US007981424B2

(12) United States Patent
Mjalli et al.

(10) Patent No.: US 7,981,424 B2
(45) Date of Patent: *Jul. 19, 2011

(54) RAGE FUSION PROTEINS, FORMULATIONS, AND METHODS OF USE THEREOF

(75) Inventors: Adnan M. M. Mjalli, Oak Ridge, NC (US); Robert Rothlein, Summerfield, NC (US); Ye Edward Tian, Jamestown, NC (US); Jeffrey C. Webster, Jamestown, NC (US); Eric J. Benjamin, Jamestown, NC (US)

(73) Assignee: Transtech Pharma, Inc., High Point, NC (US)

( * ) Notice: Subject to any disclaimer, the term of this patent is extended or adjusted under 35 U.S.C. 154(b) by 474 days.

This patent is subject to a terminal disclaimer.

(21) Appl. No.: 11/789,637

(22) Filed: Apr. 25, 2007

(65) Prior Publication Data
US 2008/0045455 A1 Feb. 21, 2008

Related U.S. Application Data

(60) Provisional application No. 60/798,455, filed on May 5, 2006.

(51) Int. Cl.
*A61K 39/00* (2006.01)
*A61K 38/16* (2006.01)
*C12P 21/00* (2006.01)

(52) U.S. Cl. ............... 424/178.1; 530/387.3; 530/402; 514/1.1

(58) Field of Classification Search .................. None
See application file for complete search history.

(56) References Cited

U.S. PATENT DOCUMENTS

| | | | |
|---|---|---|---|
| 4,867,973 A | 9/1989 | Goers et al. |
| 5,567,677 A | 10/1996 | Castensson et al. |
| 5,656,261 A | 8/1997 | Cerami et al. |
| 5,658,570 A | 8/1997 | Newman et al. |
| 5,747,035 A | 5/1998 | Presta et al. |
| 5,843,725 A | 12/1998 | Sledziewski et al. |
| 5,853,703 A | 12/1998 | Cerami et al. |
| 5,864,018 A | 1/1999 | Morser et al. |
| 5,891,341 A | 4/1999 | Li et al. |
| 6,007,865 A | 12/1999 | Cerami et al. |
| 6,018,026 A | 1/2000 | Sledziewski et al. |
| 6,225,448 B1 | 5/2001 | Tao et al. |
| 6,267,958 B1 | 7/2001 | Andya et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,380,165 B1 | 4/2002 | Al-Abed et al. |
| 6,440,749 B1 | 8/2002 | Cerami et al. |
| 6,465,422 B1 | 10/2002 | Schmidt et al. |
| 6,555,340 B1 | 4/2003 | Schmidt et al. |
| 6,555,651 B2 | 4/2003 | Stern et al. |
| 6,563,015 B1 | 5/2003 | Stern et al. |
| 6,670,136 B2 | 12/2003 | Schmidt et al. |
| 6,677,299 B2 | 1/2004 | Stern et al. |
| 6,753,150 B2 | 6/2004 | Schmidt et al. |
| 6,761,888 B1 | 7/2004 | Schenk |
| 6,790,443 B2 | 9/2004 | Stern et al. |
| 6,825,164 B1 | 11/2004 | Zlokovic et al. |
| 6,939,545 B2 | 9/2005 | Li et al. |
| 6,998,125 B2 | 2/2006 | Hanna et al. |
| 7,026,444 B2 | 4/2006 | Schmidt et al. |
| 7,081,241 B1 | 7/2006 | Schmidt et al. |
| 7,101,838 B2 | 9/2006 | Stern et al. |
| 7,125,675 B2 | 10/2006 | Schmidt et al. |
| 7,189,830 B2 | 3/2007 | Gillies et al. |
| 7,258,857 B2 | 8/2007 | Stern et al. |
| 7,470,521 B2 | 12/2008 | O'Keefe et al. |
| 2001/0039256 A1 | 11/2001 | Stern et al. |
| 2001/0053357 A1 | 12/2001 | Stern et al. |
| 2002/0002203 A1 | 1/2002 | Rahbar |
| 2002/0006391 A1 | 1/2002 | Smith et al. |
| 2002/0013256 A1 | 1/2002 | Rahbar et al. |
| 2002/0022234 A1 | 2/2002 | Al-Abed et al. |
| 2002/0037496 A1 | 3/2002 | Jacobson et al. |
| 2002/0077293 A1 | 6/2002 | Cahoon et al. |
| 2002/0082273 A1 | 6/2002 | Bush et al. |
| 2002/0086282 A1 | 7/2002 | Pillarisetti et al. |
| 2002/0102604 A1 | 8/2002 | Edwards et al. |
| 2002/0106726 A1 | 8/2002 | Schmidt et al. |
| 2002/0116725 A1 | 8/2002 | Stern et al. |
| 2002/0122799 A1 | 9/2002 | Stern et al. |

(Continued)

FOREIGN PATENT DOCUMENTS

EP 1 380 593 1/2004

(Continued)

OTHER PUBLICATIONS

Chelius et al., "Formation of Pyroglutamic Acid from N-Terminal Glutamic Acid in Immunoglobulin Gamma Antibodies" Analytical Chemistry, vol. 78, pp. 2370-2376, (2006).
Written Opinion of the International Search Authority for related PCT Application, PCT/US2007/010125, mailed Feb. 22, 2008.
International Search Report for related PCT Application, PCT/US2007/010125, mailed Feb. 22, 2008.
Patent Cooperation Treaty, International Search Report, International Application No. PCT/US2007/001686, mailed Aug. 29, 2007.
Patent Cooperation Treaty, International Search Report, International Application No. PCT/US2005/027705, mailed Nov. 10, 2005.
Jan. 11, 2008 Office Action issued in connection with U.S. Appl. No. 11/197,644.
Dec. 10, 2008 Office Action issued in connection with U.S. Appl. No. 11/197,644.

(Continued)

*Primary Examiner* — Daniel E Kolker
*Assistant Examiner* — Gregory S Emch
(74) *Attorney, Agent, or Firm* — Kilpatrick Townsend & Stockton LLP

(57) ABSTRACT

Disclosed are RAGE fusion proteins comprising RAGE polypeptide sequences linked to a second, non-RAGE polypeptide. The RAGE fusion protein may utilize a RAGE polypeptide domain comprising a RAGE ligand binding site and an interdomain linker directly linked to the N-terminus of an immunoglobulin $C_H2$ domain. Also disclosed are RAGE fusion protein formulations and the use of the RAGE fusion proteins and RAGE fusion protein formulations as therapeutics for RAGE-mediated pathologies.

52 Claims, 34 Drawing Sheets

U.S. PATENT DOCUMENTS

| | | | |
|---|---|---|---|
| 2003/0144201 | A1 | 7/2003 | Tracey et al. |
| 2004/0121372 | A1 | 6/2004 | Schmidt et al. |
| 2004/0142391 | A1 | 7/2004 | Schmidt et al. |
| 2004/0228855 | A1 | 11/2004 | Stern et al. |
| 2005/0008649 | A1 | 1/2005 | Shin et al. |
| 2005/0033017 | A1 | 2/2005 | Yamamoto et al. |
| 2005/0129682 | A1 | 6/2005 | Schmidt et al. |
| 2005/0170382 | A1 | 8/2005 | Stern et al. |
| 2005/0244849 | A1 | 11/2005 | Pittman et al. |
| 2006/0030527 | A1 | 2/2006 | Mjalli et al. |
| 2006/0040354 | A1 | 2/2006 | Goldman |
| 2006/0057679 | A1 | 3/2006 | O'Keefe et al. |
| 2006/0078562 | A1 | 4/2006 | Mjalli et al. |
| 2006/0084145 | A1 | 4/2006 | Anderson et al. |
| 2006/0140933 | A1 | 6/2006 | Pittman et al. |
| 2007/0014791 | A1 | 1/2007 | Schmidt et al. |
| 2007/0099829 | A1 | 5/2007 | Stern et al. |
| 2007/0167360 | A1 | 7/2007 | Yan et al. |
| 2008/0019986 | A1 | 1/2008 | Stern et al. |
| 2008/0045455 | A1 | 2/2008 | Mjalli |
| 2008/0075733 | A1 | 3/2008 | Mjalli et al. |
| 2008/0171701 | A1 | 7/2008 | Stern |
| 2008/0199467 | A1 | 8/2008 | Mjalli et al. |
| 2008/0207499 | A1 | 8/2008 | Barile |
| 2009/0004190 | A1 | 1/2009 | Mjalli et al. |
| 2009/0060925 | A1 | 3/2009 | Mjalli et al. |

FOREIGN PATENT DOCUMENTS

| | | |
|---|---|---|
| RU | 2219947 | 12/2003 |
| WO | WO 97/26913 | 7/1997 |
| WO | WO 97/39121 | 10/1997 |
| WO | WO 97/39125 | 10/1997 |
| WO | WO 98/22138 | 5/1998 |
| WO | WO 98/40071 | 9/1998 |
| WO | WO 99/07402 | 2/1999 |
| WO | WO 99/13912 | 3/1999 |
| WO | WO 99/18987 | 4/1999 |
| WO | WO 94/10308 | 5/1999 |
| WO | WO 99/45907 | 9/1999 |
| WO | WO 99/54485 | 10/1999 |
| WO | WO 00/18970 | 4/2000 |
| WO | WO 00/20458 | 4/2000 |
| WO | WO 00/20621 | 4/2000 |
| WO | WO 01/05422 | 1/2001 |
| WO | WO 01/12598 | 2/2001 |
| WO | WO 01/18060 | 3/2001 |
| WO | WO 01/29269 | 4/2001 |
| WO | WO 01/76584 | 10/2001 |
| WO | WO 01/79849 | 10/2001 |
| WO | WO 01/86002 | 11/2001 |
| WO | WO 01/92210 | 12/2001 |
| WO | WO 01/92892 | 12/2001 |
| WO | WO 02/14519 | 2/2002 |
| WO | WO 02/30889 | 4/2002 |
| WO | WO 02/066978 | 8/2002 |
| WO | WO 02/068636 | 9/2002 |
| WO | WO 2004/004661 | 1/2004 |
| WO | WO 2004-016229 | 2/2004 |
| WO | WO 2004/016229 | 2/2004 |
| WO | WO 2004/055055 | 7/2004 |
| WO | WO 2005/019429 | 3/2005 |
| WO | WO 2005/049852 | 6/2005 |
| WO | WO 2005/051995 | 6/2005 |
| WO | WO 2005/061538 | 7/2005 |
| WO | WO 2005/108584 | 11/2005 |
| WO | WO 2006/002971 | 1/2006 |
| WO | WO 2006/012373 | 2/2006 |
| WO | WO 2006/012415 | 2/2006 |
| WO | WO 2006-017643 | 2/2006 |
| WO | WO 2006/017643 | 2/2006 |
| WO | WO 2006/017647 | 2/2006 |
| WO | WO 2006/036922 | 4/2006 |
| WO | WO 2006/119510 | 11/2006 |
| WO | WO 2007-094926 | 8/2007 |
| WO | WO 2007/130302 | 11/2007 |
| WO | WO 08/157378 | 6/2008 |
| WO | WO 2008/100470 | 8/2008 |

OTHER PUBLICATIONS

Mohler, K. et al., Soluble Tumor Necrosis Factor (TNF) Receptors are Effective Therapeutic Agents in Lethal Endotoxemia and Function Simultaneously as Both TNF Carriers and TNF Antafonists, Journal of Immunology, vol. 151, No. 3, pp. 1548-1561, 1993.

Feb. 3, 2009 Office Action issued in connection with U.S. Appl. No. 10/990,310.

Ausubel, F. et al., Short Protocols of Molecular Biology, 4$^{th}$ Edition, Chapter 2, 1999.

Arancio, O. et al., RAGE Potentiates Aβ-induced perturbation of neuronal function in transgenic mice, EMBO Journal, Vo. 23, pp. 4096-4105, 2004.

Bucciarelli, L. et al., RAGE Blockage Stabilizes established Atherosclerosis in Diabetic Apolipoprotein E-Null Mice, Circulation vol. 106, pp. 2827-2835, 2002.

Bonnardel-Phu, E. et al., Acute Modulation of Albumin Microvascular Leakage by Advanced Glycation Ends Products in Microcirculation of Diabetic Rats in Vivo, Diabetes, vol. 48, pp. 2052-2058, 1999.

Burstein, Y. et al., Partial Amino-Acid Sequence of the Precursor of an Immunoglobulin Light Chain containing $NH_2$-Terminal Pyroglutamic Acid, Proc. Natl. Acad. Sci. USA, vol. 73, No. 8, pp. 2604-2608, 1976.

Degenhardt, T. et al., Chemical Modification of Proteins by Methylglyoxal, Cellular and Molecular Biology, vol. 44, No. 7, pp. 1139-1145, 1998.

Dyer, D. et al., Accumulation of Maillard Reaction Products in Skin Collagen in Diabetes and Aging, J. Clin. Invest., vol. 91, pp. 2463-2469, 1993.

Dyer, D. et al., Formation of Pentosidine during Nonenzymatic Browning of Proteins by Glucose, Journal of Biological Chemistry, vol. 266, No. 18, pp. 11654-11660, 1991.

Flyvbjerg, A. et al., Long Term Renal Effects of a Neutralizing RAGE Antibody in Obese Type 2 Diabetic Mice, Diabetes, vol. 53, pp. 166-172, 2004.

Guo, J. et al., Inflammation-Dependent Cerebral Deposition of Serum Amyloid A Protein in a Mouse Model of Amyloidosis, Journal of Neuroscience, vol. 22, No. 14, pp. 5900-5909, 2002.

Hammes, H. et al., Diabetic Retinopathy Risk Correlates with Intracellular Concentrations of the Glycoxidation Product $N^{\epsilon}$-(carboxymethyl) Lysine Independently of Glycohaemoglobin Concentrations, Diabetologia, vol. 42, pp. 603-607, 1999.

Hofmann, M. et al., RAGE Mediates a Novel Proinflammatory Axis: A Central Cell Surface Receptor for S100/Calgranulin Polypeptides, Cell, vol. 97, pp. 889-901, 1999.

Hofmann, M. et al., RAGE and Arthritis: the G82S Polymorphism Amplifies the Inflammatory Response, Genes and Immunity, vol. 3, pp. 123-135, 2002.

Leder, A. et al., v-Ha-ras Transgene Abrogates the Initiation Step in Mouse Skin Tumorigenesis: Effects of Phorbol Esters and Retinoic Acid, Proc. Natl. Acad, Sci. USA, vol. 81, pp. 9178-9182, 1990.

Liliensiek, B. et al., Receptor for Advanced Glycation End Products (RAGE) regulates Sepsis but not the Adaptive Immune Response, Journal of Clinical Investigation, vol. 113, No. 11, pp. 1641-1650, 2004.

Li, J. et al., Characterization and Functional Analysis of the Promoter of RAGE, the Receptor for Advanced Glycation End Products, Journal of Biological Chemistry, vol. 272, No. 26, pp. 16498-16506, 1997.

Li, J. et al., Sp1-binding Elements in the Promoter of RAGE are Essential for Amphoterin-mediated Gene Expression in Cultured Neuroblastoma Cells, Journal of Biological Chemistry, vol. 273, No. 47, pp. 30870-30878, 1998.

Lugering, N. et al., The Myeloic Related Protein MRP8/14 (27E10 antigen)-Usefulness as a Potential Marker for Disease Activity in Ulcerative Colitis and Putative Biological Function, European Journal of Clinical Investigation, vol. 25, pp. 659-664, 1995.

Luth, H. et al., Age-and-Stage-dependent Accumulation of Advanced Glycation End Products in Intracellular Deposits in Normal and Alzheimer's Disease Brains, Cerebral Cortex, vol. 15, pp. 211-220, 2005.

Miyata, T. et al., β₂-Microglobulin Modified with Advanced Glycation End Products is a Major Component of Hemodialysis-associated Amyloidosis, J. Clin. Invest., vol. 92, pp. 1243-1525, 1993.

Miyata, T. et al., The Receptor for Advanced Glycation End Products (RAGE) is a Central Mediator of the Interaction of AGE-β2 Microglobulin with Human Mononuclear Phagocytes via an Oxidant-Sensitive Pathway, J. Clin. Invest., vol. 98, No. 5, pp. 1088-1094, 1996.

Parkkinen, J. et al., Amphoterin, the 30-kDa Protein in a Family of HMG1-type Polypeptides, Journal of Biological Chemistry, vol. 268, No. 26, pp. 19726-19738, 1993.

Rammes, A. et al., Myeloid-related Protein (MRP) 8 and MRP14, Calcium-binding Proteins of the S100 Family, are Secreted by Activated Monocytes via a Novel, Tubulin-dependent Pathway, Journal of Biological Chemistry, vol. 272, No. 14, pp. 9496-9502, 1997.

Rauvala, H. et al., Isolation and Some Characteristics of an Adhesive Factor of Brain that Enhances Neurite Outgrowth in Central Neurons, Journal of Biological Chemistry, vol. 262, No. 34, pp. 16625-16635, 1987.

Renard, C. et al., The Human and Rat Recombinant Receptors for Advanced Glycation End Products have a High Degree of Homology but Different Pharmacokinetic Properties in Rats, Journal of Pharmacology and Experimental Therapeutics, vol. 290, No. 3, pp. 1458-1466, 1999.

Reddy, S. et al., Nᵉ-(Carboxymethyl)lysine is a Dominant Advanced Glycation End Product (AGE) Antigen in Tissue Proteins, Biochemistry, vol. 34, pp. 10872-10878, 1995.

Rocken, C. et all., Advanced Glycation End Products and Receptor for Advanced Glycation End Products in AA Amyloidosis, American Journal of Pathology, vol. 162, No. 4, pp. 1213-1220, 2003.

Schafer, B. et al., The S100 Family of EF-Hand Calcium-Binding Proteins: Functions and Pathology, TIBS, vol. 21, 1996.

Schleicher, E. et al., Increased Accumulation of the Glycoxidation Product Nε(carboxymethyl)lysine in Human Tissues in Diabetes and Aging, J. Clin. Invest, vol. 99, No. 3, pp. 457-468, 1997.

Schmidt, A. et al., The Dark Side of Glucose, Nature Medicine, vol. 1, No. 10, pp. 1002-1004, 1995.

Simon, R. et al., Peptoids: A Modular Approach to Drug Discovery, Proc. Natl. Acad. Sci. USA, vol. 89, pp. 9367-9371, 1992.

Schmidt, A. et al., The V-Domain of Receptor for Advanced Glycation Endproducts (RAGE) Mediates Binding of AGEs: A Novel Target for Therapy of Diabetic Complications (Abstract), Circulation, vol. 96, No. Supp. 194, pp. 137, 1987.

Taguchi, A et al., Blockade of Rage-Amphoterin Signalling Suppresses Tumour Growth and Metastases, Nature, vol. 405, pp. 354-360, 2000.

Tanaka, N. et al., The Receptor for Advanced Glycation End Products is Induced by the Glycation Products themselves and Tumor Necrosis Factor-α through Nuclear Factor-kB, and by 17β-Estradiol through Sp-1 in Human Vascular Endothelial Cells, Journal of Biological Chemistry, vol. 275, Issue 18, pp. 25781-25790, 2000.

Teillet, L. et al., Food Restriction prevents Advanced Glycation End Product Accumulation and Retards Kidney Aging in Lean Rats, J. Am. Soc. Nephrol., vol. 11, pp. 1488-1497, 2000.

Vlassara, H. et al., Advanced Glycation End-products and Atherosclerosis, The Finnish Medical Society DUODECIM, Ann. Med., vol. 28, pp. 419-426, 1996.

Wilbur, W. et al., Rapid Similarity Searches of Nucleic Acid and Protein Data Banks, Proc. Natl. Acad. Sci., USA, vol. 80, pp. 726-730, 1983.

Yan, S. et al., Receptor-dependent Cell Stress and Amyloid Accumulation in Systemic Amyloidosis, Nature Medicine, vol. 6, No. 6, pp. 643-651, 2000.

Yan, S. et al., RAGE and Amyloid-β Peptide Neuritoxicity in Alzheimer's Disease, Nature, vol. 382, pp. 685-691, 1996.

Yeh, C. et al., Requirement for p38 and p44/p42 Mitogen-Activates Protein Kinases in RAGE-Mediated Nuclear Factor-kβ Transcriptional Activation and Cytokine Secretion, Diabetes, vol. 50, pp. 1495-1504, 2001.

Zhou, Z. et al., Receptor for AGE (RAGE) Mediates Neointimal Formation in Response to Arterial Injury, Circulation, vol. 107, pp. 2238-2243, 2003.

Zhou, Z. et al., Regulation of Osteoclast Function and Bone Mann by RAGE, Journal of Experimental Medicine, vol. 203, No. 4, pp. 1067-1080, 2006.

Zimmer, D. et al., The S100 Protein Family: History, Function, and Expression, Brain Research Bulletin, vol. 37, No. 4, pp. 417-429, 1995.

Crall, F. et al., The Extramural and Intramural Coronary Arteries in Juvenile Diabetes Mellitus, American Journal of Medicine, vol. 64, pp. 221-230, 1978.

Hamby, R. et al., Reappraisal of the Role of the Diabetic State in Coronary Artery Disease, Chest, vol. 2, pp. 251-257, 1976.

Johnson, M. et al., Antioxidant with Marked Lipid-and Glucose-Lowering Activity in Diabetic Rats and Mice, Diabetes, vol. 42, pp. 1179-1186, 1993.

Kannel, W. et al., Diabetes and Glucose Tolerance as Risk Factors for Cardiovascular Disease: The Framingham Study, Diabetic Care, vol. 2, pp. 120-126, 1979.

Kannel, W. et al., Diabetes and Cardiovascular Disease—The Framingham Study, J. Am. Med. Assoc., vol. 241, pp. 2035-2038, 1979.

Needleman, S. et al., A General Method Applicable to the Search for Similarities in the Amino Acid Sequence of Two Proteins, J. Mol. Biol., vol. 48, pp. 443-453, 1970.

Park, L. et al., Suppression of Accelerated Diabetic Atherosclerosis by the Soluble Receptor for Advanced Glycation Endproducts, Nature Med., vol. 4, pp. 1025-1031, 1998.

Pearson, W. et al., Improved Tools for Biological Sequence Comparison, Proc. Natl. Acad. Sci. USA, vol. 85, pp. 2444-2448, 1998.

Pyorala, K. et al., Diabetes and Atherosclerosis, An Epidemiologic View, Diabetes/Metabolism Reviews, vol. 3, No. 2, pp. 463-524, 1987.

Smith, T. et al., Comparison of Biosequences, Advances in Applied Mathematics, Chapter 2, pp. 428-488, 1981.

Sousa, M. et al., Interaction of the Receptor for Advanced Glycation End Products (RAGE) with Transthyretin Triggers Nuclear Transcription Factor kB (NF-kB) Activation, Laboratory Investigation, vol. 80, No. 7, pp. 1101-1110, 2000.

Waller, B. et al., Status of the Coronary Arteries at Necropsy in Diabetes Mellitus with Onset after Age 30 years, Am. J. Med., vol. 69, pp. 498-506, 1980.

Yan, S. et al., Receptor-dependent Cell Stress and Amyloid Accumulation in Systemic Amyloidosis, Nature Medicine, vol. 6, pp. 643-651, 2000.

Petzold, A. et al., Cerebrospinal Fluid S100B correlates with Brain Atrophy in Alzheimer's Disease, Neuroscience Letters, vol. 336, pp. 167-170, 2003.

Yan, S. et al., Suppression of Experimental Autoimmune Encephalomyelitis by Selective Blockade of Encephalitogenic T-cell Infiltration of the Central Nervous System, nature Medicine, vol. 9, No. 3, pp. 287-293, 2003.

Lue, L. et al., Involvement of Microglial Receptor for Advanced Glycation Endproducts (RAGE) in Alzheimer's Disease: Identification of a Cellular Activation Mechanism, Experimental Neurology, vol. 171, pp. 29-45, 2001.

Ellison, J. et al., Linkage and Sequence Homology of Two Human Immunoglobulin γ heavy Chain Constant region Genes, Proc. Natl. Acad. Sci. USA, vol. 79, pp. 1984-1988, 1982.

Sasaki, N. et al., Immunohistochemical Distribution of the Receptor for Advanced Glycation End Products in Neurons and Astrocytes in Alzheimer's Disease, Brain Research, vol. 888, pp. 256-262, 2001.

Chavakis, T. et al., RAGE (Receptor for Advanced Glycation End Products): A Central Player in the Inflammatory Response, Microbes and Infection, vol. 6, pp. 1219-1225, 2004.

Jones, A. et al., Analysis of Polypeptides and Proteins, Advances Drug Delivery Reviews, vol. 10, pp. 29-90, 1993.

Bucciarelli, L. et al., RAGE is a Multiligand Receptor of the Immunoglobulin Superfamily, Implication for Homeostasis and Chronic Disease, Cell. Mol. Life Sci., vol. 59, pp. 1117-1128, 2002.

Kokkola, R. et al., RAGE is the Major Receptor for the Proinflammatory Activity of HMGB1 in Rodent Macrophages, Scandinavian Journal of Immunology, vol. 61, pp. 1-9, 2005.

Yan, S. et al., RAGE-Aβ Interactions in the Pathophysiology of Alzheimer Disease, Restorative Neurology and Neuroscience, vol. 12, pp. 167-173, 1998.

Hudson, B. et al., Blockade of Receptor for Advanced Glycation Endproducts: A New Target for Therapeutic Intervention in Diabetic Complications and Inflammatory Disorders, Archives of Biochemistry and Biophysics, vol. 419, pp. 80-88, 2003.

Morgan, B. et al., Chapter 26—Approaches to the Discovery of Non-Peptide Ligands for Peptide Receptors and Peptidases, Ann Reports Med. Chem., vol. 24, pp. 243-252, 1989.

Robertson, W. et al., Atherosclerosis in Persons with Hypertension and Diabetes Mellitus, Laboratory Investigation, vol. 18, No. 5, pp. 538-551, 1968.

Lee et al., Peptide and Protein Drug Delivery, Marcel Dekker Inc., pp. 247-301, 1990.

Schmidt, Ann Marie et al., "Isolation and Characterization of Two Binding Proteins for Advanced Glycosylation End Products from Bovine Lung Which Are Present on the Endothelial Cell Surface," The Journal of Biological Chemistry, pp. 14987-14997, vol. 267, No. 21, The American Society for Biochemistry and Molecular Biology, Inc., Jul. 25, 1992.

Wines, Bruce D. et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A1," The Journal of Immunology, 164: 5313-5318, The American Association of Immunologists, (2000).

Renard, C. et al., "Recombinant Advanced Glycation End Product Receptor Pharmacokinetics in Normal and Diabetic Rats," Molecular Pharmacology, 52: 54-62, The American Society for Pharmacology and Experimental Therapeutics, (1997).

Yan, S. D. et al., "Amyloid-β Peptide-Receptor for Advanced Glycation Endproduct Interaction Elicits Neuronal Expression of Macrophage-Colony Stimulating Factor: A Proinflammatory Pathway in Alzheimer Disease," Proc. Natl. Acad. Sci., 94: pp. 5296-5301, (1997).

Hori, et al., "The Receptor for Advanced Glycation End Products (RAGE) is a Cellular Binding Site for Amphoterin," The Journal of Biological Chemistry, 270(43); pp. 25752-25761, (1995).

Huttunen et al., Receptor for Advanced Glycation End Products-Binding COOh-Terminal Motif of Amphoterin Inhibits Invasive Migration and Metastasis, Cancer Research, 62(12); 4805-4811, (2002).

International Search Report issued Oct. 26, 2005 in connection with PCT Publication No. WO 03/025996.

Kunzendorf, U. et al., "Immunomodulation in Experimental and Clinical Nephrology Using Chimeric Proteins," Kidney Blood Press Res. 19(3-4):201-4, Department of Internal Medicine and Nephrology, Universitatsklinikum Benjamin Franklin, (1996).

Li, J., et al., "Sp1-Binding Elements in the Promoter of RAGE are Essential for Amphoterinmediated Gene Expression in Cultured Neuroblastoma Cells," The Journal of Biological Chemistry, 273(47); pp. 30870-30878, (1998).

Neeper, Michael et al., "Cloning and Expression of a Cell Surface Receptor for Advanced Glycosylation End Products of Proteins," The Journal of Biological Chemistry, pp. 14998-15004, vol. 267, No. 21, The American Society for Biochemistry and Molecular Biology, Inc., Jul. 25, 1992.

Mickle et al. "Genotype-Phenotype Relationships in Cystic Fibrosis," Med. Clin. North Am., 84(2); pp. 597-607, May 2000.

"Recombinant Human RAGE/Fc Chimera," R&D Systems, Inc., Catalog Number: 1145-Rg, Mar. 5, 2004.

Schmidt, A. et al., "Receptor for Advanced Glycation End Products (AGEs) has a Central Role in Vessel Wall Interactions and Gene Activation in Response to Circulating AGE Proteins," Proc. Natl. Acad. Sci., 91; pp. 8807-8811, (1994).

Schmidt, et al., "The Multiligand Receptor RAGE as a Progression Factor Amplifying Immune and Inflammatory Responses," J. Clin Invest. 949-955, vol. 108(7), Oct. 2001.

Stern et al., "Receptor for Advanced Glycation Endproducts (RAGE) and the Complications of Diabetes," Ageing Research Reviews, 1(1); 1-15, (2002).

Tanaka, et al., "The Receptor for Advanced Glycation End Products is Induced by the Glycation Products Themselves and Tumor Necrosis Factor-α through Nuclear Factor-kB, and by 17β-Estradiol through Sp-1 in Human Vascular Endothelial Cells," The Journal of Biological Chemistry, 275(33); pp. 25781-25790 (2000).

Apr. 24, 2006 Office Action Summary issued in connection with U.S. Appl. No. 10/643,589.

Jun. 21, 2007 Office Action Summary issued in connection with U.S. Appl. No. 10/643,589.

May 15, 2006 Interview Summary issued in connection with U.S. Appl. No. 10/643,589.

Sep. 26, 2006 Office Action issued in connection with U.S. Appl. No. 10/643,589.

Wautier, et al., "Receptor-Mediated Endothelial Cell Dysfunction in Diabetic Vasculopathy. Soluble Receptor for Advanced Glycation End Products Blocks Hyperpermeability in Diabetic Rats," J. Clin Invest., 97(1); pp. 238-243, (1996).

Yan et al., "Two-Amino Acid Molecular Switch in an Epithelial Morphogen that Regulates Binding to Two Distinct Receptors," Science 290; 523-527, (2000).

Morton, Phillip A., et al., "Differential Effects of CTLA-4 Substitutions on the Binding of Human CD80 (B7-1) and CD86 (B7-2)," The Journal of Immunology, 156: 1047-1054, The American Associates of Immunologists, (1996).

Office Action issued Oct. 24, 2007 by the Patent Office of Uzbekistan in connection with Uzbekistan Patent Application No. IAP20070074.

Oct. 18, 2007 Office Action issued in connection with U.S. Appl. No. 10/643,589.

Peppel et al., "A Tumor Necrosis Factor (TNF) Receptor-IgG Heavy Chain Chimeric Protein as a Bivalent Antagonist of TNF Activity," J. Exp. Med. 1;174 (6): 1483-9, Dec. 2000.

Rouhiainen et al., "Regulation of Monocyte Migration by Amphoterin (HMGB1)" Blood, vol. 104, pp. 1174-1176, (2004).

International Search Report mailed Dec. 15, 2005 corresponding to Application No. PCT/US2005/027694.

Written Opinion of the International Searching Authority mailed Dec. 15, 2005 corresponding to Application No. PCT/US2005/027694.

Opposition filed by ALAFAR in Jul. 2007 against Patent Application No. SP-07-7221 in Ecuador.

Office Action issued by the Patent Office of Uzbekistan on Nov. 17, 2008 corresponding to Application No. IAP20070074.

Office Action mailed Jan. 4, 2008 for U.S. Appl. No. 11/197,038.

Office Action mailed Feb. 12, 2009 for U.S. Appl. No. 11/197,038.

Office Action mailed Feb. 26, 2009 for U.S. Appl. No. 11/197,038.

First Examination Report issued by Intellectual Property Office of New Zealand on May 5, 2009 corresponding to Application No. 552128.

Search Report and Written Opinion of Octrooicentrum Nederland mailed Feb. 8, 2008 corresponding to Application No. 2000476.

Office Action issued by the Eurasian Patent Organization mailed Feb. 16, 2009 corresponding to Application No. 200870244.

International Search Report mailed Dec. 11, 2008 corresponding to Application No. PCT/US2008/001786.

Written Opinion of the International Searching Authority mailed Dec. 11, 2008 corresponding to Application No. PCT/US2008/001786.

Nickerson, P. et al., "Prolonged islet allograft acceptance in the absence of interleukin 4 expression", Transplant Immunology, Mar. 1996, vol. 4, No. 1, Mar. 1996, pp. 81-85, XP002501957 ISSN: 0966-3274 abstract.

Lekkerkerker, A.N. et al., "Potency of HIV-1 envelope glycoprotein gp120 antibodies to inhibit the interaction of DC-SIGN with HIV-1 gp120", Virology, Academic Press, Orlando, US, vol. 329, No. 2, Nov. 24, 2004 (Nov. 4, 2004), pp. 465-476, XP004613875 ISSN: 0042-6822.

Shoji-Hosaka Emi, et al., "Enhanced FC-Dependent Cellular Cytotoxicity of FC Fusion Proteins Derived From TNF Receptor II and LFA-3 By Fucose Removal From ASN-Linked Oligosaccharides," Journal of Biochemistry, Japanese Biochemical Society / OUP, Tokyo, JP, vol. 140, No. 6, Jan. 1, 2006, pp. 777-783, XP008079688, ISSN: 0021-924X.

Office Action mailed Jun. 12, 2009 by the European Patent Office (received notice Jun. 22, 2009) corresponding to Application No. 05 778 764.0 2401.

Office Action mailed Jun. 11, 2009 corresponding to U.S. Appl. No. 11/629,437.
Written Opinion of the International Searching Authority mailed Nov. 10, 2005 corresponding to Application No. PCT/US2005/027705.
Written Opinion of the International Searching Authority mailed Aug. 29, 2007 corresponding to Application No. PCT/US2007/001686.
Office Action mailed Jul. 15, 2009 corresponding to U.S. Appl. No. 11/197,038.
Office Action mailed Apr. 24, 2006 corresponding to U.S. Appl. No. 10/643,589.
Office Action mailed Sep. 26, 2006 corresponding to U.S. Appl. No. 10/643,589.
Office Action mailed Jun. 21, 2007 corresponding to U.S. Appl. No. 10/643,589.
Office Action mailed Oct. 18, 2007 corresponding to U.S. Appl. No. 10/643,589.
Office Action mailed Nov. 6, 2008 corresponding to U.S. Appl. No. 10/643,589.
Office Action mailed Mar. 18, 2009 corresponding to U.S. Appl. No. 10/643,589.
Office Action mailed Jul. 10, 2009 corresponding to U.S. Appl. No. 11/629,437.
Armour, K.L. et al., "The contrasting IgG-binding interaction of human and herpes simplex virus Fc receptors," Biochemical Society Transactions, 2002, vol. 30:495-500.
Bleck, G. T., "An Alternative Method for the Rapid Generation of Stable, High-Expressing Mammalism Cell Lines," BioProcessing Journal, Sep./Oct. 2005, pp. 1-7.
Canfield, S. M. et al., "The Binding Affinity of Human IgG for Its High Affinity Fc Receptor Is Determined by Multiple Amino Acids in the $C_H2$ Domain and Is Modulated by the Hinge Region," J. Exp. Med., 1991, vol. 173:1483-1491.
Stevenson, "Characterization of Protein and Peptide Stability and Solubility in Non-Aqueous Solvents", Current Pharmaceutical Biotechnology, 2000, vol. 2, No. 2, pp. 165-182.
Tenno, T. et al., "High-throughput construction method for expression vector of peptides for NMR study suited for isotopic labeling," Protein Engineering, Design & Selection, 2004, vol. 17:305-314.
Weiss, P. et al., "Flexible Methodology for Developing Mammalian Cell Lines," The BioPharm International Guide, Feb. 2006, pp. 30-35.
Office Action mailed Jul. 29, 2009 corresponding to European Patent Application No. 07 716 896.1.
Office Action mailed Apr. 13, 2009 corresponding to Uzbekistan Patent Application No. IAP200070074.
Decision on Grant mailed Jul. 23, 2009 corresponding to Uzbekistan Patent Application No. IAP20070074.
Written Opinion of the Austrian Patent Office mailed Jun. 17, 2009 corresponding to Singapore Patent Application No. 200700364-3.
Notice of Acceptance mailed Aug. 12, 2009 corresponding to New Zealand Patent Application No. 552128.
Office Action mailed Oct. 23, 2009 corresponding to U.S. Appl. No. 11/197,644.
Foreign reference related to U.S. Appl. No. 11/197,644: Written Opinion of the Australian Patent Office mailed Nov. 21, 2008 corresponding to Singapore Patent Application No. 200700673-7.
Foreign reference related to U.S. Appl. No. 11/197,644: Office Action mailed Apr. 16, 2009 corresponding to Indian Patent Application No. 740/DELNP/2007.
Foreign reference related to U.S. Appl. No. 11/197,644: Decision of Grant mailed Aug. 14, 2009 corresponding to Eurasian Patent Application No. 200700402.
Foreign reference related to U.S. Appl. No. 11/197,644: Decision of Grant mailed Oct. 7, 2009 corresponding to Georgian Patent Application No. AP 2005 009905.
Foreign reference related to U.S. Appl. No. 11/197,644: Office Action mailed Dec. 24, 2009 corresponding to New Zealand Patent Application No. 552842.
Foreign reference related to U.S. Appl. No. 11/197,644: Opposition filed by ALAFAR in Sep. 2007 against Patent Application No. SP-07-7297 in Ecuador.
Foreign reference related to U.S. Appl. No. 11/197,644: Office Action mailed Jan. 15, 2009 corresponding to Uzbekistan Patent Application No. IAP 2007 0073.
Foreign reference related to U.S. Appl. No. 11/197,644: Office Action mailed Mar. 2, 2009 corresponding to European Patent Application No. 05 779 648.4.
Foreign reference related to U.S. Appl. No. 11/197,644: "Recombinant Human RAGE Fc Chimera," Catalog No. 1145- RG, R&D Systems, Inc., May 7, 2009.
Foreign reference related to U.S. Appl. No. 11/197,644: Written Opinion of the Australian Patent Office mailed Mar. 5, 2008 corresponding to Singapore Patent Application No. 200700673-7.
Foreign reference related to U.S. Appl. No. 11/197,644: Search report mailed Mar. 27, 2008 corresponding to Georgian Patent Application No. AP 2005 009905.
Foreign reference related to U.S. Appl. No. 11/197,644: Office Action mailed Dec. 18, 2009 corresponding to Chinese Patent Application No. 200580025947.7.
Foreign reference related to U.S. Appl. No. 11/197,644: Ishihara, K. et al., "The receptor for advanced glycation end-products (RAGE) directly binds to ERK by a D-domain-like docking site," FEBS Letters, 2003, 550:107-113.
Foreign reference related to U.S. Appl. No. 11/197,644: Office Action mailed Sep. 15, 2009 corresponding to Ukraine Patent Application No. 2007 02216.
Foreign reference related to U.S. Appl. No. 11/197,644: Office Action mailed Jun. 18, 2008 corresponding to New Zealand Patent Application No. 552842.
Foreign reference related to U.S. Appl. No. 11/197,644: Office Action mailed Oct. 31, 2008 corresponding to Chinese Patent Application No. 200580026106.8.
Foreign reference related to U.S. Appl. No. 11/197,644: Official Notice of Readiness to Grant mailed Apr. 2009 corresponding to Eurasian Patent Application No. 200700402.
Foreign reference related to U.S. Appl. No. 11/197,644: Office Action mailed Sep. 24, 2007 corresponding to Uzbekistan Patent Application No. IAP 2007 0073.
Foreign reference related to U.S. Appl. No. 11/197,644:Office Action mailed Feb. 5, 2008 corresponding to Eurasian Patent Application No. 200700402.
Foreign reference related to U.S. Appl. No. 11/197,644: Office Action mailed Aug. 5, 2009 corresponding to Indonesia Patent Application No. W-00 2007 00370.
Foreign reference related to U.S. Appl. No. 11/197,644: Office Action mailed Dec. 1, 2009 corresponding to Australian Patent Application No. 2005271449.
Office Action mailed Mar. 24, 2010 corresponding to Ukraine Patent Application No. 200702273.
Notice of Acceptance mailed Mar. 9, 2010 corresponding to South African Patent Application No. 2009/06459.
Notice of Allowance mailed Mar. 23, 2010 corresponding to U.S. Appl. No. 11/197,038.
Notice of Allowance mailed Jan. 25, 2010 corresponding to U.S. Appl. No. 11/629,437.
Office Action mailed Apr. 8, 2010 corresponding to U.S. Appl. No. 12/069,499.
Office Action mailed Apr. 9, 2010 corresponding to Canadian Patent Application No. 2,570,324.
Preliminary Favourable Decision of Grant mailed Oct. 7, 2009 corresponding to Georgian Patent Application No. AP 2005 009904.
Notice of Allowance mailed Apr. 29, 2010 corresponding to U.S. Appl. No. 11/629,437.
Office Action mailed Jun. 23, 2010 corresponding to U.S. Appl. No. 11/197,644.
Office Action mailed May 31, 2010 corresponding to New Zealand Patent Application No. 571692.
Office Action mailed May 7, 2010 corresponding to New Zealand Patent Application No. 569545.
Office Action mailed Feb. 25, 2010 corresponding to Canadian Patent Application No. 2,575,830.

Office Action mailed May 12, 2010 corresponding to Canadian Patent Application No. 2,651,348.
Office Action mailed Jul. 30, 2010 corresponding to Canadian Patent Application No. 2,638,907.
Office Action mailed Nov. 12, 2010 corresponding to Philippine Patent Application No. 1-2006-502586.
Notice of Allowance mailed Nov. 26, 2010 corresponding to U.S. Appl. No. 11/197,038.
Notice of Abandonment mailed Oct. 22, 2010 corresponding to U.S. Appl. No. 12/069,499.
Written Opinion mailed Apr. 7, 2010 corresponding to Singapore Patent Application 200807721-6.

FIG. 1A

SEQ ID NO: 1

```
MAAGTAVGAW  VLVLSLWGAV  VGAQNITARI  GEPLVLKCKG  APKKPPQRLE
WKLNTGRTEA  WKVLSPQGGG  PWDSVARVLP  NGSLFLPAVG  IQDEGIFRCQ
AMNRNGKETK  SNYRVRVYQI  PGKPEIVDSA  SELTAGVPNK  VGTCVSEGSY
PAGTLSWHLD  GKPLVPNEKG  VSVKEQTRRH  PETGLFTLQS  ELMVTPARGG
DPRPTFSCSF  SPGLPRHRAL  RTAPIQPRVW  EPVPLEEVQL  VVEPEGGAVA
PGGTVTLTCE  VPAQPSPQIH  WMKDGVPLPL  PPSPVLILPE  IGPQDQGTYS
CVATHSSHGP  QESRAVSISI  IEPGEEGPTA  GSVGGSGLGT  LALALGILGG
LGTAALLIGV  ILWQRRQRRG  EERKAPENQE  EEEERAELNQ  SEEPEAGESS
TGGP
```

SEQ ID NO: 2

```
                        AQNITARI  GEPLVLKCKG  APKKPPQRLE
WKLNTGRTEA  WKVLSPQGGG  PWDSVARVLP  NGSLFLPAVG  IQDEGIFRCQ
AMNRNGKETK  SNYRVRVYQI  PGKPEIVDSA  SELTAGVPNK  VGTCVSEGSY
PAGTLSWHLD  GKPLVPNEKG  VSVKEQTRRH  PETGLFTLQS  ELMVTPARGG
DPRPTFSCSF  SPGLPRHRAL  RTAPIQPRVW  EPVPLEEVQL  VVEPEGGAVA
PGGTVTLTCE  VPAQPSPQIH  WMKDGVPLPL  PPSPVLILPE  IGPQDQGTYS
CVATHSSHGP  QESRAVSISI  IEPGEEGPTA  GSVGGSGLGT  LALALGILGG
LGTAALLIGV  ILWQRRQRRG  EERKAPENQE  EEEERAELNQ  SEEPEAGESS
TGGP
```

FIG. 1B

SEQ ID NO: 3

```
                          QNITARI  GEPLVLKCKG  APKKPPQRLE
WKLNTGRTEA  WKVLSPQGGG  PWDSVARVLP  NGSLFLPAVG  IQDEGIFRCQ
AMNRNGKETK  SNYRVRVYQI  PGKPEIVDSA  SELTAGVPNK  VGTCVSEGSY
PAGTLSWHLD  GKPLVPNEKG  VSVKEQTRRH  PETGLFTLQS  ELMVTPARGG
DPRPTFSCSF  SPGLPRHRAL  RTAPIQPRVW  EPVPLEEVQL  VVEPEGGAVA
PGGTVTLTCE  VPAQPSPQIH  WMKDGVPLPL  PPSPVLILPE  IGPQDQGTYS
CVATHSSHGP  QESRAVSISI  IEPGEEGPTA  GSVGGSGLGT  LALALGILGG
LGTAALLIGV  ILWQRRQRRG  EERKAPENQE  EEEERAELNQ  SEEPEAGESS
TGGP
```

FIG. 1C

SEQ ID NO: 4

```
MAAGTAVGAW VLVLSLWGAV VGAQNITARI GEPLVLKCKG APKKPPQRLE
WKLNTGRTEA WKVLSPQGGG PWDSVARVLP NGSLFLPAVG IQDEGIFRCQ
AMNRNGKETK SNYRVRVYQI PGKPEIVDSA SELTAGVPNK VGTCVSEGSY
PAGTLSWHLD GKPLVPNEKG VSVKEQTRRH PETGLFTLQS ELMVTPARGG
DPRPTFSCSF SPGLPRHRAL RTAPIQPRVW EPVPLEEVQL VVEPEGGAVA
PGGTVTLTCE VPAQPSPQIH WMKDGVPLPL PPSPVLILPE IGPQDQGTYS
CVATHSSHGP QESRAVSISI IEPGEEGPTA GSVGGSGLG
```

SEQ ID NO: 5

```
                      AQNITARI GEPLVLKCKG APKKPPQRLE
WKLNTGRTEA WKVLSPQGGG PWDSVARVLP NGSLFLPAVG IQDEGIFRCQ
AMNRNGKETK SNYRVRVYQI PGKPEIVDSA SELTAGVPNK VGTCVSEGSY
PAGTLSWHLD GKPLVPNEKG VSVKEQTRRH PETGLFTLQS ELMVTPARGG
DPRPTFSCSF SPGLPRHRAL RTAPIQPRVW EPVPLEEVQL VVEPEGGAVA
PGGTVTLTCE VPAQPSPQIH WMKDGVPLPL PPSPVLILPE IGPQDQGTYS
CVATHSSHGP QESRAVSISI IEPGEEGPTA GSVGGSGLG
```

SEQ ID NO: 6

```
                       QNITARI GEPLVLKCKG APKKPPQRLE
WKLNTGRTEA WKVLSPQGGG PWDSVARVLP NGSLFLPAVG IQDEGIFRCQ
AMNRNGKETK SNYRVRVYQI PGKPEIVDSA SELTAGVPNK VGTCVSEGSY
PAGTLSWHLD GKPLVPNEKG VSVKEQTRRH PETGLFTLQS ELMVTPARGG
DPRPTFSCSF SPGLPRHRAL RTAPIQPRVW EPVPLEEVQL VVEPEGGAVA
PGGTVTLTCE VPAQPSPQIH WMKDGVPLPL PPSPVLILPE IGPQDQGTYS
CVATHSSHGP QESRAVSISI IEPGEEGPTA GSVGGSGLG
```

FIG. 1D

SEQ ID NO: 7

```
 AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVR
```

SEQ ID NO: 8

```
  QNITARI GEPLVLKCKG APKKPPQRLE WKLNTGRTEA WKVLSPQGGG
PWDSVARVLP NGSLFLPAVG IQDEGIFRCQ AMNRNGKETK SNYRVR
```

SEQ ID NO: 9

```
 AQNITARI GEPLVLKCKG APKKPPQRLE WK
```

SEQ ID NO: 10

```
  QNITARI GEPLVLKCKG APKKPPQRLE WK
```

SEQ ID NO: 11

```
                        PEIVDSA SELTAGVPNK VGTCVSEGSY
PAGTLSWHLD GKPLVPNEKG VSVKEQTRRH PETGLFTLQS ELMVTPARGG
DPRPTFSCSF SPGLPRHRAL R
```

SEQ ID NO: 12

```
                   PRVW EPVPLEEVQL VVEPEGGAVA
PGGTVTLTCE VPAQPSPQIH WMKDGVPLPL PPSPVLILPE IGPQDQGTYS
CVATHSSHGP QESRAVS
```

SEQ ID NO: 13

```
 AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGK
```

FIG. 1 E

SEQ ID NO: 14

```
    QNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGK
```

SEQ ID NO: 15

```
   AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAG
```

SEQ ID NO: 16

```
    QNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAG
```

SEQ ID NO: 17

```
   AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQ
```

SEQ ID NO: 18

```
    QNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQ
```

FIG. 1F

SEQ ID NO: 19

```
    AQNITARI  GEPLVLKCKG  APKKPPQRLE  WKLNTGRTEA  WKVLSPQGGG
PWDSVARVLP  NGSLFLPAVG  IQDEGIFRCQ  AMNRNGKETK  SNYRVRVYQI
PGKPEIVDSA  SELTAGVPNK  VGTCVSEGSY  PAGTLSWHLD  GKPLVPNEKG
VSVKEQTRRH  PETGLFTLQS  ELMVTPARGG  DPRPTFSCSF  SPGLPRHRAL
RTAPIQPRVW  EPVPLEEVQL  VVEPEGGAVA  P
```

SEQ ID NO: 20

```
     QNITARI  GEPLVLKCKG  APKKPPQRLE  WKLNTGRTEA  WKVLSPQGGG
PWDSVARVLP  NGSLFLPAVG  IQDEGIFRCQ  AMNRNGKETK  SNYRVRVYQI
PGKPEIVDSA  SELTAGVPNK  VGTCVSEGSY  PAGTLSWHLD  GKPLVPNEKG
VSVKEQTRRH  PETGLFTLQS  ELMVTPARGG  DPRPTFSCSF  SPGLPRHRAL
RTAPIQPRVW  EPVPLEEVQL  VVEPEGGAVA  P
```

SEQ ID NO: 21

VYQIPGK

SEQ ID NO: 22

TAPIQPRVWE  PVPLEEVQLV  VEPEGGAVAP

SEQ ID NO: 23

VYQIPGKPEI  VDSASELTAG

SEQ ID NO: 24

TAPIQ

FIG. 1G

SEQ ID NO: 25
ATGGCAGCCG AACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG ACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTAC

SEQ ID NO: 26
ATGGCAGCCG AACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG ACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAG

SEQ ID NO: 27
ATGGCAGCCG AACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG ACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGT

FIG. 1H

SEQ ID NO:28

ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG GACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTGT TCCCAATAAG GTGGGGACAT GTGTGTCAGA GGGGAGCTAC
CCTGCAGGGA CTCTTAGCTG GCACTTGGAT GGGAAGCCCC TGGTGCCTAA
TGAGAAGGGA GTATCTGTGA AGGAACAGAC CAGGAGACAC CCTGAGACAG
GGCTCTTCAC ACTGCAGTCG GAGCTAATGG TGACCCCAGC CCGGGGAGGA
GATCCCCGTC CCACCTTCTC CTGTAGCTTC AGCCCAGGCC TTCCCCGACA
CCGGGCCTTG CGCACAGCCC CCATCCAGCC CCGTGTCTGG

SEQ ID NO:29

ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG GACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTGT TCCCAATAAG GTGGGGACAT GTGTGTCAGA GGGGAGCTAC
CCTGCAGGGA CTCTTAGCTG GCACTTGGAT GGGAAGCCCC TGGTGCCTAA
TGAGAAGGGA GTATCTGTGA AGGAACAGAC CAGGAGACAC CCTGAGACAG
GGCTCTTCAC ACTGCAGTCG GAGCTAATGG TGACCCCAGC CCGGGGAGGA
GATCCCCGTC CCACCTTCTC CTGTAGCTTC AGCCCAGGCC TTCCCCGACA
CCGGGCCTTG CGCACAGCCC CCATCCAGCC CCGTGTCTGG GAGCCTGTGC
CTCTGGAGGA GGTCCAATTG GTGGTGGAGC CAGAAGGTGG AGCAGTAGCT
CCT

FIG. 1I

SEQ ID NO: 38

```
        PSVF LFPPKPKDTL MISRTPEVTC VVVDVSHEDP EVKFNWYVDG
VEVHNAKTKP REEQYNSTYR VVSVLTVLHQ DWLNGKEYKC KVSNKALPAP
IEKTISKAKG QPREPQVYTL PPSRDELTKN QVSLTCLVKG FYPSDIAVEW
ESNGQPENNY KTTPPVLDSD GSFFLYSKLT VDKSRWQQGN VFSCSVMHEA
LHNHYTQKSL SLSPGK
```

SEQ ID NO: 39

```
        CCGTCAG TCTTCCTCTT CCCCCCAAAA CCCAAGGACA CCCTCATGAT
CTCCCGGACC CCTGAGGTCA CATGCGTGGT GGTGGACGTG AGCCACGAAG
ACCCTGAGGT CAAGTTCAAC TGGTACGTGG ACGGCGTGGA GGTGCATAAT
GCCAAGACAA AGCCGCGGGA GGAGCAGTAC AACAGCACGT ACCGTGTGGT
CAGCGTCCTC ACCGTCCTGC ACCAGGACTG GCTGAATGGC AAGGAGTACA
AGTGCAAGGT CTCCAACAAA GCCCTCCCAG CCCCCATCGA GAAAACCATC
TCCAAAGCCA AAGGGCAGCC CCGAGAACCA CAGGTGTACA CCCTGCCCCC
ATCCCGGGAT GAGCTGACCA AGAACCAGGT CAGCCTGACC TGCCTGGTCA
AAGGCTTCTA TCCCAGCGAC ATCGCCGTGG AGTGGGAGAG CAATGGGCAG
CCGGAGAACA ACTACAAGAC CACGCCTCCC GTGCTGGACT CCGACGGCTC
CTTCTTCCTC TACAGCAAGC TCACCGTGGA CAAGAGCAGG TGGCAGCAGG
GGAACGTCTT CTCATGCTCC GTGATGCATG AGGCTCTGCA CAACCACTAC
ACGCAGAAGA GCCTCTCCCT GTCTCCGGGT AAATGA
```

SEQ ID NO: 40

```
PCPAPELLGG PSVFLFPPKP KDTLMISRTP EVTCVVVDVS HEDPEVKFNW
YVDGVEVHNA KTKPREEQYN STYRVVSVLT VLHQDWLNGK EYKCKVSNKA
LPAPIEKTIS KAKGQPREPQ VYTLPPSRDE LTKNQVSLTC LVKGFYPSDI
AVEWESNGQP ENNYKTTPPV LDSDGSFFLY SKLTVDKSRW QQGNVFSCSV
MHEALHNHYT QKSLSLSPGK
```

FIG. 1J

SEQ ID NO: 41

```
CCGTGCCCAG CACCTGAACT CCTGGGGGGA CCGTCAGTCT TCCTCTTCCC
CCCAAAACCC AAGGACACCC TCATGATCTC CCGGACCCCT GAGGTCACAT
GCGTGGTGGT GGACGTGAGC CACGAAGACC CTGAGGTCAA GTTCAACTGG
TACGTGGACG GCGTGGAGGT GCATAATGCC AAGACAAAGC CGCGGGAGGA
GCAGTACAAC AGCACGTACC GTGTGGTCAG CGTCCTCACC GTCCTGCACC
AGGACTGGCT GAATGGCAAG GAGTACAAGT GCAAGGTCTC CAACAAAGCC
CTCCCAGCCC CCATCGAGAA AACCATCTCC AAAGCCAAAG GCAGCCCCG
AGAACCACAG GTGTACACCC TGCCCCCATC CCGGGATGAG CTGACCAAGA
ACCAGGTCAG CCTGACCTGC CTGGTCAAAG GCTTCTATCC CAGCGACATC
GCCGTGGAGT GGGAGAGCAA TGGGCAGCCG GAGAACAACT ACAAGACCAC
GCCTCCCGTG CTGGACTCCG ACGGCTCCTT CTTCCTCTAC AGCAAGCTCA
CCGTGGACAA GAGCAGGTGG CAGCAGGGGA ACGTCTTCTC ATGCTCCGTG
ATGCATGAGG CTCTGCACAA CCACTACACG CAGAAGAGCC TCTCCCTGTC
TCCGGGTAAA TGA
```

SEQ ID NO: 42

```
PCPAPELLGG PSVFLFPPKP KDTLMISRTP EVTCVVVDVS HEDPEVKFNW
YVDGVEVHNA KTKPREEQYN STYRVVSVLT VLHQDWLNGK EYKCKVSNKA
LPAPIEKTIS KAK
```

SEQ ID NO: 43

```
           GQPREPQ VYTLPPSRDE LTKNQVSLTC LVKGFYPSDI
AVEWESNGQP ENNYKTTPPV LDSDGSFFLY SKLTVDKSRW QQGNVFSCSV
MHEALHNHYT QKSLSLSPGK
```

SEQ ID NO: 44

```
ISI IEPGEEGPTA GSVGGSGLGT LA
```

FIG. 1K

SEQ ID NO: 45

```
                              pENITARI   GEPLVLKCKG   APKKPPQRLE
WKLNTGRTEA   WKVLSPQGGG   PWDSVARVLP   NGSLFLPAVG   IQDEGIFRCQ
AMNRNGKETK   SNYRVRVYQI   PGKPEIVDSA   SELTAGVPNK   VGTCVSEGSY
PAGTLSWHLD   GKPLVPNEKG   VSVKEQTRRH   PETGLFTLQS   ELMVTPARGG
DPRPTFSCSF   SPGLPRHRAL   RTAPIQPRVW   EPVPLEEVQL   VVEPEGGAVA
PGGTVTLTCE   VPAQPSPQIH   WMKDGVPLPL   PPSPVLILPE   IGPQDQGTYS
CVATHSSHGP   QESRAVSISI   IEPGEEGPTA   GSVGGSGLG
```

SEQ ID NO: 46

```
   pENITARI   GEPLVLKCKG   APKKPPQRLE   WKLNTGRTEA   WKVLSPQGGG
PWDSVARVLP   NGSLFLPAVG   IQDEGIFRCQ   AMNRNGKETK   SNYRVR
```

SEQ ID NO: 47

```
   pENITARI   GEPLVLKCKG   APKKPPQRLE   WK
```

SEQ ID NO: 48

```
   pENITARI   GEPLVLKCKG   APKKPPQRLE   WKLNTGRTEA   WKVLSPQGGG
PWDSVARVLP   NGSLFLPAVG   IQDEGIFRCQ   AMNRNGKETK   SNYRVRVYQI
PGK
```

FIG. 1L

SEQ ID NO: 49

```
   pENITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAG
```

SEQ ID NO: 50

```
   pENITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQ
```

SEQ ID NO: 51

```
   pENITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQPRVW EPVPLEEVQL VVEPEGGAVA P
```

FIG. 1M

SEQ ID NO: 52

```
     CCGTCAG TCTTCCTCTT CCCCCCAAAA CCCAAGGACA CCCTCATGAT
CTCCCGGACC CCTGAGGTCA CATGCGTGGT GGTGGACGTG AGCCACGAAG
ACCCTGAGGT CAAGTTCAAC TGGTACGTGG ACGGCGTGGA GGTGCATAAT
GCCAAGACAA AGCCGCGGGA GGAGCAGTAC AACAGCACGT ACCGTGTGGT
CAGCGTCCTC ACCGTCCTGC ACCAGGACTG GCTGAATGGC AAGGAGTACA
AGTGCAAGGT CTCCAACAAA GCCCTCCAG CCCCCATCGA GAAAACCATC
TCCAAAGCCA AAGGGCAGCC CCGAGAACCA CAGGTGTACA CCCTGCCCCC
ATCCCGGGAT GAGCTGACCA AGAACCAGGT CAGCCTGACC TGCCTGGTCA
AAGGCTTCTA TCCCAGCGAC ATCGCCGTGG AGTGGGAGAG CAATGGGCAG
CCGGAGAACA ACTACAAGAC CACGCCTCCC GTGCTGGACT CCGACGGCTC
CTTCTTCCTC TACAGCAAGC TCACCGTGGA CAAGAGCAGG TGGCAGCAGG
GGAACGTCTT CTCATGCTCC GTGATGCATG AGGCTCTGCA CAACCACTAC
ACGCAGAAGA GCCTCTCCCT GTCTCCGGG AAATGA
```

SEQ ID NO: 53

```
CCGTGCCCAG CACCTGAACT CCTGGGGGGA CCGTCAGTCT TCCTCTTCCC
CCCAAAACCC AAGGACACCC TCATGATCTC CCGGACCCCT GAGGTCACAT
GCGTGGTGGT GGACGTGAGC CACGAAGACC CTGAGGTCAA GTTCAACTGG
TACGTGGACG GCGTGGAGGT GCATAATGCC AAGACAAAGC CGCGGGAGGA
GCAGTACAAC AGCACGTACC GTGTGGTCAG CGTCCTCACC GTCCTGCACC
AGGACTGGCT GAATGGCAAG GAGTACAAGT GCAAGGTCTC CAACAAAGCC
CTCCCAGCCC CCATCGAGAA AACCATCTCC AAAGCCAAAG GCAGCCCCG
AGAACCACAG GTGTACACCC TGCCCCCATC CCGGGATGAG CTGACCAAGA
ACCAGGTCAG CCTGACCTGC CTGGTCAAAG GCTTCTATCC CAGCGACATC
GCCGTGGAGT GGGAGAGCAA TGGGCAGCCG GAGAACAACT ACAAGACCAC
GCCTCCCGTG CTGGACTCCG ACGGCTCCTT CTTCCTCTAC AGCAAGCTCA
CCGTGGACAA GAGCAGGTGG CAGCAGGGA ACGTCTTCTC ATGCTCCGTG
ATGCATGAGG CTCTGCACAA CCACTACACG CAGAAGAGCC TCTCCCTGTC
TCCGGGAAA TGA
```

```
ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCAAGA AACCACCCCA GCGGCTGGAA
TGGAAACTGA ACACAGGCCG GACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTGT TCCCAATAAG GTGGGGACAT GTGTGTCAGA GGGGAGCTAC
CCTGCAGGGA CTCTTAGCTG GCACTTGGAT GGGAAGCCCC TGGTGCCTAA
TGAGAAGGGA GTATCTGTGA AGGAACAGAC CAGGAGACAC CCTGAGACAG
GGCTCTTCAC ACTGCAGTCG GAGCTAATGG TGACCCCAGC CCGGGGAGGA
GATCCCCGTC CCACCTTCTC CTGTAGCTTC AGCCCAGGCC TTCCCCGACA
CCGGGCCTTG CGCACAGCCC CCATCCAGCC CCGTGTCTGG GAGCCTGTGC
CTCTGGAGGA GGTCCAATTG GTGGTGGAGC CAGAAGGTGG AGCAGTAGCT
CCTCCGTCAG TCTTCCTCTT CCCCCAAAA CCCAAGGACA CCCTCATGAT
CTCCCGGACC CCTGAGGTCA CATGCGTGGT GGTGGACGTG AGCCACGAAG
ACCCTGAGGT CAAGTTCAAC TGGTACGTGG ACGGCGTGGA GGTGCATAAT
GCCAAGACAA AGCCGCGGGA GGAGCAGTAC AACAGCACGT ACCGTGTGGT
CAGCGTCCTC ACCGTCCTGC ACCAGGACTG GCTGAATGGC AAGGAGTACA
AGTGCAAGGT CTCCAACAAA GCCCTCCCAG CCCCCATCGA GAAAACCATC
TCCAAAGCCA AAGGGCAGCC CCGAGAACCA CAGGTGTACA CCCTGCCCCC
ATCCCGGGAT GAGCTGACCA AGAACCAGGT CAGCCTGACC TGCCTGGTCA
AAGGCTTCTA TCCCAGCGAC ATCGCCGTGG AGTGGGAGAG CAATGGGCAG
CCGGAGAACA ACTACAAGAC CACGCCTCCC GTGCTGGACT CCGACGGCTC
CTTCTTCCTC TACAGCAAGC TCACCGTGGA CAAGAGCAGG TGGCAGCAGG
GGAACGTCTT CTCATGCTCC GTGATGCATG AGGCTCTGCA CAACCACTAC
ACGCAGAAGA GCCTCTCCCT GTCTCCGGGT AAATGA
```

(SEQ ID NO: 30)

FIG. 2A

```
ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG GACAGAAGCT GGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTGT TCCCAATAAG GTGGGGACAT GTGTGTCAGA GGGGAGCTAC
CCTGCAGGGA CTCTTAGCTG GCACTTGGAT GGGAAGCCCC TGGTGCCTAA
TGAGAAGGGA GTATCTGTGA AGGAACAGAC CAGGAGACAC CCTGAGACAG
GGCTCTTCAC ACTGCAGTCG GAGCTAATGG TGACCCCAGC CCGGGGAGGA
GATCCCCGTC CCACCTTCTC CTGTAGCTTC AGCCCAGGCC TTCCCCGACA
CCGGGCCTTG CGCACAGCCC CCATCCAGCC CCGTGTCTGG GAGCCTGTGC
CTCTGGAGGA GGTCCAATTG GTGGTGGAGC CAGAAGGTGG AGCAGTAGCT
CCTCCGTCAG TCTTCCTCTT CCCCCCAAAA CCCAAGGACA CCCTCATGAT
CTCCCGGACC CCTGAGGTCA CATGCGTGGT GGTGGACGTG AGCCACGAAG
ACCCTGAGGT CAAGTTCAAC TGGTACGTGG ACGGCGTGGA GGTGCATAAT
GCCAAGACAA AGCCGCGGGA GGAGCAGTAC AACAGCACGT ACCGTGTGGT
CAGCGTCCTC ACCGTCCTGC ACCAGGACTG GCTGAATGGC AAGGAGTACA
AGTGCAAGGT CTCCAACAAA GCCCTCCCAG CCCCCATCGA GAAAACCATC
TCCAAAGCCA AGGGCAGCC CCGAGAACCA CAGGTGTACA CCCTGCCCCC
ATCCCGGGAT GAGCTGACCA AGAACCAGGT CAGCCTGACC TGCCTGGTCA
AAGGCTTCTA TCCCAGCGAC ATCGCCGTGG AGTGGGAGAG CAATGGGCAG
CCGGAGAACA ACTACAAGAC CACGCCTCCC GTGCTGGACT CCGACGGCTC
CTTCTTCCTC TACAGCAAGC TCACCGTGGA CAAGAGCAGG TGGCAGCAGG
GGAACGTCTT CTCATGCTCC GTGATGCATG AGGCTCTGCA CAACCACTAC
ACGCAGAAGA GCCTCTCCCT GTCTCCGGG AAATGA
```

(SEQ ID NO: 54)

FIG. 2B

```
ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG GACAGAAGCT TGGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTCC GTCAGTCTTC CTCTTCCCCC CAAAACCCAA GGACACCCTC
ATGATCTCCC GGACCCCTGA GGTCACATGC GTGGTGGTGG ACGTGAGCCA
CGAAGACCCT GAGGTCAAGT TCAACTGGTA CGTGGACGGC GTGGAGGTGC
ATAATGCCAA GACAAAGCCG CGGGAGGAGC AGTACAACAG CACGTACCGT
GTGGTCAGCG TCCTCACCGT CCTGCACCAG GACTGGCTGA ATGGCAAGGA
GTACAAGTGC AAGGTCTCCA ACAAAGCCCT CCCAGCCCCC ATCGAGAAAA
CCATCTCCAA AGCCAAGGG CAGCCCCGAG AACCACAGGT GTACACCCTG
CCCCCATCCC GGGATGAGCT GACCAAGAAC CAGGTCAGCC TGACCTGCCT
GGTCAAAGGC TTCTATCCCA GCGACATCGC CGTGGAGTGG GAGAGCAATG
GGCAGCCGGA GAACAACTAC AAGACCACGC CTCCCGTGCT GGACTCCGAC
GGCTCCTTCT TCCTCTACAG CAAGCTCACC GTGGACAAGA GCAGGTGGCA
GCAGGGGAAC GTCTTCTCAT GCTCCGTGAT GCATGAGGCT CTGCACAACC
ACTACACGCA GAAGAGCCTC TCCCTGTCTC CGGGTAAATG A
```

(SEQ ID NO: 31)

FIG. 3A

```
ATGGCAGCCG GAACAGCAGT TGGAGCCTGG GTGCTGGTCC TCAGTCTGTG
GGGGGCAGTA GTAGGTGCTC AAAACATCAC AGCCCGGATT GGCGAGCCAC
TGGTGCTGAA GTGTAAGGGG GCCCCCAAGA AACCACCCCA GCGGCTGGAA
TGGAAACTGA ACACAGGCCG GACAGAAGCT GGAAGGTCC TGTCTCCCCA
GGGAGGAGGC CCCTGGGACA GTGTGGCTCG TGTCCTTCCC AACGGCTCCC
TCTTCCTTCC GGCTGTCGGG ATCCAGGATG AGGGGATTTT CCGGTGCCAG
GCAATGAACA GGAATGGAAA GGAGACCAAG TCCAACTACC GAGTCCGTGT
CTACCAGATT CCTGGGAAGC CAGAAATTGT AGATTCTGCC TCTGAACTCA
CGGCTGGTCC GTCAGTCTTC CTCTTCCCCC CAAAACCCAA GGACACCCTC
ATGATCTCCC GGACCCCTGA GGTCACATGC GTGGTGGTGG ACGTGAGCCA
CGAAGACCCT GAGGTCAAGT TCAACTGGTA CGTGGACGGC GTGGAGGTGC
ATAATGCCAA GACAAAGCCG CGGGAGGAGC AGTACAACAG CACGTACCGT
GTGGTCAGCG TCCTCACCGT CCTGCACCAG GACTGGCTGA ATGGCAAGGA
GTACAAGTGC AAGGTCTCCA ACAAAGCCCT CCCAGCCCCC ATCGAGAAAA
CCATCTCCAA AGCCAAGGG CAGCCCCGAG AACCACAGGT GTACACCCTG
CCCCCATCCC GGGATGAGCT GACCAAGAAC CAGGTCAGCC TGACCTGCCT
GGTCAAAGGC TTCTATCCCA GCGACATCGC CGTGGAGTGG GAGAGCAATG
GGCAGCCGGA GAACAACTAC AAGACCACGC CTCCCGTGCT GGACTCCGAC
GGCTCCTTCT TCCTCTACAG CAAGCTCACC GTGGACAAGA GCAGGTGGCA
GCAGGGGAAC GTCTTCTCAT GCTCCGTGAT GCATGAGGCT CTGCACAACC
ACTACACGCA GAAGAGCCTC TCCCTGTCTC CGGGAAATG A
```

(SEQ ID NO: 55).

FIG. 3B

SEQ ID NO: 32
MAAGTAVGAW VLVLSLWGAV VGAQNITARI GEPLVLKCKG APKKPPQRLE
WKLNTGRTEA WKVLSPQGGG PWDSVARVLP NGSLFLPAVG IQDEGIFRCQ
AMNRNGKETK SNYRVRVYQI PGKPEIVDSA SELTAGVPNK VGTCVSEGSY
PAGTLSWHLD GKPLVPNEKG VSVKEQTRRH PETGLFTLQS ELMVTPARGG
DPRPTFSCSF SPGLPRHRAL RTAPIQPRVW EPVPLEEVQL VVEPEGGAVA
PPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI
SKAKGQPREP QVYTLPPSRD ELTKNQVSLT CLVKGFYPSD IAVEWESNGQ
PENNYKTTPP VLDSDGSFFL YSKLTVDKSR WQQGNVFSCS VMHEALHNHY
TQKSLSLSPG K

SEQ ID NO: 33
   AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQPRVW EPVPLEEVQL VVEPEGGAVA PPSVFLFPPK PKDTLMISRT
PEVTCVVVDV SHEDPEVKFN WYVDGVEVHN AKTKPREEQY NSTYRVVSVL
TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL
YSKLTVDKSR WQQGNVFSCS VMHEALHNHY TQKSLSLSPG K

SEQ ID NO: 34
    QNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQPRVW EPVPLEEVQL VVEPEGGAVA PPSVFLFPPK PKDTLMISRT
PEVTCVVVDV SHEDPEVKFN WYVDGVEVHN AKTKPREEQY NSTYRVVSVL
TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL
YSKLTVDKSR WQQGNVFSCS VMHEALHNHY TQKSLSLSPG K

SEQ ID NO: 56
   pENITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGVPNK VGTCVSEGSY PAGTLSWHLD GKPLVPNEKG
VSVKEQTRRH PETGLFTLQS ELMVTPARGG DPRPTFSCSF SPGLPRHRAL
RTAPIQPRVW EPVPLEEVQL VVEPEGGAVA PPSVFLFPPK PKDTLMISRT
PEVTCVVVDV SHEDPEVKFN WYVDGVEVHN AKTKPREEQY NSTYRVVSVL
TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL
YSKLTVDKSR WQQGNVFSCS VMHEALHNHY TQKSLSLSPG K

FIG. 4

SEQ ID NO: 35
MAAGTAVGAW VLVLSLWGAV VGAQNITARI GEPLVLKCKG APKKPPQRLE
WKLNTGRTEA WKVLSPQGGG PWDSVARVLP NGSLFLPAVG IQDEGIFRCQ
AMNRNGKETK SNYRVRVYQI PGKPEIVDSA SELTAGPSVF LFPPKPKDTL
MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL
PPSRDELTKN QVSLTCLVKG FYPSDIAVEW ESNGQPENNY KTTPPVLDSD
GSFFLYSKLT VDKSRWQQGN VFSCSVMHEA LHNHYTQKSL SLSPGK

SEQ ID NO: 36
           AQNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGPSVF LFPPKPKDTL MISRTPEVTC VVVDVSHEDP
EVKFNWYVDG VEVHNAKTKP REEQYNSTYR VVSVLTVLHQ DWLNGKEYKC
KVSNKALPAP IEKTISKAKG QPREPQVYTL PPSRDELTKN QVSLTCLVKG
FYPSDIAVEW ESNGQPENNY KTTPPVLDSD GSFFLYSKLT VDKSRWQQGN
VFSCSVMHEA LHNHYTQKSL SLSPGK

SEQ ID NO: 37
            QNITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGPSVF LFPPKPKDTL MISRTPEVTC VVVDVSHEDP
EVKFNWYVDG VEVHNAKTKP REEQYNSTYR VVSVLTVLHQ DWLNGKEYKC
KVSNKALPAP IEKTISKAKG QPREPQVYTL PPSRDELTKN QVSLTCLVKG
FYPSDIAVEW ESNGQPENNY KTTPPVLDSD GSFFLYSKLT VDKSRWQQGN
VFSCSVMHEA LHNHYTQKSL SLSPGK

SEQ ID NO: 57
            pENITARI GEPLVLKCKG APKKPPQRLE WKLNTGRTEA WKVLSPQGGG
PWDSVARVLP NGSLFLPAVG IQDEGIFRCQ AMNRNGKETK SNYRVRVYQI
PGKPEIVDSA SELTAGPSVF LFPPKPKDTL MISRTPEVTC VVVDVSHEDP
EVKFNWYVDG VEVHNAKTKP REEQYNSTYR VVSVLTVLHQ DWLNGKEYKC
KVSNKALPAP IEKTISKAKG QPREPQVYTL PPSRDELTKN QVSLTCLVKG
FYPSDIAVEW ESNGQPENNY KTTPPVLDSD GSFFLYSKLT VDKSRWQQGN
VFSCSVMHEA LHNHYTQKSL SLSPGK

FIG. 5

FIG. 6A
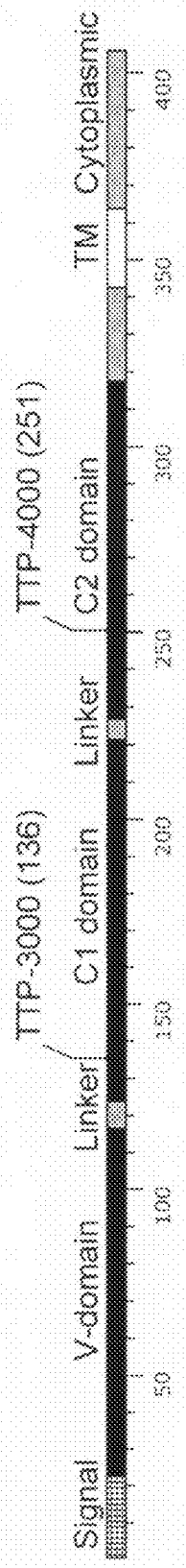
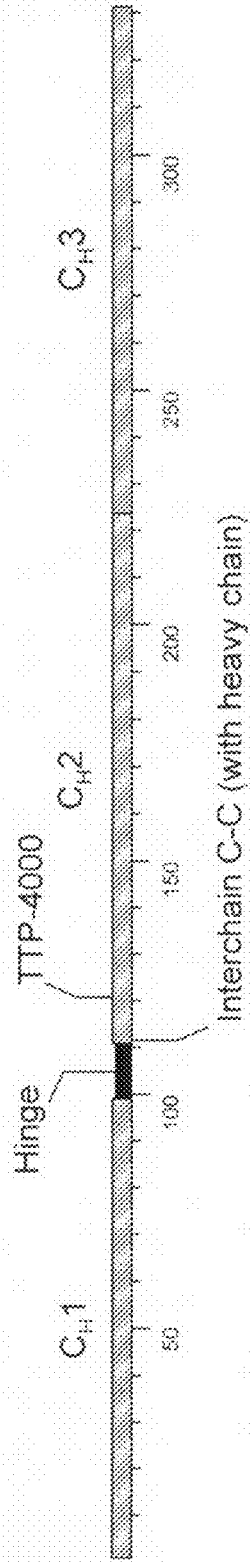

SEQUENCE LISTING

<160> NUMBER OF SEQ ID NOS: 57

<210> SEQ ID NO 1
<211> LENGTH: 404
<212> TYPE: PRT
<213> ORGANISM: Homo sapiens

<400> SEQUENCE: 1

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
        355                 360                 365

Arg Gly Glu Glu Arg Lys Ala Pro Glu Asn Gln Glu Glu Glu Glu
        370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 2
<211> LENGTH: 382
<212> TYPE: PRT
<213> ORGANISM: Homo sapiens

<400> SEQUENCE: 2

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Ser Val Gly Gly Ser Gly Leu Gly Thr Leu Ala
305                 310                 315                 320

Leu Ala Leu Gly Ile Leu Gly Gly Leu Gly Thr Ala Ala Leu Leu Ile
                325                 330                 335

```
Gly Val Ile Leu Trp Gln Arg Arg Gln Arg Gly Glu Glu Arg Lys
            340                 345                 350
Ala Pro Glu Asn Gln Glu Glu Glu Arg Ala Glu Leu Asn Gln
        355                 360                 365
Ser Glu Glu Pro Glu Ala Gly Glu Ser Ser Thr Gly Gly Pro
    370                 375                 380

<210> SEQ ID NO 3
<211> LENGTH: 381
<212> TYPE: PRT
<213> ORGANISM: Homo sapiens

<400> SEQUENCE: 3

Gln Asn Ile Thr Ala Arg Ile Gly Glu Pro Leu Val Leu Lys Cys Lys
1               5                   10                  15
Gly Ala Pro Lys Lys Pro Pro Gln Arg Leu Glu Trp Lys Leu Asn Thr
            20                  25                  30
Gly Arg Thr Glu Ala Trp Lys Val Leu Ser Pro Gln Gly Gly Pro
        35                  40                  45
Trp Asp Ser Val Ala Arg Val Leu Pro Asn Gly Ser Leu Phe Leu Pro
    50                  55                  60
Ala Val Gly Ile Gln Asp Glu Gly Ile Phe Arg Cys Gln Ala Met Asn
65                  70                  75                  80
Arg Asn Gly Lys Glu Thr Lys Ser Asn Tyr Arg Val Arg Val Tyr Gln
                85                  90                  95
Ile Pro Gly Lys Pro Glu Ile Val Asp Ser Ala Ser Glu Leu Thr Ala
            100                 105                 110
Gly Val Pro Asn Lys Val Gly Thr Cys Val Ser Glu Gly Ser Tyr Pro
        115                 120                 125
Ala Gly Thr Leu Ser Trp His Leu Asp Gly Lys Pro Leu Val Pro Asn
    130                 135                 140
Glu Lys Gly Val Ser Val Lys Glu Gln Thr Arg Arg His Pro Glu Thr
145                 150                 155                 160
Gly Leu Phe Thr Leu Gln Ser Glu Leu Met Val Thr Pro Ala Arg Gly
                165                 170                 175
Gly Asp Pro Arg Pro Thr Phe Ser Cys Ser Phe Ser Pro Gly Leu Pro
            180                 185                 190
Arg His Arg Ala Leu Arg Thr Ala Pro Ile Gln Pro Arg Val Trp Glu
        195                 200                 205
Pro Val Pro Leu Glu Glu Val Gln Leu Val Val Glu Pro Glu Gly Gly
    210                 215                 220
Ala Val Ala Pro Gly Gly Thr Val Thr Leu Thr Cys Glu Val Pro Ala
225                 230                 235                 240
Gln Pro Ser Pro Gln Ile His Trp Met Lys Asp Gly Val Pro Leu Pro
                245                 250                 255
Leu Pro Pro Ser Pro Val Leu Ile Leu Pro Glu Ile Gly Pro Gln Asp
            260                 265                 270
Gln Gly Thr Tyr Ser Cys Val Ala Thr His Ser Ser His Gly Pro Gln
        275                 280                 285
Glu Ser Arg Ala Val Ser Ile Ser Ile Ile Glu Pro Gly Glu Glu Gly
    290                 295                 300
Pro Thr Ala Gly Ser Val Gly Gly Ser Gly Leu Gly Thr Leu Ala Leu
305                 310                 315                 320
Ala Leu Gly Ile Leu Gly Gly Leu Gly Thr Ala Ala Leu Leu Ile Gly
                325                 330                 335
```

```
Val Ile Leu Trp Gln Arg Arg Gln Arg Gly Glu Arg Lys Ala
            340                 345                 350
Pro Glu Asn Gln Glu Glu Glu Glu Arg Ala Glu Leu Asn Gln Ser
            355                 360                 365
Glu Glu Pro Glu Ala Gly Glu Ser Ser Thr Gly Gly Pro
    370                 375                 380

<210> SEQ ID NO 4
<211> LENGTH: 339
<212> TYPE: PRT
<213> ORGANISM: Homo sapiens

<400> SEQUENCE: 4

Met Ala Ala Gly Thr Ala Val Gly Ala Trp Val Leu Val Leu Ser Leu
1               5                   10                  15
Trp Gly Ala Val Val Gly Ala Gln Asn Ile Thr Ala Arg Ile Gly Glu
            20                  25                  30
Pro Leu Val Leu Lys Cys Lys Gly Ala Pro Lys Lys Pro Pro Gln Arg
        35                  40                  45
Leu Glu Trp Lys Leu Asn Thr Gly Arg Thr Glu Ala Trp Lys Val Leu
    50                  55                  60
Ser Pro Gln Gly Gly Gly Pro Trp Asp Ser Val Ala Arg Val Leu Pro
65                  70                  75                  80
Asn Gly Ser Leu Phe Leu Pro Ala Val Gly Ile Gln Asp Glu Gly Ile
                85                  90                  95
Phe Arg Cys Gln Ala Met Asn Arg Asn Gly Lys Glu Thr Lys Ser Asn
            100                 105                 110
Tyr Arg Val Arg Val Tyr Gln Ile Pro Gly Lys Pro Glu Ile Val Asp
        115                 120                 125
Ser Ala Ser Glu Leu Thr Ala Gly Val Pro Asn Lys Val Gly Thr Cys
    130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
                165                 170                 175
Thr Arg Arg His Pro Glu Thr Gly Leu Phe Thr Leu Gln Ser Glu Leu
            180                 185                 190
Met Val Thr Pro Ala Arg Gly Gly Asp Pro Arg Pro Thr Phe Ser Cys
        195                 200                 205
Ser Phe Ser Pro Gly Leu Pro Arg His Arg Ala Leu Arg Thr Ala Pro
    210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
    290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
```

-continued

Gly Leu Gly

<210> SEQ ID NO 5
<211> LENGTH: 317
<212> TYPE: PRT
<213> ORGANISM: Homo sapiens

<400> SEQUENCE: 5

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Glu Pro Gly Glu Glu
    290                 295                 300

Gly Pro Thr Ala Gly Ser Val Gly Gly Ser Gly Leu Gly
305                 310                 315

<210> SEQ ID NO 6
<211> LENGTH: 316
<212> TYPE: PRT
<213> ORGANISM: Homo sapiens

<400> SEQUENCE: 6

Gln Asn Ile Thr Ala Arg Ile Gly Glu Pro Leu Val Leu Lys Cys Lys
1               5                   10                  15

Gly Ala Pro Lys Lys Pro Gln Arg Leu Glu Trp Lys Leu Asn Thr
            20                  25                  30

Gly Arg Thr Glu Ala Trp Lys Val Leu Ser Pro Gln Gly Gly Pro
        35                  40                  45

Trp Asp Ser Val Ala Arg Val Leu Pro Asn Gly Ser Leu Phe Leu Pro
 50                  55                  60

Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
                100                 105                 110

Gly Val Pro Asn Lys Val Gly Thr Cys Val Ser Glu Gly Ser Tyr Pro
            115                 120                 125

Ala Gly Thr Leu Ser Trp His Leu Asp Gly Lys Pro Leu Val Pro Asn
            130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
            180                 185                 190

Arg His Arg Ala Leu Arg Thr Ala Pro Ile Gln Pro Arg Val Trp Glu
            195                 200                 205

Pro Val Pro Leu Glu Glu Val Gln Leu Val Val Glu Pro Glu Gly Gly
 210                 215                 220

Ala Val Ala Pro Gly Gly Thr Val Thr Leu Thr Cys Glu Val Pro Ala
225                 230                 235                 240

Gln Pro Ser Pro Gln Ile His Trp Met Lys Asp Gly Val Pro Leu Pro
                245                 250                 255

Leu Pro Pro Ser Pro Val Leu Ile Leu Pro Glu Ile Gly Pro Gln Asp
            260                 265                 270

Gln Gly Thr Tyr Ser Cys Val Ala Thr His Ser Ser His Gly Pro Gln
            275                 280                 285

Glu Ser Arg Ala Val Ser Ile Ser Ile Ile Glu Pro Gly Glu Glu Gly
            290                 295                 300

Pro Thr Ala Gly Ser Val Gly Gly Ser Gly Leu Gly
305                 310                 315

<210> SEQ ID NO 7
<211> LENGTH: 94
<212> TYPE: PRT
<213> ORGANISM: Homo sapiens

<400> SEQUENCE: 7

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

```
Asn Arg Asn Gly Lys Glu Thr Lys Ser Asn Tyr Arg Val Arg
                85                  90

<210> SEQ ID NO 8
<211> LENGTH: 93
<212> TYPE: PRT
<213> ORGANISM: Homo sapiens

<400> SEQUENCE: 8

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg
                85                  90

<210> SEQ ID NO 9
<211> LENGTH: 30
<212> TYPE: PRT
<213> ORGANISM: Homo sapiens

<400> SEQUENCE: 9

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30

<210> SEQ ID NO 10
<211> LENGTH: 29
<212> TYPE: PRT
<213> ORGANISM: Homo sapiens

<400> SEQUENCE: 10

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys
            20                  25

<210> SEQ ID NO 11
<211> LENGTH: 98
<212> TYPE: PRT
<213> ORGANISM: Homo sapiens

<400> SEQUENCE: 11

Pro Glu Ile Val Asp Ser Ala Ser Glu Leu Thr Ala Gly Val Pro Asn
1               5                   10                  15

Lys Val Gly Thr Cys Val Ser Glu Gly Ser Tyr Pro Ala Gly Thr Leu
            20                  25                  30

Ser Trp His Leu Asp Gly Lys Pro Leu Val Pro Asn Glu Lys Gly Val
        35                  40                  45

Ser Val Lys Glu Gln Thr Arg Arg His Pro Glu Thr Gly Leu Phe Thr
    50                  55                  60

Leu Gln Ser Glu Leu Met Val Thr Pro Ala Arg Gly Gly Asp Pro Arg
65                  70                  75                  80
```

```
Pro Thr Phe Ser Cys Ser Phe Ser Pro Gly Leu Pro Arg His Arg Ala
                85                  90                  95

Leu Arg

<210> SEQ ID NO 12
<211> LENGTH: 91
<212> TYPE: PRT
<213> ORGANISM: Homo sapiens

<400> SEQUENCE: 12

Pro Arg Val Trp Glu Pro Val Pro Leu Glu Glu Val Gln Leu Val Val
1               5                   10                  15

Glu Pro Glu Gly Gly Ala Val Ala Pro Gly Gly Thr Val Thr Leu Thr
                20                  25                  30

Cys Glu Val Pro Ala Gln Pro Ser Pro Gln Ile His Trp Met Lys Asp
            35                  40                  45

Gly Val Pro Leu Pro Leu Pro Pro Ser Pro Val Leu Ile Leu Pro Glu
        50                  55                  60

Ile Gly Pro Gln Asp Gln Gly Thr Tyr Ser Cys Val Ala Thr His Ser
65                  70                  75                  80

Ser His Gly Pro Gln Glu Ser Arg Ala Val Ser
                85                  90

<210> SEQ ID NO 13
<211> LENGTH: 101
<212> TYPE: PRT
<213> ORGANISM: Homo sapiens

<400> SEQUENCE: 13

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Gly Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys
            100

<210> SEQ ID NO 14
<211> LENGTH: 100
<212> TYPE: PRT
<213> ORGANISM: Homo sapiens

<400> SEQUENCE: 14

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
                20                  25                  30

Gly Arg Thr Glu Ala Trp Lys Val Leu Ser Pro Gln Gly Gly Gly Pro
            35                  40                  45

Trp Asp Ser Val Ala Arg Val Leu Pro Asn Gly Ser Leu Phe Leu Pro
        50                  55                  60
```

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
            85                  90                  95

Ile Pro Gly Lys
            100

<210> SEQ ID NO 15
<211> LENGTH: 114
<212> TYPE: PRT
<213> ORGANISM: Homo sapiens

<400> SEQUENCE: 15

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly

<210> SEQ ID NO 16
<211> LENGTH: 113
<212> TYPE: PRT
<213> ORGANISM: Homo sapiens

<400> SEQUENCE: 16

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
            100                 105                 110

Gly

<210> SEQ ID NO 17
<211> LENGTH: 204
<212> TYPE: PRT
<213> ORGANISM: Homo sapiens

<400> SEQUENCE: 17

```
Ala Gln Asn Ile Thr Ala Arg Ile Gly Glu Pro Leu Val Leu Lys Cys
 1               5                  10                  15

Lys Gly Ala Pro Lys Pro Pro Gln Arg Leu Glu Trp Lys Leu Asn
             20                  25                  30

Thr Gly Arg Thr Glu Ala Trp Lys Val Leu Ser Pro Gln Gly Gly Gly
             35                  40                  45

Pro Trp Asp Ser Val Ala Arg Val Leu Pro Asn Gly Ser Leu Phe Leu
         50                  55                  60

Pro Ala Val Gly Ile Gln Asp Glu Gly Ile Phe Arg Cys Gln Ala Met
 65                  70                  75                  80

Asn Arg Asn Gly Lys Glu Thr Lys Ser Asn Tyr Arg Val Arg Val Tyr
                 85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
             115                 120                 125

Pro Ala Gly Thr Leu Ser Trp His Leu Asp Gly Lys Pro Leu Val Pro
 130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
             180                 185                 190

Pro Arg His Arg Ala Leu Arg Thr Ala Pro Ile Gln
             195                 200

<210> SEQ ID NO 18
<211> LENGTH: 203
<212> TYPE: PRT
<213> ORGANISM: Homo sapiens

<400> SEQUENCE: 18

Gln Asn Ile Thr Ala Arg Ile Gly Glu Pro Leu Val Leu Lys Cys Lys
 1               5                  10                  15

Gly Ala Pro Lys Lys Pro Pro Gln Arg Leu Glu Trp Lys Leu Asn Thr
             20                  25                  30

Gly Arg Thr Glu Ala Trp Lys Val Leu Ser Pro Gln Gly Gly Gly Pro
             35                  40                  45

Trp Asp Ser Val Ala Arg Val Leu Pro Asn Gly Ser Leu Phe Leu Pro
 50                  55                  60

Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg Val Tyr Gln
                 85                  90                  95

Ile Pro Gly Lys Pro Glu Ile Val Asp Ser Ala Ser Glu Leu Thr Ala
                100                 105                 110

Gly Val Pro Asn Lys Val Gly Thr Cys Val Ser Glu Gly Ser Tyr Pro
             115                 120                 125

Ala Gly Thr Leu Ser Trp His Leu Asp Gly Lys Pro Leu Val Pro Asn
 130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175
```

```
Gly Asp Pro Arg Pro Thr Phe Ser Cys Ser Phe Ser Pro Gly Leu Pro
            180                 185                 190

Arg His Arg Ala Leu Arg Thr Ala Pro Ile Gln
            195                 200
```

<210> SEQ ID NO 19
<211> LENGTH: 229
<212> TYPE: PRT
<213> ORGANISM: Homo sapiens

<400> SEQUENCE: 19

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro
225
```

<210> SEQ ID NO 20
<211> LENGTH: 228
<212> TYPE: PRT
<213> ORGANISM: Homo sapiens

<400> SEQUENCE: 20

```
Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
```

```
                65                  70                  75                  80
Arg Asn Gly Lys Glu Thr Lys Ser Asn Tyr Arg Val Arg Val Tyr Gln
                    85                  90                  95
Ile Pro Gly Lys Pro Glu Ile Val Asp Ser Ala Ser Glu Leu Thr Ala
                    100                 105                 110
Gly Val Pro Asn Lys Val Gly Thr Cys Val Ser Glu Gly Ser Tyr Pro
                    115                 120                 125
Ala Gly Thr Leu Ser Trp His Leu Asp Gly Lys Pro Leu Val Pro Asn
                130                 135                 140
Glu Lys Gly Val Ser Val Lys Glu Gln Thr Arg Arg His Pro Glu Thr
145                 150                 155                 160
Gly Leu Phe Thr Leu Gln Ser Glu Leu Met Val Thr Pro Ala Arg Gly
                    165                 170                 175
Gly Asp Pro Arg Pro Thr Phe Ser Cys Ser Phe Ser Pro Gly Leu Pro
                    180                 185                 190
Arg His Arg Ala Leu Arg Thr Ala Pro Ile Gln Pro Arg Val Trp Glu
                    195                 200                 205
Pro Val Pro Leu Glu Glu Val Gln Leu Val Val Glu Pro Glu Gly Gly
                    210                 215                 220
Ala Val Ala Pro
225

<210> SEQ ID NO 21
<211> LENGTH: 7
<212> TYPE: PRT
<213> ORGANISM: Homo sapiens

<400> SEQUENCE: 21

Val Tyr Gln Ile Pro Gly Lys
1               5

<210> SEQ ID NO 22
<211> LENGTH: 30
<212> TYPE: PRT
<213> ORGANISM: Homo sapiens

<400> SEQUENCE: 22

Thr Ala Pro Ile Gln Pro Arg Val Trp Glu Pro Val Pro Leu Glu Glu
1               5                   10                  15
Val Gln Leu Val Val Glu Pro Glu Gly Gly Ala Val Ala Pro
                20                  25                  30

<210> SEQ ID NO 23
<211> LENGTH: 20
<212> TYPE: PRT
<213> ORGANISM: Homo sapiens

<400> SEQUENCE: 23

Val Tyr Gln Ile Pro Gly Lys Pro Glu Ile Val Asp Ser Ala Ser Glu
1               5                   10                  15
Leu Thr Ala Gly
                20

<210> SEQ ID NO 24
<211> LENGTH: 5
<212> TYPE: PRT
<213> ORGANISM: Homo sapiens

<400> SEQUENCE: 24

Thr Ala Pro Ile Gln
```

<210> SEQ ID NO 25
<211> LENGTH: 354
<212> TYPE: DNA
<213> ORGANISM: Homo sapiens

<400> SEQUENCE: 25

| atggcagccg gaacagcagt tgagcctgg gtgctggtcc tcagtctgtg gggggcagta | 60 |
| gtaggtgctc aaaacatcac agcccggatt ggcgagccac tggtgctgaa gtgtaagggg | 120 |
| gcccccaaga aaccacccca gcggctggaa tggaaactga acacaggccg gacagaagct | 180 |
| tggaaggtcc tgtctcccca gggaggaggc cctgggaca gtgtggctcg tgtccttccc | 240 |
| aacggctccc tcttccttcc ggctgtcggg atccaggatg aggggatttt ccggtgccag | 300 |
| gcaatgaaca ggaatggaaa ggagaccaag tccaactacc gagtccgtgt ctac | 354 |

<210> SEQ ID NO 26
<211> LENGTH: 369
<212> TYPE: DNA
<213> ORGANISM: Homo sapiens

<400> SEQUENCE: 26

| atggcagccg gaacagcagt tgagcctgg gtgctggtcc tcagtctgtg gggggcagta | 60 |
| gtaggtgctc aaaacatcac agcccggatt ggcgagccac tggtgctgaa gtgtaagggg | 120 |
| gcccccaaga aaccacccca gcggctggaa tggaaactga acacaggccg gacagaagct | 180 |
| tggaaggtcc tgtctcccca gggaggaggc cctgggaca gtgtggctcg tgtccttccc | 240 |
| aacggctccc tcttccttcc ggctgtcggg atccaggatg aggggatttt ccggtgccag | 300 |
| gcaatgaaca ggaatggaaa ggagaccaag tccaactacc gagtccgtgt ctaccagatt | 360 |
| cctgggaag | 369 |

<210> SEQ ID NO 27
<211> LENGTH: 408
<212> TYPE: DNA
<213> ORGANISM: Homo sapiens

<400> SEQUENCE: 27

| atggcagccg gaacagcagt tgagcctgg gtgctggtcc tcagtctgtg gggggcagta | 60 |
| gtaggtgctc aaaacatcac agcccggatt ggcgagccac tggtgctgaa gtgtaagggg | 120 |
| gcccccaaga aaccacccca gcggctggaa tggaaactga acacaggccg gacagaagct | 180 |
| tggaaggtcc tgtctcccca gggaggaggc cctgggaca gtgtggctcg tgtccttccc | 240 |
| aacggctccc tcttccttcc ggctgtcggg atccaggatg aggggatttt ccggtgccag | 300 |
| gcaatgaaca ggaatggaaa ggagaccaag tccaactacc gagtccgtgt ctaccagatt | 360 |
| cctgggaagc cagaaattgt agattctgcc tctgaactca cggctggt | 408 |

<210> SEQ ID NO 28
<211> LENGTH: 690
<212> TYPE: DNA
<213> ORGANISM: Homo sapiens

<400> SEQUENCE: 28

| atggcagccg gaacagcagt tgagcctgg gtgctggtcc tcagtctgtg gggggcagta | 60 |
| gtaggtgctc aaaacatcac agcccggatt ggcgagccac tggtgctgaa gtgtaagggg | 120 |
| gcccccaaga aaccacccca gcggctggaa tggaaactga acacaggccg gacagaagct | 180 |

| | | |
|---|---|---|
| tggaaggtcc tgtctcccca gggaggaggc ccctgggaca gtgtggctcg tgtccttccc | 240 | |
| aacggctccc tcttccttcc ggctgtcggg atccaggatg aggggatttt ccggtgccag | 300 | |
| gcaatgaaca ggaatggaaa ggagaccaag tccaactacc gagtccgtgt ctaccagatt | 360 | |
| cctgggaagc cagaaattgt agattctgcc tctgaactca cggctggtgt tcccaataag | 420 | |
| gtggggacat gtgtgtcaga ggggagctac cctgcaggga ctcttagctg gcacttggat | 480 | |
| gggaagcccc tggtgcctaa tgagaaggga gtatctgtga aggaacagac caggagacac | 540 | |
| cctgagacag ggctcttcac actgcagtcg gagctaatgg tgaccccagc ccggggagga | 600 | |
| gatccccgtc ccaccttctc ctgtagcttc agcccaggcc ttccccgaca ccgggccttg | 660 | |
| cgcacagccc ccatccagcc ccgtgtctgg | 690 | |

<210> SEQ ID NO 29
<211> LENGTH: 753
<212> TYPE: DNA
<213> ORGANISM: Homo sapiens

<400> SEQUENCE: 29

| | | |
|---|---|---|
| atggcagccg gaacagcagt tggagcctgg gtgctggtcc tcagtctgtg gggggcagta | 60 | |
| gtaggtgctc aaaacatcac agcccggatt ggcgagccac tggtgctgaa gtgtaagggg | 120 | |
| gccccccaaga aaccacccca gcggctggaa tggaaactga acacaggccg gacagaagct | 180 | |
| tggaaggtcc tgtctcccca gggaggaggc ccctgggaca gtgtggctcg tgtccttccc | 240 | |
| aacggctccc tcttccttcc ggctgtcggg atccaggatg aggggatttt ccggtgccag | 300 | |
| gcaatgaaca ggaatggaaa ggagaccaag tccaactacc gagtccgtgt ctaccagatt | 360 | |
| cctgggaagc cagaaattgt agattctgcc tctgaactca cggctggtgt tcccaataag | 420 | |
| gtggggacat gtgtgtcaga ggggagctac cctgcaggga ctcttagctg gcacttggat | 480 | |
| gggaagcccc tggtgcctaa tgagaaggga gtatctgtga aggaacagac caggagacac | 540 | |
| cctgagacag ggctcttcac actgcagtcg gagctaatgg tgaccccagc ccggggagga | 600 | |
| gatccccgtc ccaccttctc ctgtagcttc agcccaggcc ttccccgaca ccgggccttg | 660 | |
| cgcacagccc ccatccagcc ccgtgtctgg gagcctgtgc ctctggagga ggtccaattg | 720 | |
| gtggtggagc cagaaggtgg agcagtagct cct | 753 | |

<210> SEQ ID NO 30
<211> LENGTH: 1386
<212> TYPE: DNA
<213> ORGANISM: Artificial
<220> FEATURE:
<223> OTHER INFORMATION: Artificial = synthetic construct

<400> SEQUENCE: 30

| | | |
|---|---|---|
| atggcagccg gaacagcagt tggagcctgg gtgctggtcc tcagtctgtg gggggcagta | 60 | |
| gtaggtgctc aaaacatcac agcccggatt ggcgagccac tggtgctgaa gtgtaagggg | 120 | |
| gccccccaaga aaccacccca gcggctggaa tggaaactga acacaggccg gacagaagct | 180 | |
| tggaaggtcc tgtctcccca gggaggaggc ccctgggaca gtgtggctcg tgtccttccc | 240 | |
| aacggctccc tcttccttcc ggctgtcggg atccaggatg aggggatttt ccggtgccag | 300 | |
| gcaatgaaca ggaatggaaa ggagaccaag tccaactacc gagtccgtgt ctaccagatt | 360 | |
| cctgggaagc cagaaattgt agattctgcc tctgaactca cggctggtgt tcccaataag | 420 | |
| gtggggacat gtgtgtcaga ggggagctac cctgcaggga ctcttagctg gcacttggat | 480 | |
| gggaagcccc tggtgcctaa tgagaaggga gtatctgtga aggaacagac caggagacac | 540 | |

-continued

```
cctgagacag ggctcttcac actgcagtcg gagctaatgg tgaccccagc ccggggagga      600 gatcccgtc ccaccttctc ctgtagcttc agcccaggcc ttccccgaca ccgggccttg       660
cgcacagccc ccatccagcc ccgtgtctgg gagcctgtgc ctctggagga ggtccaattg      720
gtggtggagc cagaaggtgg agcagtagct cctccgtcag tcttcctctt ccccccaaaa     780
cccaaggaca ccctcatgat ctcccggacc cctgaggtca catgcgtggt ggtggacgtg      840
agccacgaag accctgaggt caagttcaac tggtacgtgg acggcgtgga ggtgcataat     900
gccaagacaa agccgcggga ggagcagtac aacagcacgt accgtgtggt cagcgtcctc    960
accgtcctgc accaggactg gctgaatggc aaggagtaca agtgcaaggt ctccaacaaa    1020
gccctcccag cccccatcga gaaaaccatc tccaaagcca agggcagcc cgagaaccca     1080 caggtgtaca ccctgccccc atcccgggat gagctgacca gaaccaggt cagcctgacc      1140 tgcctggtca aaggcttcta tcccagcgac atcgccgtgg agtgggagag caatgggcag    1200
ccggagaaca actacaagac cacgcctccc gtgctggact ccgacggctc cttcttcctc     1260
tacagcaagc tcaccgtgga caagagcagg tggcagcagg ggaacgtctt ctcatgctcc    1320
gtgatgcatg aggctctgca caaccactac acgcagaaga gcctctcc ct gtctccgggt     1380 aaatga                                                                1386
```

<210> SEQ ID NO 31
<211> LENGTH: 1041
<212> TYPE: DNA
<213> ORGANISM: Artificial
<220> FEATURE:
<223> OTHER INFORMATION: Artificial = synthetic construct

<400> SEQUENCE: 31

```
atggcagccg gaacagcagt tggagcctgg gtgctggtcc tcagtctgtg gggggcagta      60
gtaggtgctc aaaacatcac agcccggatt ggcgagccac tggtgctgaa gtgtaagggg    120 gccccccaaga aaccaccccca gcggctggaa tggaaactga cacacaggccg acagaagct    180 tggaaggtcc tgtctcccca gggaggaggc ccctgggaca gtgtggctcg tgtccttccc      240
aacggctccc tcttccttcc ggctgtcggg atccaggatg aggggatttt ccggtgccag    300
gcaatgaaca ggaatggaaa ggagaccaag tccaactacc gagtccgtgt ctaccagatt    360
cctgggaagc cagaaattgt agattctgcc tctgaactca cggctggtcc gtcagtcttc    420
ctcttccccc caaaacccaa ggacaccctc atgatctccc ggacccctga ggtcacatgc    480
gtggtggtgg acgtgagcca cgaagaccct gaggtcaagt tcaactggta cgtggacggc    540
gtggaggtgc ataatgccaa gacaaagccg cgggaggagc agtacaacag cacgtaccgt      600
gtggtcagcg tcctcaccgt cctgcaccag gactggctga atggcaagga gtacaagtgc      660
aaggtctcca acaaagcc ct cccagccccc atcgagaaaa ccatctccaa agccaagggg    720
cagccccgag aaccacaggt gtacaccctg cccccatccc gggatgagct gaccaagaac    780
caggtcagcc tgacctgcct ggtcaaaggc ttctatccca gcgacatcgc cgtggagtgg    840
gagagcaatg gcagccgga gaacaactac aagaccacgc ctcccgtgct ggactccgac    900
ggctccttct tcctctacag caagctcacc gtggacaaga gcaggtggca gcaggggaac    960
gtcttctcat gctccgtgat gcatgaggct ctgcacaacc actacacgca gaagagcctc    1020
tccctgtctc cgggtaaatg a                                               1041
```

<210> SEQ ID NO 32
<211> LENGTH: 461
<212> TYPE: PRT

<213> ORGANISM: Artificial
<220> FEATURE:
<223> OTHER INFORMATION: Artificial = synthetic construct

<400> SEQUENCE: 32

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400
```

```
Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
                450                 455                 460

<210> SEQ ID NO 33
<211> LENGTH: 439
<212> TYPE: PRT
<213> ORGANISM: Artificial
<220> FEATURE:
<223> OTHER INFORMATION: Artificial = synthetic construct

<400> SEQUENCE: 33

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Gly Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
                115                 120                 125

Pro Ala Gly Thr Leu Ser Trp His Leu Asp Gly Lys Pro Leu Val Pro
            130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
            195                 200                 205

Glu Pro Val Pro Leu Glu Glu Val Gln Leu Val Val Glu Pro Glu Gly
        210                 215                 220

Gly Ala Val Ala Pro Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu His Gln Asp
        290                 295                 300
```

```
Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
            325                 330                 335

Glu Pro Gln Val Tyr Thr Leu Pro Pro Ser Arg Asp Glu Leu Thr Lys
        340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Met His Glu Ala Leu His Asn His Tyr Thr Gln Lys Ser
        420                 425                 430

Leu Ser Leu Ser Pro Gly Lys
        435
```

```
<210> SEQ ID NO 34
<211> LENGTH: 438
<212> TYPE: PRT
<213> ORGANISM: Artificial
<220> FEATURE:
<223> OTHER INFORMATION: Artificial = synthetic construct

<400> SEQUENCE: 34

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
            100                 105                 110

Gly Val Pro Asn Lys Val Gly Thr Cys Val Ser Glu Gly Ser Tyr Pro
        115                 120                 125

Ala Gly Thr Leu Ser Trp His Leu Asp Gly Lys Pro Leu Val Pro Asn
    130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
            180                 185                 190

Arg His Arg Ala Leu Arg Thr Ala Pro Ile Gln Pro Arg Val Trp Glu
        195                 200                 205

Pro Val Pro Leu Glu Glu Val Gln Leu Val Val Glu Pro Glu Gly Gly
    210                 215                 220

Ala Val Ala Pro Pro Ser Val Phe Leu Phe Pro Pro Lys Pro Lys Asp
```

```
                  225                 230                 235                 240

Thr Leu Met Ile Ser Arg Thr Pro Glu Val Thr Cys Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
        435

<210> SEQ ID NO 35
<211> LENGTH: 346
<212> TYPE: PRT
<213> ORGANISM: Artificial
<220> FEATURE:
<223> OTHER INFORMATION: Artificial = synthetic construct

<400> SEQUENCE: 35

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160
```

-continued

```
Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Asp Glu
                245                 250                 255

Leu Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
                275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 36
<211> LENGTH: 324
<212> TYPE: PRT
<213> ORGANISM: Artificial
<220> FEATURE:
<223> OTHER INFORMATION: Artificial = synthetic construct

<400> SEQUENCE: 36

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Gly Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Pro Ser Val Phe Leu Phe Pro Pro Lys Pro Lys Asp Thr Leu
            115                 120                 125

Met Ile Ser Arg Thr Pro Glu Val Thr Cys Val Val Val Asp Val Ser
130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175
```

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
            195                 200                 205

Ile Glu Lys Thr Ile Ser Lys Ala Lys Gly Gln Pro Arg Glu Pro Gln
            210                 215                 220

Val Tyr Thr Leu Pro Pro Ser Arg Asp Glu Leu Thr Lys Asn Gln Val
225                 230                 235                 240

Ser Leu Thr Cys Leu Val Lys Gly Phe Tyr Pro Ser Asp Ile Ala Val
            245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Lys Leu Thr
            275                 280                 285

Val Asp Lys Ser Arg Trp Gln Gln Gly Asn Val Phe Ser Cys Ser Val
            290                 295                 300

Met His Glu Ala Leu His Asn His Tyr Thr Gln Lys Ser Leu Ser Leu
305                 310                 315                 320

Ser Pro Gly Lys

<210> SEQ ID NO 37
<211> LENGTH: 323
<212> TYPE: PRT
<213> ORGANISM: Artificial
<220> FEATURE:
<223> OTHER INFORMATION: Artificial = synthetic construct

<400> SEQUENCE: 37

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
            35                  40                  45

Trp Asp Ser Val Ala Arg Val Leu Pro Asn Gly Ser Leu Phe Leu Pro
50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
            85                  90                  95

Ile Pro Gly Lys Pro Glu Ile Val Asp Ser Ala Ser Glu Leu Thr Ala
            100                 105                 110

Gly Pro Ser Val Phe Leu Phe Pro Pro Lys Pro Lys Asp Thr Leu Met
            115                 120                 125

Ile Ser Arg Thr Pro Glu Val Thr Cys Val Val Val Asp Val Ser His
            130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
            165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
            195                 200                 205

Glu Lys Thr Ile Ser Lys Ala Lys Gly Gln Pro Arg Glu Pro Gln Val
            210                 215                 220

```
Tyr Thr Leu Pro Pro Ser Arg Asp Glu Leu Thr Lys Asn Gln Val Ser
225                 230                 235                 240

Leu Thr Cys Leu Val Lys Gly Phe Tyr Pro Ser Asp Ile Ala Val Glu
            245                 250                 255

Trp Glu Ser Asn Gly Gln Pro Glu Asn Asn Tyr Lys Thr Thr Pro Pro
        260                 265                 270

Val Leu Asp Ser Asp Gly Ser Phe Phe Leu Tyr Ser Lys Leu Thr Val
    275                 280                 285

Asp Lys Ser Arg Trp Gln Gln Gly Asn Val Phe Ser Cys Ser Val Met
290                 295                 300

His Glu Ala Leu His Asn His Tyr Thr Gln Lys Ser Leu Ser Leu Ser
305                 310                 315                 320

Pro Gly Lys

<210> SEQ ID NO 38
<211> LENGTH: 210
<212> TYPE: PRT
<213> ORGANISM: Homo sapiens

<400> SEQUENCE: 38

Pro Ser Val Phe Leu Phe Pro Pro Lys Pro Lys Asp Thr Leu Met Ile
1               5                   10                  15

Ser Arg Thr Pro Glu Val Thr Cys Val Val Asp Val Ser His Glu
            20                  25                  30

Asp Pro Glu Val Lys Phe Asn Trp Tyr Val Asp Gly Val Glu Val His
            35                  40                  45

Asn Ala Lys Thr Lys Pro Arg Glu Glu Gln Tyr Asn Ser Thr Tyr Arg
50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
            100                 105                 110

Thr Leu Pro Pro Ser Arg Asp Glu Leu Thr Lys Asn Gln Val Ser Leu
        115                 120                 125

Thr Cys Leu Val Lys Gly Phe Tyr Pro Ser Asp Ile Ala Val Glu Trp
130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210

<210> SEQ ID NO 39
<211> LENGTH: 633
<212> TYPE: DNA
<213> ORGANISM: Homo sapiens

<400> SEQUENCE: 39
ccgtcagtct tcctcttccc cccaaaaccc aaggacaccc tcatgatctc ccggacccct    60
```

```
gaggtcacat gcgtggtggt ggacgtgagc cacgaagacc ctgaggtcaa gttcaactgg      120
tacgtggacg gcgtggaggt gcataatgcc aagacaaagc cgcgggagga gcagtacaac      180
agcacgtacc gtgtggtcag cgtcctcacc gtcctgcacc aggactggct gaatggcaag      240
gagtacaagt gcaaggtctc caacaaagcc ctcccagccc ccatcgagaa aaccatctcc      300
aaagccaaag ggcagccccg agaaccacag gtgtacaccc tgcccccatc ccgggatgag      360
ctgaccaaga accaggtcag cctgacctgc ctggtcaaag gcttctatcc cagcgacatc      420
gccgtggagt gggagagcaa tgggcagccg gagaacaact acaagaccac gcctcccgtg      480
ctggactccg acggctcctt cttcctctac agcaagctca ccgtggacaa gagcaggtgg      540
cagcagggga acgtcttctc atgctccgtg atgcatgagg ctctgcacaa ccactacacg      600
cagaagagcc tctccctgtc tccgggtaaa tga                                  633
```

<210> SEQ ID NO 40
<211> LENGTH: 220
<212> TYPE: PRT
<213> ORGANISM: Homo sapiens

<400> SEQUENCE: 40

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 41
<211> LENGTH: 663
<212> TYPE: DNA
<213> ORGANISM: Homo sapiens

<400> SEQUENCE: 41

```
ccgtgcccag cacctgaact cctggggggga ccgtcagtct tcctcttccc cccaaaaccc       60
```

-continued

```
aaggacaccc tcatgatctc ccggacccct gaggtcacat gcgtggtggt ggacgtgagc    120
cacgaagacc ctgaggtcaa gttcaactgg tacgtggacg gcgtggaggt gcataatgcc    180
aagacaaagc cgcgggagga gcagtacaac agcacgtacc gtgtggtcag cgtcctcacc    240
gtcctgcacc aggactggct gaatggcaag gagtacaagt gcaaggtctc caacaaagcc    300
ctcccagccc ccatcgagaa aaccatctcc aaagccaaag gcagccccg agaaccacag     360 gtgtacaccc tgcccccatc ccgggatgag ctgaccaaga accaggtcag cctgacctgc    420
ctggtcaaag gcttctatcc cagcgacatc gccgtggagt gggagagcaa tgggcagccg    480
gagaacaact acaagaccac gcctcccgtg ctggactccg acggctcctt cttcctctac    540
agcaagctca ccgtggacaa gagcaggtgg cagcagggga acgtcttctc atgctccgtg    600
atgcatgagg ctctgcacaa ccactacacg cagaagagcc tctccctgtc tccgggtaaa    660
tga                                                                  663
```

```
<210> SEQ ID NO 42
<211> LENGTH: 113
<212> TYPE: PRT
<213> ORGANISM: Homo sapiens

<400> SEQUENCE: 42

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 43
<211> LENGTH: 107
<212> TYPE: PRT
<213> ORGANISM: Homo sapiens

<400> SEQUENCE: 43

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95
```

```
Thr Gln Lys Ser Leu Ser Leu Ser Pro Gly Lys
            100                 105

<210> SEQ ID NO 44
<211> LENGTH: 25
<212> TYPE: PRT
<213> ORGANISM: Homo sapiens

<400> SEQUENCE: 44

Ile Ser Ile Ile Glu Pro Gly Glu Gly Pro Thr Ala Gly Ser Val
1               5                   10                  15

Gly Gly Ser Gly Leu Gly Thr Leu Ala
            20                  25

<210> SEQ ID NO 45
<211> LENGTH: 316
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 45

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65              70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
            100                 105                 110

Gly Val Pro Asn Lys Val Gly Thr Cys Val Ser Glu Gly Ser Tyr Pro
        115                 120                 125

Ala Gly Thr Leu Ser Trp His Leu Asp Gly Lys Pro Leu Val Pro Asn
    130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
            180                 185                 190

Arg His Arg Ala Leu Arg Thr Ala Pro Ile Gln Pro Arg Val Trp Glu
        195                 200                 205

Pro Val Pro Leu Glu Glu Val Gln Leu Val Val Glu Pro Glu Gly Gly
    210                 215                 220

Ala Val Ala Pro Gly Gly Thr Val Thr Leu Thr Cys Glu Val Pro Ala
225                 230                 235                 240

Gln Pro Ser Pro Gln Ile His Trp Met Lys Asp Gly Val Pro Leu Pro
                245                 250                 255

Leu Pro Pro Ser Pro Val Leu Ile Leu Pro Glu Ile Gly Pro Gln Asp
            260                 265                 270
```

```
Gln Gly Thr Tyr Ser Cys Val Ala Thr His Ser Ser His Gly Pro Gln
            275                 280                 285

Glu Ser Arg Ala Val Ser Ile Ser Ile Ile Glu Pro Gly Glu Glu Gly
        290                 295                 300

Pro Thr Ala Gly Ser Val Gly Gly Ser Gly Leu Gly
305                 310                 315

<210> SEQ ID NO 46
<211> LENGTH: 93
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 46

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg
                85                  90

<210> SEQ ID NO 47
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 47

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys
            20                  25

<210> SEQ ID NO 48
<211> LENGTH: 100
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 48

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60
```

```
Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg Val Tyr Gln
                 85                  90                  95

Ile Pro Gly Lys
            100

<210> SEQ ID NO 49
<211> LENGTH: 113
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 49

Xaa Asn Ile Thr Ala Arg Ile Gly Glu Pro Leu Val Leu Lys Cys Lys
  1               5                  10                  15

Gly Ala Pro Lys Lys Pro Pro Gln Arg Leu Glu Trp Lys Leu Asn Thr
                 20                  25                  30

Gly Arg Thr Glu Ala Trp Lys Val Leu Ser Pro Gln Gly Gly Gly Pro
             35                  40                  45

Trp Asp Ser Val Ala Arg Val Leu Pro Asn Gly Ser Leu Phe Leu Pro
 50                  55                  60

Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg Val Tyr Gln
                 85                  90                  95

Ile Pro Gly Lys Pro Glu Ile Val Asp Ser Ala Ser Glu Leu Thr Ala
            100                 105                 110

Gly

<210> SEQ ID NO 50
<211> LENGTH: 203
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 50

Xaa Asn Ile Thr Ala Arg Ile Gly Glu Pro Leu Val Leu Lys Cys Lys
  1               5                  10                  15

Gly Ala Pro Lys Lys Pro Pro Gln Arg Leu Glu Trp Lys Leu Asn Thr
                 20                  25                  30

Gly Arg Thr Glu Ala Trp Lys Val Leu Ser Pro Gln Gly Gly Gly Pro
             35                  40                  45

Trp Asp Ser Val Ala Arg Val Leu Pro Asn Gly Ser Leu Phe Leu Pro
 50                  55                  60

Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg Val Tyr Gln
                 85                  90                  95

Ile Pro Gly Lys Pro Glu Ile Val Asp Ser Ala Ser Glu Leu Thr Ala
            100                 105                 110

Gly Val Pro Asn Lys Val Gly Thr Cys Val Ser Glu Gly Ser Tyr Pro
            115                 120                 125
```

```
Ala Gly Thr Leu Ser Trp His Leu Asp Gly Lys Pro Leu Val Pro Asn
        130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
                180                 185                 190

Arg His Arg Ala Leu Arg Thr Ala Pro Ile Gln
                195                 200

<210> SEQ ID NO 51
<211> LENGTH: 228
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 51

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
                20                  25                  30

Gly Arg Thr Glu Ala Trp Lys Val Leu Ser Pro Gln Gly Gly Gly Pro
            35                  40                  45

Trp Asp Ser Val Ala Arg Val Leu Pro Asn Gly Ser Leu Phe Leu Pro
50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
                100                 105                 110

Gly Val Pro Asn Lys Val Gly Thr Cys Val Ser Glu Gly Ser Tyr Pro
            115                 120                 125

Ala Gly Thr Leu Ser Trp His Leu Asp Gly Lys Pro Leu Val Pro Asn
        130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
                180                 185                 190

Arg His Arg Ala Leu Arg Thr Ala Pro Ile Gln Pro Arg Val Trp Glu
                195                 200                 205

Pro Val Pro Leu Glu Glu Val Gln Leu Val Val Glu Pro Glu Gly Gly
        210                 215                 220

Ala Val Ala Pro
225

<210> SEQ ID NO 52
<211> LENGTH: 633
<212> TYPE: DNA
<213> ORGANISM: Artificial
<220> FEATURE:
<223> OTHER INFORMATION: Artificial = synthetic construct
```

<400> SEQUENCE: 52

```
ccgtcagtct tcctcttccc cccaaaaccc aaggacaccc tcatgatctc ccggacccct    60
gaggtcacat gcgtggtggt ggacgtgagc cacgaagacc ctgaggtcaa gttcaactgg   120
tacgtggacg gcgtggaggt gcataatgcc aagacaaagc cgcggggagga gcagtacaac   180
agcacgtacc gtgtggtcag cgtcctcacc gtcctgcacc aggactggct gaatggcaag   240
gagtacaagt gcaaggtctc caacaaagcc ctcccagccc ccatcgagaa aaccatctcc   300
aaagccaaag gcagccccg agaaccacag gtgtacaccc tgcccccatc ccgggatgag   360
ctgaccaaga accaggtcag cctgacctgc ctggtcaaag gcttctatcc cagcgacatc   420
gccgtggagt gggagagcaa tgggcagccg gagaacaact acaagaccac gcctcccgtg   480
ctggactccg acggctcctt cttcctctac agcaagctca ccgtggacaa gagcaggtgg   540
cagcagggga acgtcttctc atgctccgtg atgcatgagg ctctgcacaa ccactacacg   600
cagaagagcc tctccctgtc tcccgggaaa tga                                633
```

<210> SEQ ID NO 53
<211> LENGTH: 663
<212> TYPE: DNA
<213> ORGANISM: Artificial
<220> FEATURE:
<223> OTHER INFORMATION: Artificial = synthetic construct

<400> SEQUENCE: 53

```
ccgtgcccag cacctgaact cctgggggga ccgtcagtct tcctcttccc cccaaaaccc    60
aaggacaccc tcatgatctc ccggacccct gaggtcacat gcgtggtggt ggacgtgagc   120
cacgaagacc ctgaggtcaa gttcaactgg tacgtggacg gcgtggaggt gcataatgcc   180
aagacaaagc cgcggggagga gcagtacaac agcacgtacc gtgtggtcag cgtcctcacc   240
gtcctgcacc aggactggct gaatggcaag gagtacaagt gcaaggtctc caacaaagcc   300
ctcccagccc ccatcgagaa aaccatctcc aaagccaaag gcagccccg agaaccacag   360
gtgtacaccc tgcccccatc ccgggatgag ctgaccaaga accaggtcag cctgacctgc   420
ctggtcaaag gcttctatcc cagcgacatc gccgtggagt gggagagcaa tgggcagccg   480
gagaacaact acaagaccac gcctcccgtg ctggactccg acggctcctt cttcctctac   540
agcaagctca ccgtggacaa gagcaggtgg cagcagggga acgtcttctc atgctccgtg   600
atgcatgagg ctctgcacaa ccactacacg cagaagagcc tctccctgtc tcccgggaaa   660
tga                                                                 663
```

<210> SEQ ID NO 54
<211> LENGTH: 1386
<212> TYPE: DNA
<213> ORGANISM: Artificial
<220> FEATURE:
<223> OTHER INFORMATION: Artificial = synthetic construct

<400> SEQUENCE: 54

```
atggcagccg gaacagcagt tggagcctgg gtgctggtcc tcagtctgtg gggggcagta    60
gtaggtgctc aaaacatcac agcccggatt ggcgagccac tggtgctgaa gtgtaagggg   120
gccccccaaga aaccacccca gcggctggaa tggaaactga acacaggccg gacagaagct   180
tggaaggtcc tgtctcccca gggaggaggc ccctgggaca gtgtggctcg tgtccttccc   240
aacggctccc tcttccttcc ggctgtcggg atccaggatg aggggatttt ccggtgccag   300
gcaatgaaca ggaatggaaa ggagaccaag tccaactacc gagtccgtgt ctaccagatt   360
```

```
cctgggaagc cagaaattgt agattctgcc tctgaactca cggctggtgt tcccaataag     420
gtggggacat gtgtgtcaga ggggagctac cctgcaggga ctcttagctg gcacttggat     480
gggaagcccc tggtgcctaa tgagaaggga gtatctgtga aggaacagac caggagacac     540
cctgagacag ggctcttcac actgcagtcg gagctaatgg tgaccccagc ccggggagga     600
gatccccgtc ccaccttctc ctgtagcttc agcccaggcc ttccccgaca ccgggccttg     660
cgcacagccc ccatccagcc ccgtgtctgg gagcctgtgc ctctggagga ggtccaattg     720
gtggtggagc cagaaggtgg agcagtagct cctccgtcag tcttcctctt ccccccaaaa     780
cccaaggaca ccctcatgat ctcccggacc cctgaggtca catgcgtggt ggtggacgtg     840
agccacgaag accctgaggt caagttcaac tggtacgtgg acggcgtgga ggtgcataat     900
gccaagacaa agccgcggga ggagcagtac aacagcacgt accgtgtggt cagcgtcctc     960
accgtcctgc accaggactg gctgaatggc aaggagtaca gtgcaaggt ctccaacaaa     1020 gccctcccag cccccatcga aaaaccatc tccaaagcca agggcagcc ccgagaacca     1080 caggtgtaca ccctgccccc atcccgggat gagctgacca agaaccaggt cagcctgacc     1140
tgcctggtca aaggcttcta tcccagcgac atcgccgtgg agtgggagag caatgggcag     1200
ccggagaaca actacaagac cacgcctccc gtgctggact ccgacggctc cttcttcctc     1260
tacagcaagc tcaccgtgga caagagcagg tggcagcagg ggaacgtctt ctcatgctcc     1320
gtgatgcatg aggctctgca caaccactac acgcagaaga gcctctccct gtctcccggg     1380
aaatga                                                                1386

<210> SEQ ID NO 55
<211> LENGTH: 1041
<212> TYPE: DNA
<213> ORGANISM: Artificial
<220> FEATURE:
<223> OTHER INFORMATION: Artificial = synthetic construct

<400> SEQUENCE: 55
atggcagccg aacagcagt tggagcctgg gtgctggtcc tcagtctgtg gggggcagta      60
gtaggtgctc aaaacatcac agcccggatt ggcgagccac tggtgctgaa gtgtaagggg    120
gcccccaaga aaccacccca gcggctggaa tggaaactga acacaggccg gacagaagct    180
tggaaggtcc tgtctcccca gggaggaggc ccctgggaca gtgtggctcg tgtccttccc    240
aacggctccc tcttccttcc ggctgtcggg atccaggatg aggggatttt ccggtgccag    300
gcaatgaaca ggaatggaaa ggagaccaag tccaactacc gagtccgtgt ctaccagatt    360
cctgggaagc cagaaattgt agattctgcc tctgaactca cggctggtcc gtcagtcttc    420
ctcttccccc caaaacccaa ggacaccctc atgatctccc ggacccctga ggtcacatgc    480
gtggtggtgg acgtgagcca cgaagaccct gaggtcaagt tcaactggta cgtggacggc    540
gtggaggtgc ataatgccaa gacaaagccg cgggaggagc agtacaacag cacgtaccgt    600
gtggtcagcg tcctcaccgt cctgcaccag gactggctga atggcaagga gtacaagtgc    660
aaggtctcca acaaagccct cccagccccc atcgagaaaa ccatctccaa agccaaaggg    720
cagccccgag aaccacaggt gtacaccctg cccccatccc gggatgagct gaccaagaac    780
caggtcagcc tgacctgcct ggtcaaaggc ttctatccca gcgacatcgc cgtggagtgg    840
gagagcaatg ggcagccgga gaacaactac aagaccacgc ctcccgtgct ggactccgac    900
ggctccttct tcctctacag caagctcacc gtggacaaga gcaggtggca gcaggggaac    960
gtcttctcat gctccgtgat gcatgaggct ctgcacaacc actacacgca gaagagcctc   1020
```
tccctgtctc ccgggaaatg a                                              1041

<210> SEQ ID NO 56
<211> LENGTH: 438
<212> TYPE: PRT
<213> ORGANISM: Artificial
<220> FEATURE:
<223> OTHER INFORMATION: Artificial = synthetic construct
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 56

```
Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
            100                 105                 110

Gly Val Pro Asn Lys Val Gly Thr Cys Val Ser Glu Gly Ser Tyr Pro
        115                 120                 125

Ala Gly Thr Leu Ser Trp His Leu Asp Gly Lys Pro Leu Val Pro Asn
    130                 135                 140

Glu Lys Gly Val Ser Val Lys Glu Gln Thr Arg Arg His Pro Glu Thr
145                 150                 155                 160

Gly Leu Phe Thr Leu Gln Ser Glu Leu Met Val Thr Pro Ala Arg Gly
                165                 170                 175

Gly Asp Pro Arg Pro Thr Phe Ser Cys Ser Phe Ser Pro Gly Leu Pro
            180                 185                 190

Arg His Arg Ala Leu Arg Thr Ala Pro Ile Gln Pro Arg Val Trp Glu
        195                 200                 205

Pro Val Pro Leu Glu Glu Val Gln Leu Val Val Glu Pro Glu Gly Gly
    210                 215                 220

Ala Val Ala Pro Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335
```

```
Pro Gln Val Tyr Thr Leu Pro Pro Ser Arg Asp Glu Leu Thr Lys Asn
                340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
        370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 57
<211> LENGTH: 323
<212> TYPE: PRT
<213> ORGANISM: Artificial
<220> FEATURE:
<223> OTHER INFORMATION: Artificial = synthetic construct
<220> FEATURE:
<221> NAME/KEY: MISC_FEATURE
<222> LOCATION: (1)..(1)
<223> OTHER INFORMATION: Xaa=pyroglutamic acid

<400> SEQUENCE: 57

Xaa Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg Val Tyr Gln
                85                  90                  95

Ile Pro Gly Lys Pro Glu Ile Val Asp Ser Ala Ser Glu Leu Thr Ala
            100                 105                 110

Gly Pro Ser Val Phe Leu Phe Pro Lys Pro Lys Asp Thr Leu Met
        115                 120                 125

Ile Ser Arg Thr Pro Glu Val Thr Cys Val Val Val Asp Val Ser His
130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Arg Asp Glu Leu Thr Lys Asn Gln Val Ser
225                 230                 235                 240
```

-continued

```
Leu Thr Cys Leu Val Lys Gly Phe Tyr Pro Ser Asp Ile Ala Val Glu
            245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Lys Leu Thr Val
            275                 280                 285

Asp Lys Ser Arg Trp Gln Gln Gly Asn Val Phe Ser Cys Ser Val Met
        290                 295                 300

His Glu Ala Leu His Asn His Tyr Thr Gln Lys Ser Leu Ser Leu Ser
305                 310                 315                 320

Pro Gly Lys
```

RAGE FUSION PROTEINS, FORMULATIONS, AND METHODS OF USE THEREOF

CROSS REFERENCE TO RELATED APPLICATIONS

The present application claims priority under 35 U.S.C. §119(e) from U.S. Provisional Patent Application Ser. No. 60/798,455, filed May 5, 2006. The disclosure of U.S. Provisional Patent Application 60/798,455 is hereby incorporated by reference in its entirety herein.

FIELD OF THE INVENTION

The present invention relates to regulation of the Receptor for Advanced Glycated Endproducts (RAGE). More particularly, the present invention describes fusion proteins comprising a RAGE polypeptide, methods of making such fusion proteins and formulations of such RAGE fusion proteins, and the use of such RAGE fusion proteins for treatment of RAGE-based disorders.

BACKGROUND

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycation End Products (AGEs). Factors which promote formation of AGEs include delayed protein turnover (e.g. as in amyloidoses), accumulation of macromolecules having high lysine content, and high blood glucose levels (e.g. as in diabetes) (Hori et al., *J. Biol. Chem.* 270: 25752-761, (1995)). AGEs have been implicated in a variety of disorders including complications associated with diabetes and normal aging.

AGEs display specific and saturable binding to cell surface receptors on monocytes, macrophages, endothelial cells of the microvasculature, smooth muscle cells, mesengial cells, and neurons. The Receptor for Advanced Glycated Endproducts (RAGE) is a member of the immunoglobulin supergene family of molecules. The extracellular (N-terminal) domain of RAGE includes three immunoglobulin-type regions: one V (variable) type domain followed by two C-type (constant) domains (Neeper et al., *J. Biol. Chem.*, 267:14998-15004 (1992); Schmidt et al., *Circ. (Suppl.)* 96#194 (1997)). A single transmembrane spanning domain and a short, highly charged cytosolic tail follow the extracellular domain. The N-terminal, extracellular domain can be isolated by proteolysis of RAGE or by molecular biological approaches to generate soluble RAGE (sRAGE) comprised of the V and C domains.

RAGE is expressed on multiple cell types including leukocytes, neurons, microglial cells and vascular endothelium (e.g., Hori et al., *J. Biol. Chem.*, 270:25752-761 (1995)). Increased levels of RAGE are also found in aging tissues (Schleicher et al., *J. Clin. Invest.*, 99 (3): 457-468 (1997)), and the diabetic retina, vasculature and kidney (Schmidt et al., *Nature Med.*, 1: 1002-1004 (1995)).

In addition to AGEs, other compounds can bind to and modulate RAGE. RAGE binds to multiple functionally and structurally diverse ligands including amyloid beta (Aβ), serum amyloid A (SAA), Advanced Glycation End products (AGEs), S100 (a proinflammatory member of the Calgranulin family), carboxymethyl lysine (CML), amphoterin and CD11b/CD18 (Bucciarelli et al., *Cell Mol. Life. Sci.*, 59:1117-128 (2002); Chavakis et al., *Microbes Infect.*, 6:1219-1225 (2004); Kokkola et al., *Scand. J. Immunol.*, 61:1-9 (2005); Schmidt et al., *J. Clin. Invest.*, 108:949-955 (2001); Rocken et al., *Am. J. Pathol.*, 162:1213-1220 (2003)).

Binding of ligands such as AGEs, S100/calgranulin, β-amyloid, CML ($N^\epsilon$-Carboxymethyl lysine), and amphoterin to RAGE has been shown to modify expression of a variety of genes. These interactions may then initiate signal transduction mechanisms including p38 activation, p21ras, MAP kinases, Erk1-2 phosphorylation, and the activation of the transcriptional mediator of inflammatory signaling, NF-κB (Yeh et al., *Diabetes*, 50:1495-1504 (2001)). For example, in many cell types, interaction between RAGE and its ligands can generate oxidative stress, which thereby results in activation of the free radical sensitive transcription factor NF-κB, and the activation of NF-κB regulated genes, such as the cytokines IL-10 and TNF-α. Furthermore, RAGE expression is upregulated via NF-κB and shows increased expression at sites of inflammation or oxidative stress (Tanaka et al., *J. Biol. Chem.*, 275:25781-25790 (2000)). Thus, an ascending and often detrimental spiral may be fueled by a positive feedback loop initiated by ligand binding.

Activation of RAGE in different tissues and organs can lead to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.*, 97:238-243 (1995)), nephropathy (Teillet et al., *J. Am. Soc. Nephrol.*, 11:1488-1497 (2000)), arteriosclerosis (Vlassara et. al., *The Finnish Medical Society DUODECIM, Ann. Med.*, 28:419-426 (1996)), and retinopathy (Hammes et al., *Diabetologia*, 42:603-607 (1999)). RAGE has also been implicated in Alzheimer's disease (Yan et al., *Nature*, 382: 685-691 (1996)), and in tumor invasion and metastasis (Taguchi et al., *Nature*, 405:354-357 (2000)).

Despite the broad expression of RAGE and its apparent pleiotropic role in multiple diverse disease models, RAGE does not appear to be essential to normal development. For example, RAGE knockout mice are without an overt abnormal phenotype, suggesting that while RAGE can play a role in disease pathology when stimulated chronically, inhibition of RAGE does not appear to contribute to any unwanted acute phenotype (Liliensiek et al., *J. Clin. Invest.*, 113:1641-50 (2004)).

Antagonizing binding of physiological ligands to RAGE may down-regulate the pathophysiological changes brought about by excessive concentrations of AGEs and other RAGE ligands. By reducing binding of endogenous ligands to RAGE, symptoms associated with RAGE-mediated disorders may be reduced. Soluble RAGE (sRAGE) is able to effectively antagonize the binding of RAGE ligands to RAGE. However, sRAGE can have a half-life when administered in vivo that may be too short to be therapeutically useful for one or more disorders. Thus, there is a need to develop compounds that antagonize the binding of AGEs and other physiological ligands to the RAGE receptor where the compound has a desirable pharmacokinetic profile.

SUMMARY

Embodiments of the present invention comprise RAGE fusion proteins and methods of using such proteins. The present invention may be embodied in a variety of ways. Embodiments of the present invention may comprise a RAGE fusion protein comprising a RAGE polypeptide linked to a second, non-RAGE polypeptide. In one embodiment, the RAGE fusion protein comprises a RAGE ligand binding site. The RAGE fusion protein may further comprise a RAGE polypeptide directly linked to a polypeptide comprising the $C_H2$ domain of an immunoglobulin, or a portion of the $C_H2$ domain. In certain embodiments, the RAGE fusion protein comprises an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

The present invention also comprises a method to make a RAGE fusion protein. In one embodiment the method comprises linking a RAGE polypeptide to a second, non-RAGE polypeptide. In one embodiment, the RAGE polypeptide comprises a RAGE ligand binding site. The method may comprise linking a RAGE polypeptide directly to a polypeptide comprising the $C_H2$ domain of an immunoglobulin or a portion of the $C_H2$ domain. In certain embodiments, the RAGE fusion protein comprises an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

In other embodiments, the present invention may comprise methods and compositions for treating a RAGE-mediated disorder in a subject. The method may comprise administering a RAGE fusion protein of the present invention to the subject. The composition may comprise a RAGE fusion protein of the present invention in a pharmaceutically acceptable carrier.

In other embodiments, the present invention also provides formulations comprising a lyophilized mixture of a lyoprotectant, a RAGE fusion protein, and buffer. For example, in certain embodiments, the present invention may comprise a stable reconstituted formulation comprising a RAGE fusion protein in an amount of at least 50 mg/mL, and a diluent, where the reconstituted formulation has been prepared from a lyophilized mixture of the RAGE fusion protein and a lyoprotectant.

Embodiments of the present invention may also comprise articles of manufacture. In certain embodiments, the articles of manufacture may comprise a container which holds a formulation comprising a lyophilized RAGE fusion protein. The article of manufacture may also comprise instructions for reconstituting the lyophilized formulation with a diluent.

In other embodiments, the present invention may also comprise methods for preparing a stable reconstituted formulation of a RAGE fusion protein. In certain embodiments, the method may comprise reconstituting a lyophilized mixture of a RAGE fusion protein and a lyoprotectant in a diluent such that the RAGE fusion protein concentration in the reconstituted formulation is at least 50 mg/mL. For example, in one embodiment, the method may comprise the steps of lyophilizing a mixture comprising a RAGE fusion protein and a lyoprotecting amount of a lyoprotectant, and reconstituting the lyophilized mixture in a diluent.

There are various advantages that may be associated with particular embodiments of the present invention. In one embodiment, the RAGE fusion proteins of the present invention may be metabolically stable when administered to a subject. Also, the RAGE fusion proteins of the present invention may exhibit high-affinity binding for RAGE ligands. In certain embodiments, the RAGE fusion proteins of the present invention bind to RAGE ligands with affinities in the high nanomolar to low micromolar range. By binding with high affinity to physiological RAGE ligands, the RAGE fusion proteins of the present invention may be used to inhibit binding of endogenous ligands to RAGE, thereby providing a means to ameliorate RAGE-mediated diseases.

Also, the RAGE fusion proteins of the present invention may be provided in protein or nucleic acid form. In one example embodiment, the RAGE fusion protein may be administered systemically and remain in the vasculature to potentially treat vascular diseases mediated in part by RAGE. In another example embodiment, the RAGE fusion protein may be administered locally to treat diseases where RAGE ligands contribute to the pathology of the disease. Alternatively, a nucleic acid construct encoding the RAGE fusion protein may be delivered to a site by the use of an appropriate carrier such as a virus, or as a naked DNA, where transient local expression may locally inhibit the interaction between RAGE ligands and receptors. Thus, administration may be transient (e.g., as where the RAGE fusion protein is administered) or more permanent in nature (e.g., as where the RAGE fusion protein is administered as a recombinant DNA).

There are additional features of the invention which will be described hereinafter. It is to be understood that the invention is not limited in its application to the details set forth in the following claims, description and figures. The invention is capable of other embodiments and of being practiced or carried out in various ways.

BRIEF DESCRIPTION OF THE FIGURES

Various features, aspects and advantages of the present invention will become more apparent with reference to the following figures.

FIG. 1 shows various RAGE sequences and immunoglobulin sequences in accordance with alternate embodiments of the present invention: Panel A, SEQ ID NO: 1, the amino acid sequence for human RAGE; and SEQ ID NO: 2, the amino acid sequence for human RAGE without the signal sequence of amino acids 1-22; Panel B, SEQ ID NO: 3, the amino acid sequence for human RAGE without the signal sequence of amino acids 1-23; Panel C, SEQ ID NO: 4, the amino acid sequence of human sRAGE; SEQ ID NO: 5, the amino acid sequence of human sRAGE without the signal sequence of amino acids 1-22, and SEQ ID NO: 6, the amino acid sequence of human sRAGE without the signal sequence of amino acids 1-23; Panel D, SEQ ID NO: 7, an amino acid sequence comprising the V-domain of human RAGE; SEQ ID NO: 8, an alternate amino acid sequence comprising the V-domain of human RAGE; SEQ ID NO: 9, an N-terminal fragment of the V-domain of human RAGE; SEQ ID NO: 10, an alternate N-terminal fragment of the V-domain of human RAGE; SEQ ID NO: 11, the amino acid sequence for amino acids 124-221 of human RAGE; SEQ ID NO: 12, the amino acid sequence for amino acids 227-317 of human RAGE; SEQ ID NO: 13, the amino acid sequence for amino acids 23-123 of human RAGE; Panel E, SEQ ID NO: 14, the amino acid sequence for amino acids 24-123 of human RAGE; SEQ ID NO: 15, the amino acid sequence for amino acids 23-136 of human RAGE; SEQ ID NO: 16, the amino acid sequence for amino acids 24-136 of human RAGE; SEQ ID NO: 17, the amino acid sequence for amino acids 23-226 of human RAGE; SEQ ID NO: 18, the amino acid sequence for amino acids 24-226 of human RAGE; Panel F, SEQ ID NO: 19, the amino acid sequence for amino acids 23-251 of human RAGE; SEQ ID NO: 20, the amino acid sequence for amino acids 24-251 of human RAGE; SEQ ID NO: 21, a RAGE interdomain linker; SEQ ID NO: 22, a second RAGE interdomain linker; SEQ ID NO: 23, a third RAGE interdomain linker; SEQ ID NO: 24, a fourth RAGE interdomain linker; Panel G, SEQ ID NO: 25, DNA encoding human RAGE amino acids 1-118; SEQ ID NO: 26, DNA encoding human RAGE amino acids 1-123; and SEQ ID NO: 27, DNA encoding human RAGE amino acids 1-136; Panel H, SEQ ID NO: 28, DNA encoding human RAGE amino acids 1-230; and SEQ ID NO: 29, DNA encoding human RAGE amino acids 1-251; Panel I, SEQ ID NO: 38, a partial amino acid sequence for the $C_H2$ and $C_H3$ domains of human IgG; SEQ ID NO:39, DNA encoding a portion of the human $C_H2$ and $C_H3$ domains of human IgG; SEQ ID NO: 40, an amino acid sequence for the $C_H2$ and $C_H3$ domains of human IgG; Panel J, SEQ ID NO: 41, a DNA encoding the human $C_H2$ and $C_H3$ domains of human IgG; SEQ ID NO: 42, an amino acid sequence for the $C_H2$ domain of human IgG; SEQ ID NO: 43, an amino acid sequence for the $C_H3$ domain of human IgG; and SEQ ID NO: 44, a fifth RAGE interdomain linker; Panel K, SEQ ID NO: 45, the amino acid sequence of human sRAGE without the signal sequence of amino acids 1-23 where the glutamine residue at the N-terminus has cyclized to form pyroglutamic acid, SEQ ID NO: 46, an alternate amino acid sequence comprising the V-domain of human sRAGE where the glutamine residue at the N-terminus has cyclized to form pyroglutamic acid, SEQ ID NO: 47, an alternate N-terminal fragment of the V-domain of human RAGE where the glutamine residue at the N-terminus has cyclized to form pyroglutamic acid, SEQ ID NO: 48, the amino acid sequence for amino acids 24-123 of human RAGE where the glutamine residue at the N-terminus has cyclized to form pyroglutamic acid; Panel L, SEQ ID NO: 49, the amino acid sequence for amino acids 24-136 of human RAGE where the glutamine residue at the N-terminus has cyclized to form pyroglutamic acid, SEQ ID NO: 50, the amino acid sequence for amino acids 24-226 of human RAGE where the glutamine residue at the N-terminus has cyclized to form pyroglutamic acid, SEQ ID NO: 51, the amino acid sequence for amino acids 24-251 of human RAGE where the glutamine residue at the N-terminus has cyclized to form pyroglutamic acid; Panel M, SEQ ID NO: 52, an alternate DNA sequence encoding a portion of the human $C_H2$ and $C_H3$ domains of human IgG in SEQ ID NO: 38, and SEQ ID NO: 53, an alternate DNA sequence encoding the human $C_H2$ and $C_H3$ domains of human IgG in SEQ ID NO: 40.

FIG. 2 shows alternate DNA sequences SEQ ID NO: 30 (Panel A) and SEQ ID NO: 54 (Panel B) that encode a first RAGE fusion protein (TTP-4000) coding region in accordance with an embodiment of the present invention. Coding sequence 1-753 highlighted in bold encodes RAGE N-terminal protein sequence whereas sequence 754-1386 encodes human IgG Fc (γ1) protein sequence without the hinge region.

FIG. 3 shows alternate DNA sequences SEQ ID NO: 31 (Panel A) and SEQ ID NO: 55 (Panel B) that encode a second RAGE fusion protein (TTP-3000) coding region in accordance with an embodiment of the present invention. Coding sequence 1-408 highlighted in bold encodes RAGE N-terminal protein sequence, whereas sequence 409-1041 codes human IgG Fc (γ1) protein sequence without the hinge region.

FIG. 4 shows the amino acid sequences, SEQ ID NO: 32, SEQ ID NO: 33, SEQ ID NO: 34, and SEQ ID NO: 56 that each encode a four domain RAGE fusion protein in accordance with alternate embodiments of the present invention. RAGE sequence is highlighted with bold font.

FIG. 5 shows the amino acid sequences, SEQ ID NO: 35, SEQ ID NO: 36, SEQ ID NO: 37, and SEQ ID NO: 57 that each encode a three domain RAGE fusion protein in accordance with alternate embodiments of the present invention. RAGE sequence is highlighted with bold font.

DETAILED DESCRIPTION

Figure 6B:
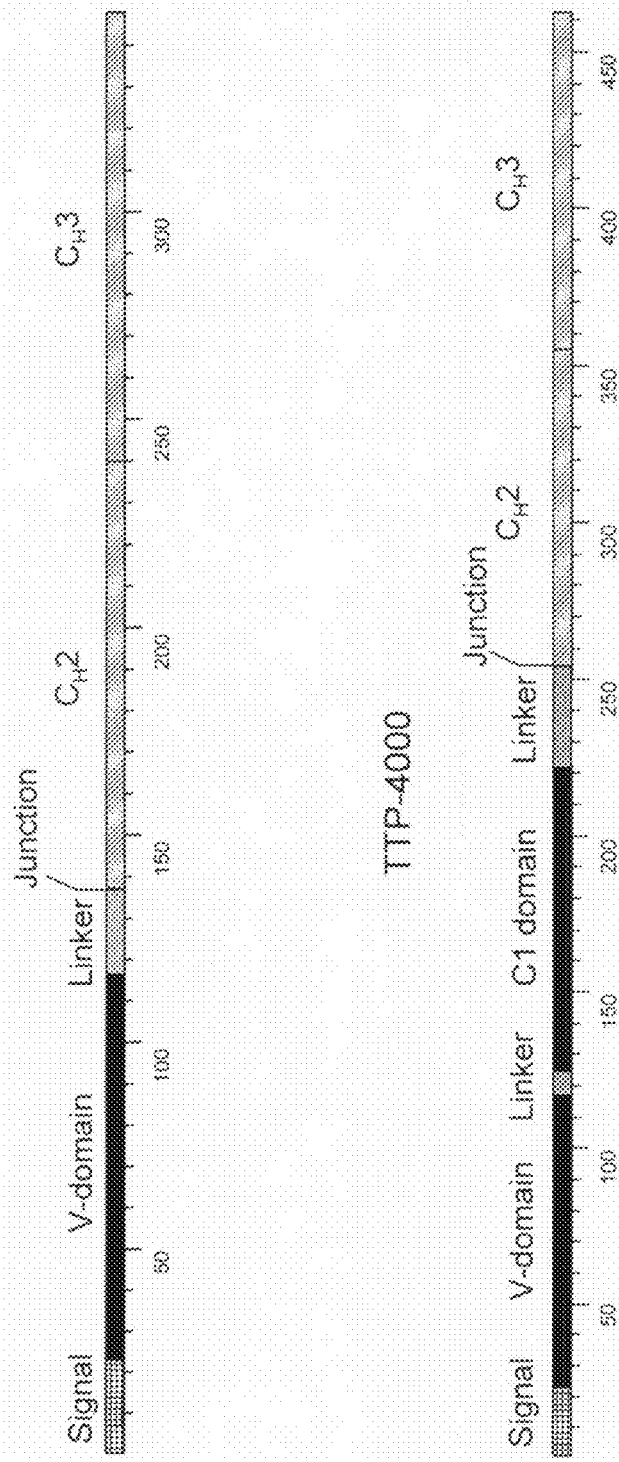
FIG. 6, Panel A, shows a comparison of the protein domains in human RAGE and human Ig gamma-1 Fc protein, and cleavage points used to make TTP-3000 (at position 136) and TTP-4000 (at position 251) in accordance with alternate embodiments of the present invention; and Panel B shows the domain structure for TTP-3000 and TTP-4000 in accordance with alternate embodiments of the present invention.

Unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, the terms "portion" and "fragment" are used interchangeably to refer to parts of a polypeptide, nucleic acid, or other molecular construct.

"Polypeptide" and "protein" are used interchangeably herein to describe protein molecules that may comprise either partial or full-length proteins.

As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid.

Unless defined otherwise, all technical and scientific terms used herein have the same meaning as commonly understood by one of ordinary skill in the art. Practitioners are particularly directed to Current Protocols in Molecular Biology (see e.g. Ausubel, F. M. et al., *Short Protocols in Molecular Biology*, 4$^{th}$ Ed., Chapter 2, John Wiley & Sons, N.Y.) for definitions and terms of the art. Abbreviations for amino acid residues are the standard 3-letter and/or 1-letter codes used in the art to refer to one of the 20 common L-amino acids.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extrachromasomal) or may be integrated into a host cell chromosome. In one embodiment, the vector may comprise an expression vector capable of producing a protein derived from at least part of a nucleic acid sequence inserted into the vector.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M NaHPO$_4$, 7% sodium dodecyl sulfate (SDS), at 65° C., and washing in 0.25 M NaHPO$_4$, 3.5% SDS followed by washing 0.1×SSC/0.1% SDS at a temperature ranging from room temperature to 68° C. depending on the length of the probe. For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [γ-$^{32}$P]ATP, or incorporation of radiolabeled nucleotides such as [α-$^{32}$P]dCTP by random primer labeling. Alternatively, probes may be labeled by incorporation of biotinylated or fluorescein labeled nucleotides, and the probe detected using Streptavidin or anti-fluorescein antibodies.

As used herein, "small organic molecules" are molecules of molecular weight less than 2,000 Daltons that contain at least one carbon atom.

The term "fusion protein" refers to a protein or polypeptide that has an amino acid sequence derived from two or more proteins. The fusion protein may also include linking regions of amino acids between amino acid portions derived from separate proteins.

As used herein, a "non-RAGE polypeptide" is any polypeptide that is not derived from RAGE or a fragment thereof. Such non-RAGE polypeptides include immunoglobulin peptides, dimerizing polypeptides, stabilizing polypeptides, amphiphilic peptides, or polypeptides comprising amino acid sequences that provide "tags" for targeting or purification of the protein.

As used herein, "immunoglobulin peptides" may comprise an immunoglobulin heavy chain or a portion thereof. In one embodiment, the portion of the heavy chain may be the Fc fragment or a portion thereof. As used herein, the Fc fragment comprises the heavy chain hinge polypeptide, and the $C_H2$ and $C_H3$ domains of the heavy chain of an immunoglobulin, in either monomeric or dimeric form. Or, the $C_H1$ and Fc fragment may be used as the immunoglobulin polypeptide. The heavy chain (or portion thereof) may be derived from any one of the known heavy chain isotypes: IgG ($\gamma$), IgM ($\mu$), IgD ($\delta$), IgE ($\epsilon$), or IgA ($\alpha$). In addition, the heavy chain (or portion thereof) may be derived from any one of the known heavy chain subtypes: IgG1 ($\gamma$1), IgG2 ($\gamma$2), IgG3 ($\gamma$3), IgG4 ($\gamma$4), IgA1 ($\alpha$1), IgA2 ($\alpha$2), or mutations of these isotypes or subtypes that alter the biological activity. An example of biological activity that may be altered includes reduction of an isotype's ability to bind to some Fc receptors as for example, by modification of the hinge region.

The terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, the percent identity of two sequences may be determined using GCG with a gap weight of 1, such that each amino acid gap is weighted as if it were a single amino acid mismatch between the two sequences.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made.

As used herein, the term "homologue" means a polypeptide having a degree of homology or identity with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA,* 80:726-730). For example, homologous sequences may be taken to include an amino acid sequences which in alternate embodiments are at least 70% identical, 75% identical, 85% identical, 90% identical, 95% identical, 96% identical, 97% identical, 98% identical, or 99% identical to each other.

As used herein, the term at least 90% identical thereto includes sequences that range from 90 to 99.99% identity to the indicated sequences and includes all ranges in between. Thus, the term at least 90% identical thereto includes sequences that are 91, 91.5, 92, 92.5, 93, 93.5, 94, 94.5, 95, 95.5, 96, 96.5, 97, 97.5, 98, 98.5, 99, 99.5 percent identical to the indicated sequence. Similarly the term "at least 70% identical includes sequences that range from 70 to 99.99% identical, with all ranges in between. The determination of percent identity is determined using the algorithms described here.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

As used herein, "immunoglobulin domain" is a sequence of amino acids that is structurally homologous, or identical to, a domain of an immunoglobulin. The length of the sequence of amino acids of an immunoglobulin domain may be any length. In one embodiment, an immunoglobulin domain may be less than 250 amino acids. In an example embodiment, an immunoglobulin domain may be about 80-150 amino acids in length. For example, the variable region, and the $C_H1$, $C_H2$, and $C_H3$ regions of an IgG are each immunoglobulin domains. In another example, the variable, the $C_H1$, $C_H2$, $C_H3$ and $C_H4$ regions of an IgM are each immunoglobulin domains.

As used herein, a "RAGE immunoglobulin domain" is a sequence of amino acids from RAGE protein that is structurally homologous, or identical to, a domain of an immunoglobulin. For example, a RAGE immunoglobulin domain may comprise the RAGE V-domain, the RAGE Ig-like C1-type 1 domain ("C1 domain"), or the RAGE Ig-like C2-type 2 domain ("C2 domain").

As used herein, an "interdomain linker" comprises a polypeptide that joins two domains together. An Fc hinge region is an example of an interdomain linker in an IgG.

As used herein, "directly linked" identifies a covalent linkage between two different groups (e.g., nucleic acid sequences, polypeptides, polypeptide domains) that does not have any intervening atoms between the two groups that are being linked.

As used herein, "ligand binding domain" refers to a domain of a protein responsible for binding a ligand. The term ligand binding domain includes homologues of a ligand binding domain or portions thereof. In this regard, deliberate amino acid substitutions may be made in the ligand binding site on the basis of similarity in polarity, charge, solubility, hydrophobicity, or hydrophilicity of the residues, as long as the binding specificity of the ligand binding domain is retained.

As used herein, a "ligand binding site" comprises residues in a protein that directly interact with a ligand, or residues involved in positioning the ligand in close proximity to those residues that directly interact with the ligand. The interaction of residues in the ligand binding site may be defined by the spatial proximity of the residues to a ligand in the model or structure. The term ligand binding site includes homologues of a ligand binding site, or portions thereof. In this regard, deliberate amino acid substitutions may be made in the ligand binding site on the basis of similarity in polarity, charge, solubility, hydrophobicity, or hydrophilicity of the residues, as long as the binding specificity of the ligand binding site is retained. A ligand binding site may exist in one or more ligand binding domains of a protein or polypeptide.

As used herein, the term "interact" refers to a condition of proximity between a ligand or compound, or portions or fragments thereof, and a portion of a second molecule of interest. The interaction may be non-covalent, for example, as a result of hydrogen-bonding, van der Waals interactions, or electrostatic or hydrophobic interactions, or it may be covalent.

As used herein, a "ligand" refers to a molecule or compound or entity that interacts with a ligand binding site, including substrates or analogues or parts thereof. As described herein, the term "ligand" may refer to compounds that bind to the protein of interest. A ligand may be an agonist, an antagonist, or a modulator. Or, a ligand may not have a biological effect. Or, a ligand may block the binding of other ligands thereby inhibiting a biological effect. Ligands may include, but are not limited to, small molecule inhibitors. These small molecules may include peptides, peptidomimetics, organic compounds and the like. Ligands may also include polypeptides and/or proteins.

As used herein, a "modulator compound" refers to a molecule which changes or alters the biological activity of a molecule of interest. A modulator compound may increase or decrease activity, or change the physical or chemical characteristics, or functional or immunological properties, of the molecule of interest. For RAGE, a modulator compound may increase or decrease activity, or change the characteristics, or functional or immunological properties of the RAGE, or a portion thereof A modulator compound may include natural and/or chemically synthesized or artificial peptides, modified peptides (e.g., phosphopeptides), antibodies, carbohydrates, monosaccharides, oligosaccharides, polysaccharides, glycolipids, heterocyclic compounds, nucleosides or nucleotides or parts thereof, and small organic or inorganic molecules. A modulator compound may be an endogenous physiological compound or it may be a natural or synthetic compound. Or, the modulator compound may be a small organic molecule. The term "modulator compound" also includes a chemically modified ligand or compound, and includes isomers and racemic forms.

An "agonist" comprises a compound that binds to a receptor to form a complex that elicits a pharmacological response specific to the receptor involved.

An "antagonist" comprises a compound that binds to an agonist or to a receptor to form a complex that does not give rise to a substantial pharmacological response and can inhibit the biological response induced by an agonist.

RAGE agonists may therefore bind to RAGE and stimulate RAGE-mediated cellular processes, and RAGE antagonists may inhibit RAGE-mediated processes from being stimulated by a RAGE agonist. For example, in one embodiment, the cellular process stimulated by RAGE agonists comprises activation of TNF-α gene transcription.

The term "peptide mimetics" refers to structures that serve as substitutes for peptides in interactions between molecules (Morgan et al., 1989, *Ann. Reports Med. Chem.*, 24:243-252). Peptide mimetics may include synthetic structures that may or may not contain amino acids and/or peptide bonds but that retain the structural and functional features of a peptide, or agonist, or antagonist. Peptide mimetics also include peptoids, oligopeptoids (Simon et al., 1972, *Proc. Natl. Acad, Sci., USA*, 89:9367); and peptide libraries containing peptides of a designed length representing all possible sequences of amino acids corresponding to a peptide, or agonist or antagonist of the invention.

The term "treating" or "treat" refers to improving a symptom of a disease or disorder and may comprise curing the disorder, substantially preventing the onset of the disorder, or improving the subject's condition. The term "treatment" as used herein, refers to the full spectrum of treatments for a given disorder from which the patient is suffering, including alleviation of one symptom or most of the symptoms resulting from that disorder, a cure for the particular disorder, or prevention of the onset of the disorder.

As used herein, the term "EC50" is defined as the concentration of an agent that results in 50% of a measured biological effect. For example, the EC50 of a therapeutic agent having a measurable biological effect may comprise the value at which the agent displays 50% of the biological effect.

As used herein, the term "IC50" is defined as the concentration of an agent that results in 50% inhibition of a measured effect. For example, the IC50 of an antagonist of RAGE binding may comprise the value at which the antagonist reduces ligand binding to the ligand binding site of RAGE by 50%.

As used herein, an "effective amount" means the amount of an agent that is effective for producing a desired effect in a subject. The term "therapeutically effective amount" denotes that amount of a drug or pharmaceutical agent that will elicit therapeutic response of an animal or human that is being sought. The actual dose which comprises the effective amount may depend upon the route of administration, the size and health of the subject, the disorder being treated, and the like.

The term "pharmaceutically acceptable carrier" as used herein may refer to compounds and compositions that are suitable for use in human or animal subjects, as for example, for therapeutic compositions administered for the treatment of a RAGE-mediated disorder or disease.

The term "pharmaceutical composition" is used herein to denote a composition that may be administered to a mammalian host, e.g., orally, parenterally, topically, by inhalation spray, intranasally, or rectally, in unit dosage formulations containing conventional non-toxic carriers, diluents, adjuvants, vehicles and the like.

The term "parenteral" as used herein, includes subcutaneous injections, intravenous, intramuscular, intracisternal injection, or infusion techniques.

As used herein "rejection" refers to the immune or inflammatory response on tissue that leads to destruction of cells, tissues or organs, or that leads to damage to cells, tissues, or organs. The rejected cells, tissue, or organ may be derived from the same subject that is mounting the rejection response, or may be transplanted from a different subject into the subject that is displaying rejection.

As used herein, the term "cell" refers to the structural and functional units of a mammalian living system that each comprise an independent living system. As is known in the art, cells include a nucleus, cytoplasm, intracellular organelles, and a cell wall which encloses the cell and allows the cell to be independent of other cells.

As used herein, the term "tissue" refers to an aggregate of cells that have a similar structure and function, or that work together to perform a particular function. A tissue may include a collection of similar cells and the intercellular substances surrounding the cells. Tissues include, but are not limited to, muscle tissue, nerve tissue, and bone.

As used herein an "organ" refers to a fully differentiated structural and functional unit in an animal that is specialized for some specific function. An organ may comprise a group of tissues that perform a specific function or group of functions. Organs include, but are not limited to, the heart, lungs, brain, eye, stomach, spleen, pancreas, kidneys, liver, intestinces, skin, uterus, bladder, and bone.

A "stable" formulation is one in which the RAGE fusion protein therein essentially retains its physical and chemical stability and biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept at 40° C. for 1 week to 1 month, at which time stability is measured. For example, the extent of aggregation following lyophilization and storage can be used as an indicator of RAGE fusion protein stability (see Examples herein). For example, a "stable" formulation may be one wherein less than about 10% and preferably less than about 5% of the RAGE fusion protein is present as an aggregate in the formulation. In other embodiments, an increase in aggregate formation following lyophilization and storage of the lyophilized formulation can be determined. For example, a "stable" lyophilized formulation may be one wherein the increase in aggregate in the lyophilized formulation is less than about 5% or less than about 3%, when the lyophilized formulation is incubated at 40° C. for at least one week. In other embodiments, stability of the RAGE fusion protein formulation may be measured using a biological activity assay such as a binding assay as described herein.

A "reconstituted" formulation is one which has been prepared by dissolving a lyophilized RAGE fusion protein formulation in a diluent such that the RAGE fusion protein is dispersed and/or dissolved in the reconstituted formulation. The reconstituted formulation may be suitable for administration (e.g. parenteral administration) to a patient to be treated with the fusion protein and, in certain embodiments of the invention, may be one which is suitable for subcutaneous administration.

By "isotonic" it is meant that the formulation of interest has an osmotic pressure from about 240 to about 340 mOsm/kg. In an embodiment, an isotonic formulation is one having an osmotic pressure that is essentially the same as human blood (285-310 mOsm/kg). Isotonicity can be measured using a vapor pressure or a freezing point depression type osmometer.

A "lyoprotectant" is a molecule which, when combined with a RAGE fusion protein, significantly prevents or reduces chemical and/or physical instability of the protein upon lyophilization and subsequent storage. Exemplary lyoprotectants include sugars such as sucrose or trehalose; a polyol such as sugar alcohols, e.g. erythritol, arabitol, xylitol, sorbitol, and mannitol; or combinations thereof. In an embodiment, the lyoprotectant may comprise a sugar. In another embodiment, the lyoprotectant may comprise a non-reducing sugar. In a further embodiment, the lyoprotectant may comprise a non-reducing sugar such as sucrose. The lyoprotectant may be added to the pre-lyophilized formulation in a "lyoprotecting amount" which means that, following lyophilization of the protein in the presence of the lyoprotecting amount of the lyoprotectant, the RAGE fusion protein essentially retains its physical and chemical stability and biological activity upon lyophilization and storage.

The "diluent" for a lyophilized formulation herein is one which is pharmaceutically acceptable (safe and non-toxic for administration to a human) and is useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution. In an embodiment, the diluent provides a reconstituted formulation suitable for injection. In another embodiment, where the diluent provides a reconstituted formulation suitable for injection, the diluent may comprise water for injection (WFI).

A "preservative" for a reconstituted formulation is a compound which can be added to the diluent or to the reconstituted formulation to essentially reduce bacterial action in the reconstituted formulation. In an embodiment, the amount of preservative may be added in an amount useful to facilitate the production of a multi-use reconstituted formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, allyl parabens such as methyl or propyl paraben, catechol, resorcinol, cyclohexanol, 3-pentanol, and m-cresol.

A "bulking agent" for a lyophilized formulation is a compound which adds mass to the lyophilized mixture and contributes to the physical structure of the lyophilized cake (e.g. facilitates the production of an essentially uniform lyophilized cake which maintains an open pore structure). Exemplary bulking agents include, but are not limited to, mannitol, glycine, and xorbitol.

RAGE Fusion Proteins

Embodiments of the present invention comprise RAGE fusion proteins, methods of making such fusion proteins, and methods of use of such fusion proteins. The present invention may be embodied in a variety of ways.

For example, embodiments of the present invention provide RAGE fusion proteins comprising a RAGE polypeptide linked to a second, non-RAGE polypeptide. In one embodiment, the RAGE fusion protein may comprise a RAGE ligand binding site. In an embodiment, the ligand binding site comprises the most N-terminal domain of the RAGE fusion protein. The RAGE ligand binding site may comprise the V domain of RAGE, or a portion thereof. In an embodiment, the RAGE ligand binding site comprises SEQ ID NO: 9 or a sequence at least 90% identical thereto, or SEQ ID NO: 10 or a sequence at least 90% identical thereto, or SEQ ID NO: 47 or a sequence at least 90% identical thereto (FIG. 1).

In an embodiment, the RAGE polypeptide may be linked to a polypeptide comprising an immunoglobulin domain or a portion (e.g., a fragment thereof) of an immunoglobulin domain. In one embodiment, the polypeptide comprising an immunoglobulin domain comprises at least a portion of at least one of the $C_H2$ or the $C_H3$ domains of a human IgG.

In certain embodiments, the RAGE fusion protein comprises an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

A RAGE protein or polypeptide may comprise full-length human RAGE protein (e.g., SEQ ID NO: 1), or a fragment of human RAGE. As used herein, a fragment of a RAGE polypeptide is at least 5 amino acids in length, may be greater than 30 amino acids in length, but is less than the full amino acid sequence. In alternate embodiments of the fusion proteins, compositions, and methods of the present invention, the RAGE polypeptide may comprise a sequence that is at least about 70%, 75%, 80%, 85%, 90%, 95%, 96%, 97%, 98%, or 99% identical to human RAGE, or a fragment thereof. For example, in one embodiment, the RAGE polypeptide may comprise human RAGE, or a fragment thereof, with Glycine as the first residue rather than a Methionine (see e.g., Neeper et al., (1992)). Or, the human RAGE may comprise full-length RAGE with the signal sequence removed (e.g., SEQ ID NO: 2 or SEQ ID NO: 3) (FIGS. 1A and 1B) or a portion of that amino acid sequence.

The RAGE fusion proteins of the present invention may also comprise sRAGE (e.g., SEQ ID NO: 4), a polypeptide at least 90% identical to sRAGE, or a fragment of sRAGE. As used herein, sRAGE is the RAGE protein that does not include the transmembrane region or the cytoplasmic tail (Park et al., *Nature Med.*, 4:1025-1031 (1998)). For example, the RAGE polypeptide may comprise human sRAGE, or a fragment thereof, with Glycine as the first residue rather than a Methionine (See e.g., Neeper et al., (1992)). Or, a RAGE polypeptide may comprise human sRAGE with the signal sequence removed (See e.g., SEQ ID NO: 5 or SEQ ID NO: 6, or SEQ ID NO: 45 in FIG. 1) or a portion of that amino acid sequence.

In other embodiments, the RAGE protein may comprise a RAGE V domain (see e.g., SEQ ID NO: 7, SEQ ID NO: 8, or SEQ ID NO: 46 in FIG. 1) (Neeper et al., (1992); Schmidt et al. (1997)). Or, a sequence at least 90% identical to the RAGE V domain or a fragment thereof may be used.

Or, the RAGE protein may comprise a fragment of the RAGE V domain (e.g., SEQ ID NO: 9, SEQ ID NO: 10 or SEQ ID NO: 47 in FIG. 1). In one embodiment the RAGE protein may comprise a ligand binding site. In an embodiment, the ligand binding site may comprise SEQ ID NO: 9, or a sequence at least 90% identical thereto, or SEQ ID NO: 10, or a sequence at least 90% identical thereto, or SEQ ID NO: 47, or a sequence at least 90% identical thereto. In yet another embodiment, the RAGE fragment is a synthetic peptide.

In another embodiment, the ligand binding site may comprise amino acids 23-53 of SEQ ID NO: 1 (FIG. 1). In another embodiment, the ligand binding site may comprise amino acids 24-52 of SEQ. ID NO: 1. In another embodiment, the ligand binding site may comprise amino acids 31-52 of SEQ ID NO: 1. In another embodiment, the ligand binding site may comprise amino acids 31-116 of SEQ ID NO: 1. In another embodiment, the ligand binding site may comprise amino acids 19-52 of SEQ ID NO: 1. For example, the ligand binding site may comprise, a RAGE V domain or a portion thereof such as the RAGE ligand binding domain (e.g., amino acids 1-118, 23-118, 24-118, 31-118, 1-116, 23-116, 24-116, 31-116, 1-54, 23-54, 24-54, 31-54, 1-53, 23-53, 24-53, or 31-53 of SEQ ID NO: 1, or fragments thereof). Or fragments of the polypeptides that functionally bind a RAGE ligand may be used. Or, a sequence at least 70%, 75%, 80%, 85%, 90%, 95%, 97%, 98% or 99% identical to the RAGE V domain or a fragment thereof (e.g., as described above) may be used. Further, as is known in the art, in embodiments where the N-terminus of the fusion protein is glutamine, as for example upon removal of the signal sequence comprising residues 1-23 of SEQ ID NO: 1 (e.g., Q24 for a polypeptide comprise amino acids 24-118 or SEQ ID NO: 1), the glutamine may cyclize to form pyroglutamic acid (pE).

Thus, the RAGE polypeptide used in the RAGE fusion proteins of the present invention may comprise a fragment of full length RAGE. As is known in the art, RAGE comprises three immunoglobulin-like polypeptide domains, the V domain, and the C1 and C2 domains each linked to each other by an interdomain linker. Full-length RAGE also includes a transmembrane polypeptide and a cytoplasmic tail downstream (C-terminal) of the C2 domain, and linked to the C2 domain.

In an embodiment, the RAGE polypeptide does not include any signal sequence residues. The signal sequence of RAGE may comprise either residues 1-22 or residues 1-23 of full length RAGE. Further, as is known in the art, in embodiments where the N-terminus of the fusion protein is glutamine, (e.g., the signal sequence comprises residues 1-23), the N-terminal glutamine (Q24) may cyclize to form pyroglutamic acid (pE). Example constructs of such molecules are polypeptides having the amino acid sequences as set forth in SEQ ID NOs: 45, 46, 47, 48, 49, 50, and 51 (FIG. 1), as well as RAGE fusion proteins having the amino acid sequences as set forth in SEQ ID NOs: 56 and 57 (FIG. 4).

As recognized in the art, the $C_H3$ region of the RAGE fusion proteins of the present invention may have the C-terminal amino acid cleaved off through a post-translational modification when expressed in certain recombinant systems. (See e.g., Li, et al., *BioProcessing J.*, 4:23-30 (2005)). In an embodiment, the C-terminal amino acid cleaved off is lysine (K). Thus, in alternate embodiments, the RAGE fusion protein of the present invention may comprise a polypeptide having the amino acid sequence as set forth in SEQ ID NOs: 32-37, 56 and 57 without the C-terminal lysine (K).

Thus in various embodiments, the RAGE polypeptide may comprise amino acids 23-116 of human RAGE (SEQ ID NO: 7) or a sequence at least 90% identical thereto, or amino acids 24-116 of human RAGE (SEQ ID NO: 8) or a sequence at least 90% identical thereto, or amino acids 24-116 of human RAGE where Q24 cyclizes to form pE (SEQ ID NO: 46) or a sequence at least 90% identical thereto, corresponding to the V domain of RAGE. Or, the RAGE polypeptide may comprise amino acids 124-221 of human RAGE (SEQ ID NO: 11) or a sequence at least 90% identical thereto, corresponding to the C1 domain of RAGE. In another embodiment, the RAGE polypeptide may comprise amino acids 227-317 of human RAGE (SEQ ID NO: 12) or a sequence at least 90% identical thereto, corresponding to the C2 domain of RAGE. Or, the RAGE polypeptide may comprise amino acids 23-123 of human RAGE (SEQ ID NO: 13) or a sequence at least 90% identical thereto, or amino acids 24-123 of human RAGE (SEQ ID NO: 14) or a sequence at least 90% identical thereto, corresponding to the V domain of RAGE and a downstream interdomain linker. Or, the RAGE polypeptide may comprise amino acids 24-123 of human RAGE where Q24 cyclizes to form pE (SEQ ID NO: 48) or a sequence at least 90% identical thereto. Or, the RAGE polypeptide may comprise amino acids 23-226 of human RAGE (SEQ ID NO: 17) or a sequence at least 90% identical thereto, or amino acids 24-226 of human RAGE (SEQ ID NO: 18) or a sequence at least 90% identical thereto, corresponding to the V-domain, the C1 domain and the interdomain linker linking these two domains. Or, the RAGE polypeptide may comprise amino acids 24-226 of human RAGE where Q24 cyclizes to form pE (SEQ ID NO: 50), or a sequence at least 90% identical thereto. Or, the RAGE polypeptide may comprise amino acids 23-339 of human RAGE (SEQ ID NO: 5) or a sequence at least 90% identical thereto, or 24-339 of human RAGE (SEQ ID NO: 6) or a sequence at least 90% identical thereto, corresponding to sRAGE (i.e., encoding the V, C1, and C2 domains and interdomain linkers). Or, the RAGE polypeptide may comprise amino acids 24-339 of human RAGE where Q24 cyclizes to form pE (SEQ ID NO: 45) or a sequence at least 90% identical thereto. Or, fragments of each of these sequences may be used. See FIG. 1 for the amino acid sequences of these polypeptides.

The RAGE fusion protein may include several types of peptides that are not derived from RAGE or a fragment thereof. The second polypeptide of the RAGE fusion protein may comprise a polypeptide derived from an immunoglobulin. In one embodiment, the immunoglobulin polypeptide may comprise an immunoglobulin heavy chain or a portion (i.e., fragment) thereof. For example, the heavy chain fragment may comprise a polypeptide derived from the Fc fragment of an immunoglobulin, wherein the Fc fragment comprises the heavy chain hinge polypeptide, and $C_H2$ and $C_H3$ domains of the immunoglobulin heavy chain as a monomer. The heavy chain (or portion thereof) may be derived from any one of the known heavy chain isotypes: IgG (γ), IgM (μ), IgD (δ), IgE (ε), or IgA (α). In addition, the heavy chain (or portion thereof) may be derived from any one of the known heavy chain subtypes: IgG1 (γ1), IgG2 (γ2), IgG3 (γ3), IgG4 (γ4), IgA1 (α1), IgA2 (α2), or mutations of these isotypes or subtypes that alter the biological activity. The second polypeptide may comprise the $C_H2$ and $C_H3$ domains of a human IgG1 or portions of either, or both, of these domains. As an example embodiment, the polypeptide comprising the $C_H2$ and $C_H3$ domains of a human IgG1 or a portion thereof may comprise SEQ ID NO: 40 (FIG. 1) or a portion thereof. In one embodiment, the polypeptide comprising the $C_H2$ and $C_H3$ domains of a human IgG1, or a portion thereof, may comprise SEQ ID NO: 38 or a fragment thereof. The immunoglobulin peptide may be encoded by the nucleic acid sequence of SEQ ID NO: 39 or SEQ ID NO: 41 (FIG. 1). The immunoglobulin sequence in SEQ ID NO: 38 or SEQ ID NO: 40 may also be encoded by SEQ ID NO: 52 or SEQ ID NO: 53 (FIG. 1), where silent base changes for the codons that encode for proline (CCG to CCC) and glycine (GGT to GGG) at the C-terminus of the sequence remove a cryptic RNA splice site near the terminal codon (i.e., nucleotides 622-627 of SEQ ID NO: 39 are modified to generate SEQ ID NO: 52 or nucleotides 652-657 of SEQ ID NO: 41 are modified to generate SEQ ID NO: 53).

The hinge region of the Fc portion of the immunoglobulin chain may be proinflammatory in vivo. Thus, in one embodiment, the RAGE fusion protein of the present invention comprises an interdomain linker derived from RAGE rather than an interdomain hinge polypeptide derived from an immunoglobulin.

Thus in certain embodiments, the RAGE fusion protein may comprise a RAGE polypeptide directly linked to a polypeptide comprising a $C_H2$ domain of an immunoglobulin, or a fragment or portion of the $C_H2$ domain of an immunoglobulin. In one embodiment, the $C_H2$ domain, or a fragment thereof comprises SEQ ID NO: 42 (FIG. 1). In an embodiment, the fragment of SEQ ID NO: 42 comprises SEQ ID NO: 42 with the first ten amino acids comprising at least a portion of the Fc hinge region removed. In one embodiment, the RAGE polypeptide may comprise a ligand binding site. The RAGE ligand binding site may comprise the V domain of RAGE, or a portion thereof. In an embodiment, the RAGE ligand binding site comprises SEQ ID NO: 9 or a sequence at least 90% identical thereto, or SEQ ID NO: 10 or a sequence at least 90% identical thereto, or SEQ ID NO: 47, or a sequence at least 90% identical thereto.

The RAGE polypeptide used in the RAGE fusion proteins of the present invention may comprise a RAGE immunoglobulin domain. Additionally or alternatively, the fragment of RAGE may comprise an interdomain linker. Or, the RAGE polypeptide may comprise a RAGE immunoglobulin domain linked to an upstream (i.e., closer to the N-terminus) or downstream (i.e., closer to the C-terminus) interdomain linker. In yet another embodiment, the RAGE polypeptide may comprise two (or more) RAGE immunoglobulin domains each linked to each other by an interdomain linker. The RAGE polypeptide may further comprise multiple RAGE immunoglobulin domains linked to each other by one or more interdomain linkers and having a terminal interdomain linker attached to the N-terminal RAGE immunoglobulin domain and/or the C-terminal immunoglobulin domain. Additional combinations of RAGE immunoglobulin domains and interdomain linkers are within the scope of the present invention.

In one embodiment, the RAGE polypeptide comprises a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a fragment thereof. The polypeptide comprising a $C_H2$ domain of an immunoglobulin may comprise the $C_H2$ and $C_H3$ domains of a human IgG1 or a portion of either, or both, of these domains. As example embodiments, the polypeptide comprising the $C_H2$ and $C_H3$ domains, or a portion thereof, of a human IgG1 may comprise SEQ ID NO: 40 or a portion thereof. In one embodiment, the polypeptide comprising the $C_H2$ and $C_H3$ domains of a human IgG1, or a portion thereof, may comprise SEQ ID NO: 38 or a fragment thereof. Or, the human IgG1 may comprise SEQ ID NO: 38 or SEQ ID NO: 40 with the terminal lysine (K) removed.

As described above, the RAGE fusion protein of the present invention may comprise a single or multiple domains from RAGE. Also, the RAGE polypeptide comprising an interdomain linker linked to a RAGE polypeptide domain may comprise a fragment of full-length RAGE protein. For example, the RAGE polypeptide may comprise amino acids 23-136 of human RAGE (SEQ ID NO: 15) or a sequence at least 90% identical thereto or amino acids 24-136 of human RAGE (SEQ ID NO: 16) or a sequence at least 90% identical thereto, or amino acids 24-136 of human RAGE where Q24 cyclizes to form pE (SEQ ID NO: 49), or a sequence at least 90% identical thereto, corresponding to the V domain of RAGE and a downstream interdomain linker. Or, the RAGE polypeptide may comprise amino acids 23-251 of human RAGE (SEQ ID NO: 19) or a sequence at least 90% identical thereto, or amino acids 24-251 of human RAGE (SEQ ID NO: 20) or a sequence at least 90% identical thereto, or amino acids 24-251 of human RAGE where Q24 cyclizes to form pE (SEQ ID NO: 51), or a sequence at least 90% identical thereto, corresponding to the V-domain, the C1 domain, the interdomain linker linking these two domains, and a second interdomain linker downstream of C1.

For example, in one embodiment, the RAGE fusion protein may comprise two immunoglobulin domains derived from RAGE protein and two immunoglobulin domains derived from a human Fc polypeptide. The RAGE fusion protein may comprise a first RAGE immunoglobulin domain and a first RAGE interdomain linker linked to a second RAGE immunoglobulin domain and a second RAGE interdomain linker, such that the N-terminal amino acid of the first interdomain linker is linked to the C-terminal amino acid of the first RAGE immunoglobulin domain, the N-terminal amino acid of the second RAGE immunoglobulin domain is linked to C-terminal amino acid of the first interdomain linker, the N-terminal amino acid of the second interdomain linker is linked to C-terminal amino acid of the second RAGE immunoglobulin domain, and the C-terminal amino acid of the RAGE second interdomain linker is directly linked to the N-terminal amino acid of the $C_H2$ immunoglobulin domain. In alternate embodiments, the four domain RAGE fusion protein is encoded by SEQ ID NO: 30 or SEQ ID NO: 54 (FIG. 2). In one embodiment, a four domain RAGE fusion protein may comprise SEQ ID NO: 32 (FIG. 4). In alternate embodiments, a four domain RAGE fusion protein comprises SEQ ID NO: 33, SEQ ID NO: 34, or SEQ ID NO: 56 (FIG. 4).

Alternatively, a three domain RAGE fusion protein may comprise one immunoglobulin domain derived from RAGE and two immunoglobulin domains derived from a human Fc polypeptide. For example, the RAGE fusion protein may comprise a single RAGE immunoglobulin domain linked via a RAGE interdomain linker to the N-terminal amino acid of a $C_H2$ immunoglobulin domain or a portion of a $C_H2$ immunoglobulin domain. In alternate embodiments, the three domain RAGE fusion protein is encoded by SEQ ID NO: 31 or SEQ ID NO: 55 (FIG. 3). In one embodiment, a three domain RAGE fusion protein may comprise SEQ ID NO: 35 (FIG. 5). In alternate embodiments, a three domain RAGE fusion protein may comprise SEQ ID NO: 36, SEQ ID NO: 37, or SEQ ID NO: 57 (FIG. 5).

A RAGE interdomain linker fragment may comprise a peptide sequence that is naturally downstream of, and thus, linked to, a RAGE immunoglobulin domain. For example, for the RAGE V domain, the interdomain linker may comprise amino acid sequences that are naturally downstream from the V domain. In an embodiment, the linker may comprise SEQ ID NO: 21, corresponding to amino acids 117-123 of full-length RAGE. Or, the linker may comprise a peptide having additional portions of the natural RAGE sequence. For example, an interdomain linker comprising several amino acids (e.g., 1-3, 1-5, or 1-10, or 1-15 amino acids) upstream and downstream of SEQ ID NO: 21 may be used. Thus, in one embodiment, the interdomain linker comprises SEQ ID NO: 23 comprising amino acids 117-136 of full-length RAGE. Or, fragments of SEQ ID NO: 21 deleting, for example, 1, 2, or 3, amino acids from either end of the linker may be used. In alternate embodiments, the linker may comprise a peptide that is at least 70%, 75%, 80%, 85%, 90%, 95%, 96%, 97%, 98%, or 99% identical to SEQ ID NO: 21 or SEQ ID NO: 23.

For the RAGE C1 domain, the linker may comprise peptide sequence that is naturally downstream of the C1 domain. In an embodiment, the linker may comprise SEQ ID NO: 22, corresponding to amino acids 222-251 of full-length RAGE. Or, the linker may comprise a peptide having additional portions of the natural RAGE sequence. For example, a linker comprising several (1-3, 1-5, or 1-10, or 1-15 amino acids) amino acids upstream and downstream of SEQ ID NO: 22 may be used. Or, fragments of SEQ ID NO: 22 may be used, deleting for example, 1-3, 1-5, or 1-10, or 1-15 amino acids from either end of the linker. For example, in one embodiment, a RAGE interdomain linker may comprise SEQ ID NO: 24, corresponding to amino acids 222-226. In alternate embodiments, the linker may comprise a peptide that is at least 70%, 75%, 80%, 85%, 90%, 95%, 96%, 97%, 98%, or 99% identical to SEQ ID NO: 22 or SEQ ID NO: 24.

Or an interdomain linker may comprise SEQ ID NO: 44, corresponding to RAGE amino acids 318-342. In alternate embodiments, the linker may comprise a peptide that is at least 70%, 75%, 80%, 85%, 90%, 95%, 96%, 97%, 98%, or 99% identical to SEQ ID NO: 44.

Furthermore, one of skill will recognize that individual substitutions, deletions or additions which alter, add or delete a single amino acid or a small percentage of amino acids (typically less than about 5%, more typically less than about 1%) in an encoded sequence are conservatively modified variations where the alterations result in the substitution of an amino acid with a chemically similar amino acid. Conservative substitution tables providing functionally similar amino acids are well known in the art. The following example groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid. A "conservative substitution" also refers to utilizing a substituting amino acid which is identical to the amino acid being substituted except that a functional group in the side chain is protected with a suitable protecting group.

As is known in the art, amino acids may become chemically modified from their natural structure, either by enzymatic or non-enzymatic reaction mechanisms. For example, in one embodiment, an N-terminal glutamic acid or glutamine may cyclize, with loss of water, to form pyroglutamic acid (pyroE or pE) (Chelius et al., *Anal. Chem.*, 78: 2370-2376 (2006) and Burstein et al., *Proc. National Acad. Sci.*, 73:2604-2608 (1976)). Alternatively, a fusion protein having an N-terminal pyroglutamic acid could potentially be accessed through a nucleic acid sequence encoding for glutamic acid at the position in the protein that via post-translational processing becomes the N-terminus (e.g., where residue 24 of SEQ ID NO: 1 is glutamate rather than a glutamine).

Methods of Producing RAGE Fusion Proteins

The present invention also comprises a method to make a RAGE fusion protein. Thus, in one embodiment, the present invention comprises a method of making a RAGE fusion protein comprising the step of covalently linking a RAGE polypeptide linked to a second, non-RAGE polypeptide wherein the RAGE polypeptide comprises a RAGE ligand binding site. For example, the linked RAGE polypeptide and the second, non-RAGE polypeptide may be encoded by a recombinant DNA construct. The method may further comprise the step of incorporating the DNA construct into an expression vector. Also, the method may comprise the step of inserting the expression vector into a host cell.

For example, embodiments of the present invention provide RAGE fusion proteins comprising a RAGE polypeptide linked to a second, non-RAGE polypeptide. In one embodiment, the RAGE fusion protein may comprise a RAGE ligand binding site. In an embodiment, the ligand binding site comprises the most N-terminal domain of the RAGE fusion protein. The RAGE ligand binding site may comprise the V domain of RAGE, or a portion thereof. In an embodiment, the RAGE ligand binding site comprises SEQ ID NO: 9 or a sequence at least 90% identical thereto, or SEQ ID NO: 10 or a sequence at least 90% identical thereto, or SEQ ID NO: 47, or a sequence at least 90% identical thereto.

In an embodiment, the RAGE polypeptide may be linked to a polypeptide comprising an immunoglobulin domain or a portion (e.g., a fragment thereof) of an immunoglobulin domain. In one embodiment, the polypeptide comprising an immunoglobulin domain comprises at least a portion of at least one of the $C_H2$ or the $C_H3$ domains of a human IgG.

Thus, embodiments of the present invention may comprise isolated DNA molecules that encode the RAGE fusion proteins of the present invention. In certain embodiments, the DNA molecules encode for a RAGE fusion protein comprising an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine. Thus, in certain embodiments, the present invention may comprise a DNA molecule having the sequence as set forth in SEQ ID NO: 54 or SEQ ID NO: 55, or a sequence at least 90% identical thereto.

The RAGE fusion protein may be engineered by recombinant DNA techniques. For example, in one embodiment, the present invention may comprise an isolated nucleic acid sequence comprising, complementary to, or having significant identity with, a polynucleotide sequence that encodes for a RAGE polypeptide linked to a second, non-RAGE polypeptide. In an embodiment, the RAGE polypeptide may comprise a RAGE ligand binding site.

The RAGE protein or polypeptide may comprise full-length human RAGE (e.g., SEQ ID NO: 1), or a fragment of human RAGE. In an embodiment, the RAGE polypeptide does not include any signal sequence residues. The signal sequence of RAGE may comprise either residues 1-22 or residues 1-23 of full length RAGE (SEQ ID NO: 1). In alternate embodiments, the RAGE polypeptide may comprise a sequence that is at least 70%, 75%, 80%, 85%, 90%, 95%, 96%, 97%, 98%, or 99% identical to human RAGE, or a fragment thereof. For example, in one embodiment, the RAGE polypeptide may comprise human RAGE, or a fragment thereof, with Glycine as the first residue rather than a Methionine (see e.g., Neeper et al., (1992)). Or, the human RAGE may comprise full-length RAGE with the signal sequence removed (e.g., SEQ ID NO: 2 or SEQ ID NO: 3) (FIGS. 1A and 1B) or a portion of that amino acid sequence. The RAGE fusion proteins of the present invention may also comprise sRAGE (e.g., SEQ ID NO: 4), a polypeptide at least 90% identical to sRAGE, or a fragment of sRAGE. For example, the RAGE polypeptide may comprise human sRAGE, or a fragment thereof, with Glycine as the first residue rather than a Methionine (see e.g., Neeper et al., (1992)). Or, the human RAGE may comprise sRAGE with the signal sequence removed (See e.g., SEQ ID NO: 5, SEQ ID NO: 6 or SEQ ID NO: 45 in FIG. 1) or a portion of that amino acid sequence. In other embodiments, the RAGE protein may comprise a V domain (See e.g., SEQ ID NO: 7, SEQ ID NO: 8 or SEQ ID NO: 46 in FIG. 1). Or, a sequence at least 90% identical to the V domain or a fragment thereof may be used. Or, the RAGE protein may comprise a fragment of RAGE comprising a portion of the V domain (See e.g., SEQ ID NO: 9, SEQ ID NO: 10 or SEQ ID NO: 47 in FIG. 1). In an embodiment, the ligand binding site may comprise SEQ ID NO: 9, or a sequence at least 90% identical thereto, or SEQ ID NO: 10, or a sequence at least 90% identical thereto, or SEQ ID NO: 47, or a sequence at least 90% identical thereto. In yet another embodiment, the RAGE fragment is a synthetic peptide.

In an embodiment, the nucleic acid sequence comprises SEQ ID NO: 25 to encode amino acids 1-118 of human RAGE or a fragment thereof. For example, a sequence comprising nucleotides 1-348 of SEQ ID NO: 25 may be used to encode amino acids 1-116 of human RAGE. Or, the nucleic acid may comprise SEQ ID NO: 26 to encode amino acids 1-123 of human RAGE. Or, the nucleic acid may comprise SEQ ID NO: 27 to encode amino acids 1-136 of human RAGE. Or, the nucleic acid may comprise SEQ ID NO: 28 to encode amino acids 1-230 of human RAGE. Or, the nucleic acid may comprise SEQ ID NO: 29 to encode amino acids 1-251 of human RAGE. Or fragments of these nucleic acid sequences may be used to encode RAGE polypeptide fragments.

The RAGE fusion protein may include several types of peptides that are not derived from RAGE or a fragment thereof. The second polypeptide of the RAGE fusion protein may comprise a polypeptide derived from an immunoglobulin. The heavy chain (or portion thereof) may be derived from any one of the known heavy chain isotypes: IgG ($\gamma$), IgM ($\mu$), IgD ($\delta$), IgE ($\epsilon$), or IgA ($\alpha$). In addition, the heavy chain (or portion thereof) may be derived from any one of the known heavy chain subtypes: IgG1 ($\gamma$1), IgG2 ($\gamma$2), IgG3 ($\gamma$3), IgG4 ($\gamma$4), IgA1 ($\alpha$1), IgA2 ($\alpha$2), or mutations of these isotypes or subtypes that alter the biological activity. The second polypeptide may comprise the $C_H2$ and $C_H3$ domains of a human IgG1 or a portion of either, or both, of these domains. As an example embodiments, the polypeptide comprising the $C_H2$ and $C_H3$ domains of a human IgG1 or a portion thereof may comprise SEQ ID NO: 38 or SEQ ID NO: 40. In one embodiment, the polypeptide comprising the $C_H2$ and $C_H3$ domains of a human IgG1, or a portion thereof, may comprise SEQ ID NO: 38 or a fragment thereof. The immunoglobulin peptide may be encoded by the nucleic acid sequence of SEQ ID NO: 39 or SEQ ID NO: 41. In alternate embodiments, the immunoglobulin sequence in SEQ ID NO: 38 or SEQ ID NO: 40 may also be encoded by SEQ ID NO: 52 or SEQ ID NO: 53, respectively.

The hinge region of the Fc portion of the immunoglobulin chain may be proinflammatory in vivo. Thus, the RAGE fusion protein of the present invention may comprise an interdomain linker derived from RAGE rather than an interdomain hinge polypeptide derived from an immunoglobulin.

Thus, in one embodiment, the present invention comprises a method of making a RAGE fusion protein comprising the step of covalently linking a RAGE polypeptide to a polypeptide comprising a $C_H2$ domain of an immunoglobulin or a portion of a $C_H2$ domain of an immunoglobulin. In one embodiment, the RAGE fusion protein may comprise a RAGE ligand binding site. The RAGE ligand binding site may comprise the V domain of RAGE, or a portion thereof. In an embodiment, the RAGE ligand binding site comprises SEQ ID NO: 9 or a sequence at least 90% identical thereto, or SEQ ID NO: 10 or a sequence at least 90% identical thereto, or SEQ ID NO: 47, or a sequence at least 90% identical thereto.

In one embodiment, the RAGE fusion protein may be encoded by a recombinant DNA construct. The method may comprise the step of incorporating the DNA construct into an expression vector. Also, the method may comprise transfecting the expression vector into a host cell. Thus, embodiments of the present invention also comprise expression vectors encoding DNA molecules that encode the RAGE fusion proteins of the present invention. In certain embodiments, the DNA molecules encode for a RAGE fusion protein comprising an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

Yet other embodiments of the present invention also comprise cells transfected with an expression vector encoding DNA molecules that encode the RAGE fusion proteins of the present invention. In certain embodiments, the DNA molecules encode for a RAGE fusion protein comprising an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

For example, in one embodiment, the present invention comprises a nucleic acid encoding a RAGE polypeptide directly linked to a polypeptide comprising a $C_H2$ domain of an immunoglobulin, or a fragment thereof. In one embodiment, the $C_H2$ domain, or a fragment thereof, comprises SEQ ID NO: 42. In an embodiment, the fragment of SEQ ID NO: 42 comprises SEQ ID NO: 42 with the first ten amino acids removed. The second polypeptide may comprise the $C_H2$ and $C_H3$ domains of a human IgG1. As example embodiments, the polypeptide comprising the $C_H2$ and $C_H3$ domains of a human IgG1 may comprise SEQ ID NO: 38 or SEQ ID NO: 40. In one embodiment, the polypeptide comprising the $C_H2$ and $C_H3$ domains of a human IgG1, or a portion thereof, may comprise SEQ ID NO: 38 or a fragment thereof. The immunoglobulin peptide may be encoded by the nucleic acid sequence of SEQ ID NO: 39 or SEQ ID NO: 41. The immunoglobulin sequence in SEQ ID NO: 38 or SEQ ID NO: 40 may also be encoded by SEQ ID NO: 52 or SEQ ID NO: 53, where silent base changes for the codons that encode for proline (CCG to CCC) and glycine (GGT to GGG) at the C-terminus of the sequence remove a cryptic RNA splice site near the terminal codon (i.e., nucleotides 622-627 of SEQ ID NO: 39 are modified to generate SEQ ID NO: 52 or nucleotides 652-657 of SEQ ID NO: 41 are modified to generate SEQ ID NO: 53).

In one embodiment, the RAGE polypeptide may comprise a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a fragment thereof. The polypeptide comprising a $C_H2$ domain of an immunoglobulin, or a portion thereof, may comprise a polypeptide comprising the $C_H2$ and $C_H3$ domains of a human IgG1 or a portion of both, or either, of these domains. As example embodiments, the polypeptide comprising the $C_H2$ and $C_H3$ domains of a human IgG1, or a portion thereof, may comprise SEQ ID NO: 38 or SEQ ID NO: 40. In one embodiment, the polypeptide comprising the $C_H2$ and $C_H3$ domains of a human IgG1, or a portion thereof, may comprise SEQ ID NO: 38 or a fragment thereof. In certain embodiments, the polypeptide comprising the $C_H2$ and $C_H3$ domains of a human IgG1, or a portion thereof, may comprise SEQ ID NO: 38 or SEQ ID NO: 40 with the C-terminal lysine (K) removed.

The RAGE fusion protein of the present invention may comprise a single or multiple domains from RAGE. Also, the RAGE polypeptide comprising an interdomain linker linked to a RAGE immunoglobulin domain may comprise a fragment of a full-length RAGE protein. For example, in one embodiment, the RAGE fusion protein may comprise two immunoglobulin domains derived from RAGE protein and two immunoglobulin domains derived from a human Fc polypeptide. The RAGE fusion protein may comprise a first RAGE immunoglobulin domain and a first interdomain linker linked to a second RAGE immunoglobulin domain and a second RAGE interdomain linker, such that the N-terminal amino acid of the first interdomain linker is linked to the C-terminal amino acid of the first RAGE immunoglobulin domain, the N-terminal amino acid of the second RAGE immunoglobulin domain is linked to C-terminal amino acid of the first interdomain linker, the N-terminal amino acid of the second interdomain linker is linked to C-terminal amino acid of the RAGE second immunoglobulin domain, and the C-terminal amino acid of the RAGE second interdomain linker is directly linked to the N-terminal amino acid of the polypeptide comprising a $C_H2$ immunoglobulin domain or fragment thereof. For example, the RAGE polypeptide may comprise amino acids 23-251 of human RAGE (SEQ ID NO: 19) or a sequence at least 90% identical thereto, or amino acids 24-251 of human RAGE (SEQ ID NO: 20) or a sequence at least 90% identical thereto, or amino acids 24-251 of human RAGE where Q24 cyclizes to form pE (SEQ ID NO: 51) or a sequence at least 90% identical thereto, corresponding to the V-domain, the C1 domain, the interdomain linker linking these two domains, and a second interdomain linker downstream of C1. In one embodiment, a nucleic acid construct comprising SEQ ID NO: 30 or a fragment thereof may encode for a four domain RAGE fusion protein (FIG. 2A). In another embodiment, nucleic acid construct comprising SEQ ID NO: 54 (FIG. 2B) may encode for a four domain RAGE fusion protein, where silent base changes for the codons that encode for proline (CCG to CCC) and glycine (GGT to GGG) at the C-terminus of the sequence are entered to remove a cryptic RNA splice site near the terminal codon (i.e., at nucleotides 1375-1380 of SEQ ID NO: 30 are modified to generate SEQ ID NO: 54).

Alternatively, a three domain RAGE fusion protein may comprise one immunoglobulin domain derived from RAGE and two immunoglobulin domains derived from a human Fc polypeptide. For example, the RAGE fusion protein may comprise a single RAGE immunoglobulin domain linked via a RAGE interdomain linker to the N-terminal amino acid of the polypeptide comprising a $C_H2$ immunoglobulin domain or a fragment thereof. For example, the RAGE polypeptide may comprise amino acids 23-136 of human RAGE (SEQ ID NO: 15) or a sequence at least 90% identical thereto or amino acids 24-136 of human RAGE (SEQ ID NO: 16) or a sequence at least 90% identical thereto, or amino acids 24-136 of human RAGE where Q24 cyclizes to form pE (SEQ ID NO: 49) or a sequence at least 90% identical thereto, corresponding to the V domain of RAGE and a downstream interdomain linker (FIG. 1). In one embodiment, a nucleic acid construct comprising SEQ ID NO: 31 or a fragment thereof may encode for a three domain RAGE fusion protein (FIG. 3A). In another embodiment, nucleic acid construct comprising SEQ ID NO: 55 may encode for a three domain RAGE fusion protein, where silent base changes for the codons that encode for proline (CCG to CCC) and glycine (GGT to GGG) at the C-terminus of the sequence remove a cryptic RNA splice site near the terminal codon (i.e., nucleotides 1030-1035 of SEQ ID NO: 31 are modified to generate SEQ ID NO: 55) (FIG. 3B).

A RAGE interdomain linker fragment may comprise a peptide sequence that is naturally downstream of, and thus, linked to, a RAGE immunoglobulin domain. For example, for the RAGE V domain, the interdomain linker may comprise amino acid sequences that are naturally downstream from the V domain. In an embodiment, the linker may comprise SEQ ID NO: 21, corresponding to amino acids 117-123 of full-length RAGE. Or, the linker may comprise a peptide having additional portions of the natural RAGE sequence. For example, an interdomain linker comprising several amino acids (e.g., 1-3, 1-5, or 1-10, or 1-15 amino acids) upstream and downstream of SEQ ID NO: 21 may be used. Thus, in one embodiment, the interdomain linker comprises SEQ ID NO: 23 comprising amino acids 117-136 of full-length RAGE. Or, fragments of SEQ ID NO: 21 deleting, for example, 1, 2, or 3, amino acids from either end of the linker may be used. In alternate embodiments, the linker may comprise a sequence that is at least 70%, 75%, 80%, 85%, 90%, 95%, 96%, 97%, 98%, or 99% identical to SEQ ID NO: 21 or SEQ ID NO: 23.

For the RAGE C1 domain, the linker may comprise a peptide sequence that is naturally downstream of the C1 domain. In an embodiment, the linker may comprise SEQ ID NO: 22, corresponding to amino acids 222-251 of full-length RAGE. Or, the linker may comprise a peptide having additional portions of the natural RAGE sequence. For example, a linker comprising several (1-3, 1-5, or 1-10, or 1-15 amino acids) amino acids upstream and downstream of SEQ ID NO: 22 may be used. Or, fragments of SEQ ID NO: 22 may be used, deleting for example, 1-3, 1-5, or 1-10, or 1-15 amino acids from either end of the linker. For example, in one embodiment, a RAGE interdomain linker may comprise SEQ ID NO: 24, corresponding to amino acids 222-226. In alternate embodiments, the linker may comprise a sequence that is at least 70%, 75%, 80%, 85%, 90%, 95%, 96%, 97%, 98%, or 99% identical to SEQ ID NO: 22 or SEQ ID NO: 24.

Or an interdomain linker may comprise SEQ ID NO: 44, corresponding to RAGE amino acids 318-342. In alternate embodiments, the linker may comprise a sequence that is at least 70%, 75%, 80%, 85%, 90%, 95%, 96%, 97%, 98%, or 99% identical to SEQ ID NO: 44.

The method may further comprise the step of incorporating the DNA construct into an expression vector. Thus, in a embodiment, the present invention comprises an expression vector that encodes for a RAGE fusion protein comprising a RAGE polypeptide directly linked to a polypeptide comprising a $C_H2$ domain of an immunoglobulin or a portion of a $C_H2$ domain of an immunoglobulin. In an embodiment, the RAGE polypeptide comprise constructs, such as those described herein, having a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a portion thereof. For example, the expression vector used to transfect the cells may comprise the nucleic acid sequence SEQ ID NO: 30, or a fragment thereof, SEQ ID NO: 54, or a fragment thereof, SEQ ID NO: 31, or a fragment thereof, or SEQ ID NO: 55, or a fragment thereof.

The method may further comprise the step of transfecting a cell with the expression vector of the present invention. Thus, in an embodiment, the present invention comprises a cell transfected with the expression vector that expressed the RAGE fusion protein of the present invention, such that the cell expresses a RAGE fusion protein comprising a RAGE polypeptide directly linked to a polypeptide comprising a $C_H2$ domain of an immunoglobulin or a portion of a $C_H2$ domain of an immunoglobulin. In an embodiment, the RAGE polypeptide comprise constructs, such as those described herein, having a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a portion thereof. For example, the expression vector may comprise the nucleic acid sequence SEQ ID NO: 30, or a fragment thereof, SEQ ID NO: 54, or a fragment thereof, SEQ ID NO: 31, or a fragment thereof, or SEQ ID NO: 55, or a fragment thereof.

For example, plasmids may be constructed to express RAGE-IgG fusion proteins by fusing different lengths of a 5' cDNA sequence of human RAGE with a 3' cDNA sequence of human IgG1 Fc (γ1). The expression cassette sequences may be inserted into an expression vector such as pcDNA3.1 expression vector (Invitrogen, CA) using standard recombinant techniques.

Also, the method may comprise transfecting the expression vector into a host cell. RAGE fusion proteins may be expressed in mammalian expression systems, including systems in which the expression constructs are introduced into the mammalian cells using virus such as retrovirus or adenovirus. Mammalian cell lines available as hosts for expression are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, and a number of other cell lines. Cell lines may be selected through determining which cell lines have high expression levels of a RAGE fusion protein. Other cell lines that may be used are insect cell lines, such as Sf9 cells. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*. When recombinant expression vectors encoding RAGE fusion protein genes are introduced into mammalian host cells, the RAGE fusion proteins are produced by culturing the host cells for a period of time sufficient to allow for expression of the RAGE fusion protein in the host cells or secretion of the RAGE fusion protein into the culture medium in which the host cells are grown. RAGE fusion proteins may be recovered from the culture medium using standard protein purification methods.

Nucleic acid molecules encoding RAGE fusion proteins and expression vectors comprising these nucleic acid molecules may be used for transfection of a suitable mammalian, plant, bacterial or yeast host cell. Transformation may be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

An expression vector may also be delivered to an expression system using DNA biolistics, wherein the plasmid is precipitated onto microscopic particles, preferably gold, and the particles are propelled into a target cell or expression system. DNA biolistics techniques are well-known the art and devices, e.g., a "gene gun", are commercially available for delivery of the microparticles in to a cell (e.g., Helios Gene Gun, Bio-Rad Labs., Hercules, Calif.) and into the skin (PMED Device, PowderMed. Ltd., Oxford, UK).

Expression of RAGE fusion proteins from production cell lines may be enhanced using a number of known techniques. For example, the glutamine synthetase gene expression system (the GS system) and the plasma-encoded neomycin resistance system are common approaches for enhancing expression under certain conditions.

RAGE fusion proteins expressed by different cell lines may have different glycosylation patterns from each other. However, all RAGE fusion proteins encoded by the nucleic acid molecules provided herein, or comprising the amino acid sequences provided herein are part of the instant invention, regardless of the glycosylation of the RAGE fusion protein.

In one embodiment, a recombinant expression vector may be transfected into Chinese Hamster Ovary cells (CHO) and expression optimized. In alternate embodiments, the cells may produce 0.1 to 20 grams/liter, or 0.5 to 10 grams/liter, or about 1-2 grams/liter.

As is known in the art, such nucleic acid constructs may be modified by mutation, as for example, by PCR amplification of a nucleic acid template with primers comprising the mutation of interest. In this way, polypeptides comprising varying affinity for RAGE ligands may be designed. In one embodiment, the mutated sequences may be 90% or more identical to the starting DNA. As such, variants may include nucleotide sequences that hybridize under stringent conditions (i.e., equivalent to about 20-27° C. below the melting temperature (TM) of the DNA duplex in 1 molar salt).

The coding sequence may be expressed by transfecting the expression vector into an appropriate host. For example, the recombinant vectors may be stably transfected into Chinese Hamster Ovary (CHO) cells, and cells expressing the RAGE fusion protein selected and cloned. In an embodiment, cells expressing the recombinant construct are selected for plasmid-encoded neomycin resistance by applying antibiotic G418. Individual clones may be selected and clones expressing high levels of recombinant protein as detected by Western Blot analysis of the cell supernatant may be expanded, and the gene product purified by affinity chromatography using Protein A columns.

Sample embodiments of recombinant nucleic acids that encode the RAGE fusion proteins of the present invention are shown in FIGS. 2 and 3. For example, as described above, the RAGE fusion protein produced by the recombinant DNA construct may comprise a RAGE polypeptide linked to a second, non-RAGE polypeptide. The RAGE fusion protein may comprise two domains derived from RAGE protein and two domains derived from an immunoglobulin. Example nucleic acid constructs encoding a RAGE fusion protein, TTP-4000 (TT4), having this type of structure is shown in FIG. 2 (SEQ ID NO: 30 and SEQ ID NO: 54). As shown for SEQ ID NO: 30 and SEQ ID NO: 54, coding sequence 1-753 (highlighted in bold) encodes the RAGE N-terminal protein sequence whereas the sequence from 754-1386 encodes the IgG Fc protein sequence without the hinge.

When derived from SEQ ID NO: 30 or SEQ ID NO: 54, or a sequence at least 90% identical thereto, the RAGE fusion protein may comprise the four domain amino acid sequence of SEQ ID NO: 32, or the polypeptide with the signal sequence removed (see e.g., SEQ ID NO: 33, SEQ ID NO: 34 or SEQ ID NO: 56 in FIG. 4). In SEQ ID NO: 32, SEQ ID NO: 33, SEQ ID NO: 34 or SEQ ID NO: 56, the RAGE amino acid sequence is highlighted with bold font. The immunoglobulin sequence is the $C_H2$ and $C_H3$ immunoglobulin domains of IgG without the hinge region.

FIG. 6 shows a comparison of the polypeptide domains found in RAGE and IgG (FIG. 6A) and the domain structure of the RAGE fusion proteins TTP-3000 and TTP-4000. As shown in FIG. 6B, the first 251 amino acids of the full-length TTP-4000 RAGE fusion protein contains as the RAGE polypeptide sequence a signal sequence comprising amino acids 1-22/23, the V immunoglobulin domain (including the ligand binding site) comprising amino acids 23/24-116, an interdomain linker comprising amino acids 117 to 123, a second immunoglobulin domain (C1) comprising amino acids 124-221, and a downstream interdomain linker comprising amino acids 222-251.

In an embodiment, the RAGE fusion protein may not necessarily comprise the second RAGE immunoglobulin domain. For example, the RAGE fusion protein may comprise one immunoglobulin domain derived from RAGE and two immunoglobulin domains derived from a human Fc polypeptide. Example nucleic acid constructs encoding this type of RAGE fusion protein is shown in FIG. 3 (SEQ ID NO: 31 and SEQ ID NO: 55). As shown in SEQ ID NO: 31 and SEQ ID NO: 55, the coding sequence from nucleotides 1 to 408 (highlighted in bold) encodes the RAGE N-terminal protein sequence, whereas the sequence from 409-1041 codes the IgG1 Fc (γ1) protein sequence.

When derived from SEQ ID NO: 31 or SEQ ID NO: 55, or a sequence at least 90% identical thereto, the RAGE fusion protein may comprise the three domain amino acid sequence of SEQ ID NO: 35, or the polypeptide with the signal sequence removed (see e.g., SEQ ID NO: 36, SEQ ID NO: 37 or SEQ ID NO: 57 in FIG. 5). In SEQ ID NO: 35, SEQ ID NO: 36, SEQ ID NO: 37 or SEQ ID NO: 57 in FIG. 5, the RAGE amino acid sequence is highlighted with bold font. As shown in FIG. 6B, the first 136 amino acids of the full-length TTP-3000 RAGE fusion protein contains as the RAGE polypeptide a signal sequence comprising amino acids 1-22/23, the V immunoglobulin domain (including the ligand binding site) comprising amino acids 23/24-116, and an interdomain linker comprising amino acids 117 to 136. The sequence from 137 to 346 includes the $C_H2$ and $C_H3$ immunoglobulin domains of IgG without the hinge region.

The RAGE fusion proteins of the present invention may comprise improved in vivo stability over RAGE polypeptides not comprising a second polypeptide. The RAGE fusion protein may be further modified to increase stability, efficacy, potency and bioavailability. Thus, the RAGE fusion proteins of the present invention may be modified by post-translational processing or by chemical modification. For example, the RAGE fusion protein may be synthetically prepared to include L-, D-, or unnatural amino acids, alpha-disubstituted amino acids, or N-alkylamino acids. Additionally, proteins may be modified by acetylation, acylation, ADP-ribosylation, amidation, attachment of lipids such as phosphatidyinositol, formation of disulfide bonds, and the like. Furthermore, polyethylene glycol can be added to increase the biological stability of the RAGE fusion protein.

Binding of RAGE Antagonists to RAGE Fusion Proteins

The RAGE fusion proteins of the present invention may comprise a number of applications. For example, the RAGE fusion protein of the present invention may be used in a binding assay to identify RAGE ligands, such as RAGE agonists, antagonists, or modulators.

For example, in one embodiment, the present invention provides a method for detection of RAGE modulators comprising: (a) providing a RAGE fusion protein comprising a RAGE polypeptide linked to a second, non-RAGE polypeptide, where the RAGE polypeptide comprises a ligand binding site; (b) mixing a compound of interest and a ligand having a known binding affinity for RAGE with the RAGE fusion protein; and (c) measuring binding of the known RAGE ligand to the RAGE fusion protein in the presence of the compound of interest. In an embodiment, the ligand binding site comprises the most N-terminal domain of the RAGE fusion protein.

The RAGE fusion proteins may also provide kits for the detection of RAGE modulators. For example, in one embodiment, a kit of the present invention may comprise (a) a compound having known binding affinity to RAGE as a positive control; (b) a RAGE fusion protein comprising a RAGE polypeptide linked to a second, non-RAGE polypeptide, wherein the RAGE polypeptide comprises a RAGE ligand binding site; and (c) instructions for use. In an embodiment, the ligand binding site comprises the most N-terminal domain of the RAGE fusion protein.

For example, the RAGE fusion protein may be used in a binding assay to identify potential RAGE ligands. In one example embodiment of such a binding assay, a known RAGE ligand may coated onto a solid substrate (e.g., Maxisorb plates) at a concentration of about 5 micrograms per well, where each well contains a total volume of about 100 microliters (μL). The plates may be incubated at 4° C. overnight to allow the ligand to absorb or bind to the substrate. Alternatively, shorter incubation periods at higher temperature (e.g., room temperature) may be used. After a period of time to allow for the ligand to bind to the substrate, the assay wells may be aspirated and a blocking buffer (e.g., 1% BSA in 50 mM imidizole buffer, pH 7.2) may be added to block nonspecific binding. For example, blocking buffer may be added to the plates for 1 hour at room temperature. The plates may then be aspirated and/or washed with a wash buffer. In one embodiment, a buffer comprising 20 mM Imidizole, 150 mM NaCl, 0.05% Tween-20, 5 mM $CaCl_2$ and 5 mM $MgCl_2$, pH 7.2 may be used as a wash buffer. The RAGE fusion protein may then added at increasing dilutions to the assay wells. The RAGE fusion protein may then be allowed to incubate with the immobilized ligand in the assay well such that binding can attain equilibrium. In one embodiment, the RAGE fusion protein is allowed to incubate with the immobilized ligand for about one hour at 37° C. In alternate embodiments, longer incubation periods at lower temperatures may be used. After the RAGE fusion protein and immobilized ligand have been incubated, the plate may be washed to remove any unbound RAGE fusion protein. The RAGE fusion protein bound to the immobilized ligand may be detected in a variety of ways. In one embodiment, detection employs an ELISA. Thus, in one embodiment, an immunodetection complex containing a monoclonal mouse anti-human IgG1, biotinylated goat anti-mouse IgG, and an avidin linked alkaline phosphatase may be added to the RAGE fusion protein immobilized in the assay well. The immunodetection complex may be allowed to bind to the immobilized RAGE fusion protein such that binding between the RAGE fusion protein and the immunodetection complex attains equilibrium. For example, the complex may be allowed to bind to the RAGE fusion protein for one hour at room temperature. At that point, any unbound complex may be removed by washing the assay well with wash buffer. The bound complex may be detected by adding the alkaline phosphatase substrate, para-nitrophenylphosphate (PNPP), and measuring conversion of PNPP to para-nitrophenol (PNP) as an increase in absorbance at 405 nm.

Figure 7:
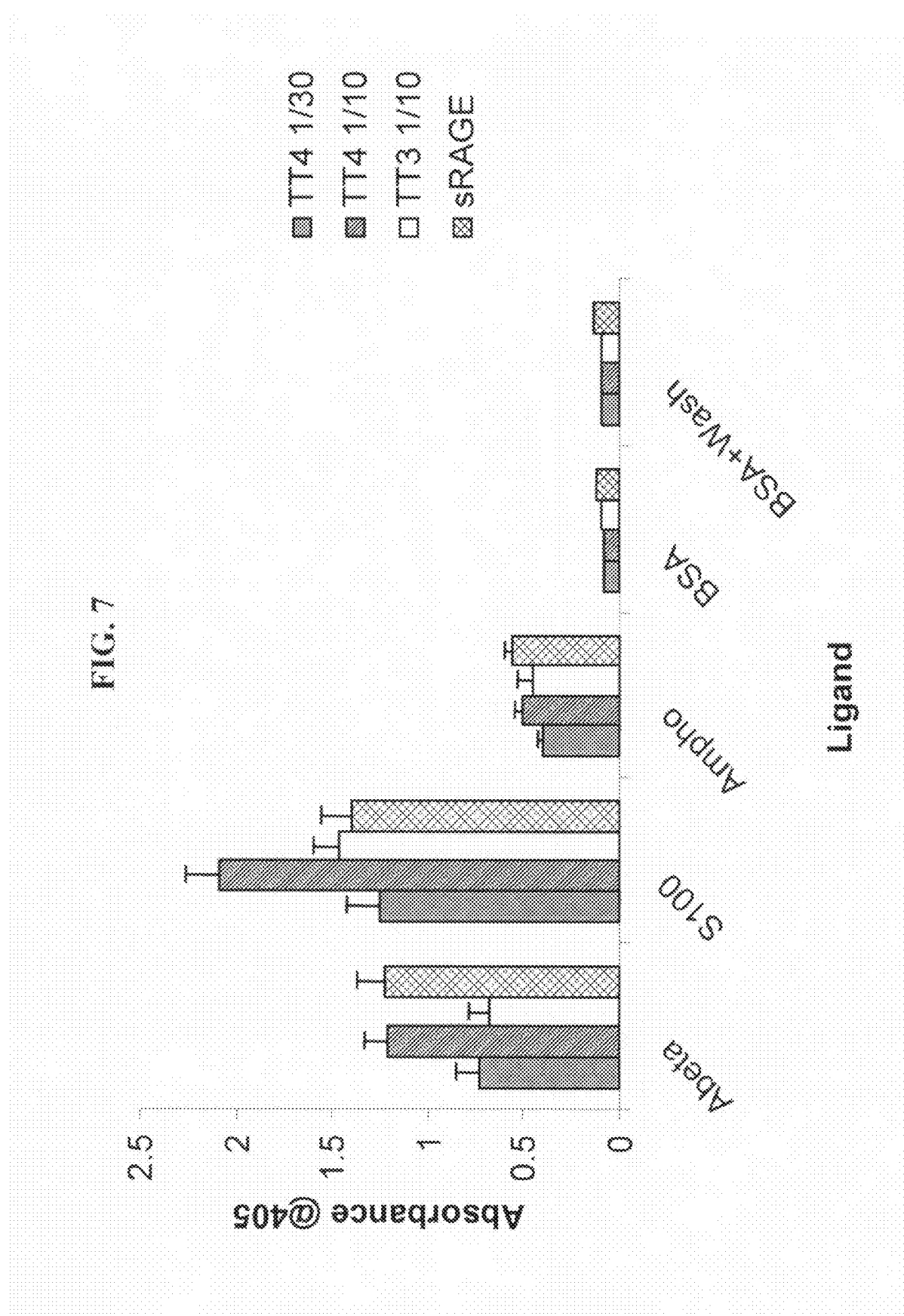
FIG. 7 shows results of an in vitro binding assay for sRAGE, and a first RAGE fusion protein TTP-4000 (TT4) and a second RAGE fusion protein TTP-3000 (TT3), to the RAGE ligands amyloid-beta (A-beta), S100b (S100), and amphoterin (Ampho), in accordance with an embodiment of the present invention.

In an embodiment, RAGE ligand bind to the RAGE fusion protein with nanomolar (nM) or micromolar (μM) affinity. An experiment illustrating binding of RAGE ligands to RAGE fusion proteins of the present invention is shown in FIG. 7. Solutions of TTP-3000 (TT3) and TTP-4000 (TT4) having initial concentrations of 1.082 mg/mL, and 370 μg/mL, respectively, were prepared. As shown FIG. 7, at various dilutions, the RAGE fusion proteins TTP-3000 and TTP-4000 are able to bind to immobilized RAGE ligands Amyloid-beta (Abeta) (Amyloid Beta (1-40) from Biosource), S100b (S100), and amphoterin (Ampho), resulting in an increase in absorbance. In the absence of ligand (i.e., coating with only BSA) there was no increase in absorbance.

The binding assay of the present invention may be used to quantify ligand binding to RAGE. In alternate embodiments, RAGE ligands may bind to the RAGE fusion protein of the present invention with binding affinities ranging from 0.1 to 1000 nanomolar (nM), or from 1 to 500 nM, or from 10 to 80 nM.

Figure 8:
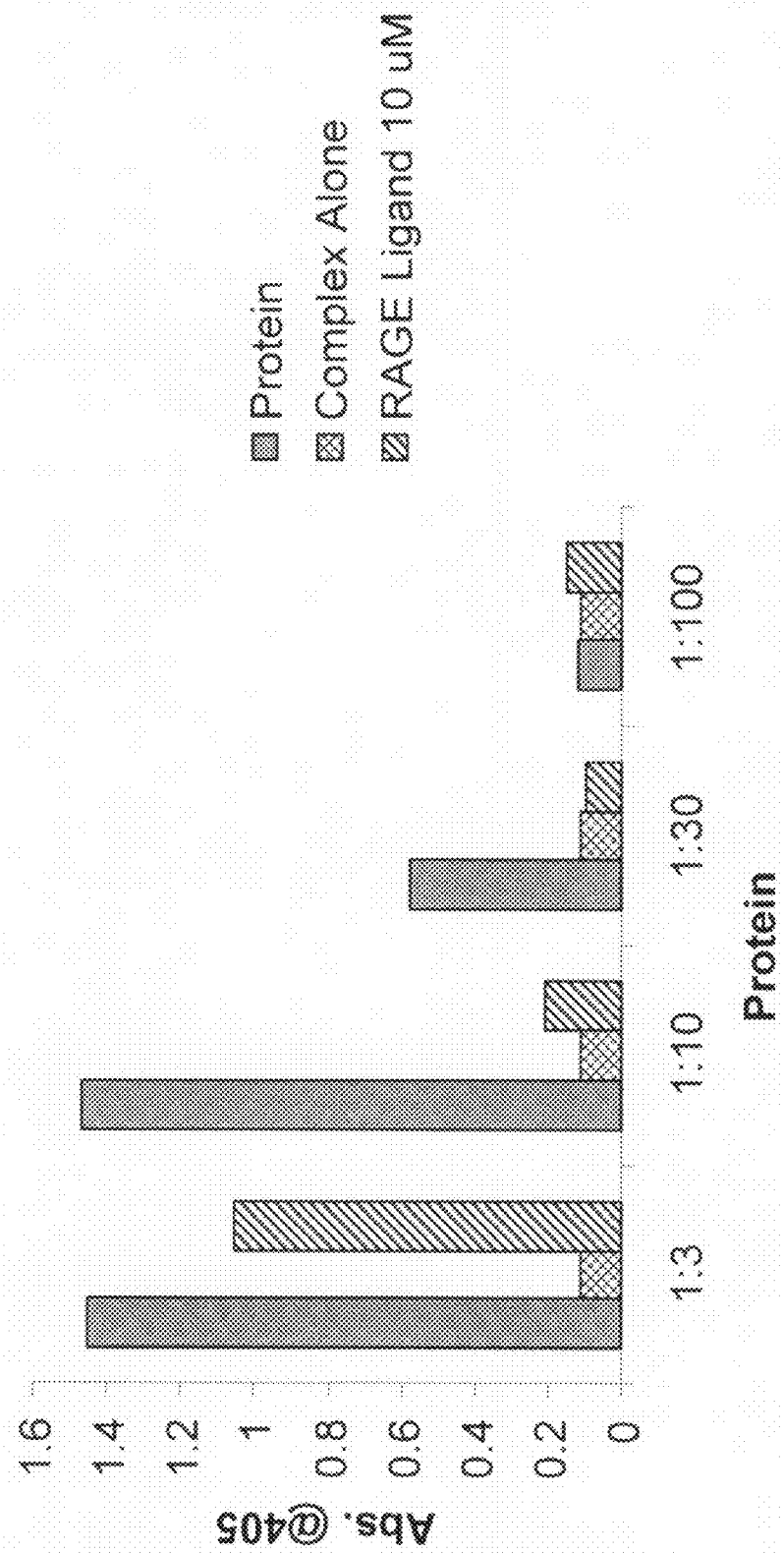
FIG. 8 shows results of an in vitro binding assay for a first RAGE fusion protein TTP-4000 (TT4) ("Protein") to amyloid-beta as compared to a negative control only including the immunodetection reagents ("Complex Alone"), and antagonism of such binding by a RAGE antagonist ("RAGE Ligand") in accordance with an embodiment of the present invention.
Figure 9:
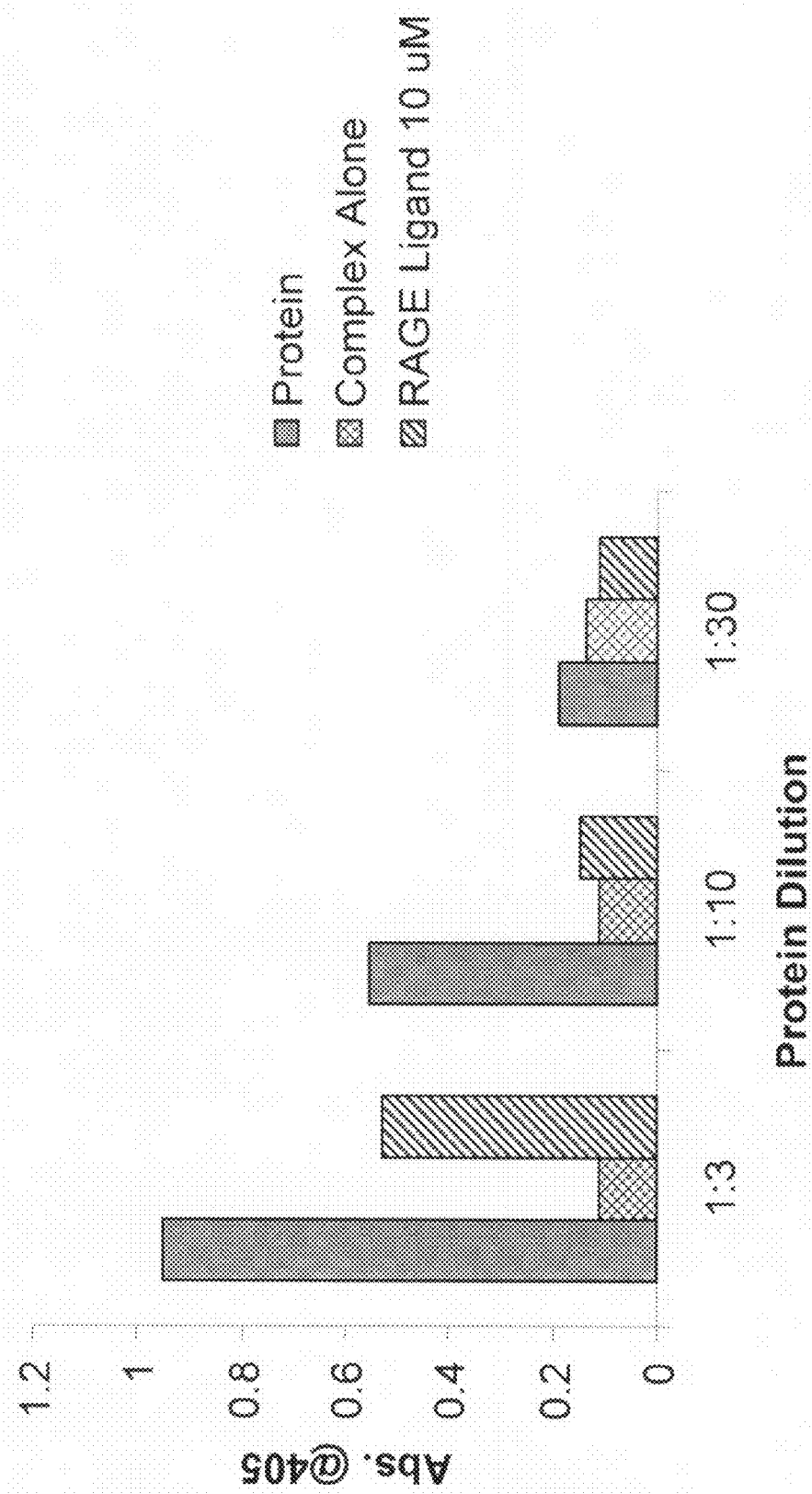
FIG. 9 shows results of an in vitro binding assay for a second RAGE fusion protein TTP-3000 (TT3) ("Protein") to amyloid-beta as compared to a negative control only including the immunodetection reagents ("Complex Alone"), and antagonism of such binding by a RAGE antagonist ("RAGE Ligand") in accordance with an embodiment of the present invention.

The RAGE fusion protein of the present invention may also be used to identify compounds having the ability to bind to RAGE. As shown in FIGS. 8 and 9, respectively, a RAGE ligand may be assayed for its ability to compete with immobilized amyloid beta for binding to TTP-4000 (TT4) or TTP-3000 (TT3) RAGE fusion proteins. Thus, it may be seen that a RAGE ligand at a final assay concentration (FAC) of 10 μM can displace binding of RAGE fusion protein to amyloid-beta at concentrations of 1:3, 1:10, 1:30, and 1:100 of the initial TTP-4000 solution (FIG. 8) or TTP-3000 (FIG. 9).

Modulation of Cellular Effectors

Embodiments of the RAGE fusion proteins of the present invention may be used to modulate a biological response mediated by RAGE. For example, the RAGE fusion proteins may be designed to modulate RAGE-induced increases in gene expression. Thus, in an embodiment, RAGE fusion proteins of the present invention may be used to modulate the function of biological enzymes. For example, the interaction between RAGE and its ligands may generate oxidative stress and activation of NF-κB, and NF-κB regulated genes, such as the cytokines IL-1β, TNF-α, and the like. In addition, several other regulatory pathways, such as those involving p21ras, MAP kinases, ERK1, and ERK2, have been shown to be activated by binding of AGEs and other ligands to RAGE.

Figure 10:
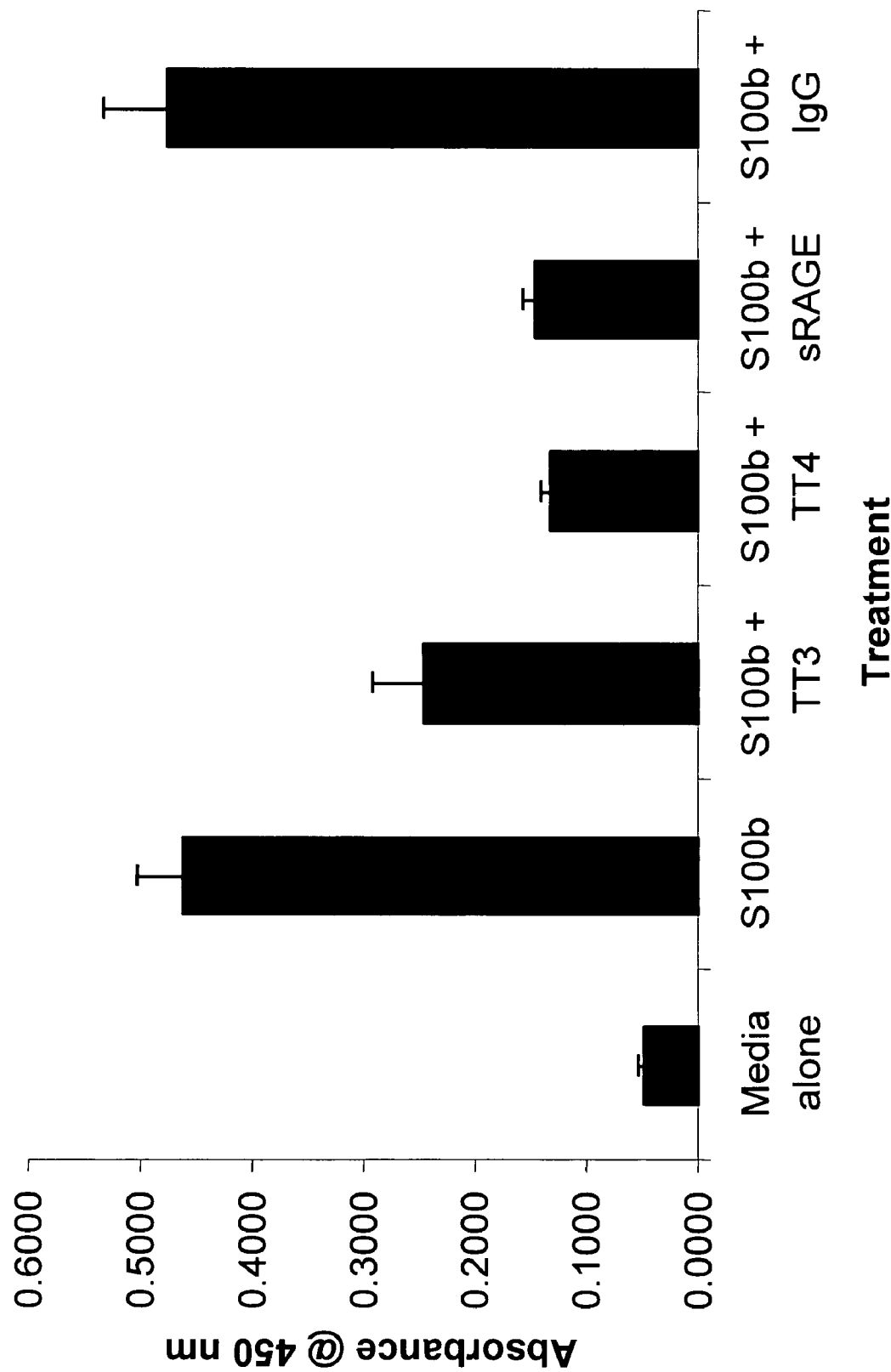
FIG. 10 shows results of a cell-based assay measuring the inhibition of S100b-RAGE induced production of TNF-α by RAGE fusion proteins TTP-3000 (TT3) and TTP-4000 (TT4), and sRAGE in accordance with an embodiment of the present invention.

Use of the RAGE fusion proteins of the present invention to modulate expression of the cellular effector TNF-α is shown in FIG. 10. THP-1 myeloid cells may be cultured in RPMI-1640 media supplemented with 10% FBS and induced to secrete TNF-α via stimulation of RAGE with S100b. When such stimulation occurs in the presence of a RAGE fusion protein, induction of TNF-α by S100b binding to RAGE may be inhibited. Thus, as shown in FIG. 10, addition of 10 μg TTP-3000 (TT3) or TTP-4000 (TT4) RAGE fusion protein reduces S100b induction of TNF-α by about 50% to 75%. RAGE fusion protein TTP-4000 may be at least as effective in blocking S100b induction of TNF-α as is sRAGE (FIG. 10). Specificity of the inhibition for the RAGE sequences of TTP-4000 and TTP-3000 is shown by the experiment in which IgG alone was added to S100b stimulated cells. Addition of IgG and S100b to the assay shows the same levels of TNF-α as S100b alone.

In another cell-based assay, the ability of TTP-4000 to prevent the RAGE ligand HMGB1 from interacting with RAGE and other HMGB1 receptors was evaluated. Unlike anti-RAGE antibodies that bind to RAGE and to prevent the interaction of a RAGE ligand with RAGE, TTP-4000 may block the interaction of a RAGE ligand with RAGE by binding to the RAGE ligand. HMGB1 has been reported to be a ligand for RAGE and the Toll-Like Receptors 2 and 4 (Park et al., *J Biol. Chem.*, 2004; 279(9):7370-7). All three of these receptors (RAGE, Toll-like receptor 2, and Toll-like receptor 4) are expressed on THP-1 cells (Parker, et al., *J. Immunol.*, 2004, 172(8):4977-86.).

Figure 11:
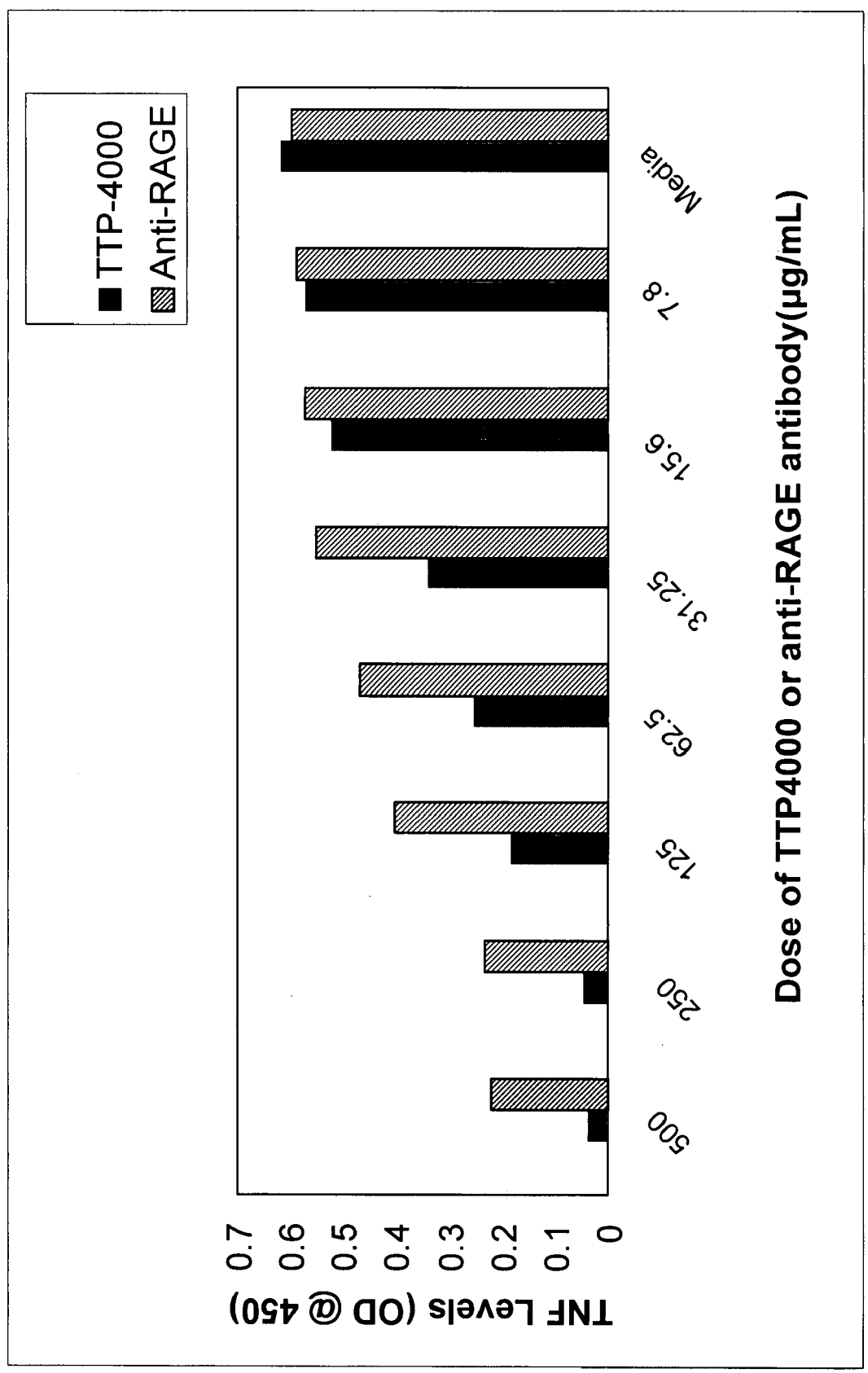
FIG. 11 shows results of a cell-based assay measuring the inhibition of HMGB1-RAGE induced production of TNF-α by RAGE fusion protein TTP-4000 and an anti-RAGE antibody in accordance with an embodiment of the present invention.

In this experiment, THP-1 cells were stimulated to produce TNF-α by HMGB1 (50 mg/mL) in the presence or absence of either TTP4000 or anti-RAGE antibodies. Under the conditions used in the assay, HMGB1 should be the only inducer of TNF-α. The results in FIG. 11 demonstrate that the anti-RAGE antibody and RAGE fusion protein TTP-4000 block HMGB1 from interacting with RAGE expressed on the THP-1 cells, and that TTP-4000 inhibits HMGB1-induced TNF-α production to a greater extent than does the anti-RAGE antibody. Thus, the data indicate that TTP-4000 may inhibit HMGB1 activity to a greater extent than anti-RAGE antibody by inhibiting HMGB1 from interacting with Toll-like receptors 2 and 4, as well as RAGE present on THP-1 cells.

Physiological Characteristics of RAGE Fusion Proteins

While sRAGE can have a therapeutic benefit in the modulation of RAGE-mediated diseases, human sRAGE may have limitations as a stand-alone therapeutic based on the relatively short half-life of sRAGE in plasma. For example, whereas rodent sRAGE has a half-life in normal and diabetic rats of approximately 20 hours, human sRAGE has a half-life of less than 2 hours when assessed by retention of immunoreactivity sRAGE (Renard et al., *J. Pharmacol. Exp. Ther.*, 290:1458-1466 (1999)).

To generate a RAGE therapeutic that has similar binding characteristics as sRAGE, but a more stable pharmacokinetic profile, a RAGE fusion protein comprising a RAGE ligand binding site linked to one or more human immunoglobulin domains may be used. As is known in the art, the immunoglobulin domains may include the Fc portion of the immunoglobulin heavy chain.

The immunoglobulin Fc portion may confer several attributes to a RAGE fusion protein. For example, the Fc fusion protein may increase the serum half-life of such fusion proteins, often from hours to several days. The increase in pharmacokinetic stability is generally a result of the interaction of the linker between $C_H2$ and $C_H3$ regions of the Fc fragment with the FcRn receptor (Wines et al., *J. Immunol.*, 164:5313-5318 (2000)).

Although fusion proteins comprising an immunoglobulin Fc polypeptide may provide the advantage of increased stability, immunoglobulin fusion proteins may elicit an inflammatory response when introduced into a host. The inflammatory response may be due, in large part, to the Fc portion of the immunoglobulin of the fusion protein. The proinflammatory response may be a desirable feature if the target is expressed on a diseased cell type that needs to be eliminated (e.g., a cancer cell, an or a population of lymphocytes causing an autoimmune disease). The proinflammatory response may be a neutral feature if the target is a soluble protein, as most soluble proteins do not activate immunoglobulins. However, the proinflammatory response may be a negative feature if the target is expressed on cell types whose destruction would lead to untoward side-effects. Also, the proinflammatory response may be a negative feature if an inflammatory cascade is established at the site of a fusion protein binding to a tissue target, since many mediators of inflammation may be detrimental to surrounding tissue, and/or may cause systemic effects.

The primary proinflammatory site on immunoglobulin Fc fragments resides on the hinge region between the $C_H1$ and $C_H2$. This hinge region interacts with the FcR1-3 on various leukocytes and trigger these cells to attack the target. (Wines et al., *J. Immunol.*, 164:5313-5318 (2000)).

As therapeutics for RAGE-mediated diseases, RAGE fusion proteins may not require the generation of an inflammatory response. Thus, embodiments of the RAGE fusion proteins of the present invention may comprise a RAGE fusion protein comprising a RAGE polypeptide linked to an immunoglobulin domain(s) where the Fc hinge region from the immunoglobulin is removed and replaced with a RAGE polypeptide. In this way, interaction between the RAGE fusion protein and Fc receptors on inflammatory cells may be minimized. It may be important, however, to maintain proper stacking and other three-dimensional structural interactions between the various immunoglobulin domains of the RAGE fusion protein. Thus, embodiments of the RAGE fusion proteins of the present invention may substitute the biologically inert, but structurally similar RAGE interdomain linker that separates the V and C1 domains of RAGE, or the linker that separates the C1 and C2 domains of RAGE, in lieu of the normal hinge region of the immunoglobulin heavy chain. Thus, the RAGE polypeptide of the RAGE fusion protein may comprise an interdomain linker sequence that is naturally found downstream of a RAGE immunoglobulin domain to form a RAGE immunglobulin domain/linker fragment. In this way, the three dimensional interactions between the immunoglobulin domains contributed by either RAGE or the immunoglobulin may be maintained.

Figure 12:
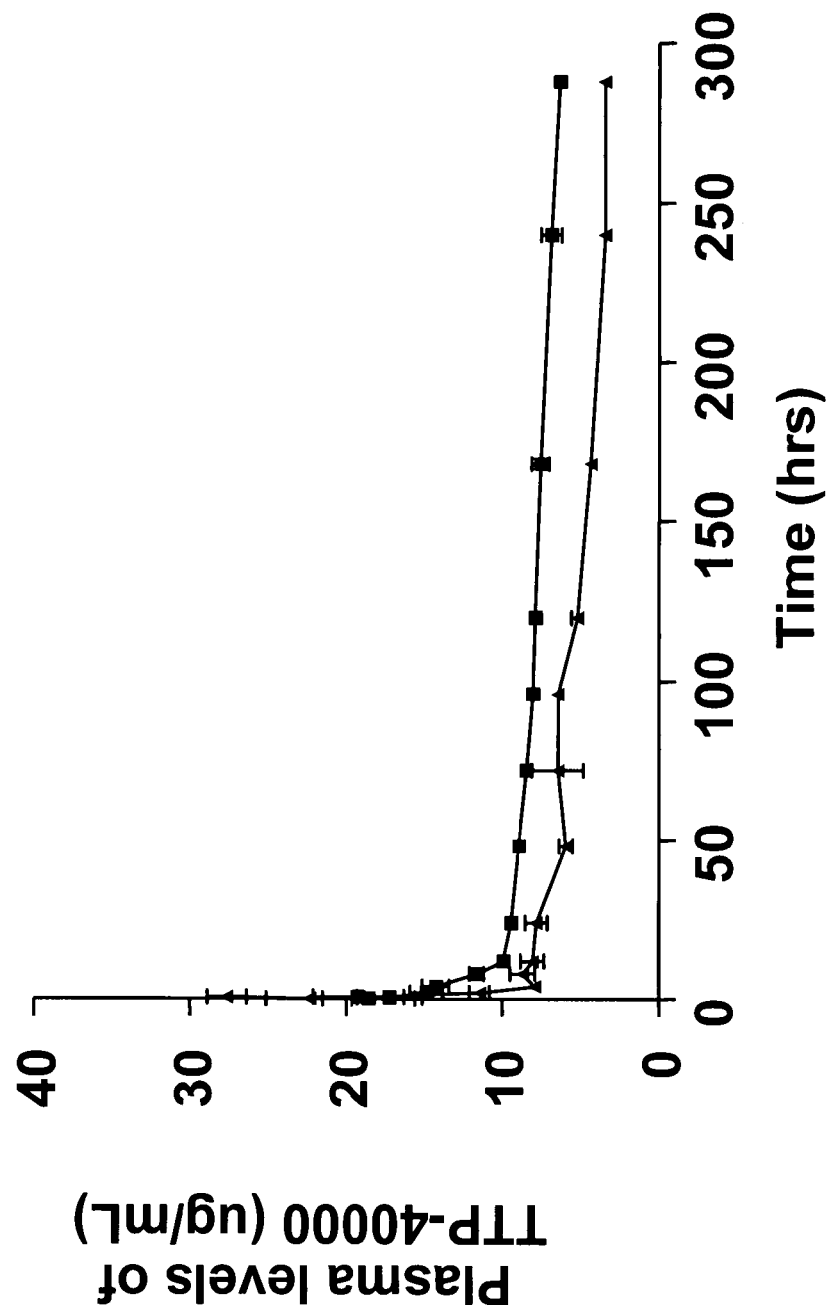
FIG. 12 shows a pharmacokinetic profile for RAGE fusion protein TTP-4000 in accordance with an embodiment of the present invention wherein each curve represents a different animal under the same experimental conditions.

In an embodiment, a RAGE fusion protein of the present invention may comprise a substantial increase in pharmacokinetic stability as compared to sRAGE. For example, FIG. 12 shows that once the RAGE fusion protein TTP-4000 has saturated its ligands, it may retain a half-life of greater than 300 hours. This may be contrasted with the half-life for sRAGE of only a few hours in human plasma.

Figure 13:
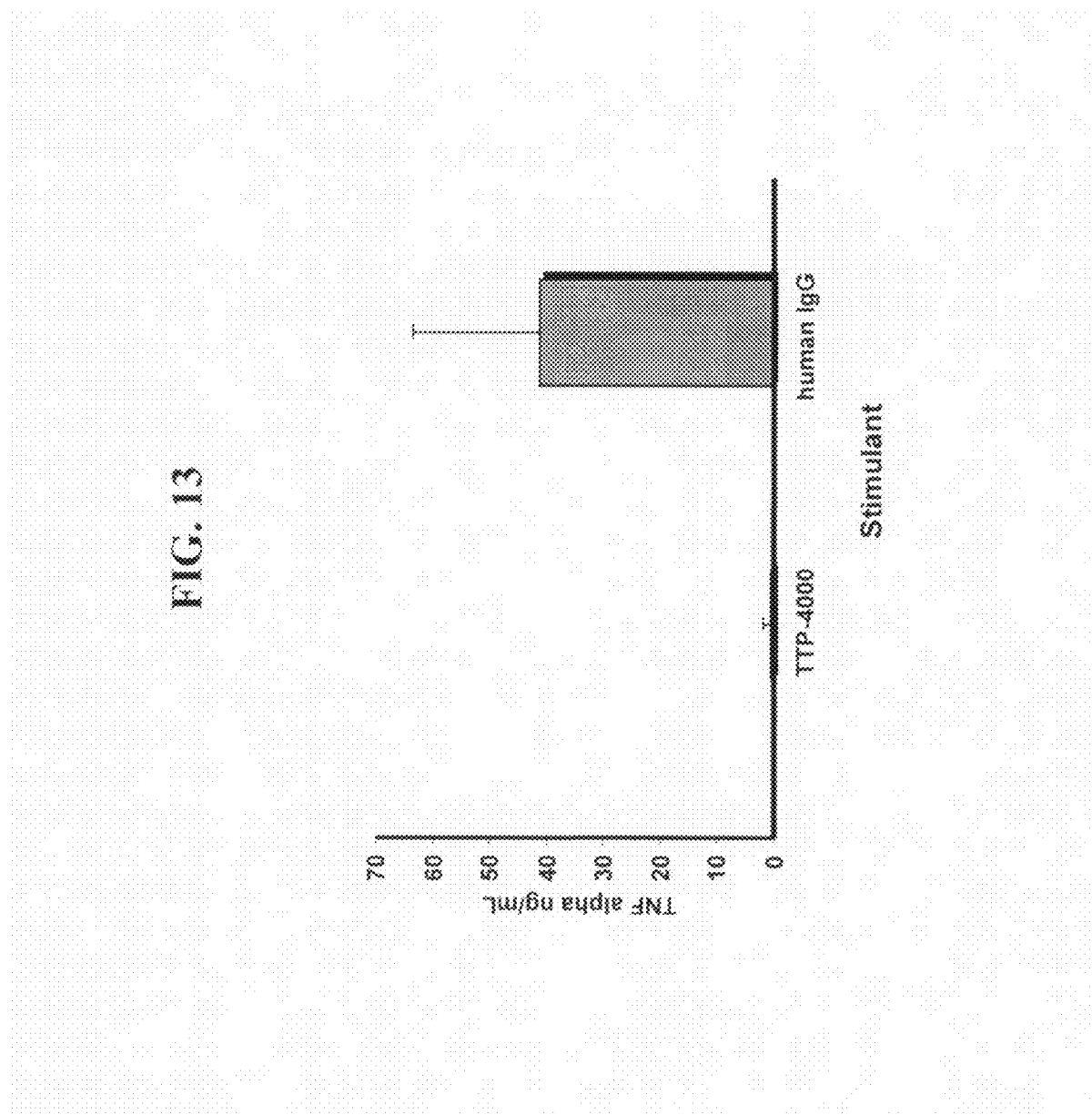
FIG. 13 shows relative levels of TNF-α release from THP-1 cells due to stimulation by RAGE fusion protein TTP-4000 and human IgG stimulation as a measure of an inflammatory response in accordance with an embodiment of the present invention.

Thus, in an embodiment, the RAGE fusion proteins of the present invention may be used to antagonize binding of physiological ligands to RAGE as a means to treat RAGE-mediated diseases without generating an unacceptable amount of inflammation. The RAGE fusion proteins of the present invention may exhibit a substantial decrease in generating a proinflammatory response as compared to IgG. For example, as shown in FIG. 13, the RAGE fusion protein TTP-4000 does not stimulate TNF-α release from cells under conditions where human IgG stimulation of TNF-α release is detected.

Treatment of Disease with RAGE Fusion Proteins

The present invention may also comprise methods for the treatment of RAGE-mediated disorder in a human subject. In an embodiment, the method may comprise administering to a subject a RAGE fusion protein comprising a RAGE polypeptide comprising a RAGE ligand binding site linked to a second, non-RAGE polypeptide.

In certain embodiments, the RAGE formulation comprises a lyophilized RAGE fusion protein. In certain embodiments, the present invention may comprise methods of treating a RAGE-mediated disorder in a subject comprising administering to a subject a therapeutically effective amount of a reconstituted formulation comprising a RAGE fusion protein, a lyoprotectant, and a buffer.

Any of the embodiments of the RAGE fusion proteins described herein may be used for treatment of disease in the therapeutic compositions and formulations of the present invention. Thus, the RAGE fusion protein may comprise a sequence derived from a RAGE ligand binding site linked to an immunoglobulin polypeptide. Embodiments of the RAGE fusion protein may comprise a RAGE polypeptide directly linked to a polypeptide comprising a $C_H2$ domain of an immunoglobulin or a portion of a $C_H2$ domain of an immunoglobulin. In certain embodiments, the RAGE polypeptide may comprise a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a portion thereof. For example, certain embodiments of the fusion protein may comprise a first RAGE immunoglobulin domain and a first RAGE interdomain linker linked to a second RAGE immunoglobulin domain and a second RAGE interdomain linker, such that the N-terminal amino acid of the first interdomain linker is linked to the C-terminal amino acid of the first RAGE immunoglobulin domain, the N-terminal amino acid of the second RAGE immunoglobulin domain is linked to C-terminal amino acid of the first interdomain linker, the N-terminal amino acid of the second interdomain linker is linked to C-terminal amino acid of the second RAGE immunoglobulin domain, and the C-terminal amino acid of the RAGE second interdomain linker is directly linked to the N-terminal amino acid of the $C_H2$ immunoglobulin domain or a portion of a $C_H2$ domain of an immunoglobulin.

In alternate embodiments of this multi-domain fusion protein, the RAGE polypeptide may comprise the amino acid sequence as set forth in SEQ ID NO: 10, or a sequence at least 90% identical thereto, or the amino acid sequence as set forth in SEQ ID NO: 47, or a sequence at least 70%, 75%, 80%, 85%, 90%, 95%, 96%, 97%, 98%, or 99% identical thereto. In other alternate embodiments, the RAGE fusion protein may comprise the amino acid sequence as set forth in at least one of SEQ ID NOs: 32, 33, 34, 35, 36, 37, 56, or 57, or a sequence at least 70%, 75%, 80%, 85%, 90%, 95%, 96%, 97%, 98%, or 99% identical thereto. For example, in certain embodiments, a sequence at least 90% identical to SEQ ID NOs: 32, 33, 34, 56, 35, 36, 37, or 57 comprises the polypeptide of SEQ ID NOs: 32, 33, 34, 56, 35, 36, 37, or 57 without the C-terminal lysine. Or, other embodiments as described herein may constitute the RAGE fusion protein used in the formulations of the present invention.

A variety of lyoprotectants may be used in the lyophilized RAGE fusion protein formulation. In some embodiments, the lyoprotectant may comprise a non-reducing sugar. For example, the non-reducing sugar may comprise sucrose, mannitol, or trehalose. Also, a variety of buffers may be used in the lyophilized RAGE fusion protein formulation. In certain embodiments, the buffer may comprise histidine.

The lyophilized RAGE fusion protein may comprise additional components. In certain embodiments, the RAGE fusion protein formulation may further comprise at least one of a surfactant, a chelating agent or a bulking agent. In one embodiment, the reconstituted RAGE fusion protein formulation comprises about 40-100 mg/mL RAGE fusion protein comprising the sequence as set forth in SEQ ID NOs: 32, 33, 34, 56, 35, 36, 37, or 57; about 2 mM to about 50 mM histidine; about 60 mM to about 65 mM sucrose; about 0.001% to about 0.05% Tween 80; and a pH of about 6.0 to 6.5. For example, the reconstituted RAGE fusion protein formulation may, in certain embodiments, comprise about 40-50 mg/mL RAGE fusion protein comprising the sequence as set forth in SEQ ID NOs: 32, 33, 34, 56, 35, 36, 37, or 57; about 10 mM histidine, about 65 mM sucrose, about 0.01% Tween 80, and at a pH of about 6.0. Or, other concentrations of the RAGE fusion protein may be used in the formulations for treatment of RAGE-mediated disorders as is required.

The RAGE fusion protein formulation may comprise a stable therapeutic agent that is formulated for use in a clinic or as a prescription medicine. For example, in certain embodiments, the RAGE fusion protein formulation may exhibits less than 10%, or less than 5%, or less than 3% decomposition after one week at 40 degrees Centigrade.

Also, the RAGE fusion protein formulation may be stable upon reconstitution in a diluent. In certain embodiments, less than about 10%, or about 5%, or about 4%, or about 3%, or about 2%, or or about 1% of the RAGE fusion protein is present as an aggregate in the RAGE fusion protein formulation.

The reconstituted RAGE fusion protein formulation may be suitable for administration by various routes and as is required for treatment of the RAGE-mediated disorder of interest. Administration of the RAGE fusion protein of the present invention may employ intraperitoneal (IP) injection. Alternatively, the RAGE fusion protein may be administered orally, intranasally, or as an aerosol. In another embodiment, administration is intravenous (IV). The RAGE fusion protein may also be injected subcutaneously. In another embodiment, administration of the RAGE fusion protein is intra-arterial. In another embodiment, administration is sublingual. Also, administration may employ a time-release capsule. In yet another embodiment, administration may be transrectal, as by a suppository or the like. For example, subcutaneous administration may be useful to treat chronic disorders when the self-administration is desirable.

As described in more detail herein, RAGE has been implicated in the pathogenesis of a variety of disease states, and the RAGE fusion proteins of the present invention have been found to be effective in ameliorating such disease states. Thus, the RAGE fusion protein formulations of the present invention may be used to treat a variety of RAGE-mediated disorders.

In certain embodiments, a reconstituted RAGE fusion protein formulation of the present invention may be used to treat a symptom of diabetes or a symptom of diabetic late complications. For example, the symptom of diabetes or diabetic late complications comprises at least one of diabetic nephropathy, diabetic retinopathy, a diabetic foot ulcer, a cardiovascular complication, or diabetic neuropathy.

In other embodiments, a reconstituted RAGE fusion protein formulation of the present invention may be used to treat at least one of amyloidosis, Alzheimer's disease, cancer, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, or impaired wound healing.

Or, the reconstituted RAGE fusion protein formulation may be used to treat osteoporosis. For example, in certain embodiments, administration of a RAGE fusion protein formulation of the present invention increases bone density of subject or reduces the rate of a decrease in bone density of a subject.

In some embodiments, the autoimmunity treated using the RAGE fusion protein formulations of the present invention may comprise rejection of at least one of skin cells, pancreatic cells, nerve cells, muscle cells, endothelial cells, heart cells, liver cells, kidney cells, a heart, bone marrow cells, bone, blood cells, artery cells, vein cells, cartilage cells, thyroid, cells, or stem cells. Or, the reconstituted RAGE fusion protein formulation may be used to treat kidney failure.

In certain embodiments, the reconstituted RAGE fusion protein formulation may used to treat inflammation and/or rejection associated with transplantation of at least one of an organ, a tissue, or a plurality of cells from a first site to a second site. The first and second sites may either be in different subjects, or in the same subject. Transplantation of a variety of different cell types may be improved using the RAGE fusion protein formulations of the present invention. For example, the transplanted cells, tissue, or organ may comprise a cell, tissue or organ of a pancreas, skin, liver, kidney, heart, bone marrow, blood, bone, muscle, artery, vein, cartilage, thyroid, nervous system, or stem cells.

Examples of using RAGE fusion proteins of the present invention in the treatment of such diseases and disorders are disclosed herein.

For example, a variety of animal models have been used to validate the use of compounds that modulate RAGE as therapeutics. Examples of these models are as follows:
  a) sRAGE inhibited neointimal formation in a rat model of restenosis following arterial injury in both diabetic and normal rats by inhibiting endothelial, smooth muscle and macrophage activation via RAGE (Zhou et al., *Circulation* 107:2238-2243 (2003));
  b) Inhibition of RAGE/ligand interactions, using either sRAGE or an anti-RAGE antibody, reduced amyloid plaque formation in a mouse model of systemic amyloidosis (Yan et al., *Nat. Med.*, 6:643-651 (2000)). Accompanying the reduction in amyloid plaques was a reduction in the inflammatory cytokines, interleukin-6 (IL-6) and macrophage colony stimulating factor (M-CSF) as well as reduced activation of NF-kB in the treated animals;
  c) RAGE transgenic mice (RAGE overexpressers and RAGE dominant negative expressers) exhibit plaque formation and cognitive deficits in a mouse model of AD (Arancio et al., *EMBO J.*, 23:4096-4105 (2004));
  d) Treatment of diabetic rats with sRAGE reduced vascular permeability (Bonnardel-Phu et al., *Diabetes*, 48:2052-2058 (1999));
  e) Treatment with sRAGE reduced atherosclerotic lesions in diabetic apolipoprotein E-null mice and prevented the functional and morphological indices of diabetic nephropathy in db/db mice (Hudson et al., *Arch. Biochem. Biophys.*, 419:80-88 (2003)); and
  f) sRAGE attenuated the severity of inflammation in a mouse model of collagen-induced arthritis (Hofmann et al., *Genes Immunol.*, 3:123-135 (2002)), a mouse model of experimental allergic encephalomyelitis (Yan et al., *Nat. Med.* 9:28-293 (2003)) and a mouse model of inflammatory bowel disease (Hofmann et al., *Cell*, 97:889-901 (1999)).

Thus, in an embodiment, the RAGE fusion proteins of the present invention may be used to treat a symptom of diabetes and/or complications resulting from diabetes mediated by RAGE. In alternate embodiments, the symptom of diabetes or diabetic late complications may comprise diabetic nephropathy, diabetic retinopathy, a diabetic foot ulcer, a cardiovascular complication of diabetes, or diabetic neuropathy.

Originally identified as a receptor for molecules whose expression is associated with the pathology of diabetes, RAGE itself is essential to the pathophysiology of diabetic complications. In vivo, inhibition of RAGE interaction with its ligand(s) has been shown to be therapeutic in multiple models of diabetic complications and inflammation (Hudson et al., *Arch. Biochem. Biophys.*, 419:80-88 (2003)). For example, a two-month treatment with anti-RAGE antibodies normalized kidney function and reduced abnormal kidney histopathology in diabetic mice (Flyvbjerg et al., *Diabetes* 53:166-172 (2004)). Furthermore, treatment with a soluble form of RAGE (sRAGE) which binds to RAGE ligands and inhibits RAGE/ligand interactions, reduced atherosclerotic lesions in diabetic apolipoprotein E-null mice and attenuated the functional and morphological pathology of diabetic nephropathy in db/db mice (Bucciarelli et al., *Circulation* 106: 2827-2835 (2002)).

Also, it has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer et al., *J. Clin. Invest.*, 91:2463-2469 (1993); Reddy et al., *Biochem.*, 34:10872-10878 (1995); Dyer et al., *J. Biol. Chem.*, 266:11654-11660 (1991); Degenhardt et al., *Cell Mol. Biol.*, 44:1139-1145 (1998)). Accumulation of AGEs in the vasculature can occur focally, as in the joint amyloid composed of AGE-$\beta_2$-microglobulin found in patients with dialysis-related amyloidosis (Miyata et al., *J. Clin. Invest.*, 92:1243-1252 (1993); Miyata et al., *J. Clin. Invest.*, 98:1088-1094 (1996)), or generally, as exemplified by the vasculature and tissues of patients with diabetes (Schmidt et al., *Nature Med.*, 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li et al., *J. Biol. Chem.*, 272:16498-16506 (1997); Li et al., *J. Biol. Chem.*, 273:30870-30878 (1998); Tanaka et al., *J. Biol. Chem.*, 275:25781-25790 (2000)). RAGE expression is increased in endothelium, smooth muscle cells and infiltrating mononuclear phagocytes in diabetic vasculature. Also, studies in cell culture have demonstrated that AGE-RAGE interaction causes changes in cellular properties important in vascular homeostasis.

Figure 14A:
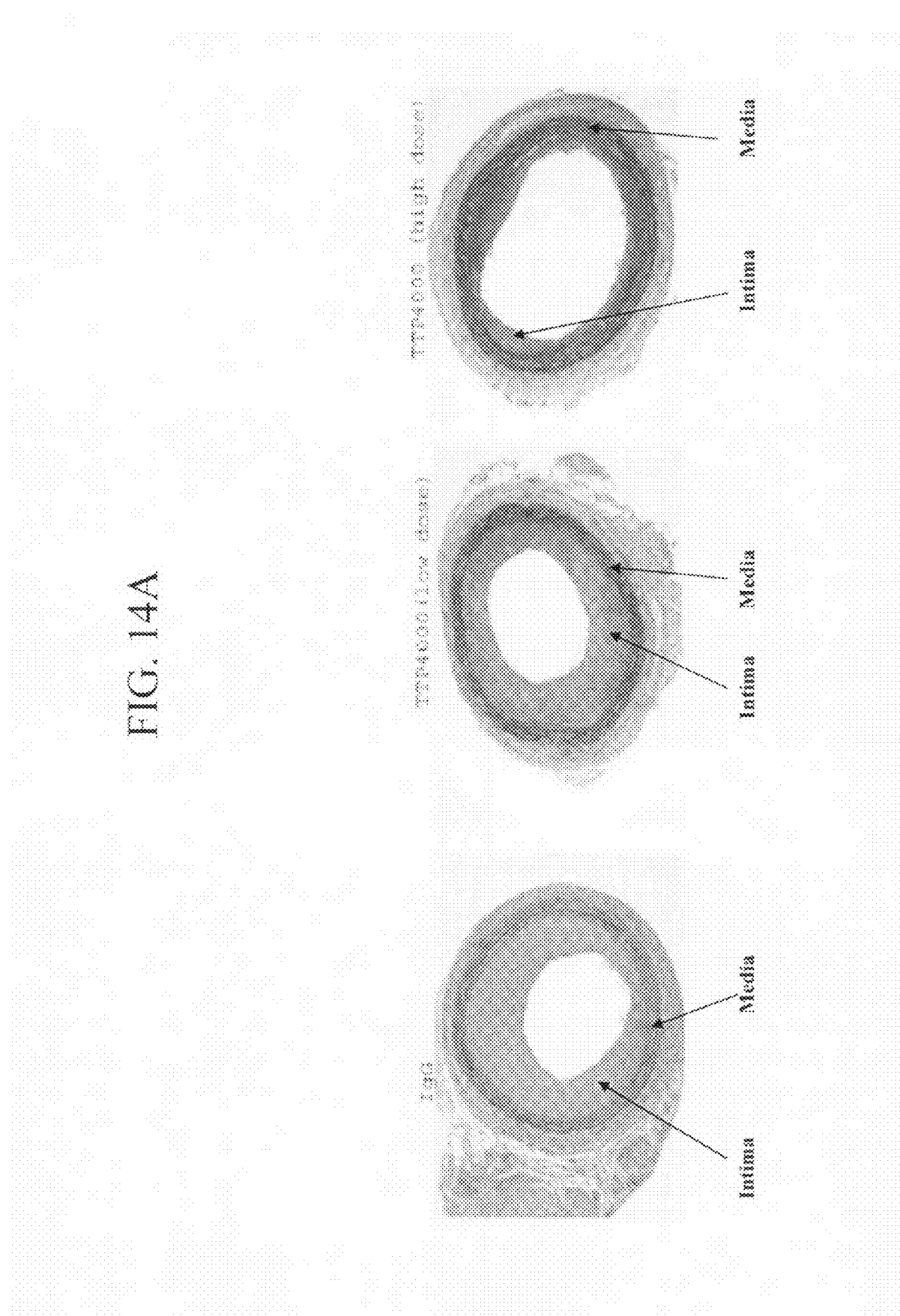
FIG. 14 shows the use of RAGE fusion protein TTP-4000 to reduce restenosis in diabetic animals in accordance with alternate embodiments of the present invention, wherein panel A shows that TTP-4000 RAGE-fusion protein reduced the intima/media ratio as compared to a negative control (IgG), and panel B shows that TTP-4000 RAGE-fusion protein reduced vascular smooth muscle cell proliferation in a dose-responsive manner.
Figure 14B:
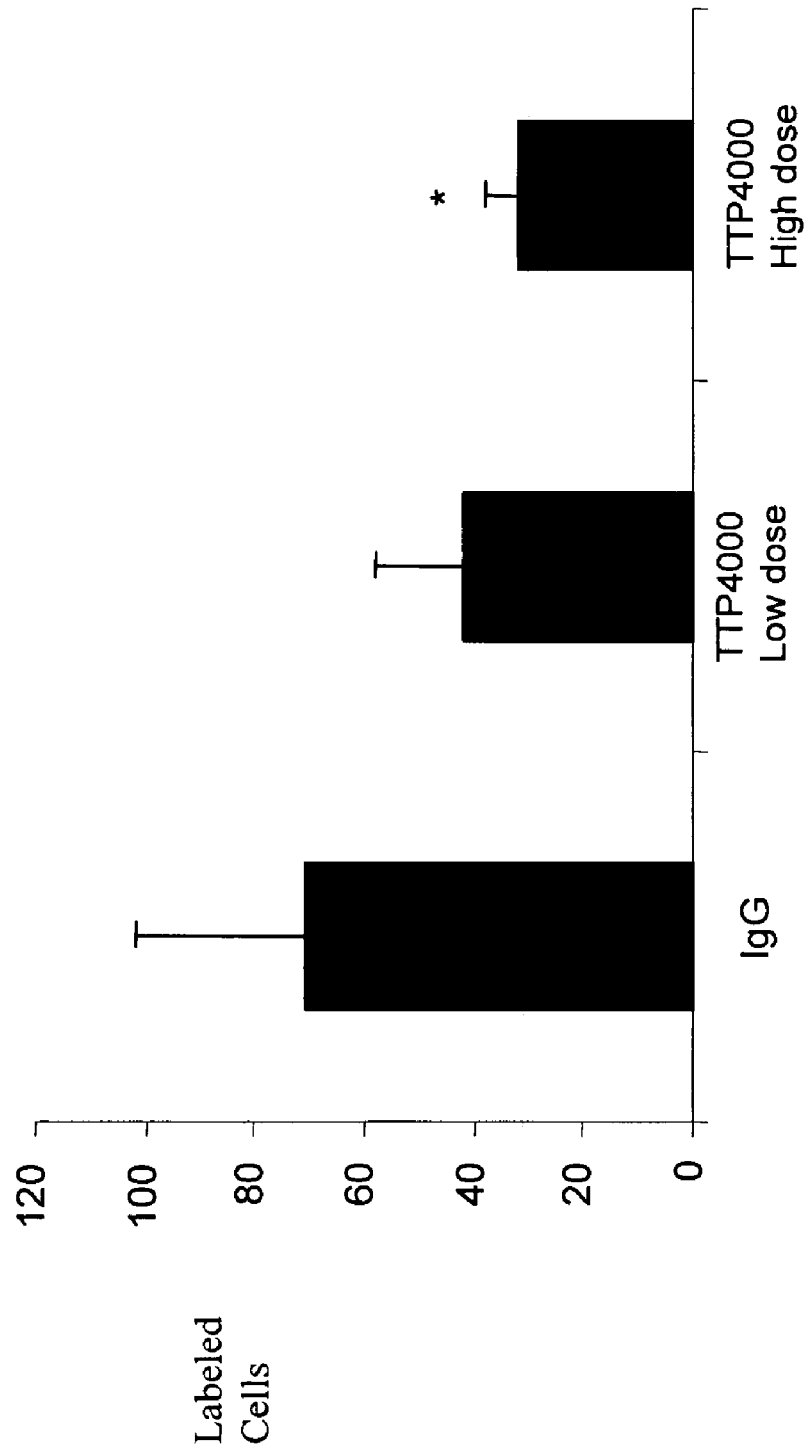

Use of the RAGE fusion proteins in the treatment of diabetes related pathology is illustrated in FIG. 14. The RAGE fusion protein TTP-4000 was evaluated in a diabetic rat model of restenosis which involved measuring smooth muscle proliferation and intimal expansion following vascular injury. As illustrated in FIG. 14, TTP-4000 treatment may significantly reduce the intima/media (I/M) ratio (FIG. 14A; Table 1) in diabetes-associated restenosis in a dose-responsive manner. Also, TTP-4000 treatment may significantly reduce restenosis-associated vascular smooth muscle cell proliferation in a dose-responsive manner (FIG. 14B).

TABLE 1

| Effect of TTP-4000 in Rat Model of Restenosis | | | |
|---|---|---|---|
| | IgG (n = 9) | TTP-4000 (n = 9) Low dose** (0.3 mg/animal qod × 4) | TTP-4000 (n = 9) High dose** (1.0 mg/animal qod × 4) |
| Intimal area (mm$^2$) | 0.2 ± 0.03 | 0.18 ± 0.04 | 0.16 ± 0.02 |
| Medial area (mm$^2$) | 0.12 ± 0.01 | 0.11 ± 0.02 | 0.11 ± 0.01 |
| I/M ratio | 1.71 ± 0.27 | 1.61 ± 0.26 | 1.44* ± 0.15 |

*$P < 0.05$;
**For both high and low dose, a loading dose of 3 mg/animal was used.

In other embodiments, the RAGE fusion proteins of the present invention may also be used to treat or reverse amyloidoses and Alzheimer's disease. RAGE is a receptor for amyloid beta (Aβ) as well as other amyloidogenic proteins including SAA and amylin (Yan et al., *Nature*, 382:685-691 (1996); Yan et al., *Proc. Natl. Acad. Sci., USA*, 94:5296-5301 (1997); Yan et al., *Nat. Med.*, 6:643-651 (2000); Sousa et al., *Lab Invest.*, 80:1101-1110 (2000)). Also, the RAGE ligands, including AGEs, S100b and Aβ proteins, are found in tissue surrounding the senile plaque in man (Luth et al., *Cereb. Cortex* 15:211-220 (2005); Petzold et al, *Neurosci. Lett.*, 336: 167-170 (2003); Sasaki et al., *Brain Res.*, 12:256-262 (2001; Yan et al., *Restor. Neurol Neruosci.*, 12:167-173 (1998)). It has been shown that RAGE binds β-sheet fibrillar material regardless of the composition of the subunits (amyloid-β peptide, amylin, serum amyloid A, prion-derived peptide) (Yan et al., *Nature*, 382:685-691 (1996); Yan et al., *Nat. Med.*, 6:643-651 (2000)). In addition, deposition of amyloid has been shown to result in enhanced expression of RAGE. For example, in the brains of patients with Alzheimer's disease (AD), RAGE expression increases in neurons and glia (Yan, et al., *Nature* 382:685-691 (1996)). Concurrent with expression of RAGE ligands, RAGE is upregulated in astrocytes and microglial cells in the hippocampus of individuals with AD but is not upregulated in individuals that do not have AD (Lue et al., *Exp. Neurol.*, 171:29-45 (2001)). These findings suggest that cells expressing RAGE are activated via RAGE/ RAGE ligand interactions in the vicinity of the senile plaque. Also, in vitro, Aβ-mediated activation of microglial cells can be blocked with antibodies directed against the ligand-binding domain of RAGE (Yan et al., *Proc. Natl. Acad. Sci., USA*, 94:5296-5301 (1997)). It has also been demonstrated that RAGE can serve as a focal point for fibril assembly (Deane et al., *Nat. Med.* 9:907-913 (2003)).

Also, in vivo inhibition of RAGE/ligand interactions using either sRAGE or an anti-RAGE antibody can reduce amyloid plaque formation in a mouse model of systemic amyloidosis (Yan et al., *Nat. Med.*, 6:643-651 (2000)). Double transgenic mice that over-express human RAGE and human amyloid precursor protein (APP) with the Swedish and London mutations (mutant hAPP) in neurons develop learning defects and neuropathological abnormalities earlier than their single mutant hAPP transgenic counterparts. In contrast, double transgenic mice with diminished Aβ signaling capacity due to neurons expressing a dominant negative form of RAGE on the same mutant hAPP background, show a delayed onset of neuropathological and learning abnormalities compared to their single APP transgenic counterpart (Arancio et al., *EMBO J.*, 23:4096-4105 (2004)).

In addition, inhibition of RAGE-amyloid interaction has been shown to decrease expression of cellular RAGE and cell stress markers (as well as NF-κB activation), and diminish amyloid deposition (Yan et al., *Nat. Med.*, 6:643-651 (2000)) suggesting a role for RAGE-amyloid interaction in both perturbation of cellular properties in an environment enriched for amyloid (even at early stages) as well as in amyloid accumulation.

Figure 15A:
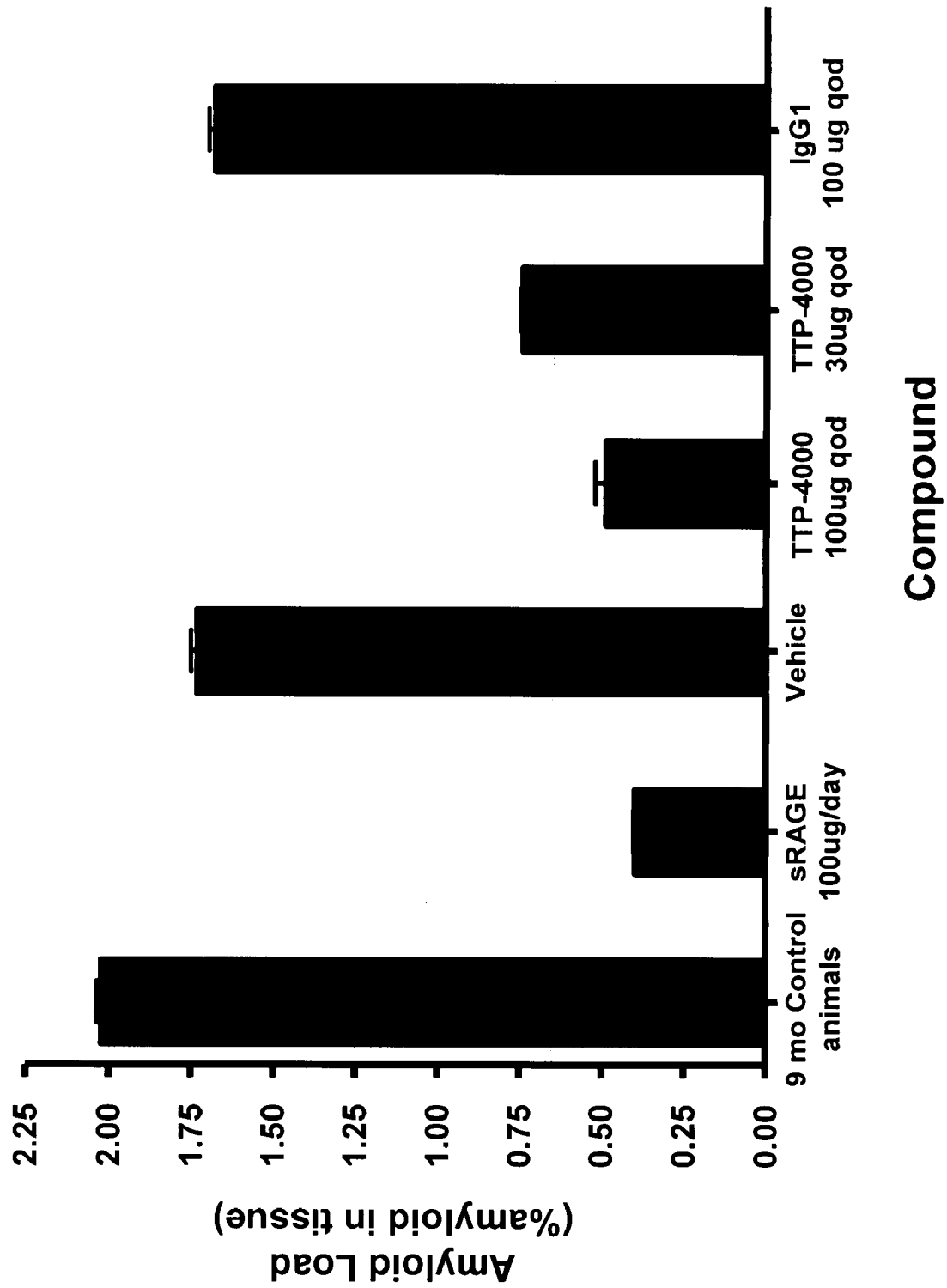
FIG. 15 shows use of RAGE fusion protein TTP-4000 to reduce amyloid formation and cognitive dysfunction in animals with Alzheimer's Disease (AD) in accordance with alternate embodiments of the present invention wherein panel A shows TTP-4000 RAGE-fusion protein reduced amyloid load in the brain, and panel B shows TTP-4000 RAGE-fusion protein improved cognitive function.
Figure 15B:
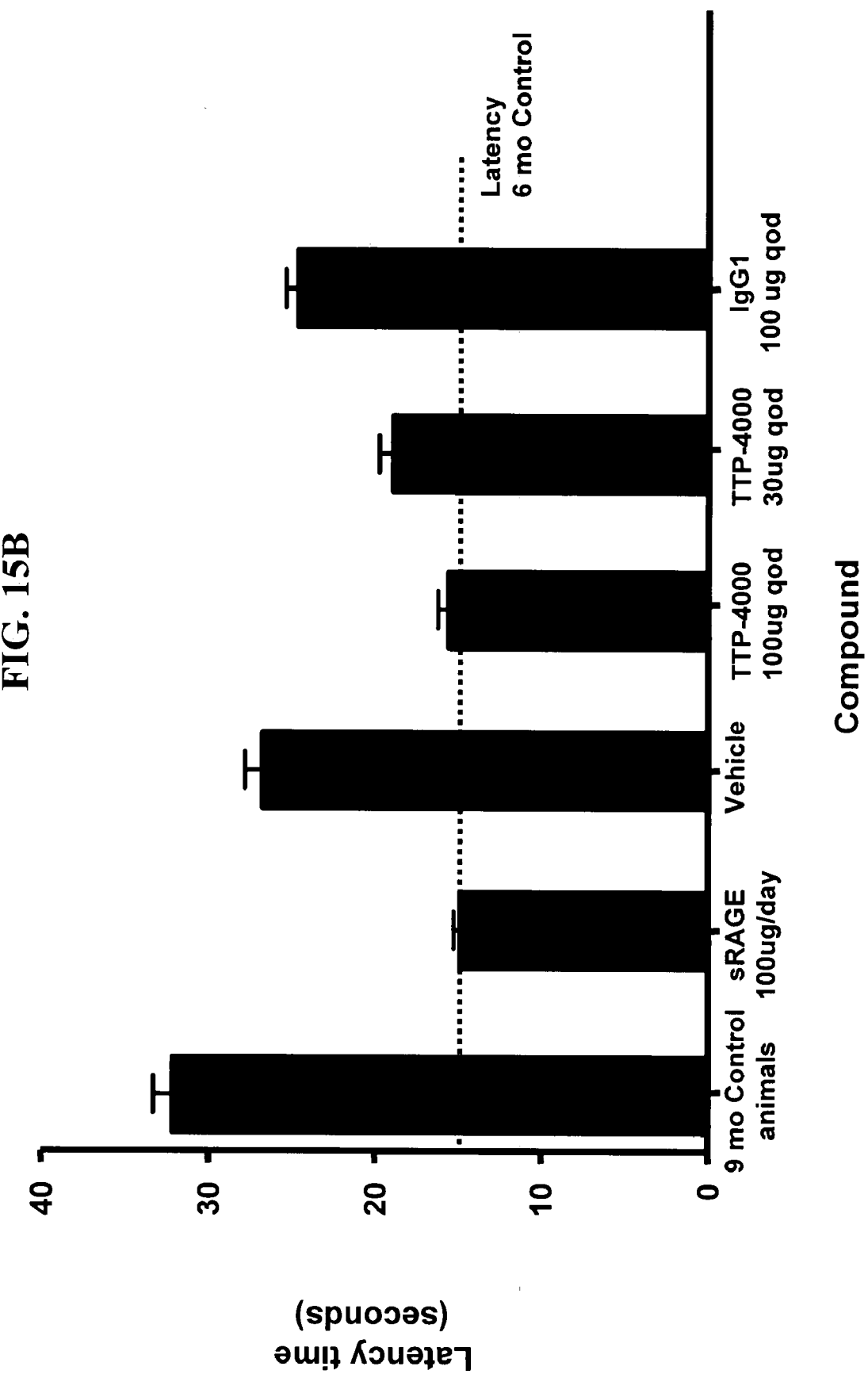

Thus, the RAGE fusion proteins of the present invention may also be used to treat reduce amyloidosis and to reduce amyloid plaques and cognitive dysfunction associated with Alzheimer's Disease (AD). As described above, sRAGE has been shown to reduce both amyloid plaque formation in the brain and subsequent increase in inflammatory markers in an animal model of AD. FIGS. 15A and 15B show that mice that have AD, and are treated for 3 months with either TTP-4000 or mouse sRAGE had fewer amyloid beta (Aβ) plaques and less cognitive dysfunction than animals that received a vehicle or a human IgG negative control (IgG1). Like sRAGE, TTP-4000 may also reduce the inflammatory cytokines IL-1 and TNF-α (data not shown) associated with AD.

Also, RAGE fusion proteins of the present invention may be used to treat atherosclerosis and other cardiovascular disorders. Thus, it has been shown that ischemic heart disease is particularly high in patients with diabetes (Robertson, et al., *Lab Invest.*, 18:538-551 (1968); Kannel et al, *J. Am. Med. Assoc.*, 241:2035-2038 (1979); Kannel et al., *Diab. Care*, 2:120-126 (1979)). In addition, studies have shown that atherosclerosis in patients with diabetes is more accelerated and extensive than in patients not suffering from diabetes (see e.g. Waller et al., *Am. J. Med.*, 69:498-506 (1980); Crall et al, *Am. J. Med.* 64:221-230 (1978); Hamby et al., *Chest*, 2:251-257 (1976); and Pyorala et al., *Diab. Metab. Rev.*, 3:463-524 (1978)). Although the reasons for accelerated atherosclerosis in the setting of diabetes are many, it has been shown that reduction of AGEs can reduce plaque formation.

For example, the RAGE fusion proteins of the present invention may also be used to treat stroke. When TTP-4000 was compared to sRAGE in a disease relevant animal model of stroke, TTP-4000 was found to provide a significantly greater reduction in infarct volume. In this model, the middle carotid artery of a mouse is ligated and then reperfused to form an infarct. To assess the efficacy of RAGE fusion proteins to treat or prevent stroke, mice were treated with sRAGE or TTP-4000 or control immunoglobulin just prior to reperfusion. As can be seen in Table 2, TTP-4000 was more efficacious than sRAGE in limiting the area of infarct in these animals suggesting that TTP-4000, because of its better half-life in plasma, was able to maintain greater protection than sRAGE.

TABLE 2

Reduction of Infarct in Stroke

|  | % Reduction of Infarct** |
| --- | --- |
| sRAGE | 15%* |
| TTP-4000 (300 μg) | 38%* |
| TTP-4000 (300 μg) | 21%* |
| TTP-4000 (300 μg) | 10%* |
| IgG Isotype control (300 μg) | 4% |

*Significant to p < 0.001;
**Compared to saline

In another embodiment, the RAGE fusion proteins of the present invention may be used to treat cancer. In one embodiment, the cancer treated using the RAGE fusion proteins of the present invention comprises cancer cells that express RAGE. For example, cancers that may be treated with the RAGE fusion protein of the present invention include some lung cancers, some gliomas, some papillomas, and the like. Amphoterin is a high mobility group I nonhistone chromosomal DNA binding protein (Rauvala et al., *J. Biol. Chem.*, 262:16625-16635 (1987); Parkikinen et al., *J. Biol. Chem.* 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi et al., *Nature* 405:354-360 (2000)), and spontaneously arising papillomas in mice expressing the v-Ha-ras transgene (Leder et al., *Proc. Natl. Acad. Sci.*, 87:9178-9182 (1990)).

In yet another embodiment, the RAGE fusion proteins of the present invention may be used to treat inflammation. In alternate embodiments, the RAGE fusion proteins of the present invention may be used to treat inflammation associated with inflammatory bowel disease, inflammation associated with rheumatoid arthritis, inflammation associated with psoriasis, inflammation associated with multiple sclerosis, inflammation associated with hypoxia, inflammation associated with stroke, inflammation associated with heart attack, inflammation associated with hemorrhagic shock, inflammation associated with sepsis, inflammation associated with organ transplantation, inflammation associated with impaired wound healing, or inflammation associated with rejection of self (e.g., autoimmune) or non-self (e.g., transplanted) cells, tissue, or organs.

For example, following thrombolytic treatment, inflammatory cells such as granulocytes infiltrate the ischemic tissue and produce oxygen radicals that can destroy more cells than were killed by the hypoxia. Inhibiting the receptor on the neutrophil responsible for the neutrophils being able to infiltrate the tissue with antibodies or other protein antagonists has been shown to ameliorate the response. Since RAGE is a ligand for this neutrophil receptor, a RAGE fusion protein containing a fragment of RAGE may act as a decoy and prevent the neutrophil from trafficking to the reperfused site and thus prevent further tissue destruction. The role of RAGE in prevention of inflammation may be indicated by studies showing that sRAGE inhibited neointimal expansion in a rat model of restenosis following arterial injury in both diabetic and normal rats, presumably by inhibiting endothelial, smooth muscle cell proliferation and macrophage activation via RAGE (Zhou et al., *Circulation*, 107:2238-2243 (2003)). In addition, sRAGE inhibited models of inflammation including delayed-type hypersensitivity, experimental autoimmune encephalitis and inflammatory bowel disease (Hofman et al., *Cell*, 97:889-901 (1999)).

In an embodiment, the RAGE fusion proteins of the present invention may be used to treat auto-immune based disorders. For example, in an embodiment, the RAGE fusion proteins of the present invention may be used to treat kidney failure. Thus, the RAGE fusion proteins of the present invention may be used to treat systemic lupus nephritis or inflammatory lupus nephritis. For example, the S100/calgranulins have been shown to comprise a family of closely related calcium-binding polypeptides characterized by two EF-hand regions linked by a connecting peptide (Schafer et al., *TIBS*, 21:134-140 (1996); Zimmer et al., *Brain Res. Bull.*, 37:417-429 (1995); Rammes et al., *J. Biol. Chem.*, 272:9496-9502 (1997); Lugering et al., *Eur. J. Clin. Invest.*, 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S-100/calgranulins) has a proximal role in the inflammatory cascade.

Type I diabetes is an autoimmune disorder that may be prevented or ameliorated by treatment with the RAGE fusion proteins of the present invention. For example, it has been shown that sRAGE may allow for the transfer of splenocytes from non-obese diabetic (NOD) mice to NOD-mice with severe combined immunodeficiency (NOD-scid mice). NOD-scid mice do not display diabetes spontaneously, but require the presence of immunocytes capable of destroying islet cells such that diabetes is then induced. It was found that NOD-scid recipients treated with sRAGE displayed reduced onset of diabetes induced by splenocytes transferred from a diabetic (NOD) mouse as compared to NOD-scid recipients not treated with sRAGE (U.S. Patent Publication 2002/0122799). As stated in US 2002/0122799, the experimental results using sRAGE in this model are relevant to human disease such as clinical settings in which future immune therapies and islet transplantation may occur.

Thus, in an embodiment, a RAGE fusion protein of the present invention may be used to treat inflammation associated with transplantation of at least one of an organ, a tissue, or a plurality of cells from a first site to a second site. The first and second sites may be in different subjects, or in the same subject. In alternate embodiments, the transplanted cells, tissue or organ comprise cells of a pancreas, skin, liver, kidney, heart, lung, bone marrow, blood, bone, muscle, endothelial cells, artery, vein, cartilage, thyroid, nervous system, or stem cells. For example, administration of the RAGE fusion proteins of the present invention may be used to facilitate transplantation of islet cells from a first non-diabetic subject to a second diabetic subject.

In another embodiment, the present invention may provide a method of treating osteoporosis by administering to a subject a therapeutically effective amount of a RAGE fusion protein of the present invention. (Zhou et al., *J. Exp. Med.*, 203:1067-1080 (2006)). In an embodiment, the method of treating osteoporosis may further comprise the step of increasing bone density of the subject or reducing the rate of decrease in bone density of a subject.

Thus, in various selected embodiments, the present invention may provide a method for inhibiting the interaction of an AGE with RAGE in a subject by administering to the subject a therapeutically effective amount of a RAGE fusion protein of the present invention. The subject treated using the RAGE fusion proteins of the present invention may be an animal. In an embodiment, the subject is a human. The subject may be suffering from an AGE-related disease such as diabetes, diabetic complications such as nephropathy, neuropathy, retinopathy, foot ulcer, amyloidoses, or renal failure, and inflammation. Or, the subject may be an individual with Alzheimer's disease. In an alternative embodiment, the subject may be an individual with cancer. In yet other embodiments, the subject may be suffering from systemic lupus erythmetosis or inflammatory lupus nephritis. Other diseases may be mediated by RAGE and thus, may be treated using the RAGE fusion proteins of the present invention. Thus, in additional alternative embodiments of the present invention, the RAGE fusion proteins may be used for treatment of Crohn's disease, arthritis, vasculitis, nephropathies, retinopathies, and neuropathies in human or animal subjects. In other embodiments, inflammation involving both autoimmune responses (e.g., rejection of self) and non-autoimmune responses (e.g., rejection of non-self) may be mediated by RAGE and thus, may be treated using the RAGE fusion proteins of the present invention.

A therapeutically effective amount may comprise an amount which is capable of preventing the interaction of RAGE with an AGE or other types of endogenous RAGE ligands in a subject. Accordingly, the amount will vary with the subject being treated. Administration of the compound may be hourly, daily, weekly, monthly, yearly, or as a single event. In various alternative embodiments, the effective amount of the RAGE fusion protein may range from about 1 ng/kg body weight to about 100 mg/kg body weight, or from about 10 µg/kg body weight to about 50 mg/kg body weight, or from about 100 μg/kg body weight to about 20 mg/kg body weight. The actual effective amount may be established by dose/response assays using methods standard in the art (Johnson et al., *Diabetes.* 42: 1179, (1993)). Thus, as is known to those in the art, the effective amount may depend on bioavailability, bioactivity, and biodegradability of the compound.

Compositions

The present invention may comprise a composition comprising a RAGE fusion protein of the present invention mixed with a pharmaceutically acceptable carrier. The RAGE fusion protein may comprise a RAGE polypeptide linked to a second, non-RAGE polypeptide. In one embodiment, the RAGE fusion protein may comprise a RAGE ligand binding site. In an embodiment, the ligand binding site comprises the most N-terminal domain of the RAGE fusion protein. The RAGE ligand binding site may comprise the V domain of RAGE, or a portion thereof. In an embodiment, the RAGE ligand binding site comprises SEQ ID NO: 9 or a sequence at least 90% identical thereto, or SEQ ID NO: 10 or a sequence at least 90% identical thereto, or SEQ ID NO: 47 or a sequence at least 90% identical thereto.

In an embodiment, the RAGE polypeptide may be linked to a polypeptide comprising an immunoglobulin domain or a portion (e.g., a fragment thereof) of an immunoglobulin domain. In one embodiment, the polypeptide comprising an immunoglobulin domain comprises at least a portion of at least one of the $C_H2$ or the $C_H3$ domains of a human IgG.

In certain embodiments, the RAGE fusion protein comprises an amino acid sequence as set forth in SEQ ID NO: 56 or SEQ ID NO: 57, or a sequence at least 70%, 75%, 80%, 85%, 90%, 95%, 96%, 97%, 98%, or 99% identical thereto. For example, in some embodiments, a sequence at least 90% identical to SEQ ID NO: 56 or SEQ ID NO: 57 comprises the sequence of SEQ ID NO: 56 or SEQ ID NO: 57 without the C-terminal lysine.

The RAGE protein or polypeptide may comprise full-length human RAGE (e.g., SEQ ID NO: 1), or a fragment of human RAGE. In an embodiment, the RAGE polypeptide does not include any signal sequence residues. The signal sequence of RAGE may comprise either residues 1-22 or residues 1-23 of full length RAGE (SEQ ID NO: 1). In alternate embodiments, the RAGE polypeptide may comprise a sequence that is at least 70%, 75%, 80%, 85%, 90%, 95%, 96%, 97%, 98%, or 99% identical to human RAGE, or a fragment thereof. For example, in one embodiment, the RAGE polypeptide may comprise human RAGE, or a fragment thereof, with Glycine as the first residue rather than a Methionine (see e.g., Neeper et al., (1992)). Or, the human RAGE may comprise full-length RAGE with the signal sequence removed (e.g., SEQ ID NO: 2 or SEQ ID NO: 3) (FIGS. 1A and 1B) or a portion of that amino acid sequence.

The RAGE fusion proteins of the present invention may also comprise sRAGE (e.g., SEQ ID NO: 4), a polypeptide at least 90% identical to sRAGE, or a fragment of sRAGE. For example, the RAGE polypeptide may comprise human sRAGE, or a fragment thereof, with Glycine as the first residue rather than a Methionine (see e.g., Neeper et al., (1992)). Or, the human RAGE may comprise sRAGE with the signal sequence removed (See e.g., SEQ ID NO: 5, SEQ ID NO: 6 or SEQ ID NO: 45 in FIG. 1) or a portion of that amino acid sequence. In other embodiments, the RAGE protein may comprise a V domain (See e.g., SEQ ID NO: 7, SEQ ID NO: 8 or SEQ ID NO: 46 in FIG. 1). Or, a sequence at least 90% identical to the V domain or a fragment thereof may be used. Or, the RAGE protein may comprise a fragment of RAGE comprising a portion of the V domain (See e.g., SEQ ID NO: 9, SEQ ID NO: 10, or SEQ ID NO: 47 in FIG. 1). In an embodiment, the ligand binding site may comprise SEQ ID NO: 9, or a sequence at least 90% identical thereto, or SEQ ID NO: 10, or a sequence at least 90% identical thereto, or SEQ ID NO: 47, or a sequence at least 90% identical thereto. In yet another embodiment, the RAGE fragment is a synthetic peptide.

For example, the RAGE polypeptide may comprise amino acids 23-116 of human RAGE (SEQ ID NO: 7) or a sequence at least 90% identical thereto, or amino acids 24-116 of human RAGE (SEQ ID NO: 8) or a sequence at least 90% identical thereto, or amino acids 24-116 of human RAGE where Q24 cyclizes to form pE (SEQ ID NO: 46), or a sequence at least 90% identical thereto, corresponding to the V domain of RAGE. Or, the RAGE polypeptide may comprise amino acids 124-221 of human RAGE (SEQ ID NO: 11) or a sequence at least 90% identical thereto, corresponding to the C1 domain of RAGE. In another embodiment, the RAGE polypeptide may comprise amino acids 227-317 of human RAGE (SEQ ID NO: 12) or a sequence at least 90% identical thereto, corresponding to the C2 domain of RAGE. Or, the RAGE polypeptide may comprise amino acids 23-123 of human RAGE (SEQ ID NO: 13) or a sequence at least 90% identical thereto, or amino acids 24-123 of human RAGE (SEQ ID NO: 14) or a sequence at least 90% identical thereto, corresponding to the V domain of RAGE and a downstream interdomain linker. Or, the RAGE polypeptide may comprise amino acids 24-123 of human RAGE where Q24 cyclizes to form pE (SEQ ID NO: 48), or a sequence at least 90% identical thereto. Or, the RAGE polypeptide may comprise amino acids 23-226 of human RAGE (SEQ ID NO: 17) or a sequence at least 90% identical thereto, or amino acids 24-226 of human RAGE (SEQ ID NO: 18) or a sequence at least 90% identical thereto, corresponding to the V-domain, the C1 domain and the interdomain linker linking these two domains. Or, the RAGE polypeptide may comprise amino acids 24-226 of human RAGE where Q24 cyclizes to form pE (SEQ ID NO: 50), or a sequence 90% identical thereto. Or, the RAGE polypeptide may comprise amino acids 23-339 of human RAGE (SEQ ID NO: 5) or a sequence at least 90% identical thereto, or 24-339 of human RAGE (SEQ ID NO: 6) or a sequence at least 90% identical thereto, corresponding to sRAGE (i.e., encoding the V, C1, and C2 domains and interdomain linkers). Or, the RAGE polypeptide may comprise amino acids 24-339 of human RAGE where Q24 cyclizes to form pE (SEQ ID NO: 45), or a sequence at least 90% identical thereto. Or, fragments of each of these sequences may be used.

In another embodiment, the ligand binding site may comprise amino acids 22-51 of SEQ ID NO: 1. In another embodiment, the ligand binding site may comprise amino acids 23-51 of SEQ. ID NO: 1. In another embodiment, the ligand binding site may comprise amino acids 31-51 of SEQ ID NO: 1. In another embodiment, the ligand binding site may comprise amino acids 31-116 of SEQ ID NO: 1. For example, the ligand binding site may comprise, a RAGE V domain or a portion thereof such as the RAGE ligand binding domain (e.g., amino acids 1-118, 23-118, 24-118, 31-118, 1-116, 23-116, 24-116, 31-116, 1-54, 23-54, 24-54, 31-54, 1-53, 23-53, 24-53, or 31-53 of SEQ ID NO: 1, or fragments thereof) (FIG. 1). Or fragments of the polypeptides that functionally bind a RAGE ligand may be used. Or, a sequence at least 70%, 75%, 80%, 85%, 90%, 95%, 97%, 98% or 99% identical to the RAGE V domain or a fragment thereof (e.g., as described above) may be used. Further, as is known in the art, in embodiments where the N-terminus of the fusion protein is glutamine, as for example upon removal of the signal sequence comprising residues 1-23 of SEQ ID NO: 1 (e.g., Q24 for a polypeptide comprise amino acids 24-118 or SEQ ID NO: 1), the glutamine may cyclize to form pyroglutamic acid (pE).

The RAGE fusion protein may include several types of peptides that are not derived from RAGE or a fragment thereof. The second polypeptide of the RAGE fusion protein may comprise a polypeptide derived from an immunoglobulin. The heavy chain (or portion thereof) may be derived from any one of the known heavy chain isotypes: IgG (γ), IgM (μ), IgD (δ), IgE (ε), or IgA (α). In addition, the heavy chain (or portion thereof) may be derived from any one of the known heavy chain subtypes: IgG1 (γ1), IgG2 (γ2), IgG3 (γ3), IgG4 (γ4), IgA1 (α1), IgA2 (α2), or mutations of these isotypes or subtypes that alter the biological activity. The second polypeptide may comprise the $C_H2$ and $C_H3$ domains of a human IgG1 or a portion of either, or both, of these domains. As an example embodiments, the polypeptide comprising the $C_H2$ and $C_H3$ domains of a human IgG1 or a portion thereof may comprise SEQ ID NO: 40 or a portion thereof. In an embodiment, the polypeptide comprising the $C_H2$ and $C_H3$ domains of a human IgG1 or a portion thereof may comprise SEQ ID NO: 38, or a portion thereof. For example, the polypeptide comprising the $C_H2$ and $C_H3$ domains of a human IgG1 or a portion thereof may comprise SEQ ID NO: 38 or SEQ ID NO: 40 with the terminal lysine (K) removed. The immunoglobulin peptide may be encoded by the nucleic acid sequence of SEQ ID NO: 39 or SEQ ID NO: 41. The immunoglobulin sequence in SEQ ID NO: 38 or SEQ ID NO: 40 may also be encoded by SEQ ID NO: 52 or SEQ ID NO: 53, respectively.

The Fc portion of the immunoglobulin chain may be proinflammatory in vivo. Thus, in one embodiment, the RAGE fusion protein of the present invention comprises an interdomain linker derived from RAGE rather than an interdomain hinge polypeptide derived from an immunoglobulin.

Thus in one embodiment, the RAGE fusion protein may further comprise a RAGE polypeptide directly linked to a polypeptide comprising a $C_H2$ domain of an immunoglobulin, or a fragment thereof. In one embodiment, the $C_H2$ domain, or a fragment thereof comprises SEQ ID NO: 42. In an embodiment, the fragment of SEQ ID NO: 42 comprises SEQ ID NO: 42 with the first ten amino acids removed.

In one embodiment, the RAGE polypeptide comprises a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a fragment thereof. The polypeptide comprising a $C_H2$ domain of an immunoglobulin, or a portion thereof, may comprise the $C_H2$ and $C_H3$ domains of a human IgG1, or a portion of both, or either, of these domains. As example embodiments, the polypeptide comprising the $C_H2$ and $C_H3$ domains of a human IgG1, or a portion thereof, may comprise SEQ ID NO: 40 or a portion thereof. In an embodiment, the polypeptide comprising the $C_H2$ and $C_H3$ domains of a human IgG1 or a portion thereof may comprise SEQ ID NO: 38, or a portion thereof. For example, the polypeptide comprising the $C_H2$ and $C_H3$ domains of a human IgG1 or a portion thereof may comprise SEQ ID NO: 38 or SEQ ID NO: 40 with the terminal lysine (K) removed.

The RAGE fusion protein of the present invention may comprise a single or multiple domains from RAGE. Also, the RAGE polypeptide comprising an interdomain linker linked to a RAGE immunoglobulin domain may comprise a fragment of a full-length RAGE protein. For example, in one embodiment, the RAGE fusion protein may comprise two immunoglobulin domains derived from RAGE protein and two immunoglobulin domains derived from a human Fc polypeptide. The RAGE fusion protein may comprise a first RAGE immunoglobulin domain and a first interdomain linker linked to a second RAGE immunoglobulin domain and a second RAGE interdomain linker, such that the N-terminal amino acid of the first interdomain linker is linked to the C-terminal amino acid of the first RAGE immunoglobulin domain, the N-terminal amino acid of the second RAGE immunoglobulin domain is linked to C-terminal amino acid of the first interdomain linker, the N-terminal amino acid of the second interdomain linker is linked to C-terminal amino acid of the RAGE second immunoglobulin domain, and the C-terminal amino acid of the RAGE second interdomain linker is directly linked to the N-terminal amino acid of the polypeptide comprising a $C_H2$ immunoglobulin domain or fragment thereof. For example, the RAGE polypeptide may comprise amino acids 23-251 of human RAGE (SEQ ID NO: 19) or a sequence at least 90% identical thereto, or amino acids 24-251 of human RAGE (SEQ ID NO: 20) or a sequence at least 90% identical thereto, or amino acids 24-251 of human RAGE where Q24 cyclizes to form pE, or a sequence at least 90% identical thereto (SEQ ID NO: 51), corresponding to the V-domain, the C1 domain, the interdomain linker linking these two domains, and a second interdomain linker downstream of C1. In one embodiment, a nucleic acid construct comprising SEQ ID NO: 30 or a fragment thereof may encode for a four domain RAGE fusion protein. In another embodiment, nucleic acid construct comprising SEQ ID NO: 54 may encode for a four domain RAGE fusion protein, where silent base changes for the codons that encode for proline (CCG to CCC) and glycine (GGT to GGG) at the C-terminus of the sequence are entered to remove a cryptic RNA splice site near the terminal codon (i.e., at nucleotides 1375-1380 of SEQ ID NO: 30 are modified to generate SEQ ID NO: 54).

Alternatively, a three domain RAGE fusion protein may comprise one immunoglobulin domain derived from RAGE and two immunoglobulin domains derived from a human Fc polypeptide. For example, the RAGE fusion protein may comprise a single RAGE immunoglobulin domain linked via a RAGE interdomain linker to the N-terminal amino acid of the polypeptide comprising a $C_H2$ immunoglobulin domain or a fragment thereof. For example, the RAGE polypeptide may comprise amino acids 23-136 of human RAGE (SEQ ID NO: 15) or a sequence at least 90% identical thereto or amino acids 24-136 of human RAGE (SEQ ID NO: 16) or a sequence at least 90% identical thereto, or amino acids 24-136 of human RAGE where Q24 cyclizes to form pE, or a sequence at least 90% identical thereto (SEQ ID NO: 49), corresponding to the V domain of RAGE and a downstream interdomain linker. In one embodiment, a nucleic acid construct comprising SEQ ID NO: 31 or a fragment thereof may encode for a three domain RAGE fusion protein. In another embodiment, nucleic acid construct comprising SEQ ID NO: 55 may encode for a three domain RAGE fusion protein, where silent base changes for the codons that encode for proline (CCG to CCC) and glycine (GGT to GGG) at the C-terminus of the sequence are entered to remove a cryptic RNA splice site near the terminal codon (i.e., nucleotides 1030-1035 of SEQ ID NO: 31 are modified to generate SEQ ID NO: 55).

A RAGE interdomain linker fragment may comprise a peptide sequence that is naturally downstream of, and thus, linked to, a RAGE immunoglobulin domain. For example, for the RAGE V domain, the interdomain linker may comprise amino acid sequences that are naturally downstream from the V domain. In an embodiment, the linker may comprise SEQ ID NO: 21, corresponding to amino acids 117-123 of full-length RAGE. Or, the linker may comprise a peptide having additional portions of the natural RAGE sequence. For example, an interdomain linker comprising several amino acids (e.g., 1-3, 1-5, or 1-10, or 1-15 amino acids) upstream and downstream of SEQ ID NO: 21 may be used. Thus, in one embodiment, the interdomain linker comprises SEQ ID NO: 23 comprising amino acids 117-136 of full-length RAGE. Or, fragments of SEQ ID NO: 21 deleting, for example, 1, 2, or 3, amino acids from either end of the linker may be used. In alternate embodiments, the linker may comprise a sequence that is at least 70%, 75%, 80%, 85%, 90%, 95%, 96%, 97%, 98%, or 99% identical to SEQ ID NO: 21 or SEQ ID NO: 23.

For the RAGE C1 domain, the linker may comprise a peptide sequence that is naturally downstream of the C1 domain. In an embodiment, the linker may comprise SEQ ID NO: 22, corresponding to amino acids 222-251 of full-length RAGE. Or, the linker may comprise a peptide having additional portions of the natural RAGE sequence. For example, a linker comprising several (1-3, 1-5, or 1-10, or 1-15 amino acids) amino acids upstream and downstream of SEQ ID NO: 22 may be used. Or, fragments of SEQ ID NO: 22 may be used, deleting for example, 1-3, 1-5, or 1-10, or 1-15 amino acids from either end of the linker. For example, in one embodiment, a RAGE interdomain linker may comprise SEQ ID NO: 24, corresponding to amino acids 222-226. In alternate embodiments, the linker may comprise a sequence that is at least 70%, 75%, 80%, 85%, 90%, 95%, 96%, 97%, 98%, or 99% identical to SEQ ID NO: 22 or SEQ ID NO: 24.

Or an interdomain linker may comprise SEQ ID NO: 44, corresponding to RAGE amino acids 318-342. In alternate embodiments, the linker may comprise a sequence that is at least 70%, 75%, 80%, 85%, 90%, 95%, 96%, 97%, 98%, or 99% identical to SEQ ID NO: 44.

Pharmaceutically acceptable carriers may comprise any of the standard pharmaceutically accepted carriers known in the art. In one embodiment, the pharmaceutical carrier may be a liquid and the RAGE fusion protein or nucleic acid construct may be in the form of a solution. In another embodiment, the pharmaceutically acceptable carrier may be a solid in the form of a powder, a lyophilized powder, or a tablet. Or, the pharmaceutical carrier may be a gel, suppository, or cream. In alternate embodiments, the carrier may comprise a liposome, a microcapsule, a polymer encapsulated cell, or a virus. Thus, the term pharmaceutically acceptable carrier encompasses, but is not limited to, any of the standard pharmaceutically accepted carriers, such as water, alcohols, phosphate buffered saline solution, sugars (e.g., sucrose or mannitol), oils or emulsions such as oil/water emulsions or a trigyceride emulsion, various types of wetting agents, tablets, coated tablets and capsules.

In certain embodiments, the RAGE fusion proteins may be present in a neutral form (including zwitter ionic forms) or as a positively or negatively-charged species. In some embodiments, the RAGE fusion proteins may be complexed with a counterion to form a pharmaceutically acceptable salt.

The terms "pharmaceutically acceptable salt" refer to a complex comprising one or more RAGE fusion proteins and one or more counterions, where the counterions are derived from pharmaceutically acceptable inorganic and organic acids and bases.

Pharmaceutically acceptable inorganic bases include metallic ions. More preferred metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the RAGE fusion proteins of the present invention can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl) piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino) ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

Administration of the RAGE fusion proteins of the present invention may employ various routes. Thus, administration of the RAGE fusion protein of the present invention may employ intraperitoneal (IP) injection. Alternatively, the RAGE fusion protein may be administered orally, intranasally, or as an aerosol. In another embodiment, administration is intravenous (IV). The RAGE fusion protein may also be injected subcutaneously. In another embodiment, administration of the RAGE fusion protein is intra-arterial. In another embodiment, administration is sublingual. Also, administration may employ a time-release capsule. For example, subcutaneous administration may be useful to treat chronic disorders when the self-administration is desirable.

In a further aspect of the present invention, the RAGE fusion proteins of the invention may be utilized in adjuvant therapeutic or combination therapeutic treatments with other known therapeutic agents. The following is a non-exhaustive listing of adjuvants and additional therapeutic agents which may be utilized in combination with the RAGE fusion protein modulators of the present invention:

Pharmacologic Classifications of Anticancer Agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil, Azathioprine, 6-Mercaptopurine, and cytotoxic cancer chemotherapeutic agents
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins Pharmacologic Classifications of Treatment for Rheumatoid Arthritis
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids, such as beclomethasone, methylprednisolone, betamethasone, prednisone, dexamethasone, and hydrocortisone Pharmacologic Classifications of Treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic Classifications of Treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In an embodiment, the compositions of the present invention may comprise a therapeutically effective amount of a RAGE fusion protein in combination with a single or multiple additional therapeutic agents. In addition to the agents heretofore described, the following therapeutic agents may be used in combination with the RAGE fusion proteins of the present invention: immunosuppressants, such as cyclosporin, tacrolimus, rapamycin and other FK-506 type immunosuppressants.

In one embodiment, the present invention may therefore provide a method of treating RAGE mediated diseases, the method comprising administering to a subject in need thereof, a therapeutically effective amount of a RAGE fusion protein in combination with therapeutic agents selected from the group consisting of alkylating agents, antimetabolites, plant alkaloids, antibiotics, hormones, biologic response modifiers, analgesics, NSAIDs, DMARDs, biologic response modifiers (e.g., glucocorticoids), sulfonylureas, biguanides, insulin, cholinesterase inhibitors, antipsychotics, antidepressants, anticonvulsants, and immunosuppressants, such as cyclosporin, tacrolimus, rapamycin and other FK-506 type immunosuppressants. In a further embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, biologic response modifiers (e.g., glucocorticoids), sulfonylureas, biguanides, insulin, cholinesterase inhibitors, antipsychotics, antidepressants, anticonvulsants, and immunosuppressants, such as cyclosporin, tacrolimus, rapamycin and other FK-506 type immunosuppressants.

Lyophilized Formulations

In other embodiments, the present invention also provides formulations comprising a RAGE fusion protein. Embodiments of the formulations may comprise a lyophilized mixture of a lyoprotectant, a RAGE fusion protein, and buffer.

A variety of lyoprotectants may be used in the lyophilized RAGE fusion protein formulations of the present invention. In some embodiments, the lyoprotectant may comprise a non-reducing sugar. For example, the non-reducing sugar may comprise sucrose, mannitol, or trehalose. Also, a variety of buffers may be used in the lyophilized RAGE fusion protein formulation. In certain embodiments, the buffer may comprise histidine.

The lyophilized RAGE fusion protein may comprise additional components. In certain embodiments, the RAGE fusion protein formulation may further comprise at least one of a surfactant, a chelating agent or a bulking agent. In one embodiment, the reconstituted RAGE fusion protein formulation comprises about 40-100 mg/mL RAGE fusion protein comprising the sequence as set forth in SEQ ID NOs: 32, 33, 34, 56, 35, 36, 37, or 57; about 2 mM to about 50 mM histidine; about 60 mM to about 65 mM sucrose; about 0.001% to about 0.05% Tween 80; and a pH of about 6.0 to 6.5. For example, the reconstituted RAGE fusion protein formulation may, in certain embodiments, comprise about 40-50 mg/mL RAGE fusion protein comprising the sequence as set forth in SEQ ID NOs: 32, 33, 34, 56, 35, 36, 37, or 57; about 10 mM histidine; about 65 mM sucrose; about 0.01% Tween 80; and at a pH of about 6.0. Or, other concentrations of the RAGE fusion protein may be used as further described herein.

In one embodiment, the present invention comprises a reconstituted formulation comprising a lyophylized RAGE fusion protein reconstituted in a diluent, wherein the RAGE fusion protein concentration in the reconstituted formulation is within the range from about 1 mg/mL to about 400 mg/mL. Or, other concentrations of the RAGE fusion protein may be used as described herein.

In other embodiments, the present invention may also comprise methods for preparing stable reconstituted formulation of a RAGE fusion protein. The reconstituted formulation may comprise a concentration that is suitable for direct use (e.g., direct administration to a subject) or that may be further diluted and/or mixed with a delivery agent.

In certain embodiments, the method may comprise reconstituting a lyophilized mixture of the RAGE fusion protein and a lyoprotectant in a diluent such that the RAGE fusion protein concentration in the reconstituted formulation is in a range from about 1 mg/mL to about 400 mg/mL. Or, other concentrations as described herein may be used as described herein.

A variety of lyoprotectants may be used in the reconstituted RAGE fusion protein formulations of the present invention. In some embodiments, the lyoprotectant may comprise a non-reducing sugar. For example, the non-reducing sugar may comprise sucrose, mannitol, or trehalose. Also, a variety of buffers may be used in the lyophilized RAGE fusion protein formulation. In certain embodiments, the buffer may comprise histidine.

The reconstituted RAGE fusion protein formulation may comprise additional components. In certain embodiments, the RAGE fusion protein formulation may further comprise at least one of a surfactant, a chelating agent or a bulking agent. In one embodiment, the reconstituted RAGE fusion protein formulation comprises about 40-100 mg/mL RAGE fusion protein comprising the sequence as set forth in SEQ ID NOs: 32, 33, 34, 56, 35, 36, 37, or 57; about 2 mM to about 50 mM histidine; about 60 mM to about 65 mM sucrose; about 0.001% to about 0.05% Tween 80; and a pH of about 6.0 to 6.5. For example, the reconstituted RAGE fusion protein formulation may, in certain embodiments, comprise about 40-50 mg/mL RAGE fusion protein comprising the sequence as set forth in SEQ ID NOs: 32, 33, 34, 56, 35, 36, 37, or 57; about 10 mM histidine, about 65 mM sucrose, about 0.01% Tween 80, and at a pH of about 6.0.

A variety of diluents suitable for pharmaceuticals may be used to reconstitute the lyophilized RAGE fusion protein. In an embodiment, the lyophilized RAGE fusion protein is sterile. Also in an embodiment, the diluent is sterile. In one embodiment, the diluent may comprise water for injection (WFI). Also, in certain embodiments, the amount of diluent added is based on the therapeutic dosage and the pharmacokinetic profile of the RAGE fusion protein, as well as the biocompatibility of the formulation and carrier being administered. In an embodiment, the reconstituted formulation is isotonic.

The RAGE fusion protein formulation may comprise a stable therapeutic agent that is formulated for use in a clinic or as a prescription medicine. For example, in certain embodiments, the reconstituted RAGE fusion protein formulation may exhibit less than 10%, or less than 5%, or less than 3% decomposition after one week at 40 degrees Centigrade.

Also, the RAGE fusion protein formulation may be stable upon reconstitution in a diluent. In certain embodiments, less than about 10%, or about 5%, or about 4%, or about 3%, or about 2%, or about 1% of the RAGE fusion protein is present as an aggregate in the RAGE fusion protein formulation.

The reconstituted RAGE fusion protein formulation may be suitable for administration by various routes and as is required for treatment of the RAGE-mediated disorder of interest. In certain embodiments, the reconstituted RAGE fusion protein formulation is suitable for at least one of intravenous, intraperitoneal, or subcutaneous administration of the formulation to a subject.

For example, in certain embodiments, the present invention may comprise a stable reconstituted formulation comprising a RAGE fusion protein in a concentration of at least 10 mg/mL, or at least 20 mg/mL, or at least 50 mg/mL and a diluent, where the reconstituted formulation has been prepared from a lyophilized mixture of the RAGE fusion protein and a lyoprotectant. In alternate embodiments, the RAGE fusion protein concentration in the reconstituted formulation may be at least 100 mg/mL, or at least 200 mg/mL, or at least 400 mg/mL. In yet alternate embodiments, the RAGE fusion protein concentration in the reconstituted formulation is in an amount within the range of about 0.5 mg/mL to about 400 mg/mL, or about 1 mg/mL to about 200 mg/mL, or about 40 mg/mL to about 400 mg/mL, about 40 to 100 mg/mL, or about 40-50 mg/mL. The formulation may also comprise a buffer.

In yet other embodiments, the present invention may comprise articles of manufacture that include RAGE fusion proteins. For example, in certain embodiments, the article of manufacture may comprise a container which holds a lyophylized RAGE fusion protein, and instructions for reconstituting the lyophilized formulation with a diluent. In certain embodiments, the articles of manufacture may comprise a container which holds a formulation comprising a lyophilized mixture of a lyoprotectant, a RAGE fusion protein, and buffer. The article of manufacture may also comprise instructions for reconstituting the lyophilized formulation with a diluent.

A variety of lyoprotectants may be used in the articles of manufacture of the present invention. In some embodiments, the lyoprotectant may comprise a non-reducing sugar. For example, the non-reducing sugar may comprise sucrose, mannitol, or trehalose. Also, a variety of buffers may be used in the lyophilized RAGE fusion protein formulation. In certain embodiments, the buffer may comprise histidine.

The RAGE fusion protein formulation of the articles of manufacture of the present invention may comprise additional components. In certain embodiments, the lyophilized RAGE fusion protein formulation may further comprise at least one of a surfactant, a chelating agent or a bulking agent. In one embodiment of the articles of manufacture of the present invention, upon reconstitution according to the instructions provided, the RAGE fusion protein formulation comprises about 40-100 mg/mL RAGE fusion protein comprising the sequence as set forth in SEQ ID NOs: 32, 33, 34, 56, 35, 36, 37, or 57; about 2 mM to about 50 mM histidine; about 60 mM to about 65 mM sucrose; about 0.001% to about 0.05% Tween 80; and a pH of about 6.0 to 6.5. For example, the reconstituted RAGE fusion protein formulation may, in certain embodiments, comprise about 40-50 mg/mL RAGE fusion protein comprising the sequence as set forth in SEQ ID NOs: 32, 33, 34, 56, 35, 36, 37, or 57; about 10 mM histidine; about 65 mM sucrose; about 0.01% Tween 80; and at a pH of about 6.0. Or other concentrations of the RAGE fusion protein may be used as described herein.

A variety of diluents suitable for pharmaceuticals may be provided for reconstituting the lyophilized RAGE fusion protein. In an embodiment, the lyophilized formulation is sterile. Alternatively or additionally, the diluent may be sterile. In one embodiment, the diluent may comprise water for injection (WFI). Thus, the article of manufacture may further comprise a second container which holds a diluent for reconstituting the lyophilized formulation, wherein the diluent is water for injection (WFI). In an embodiment, the reconstituted formulation is isotonic.

Also, in certain embodiments, the amount of diluent added is based on the therapeutic dosage and the pharmacokinetic profile of the RAGE fusion protein, as well as the biocompatibility of the formulation and carrier being administered. In alternate embodiment, the instructions are for reconstituting the lyophilized formulation so as to have the concentrations as described herein. For example, in certain embodiments, the instructions are for reconstituting the lyophilized formulation such that the RAGE fusion protein concentration in the reconstituted formulation is within the range from about 40 mg/mL to about 100 mg/mL.

The RAGE fusion protein formulation provided as the article of manufacture may comprise a stable therapeutic agent that is formulated for use in a clinic or as a prescription medicine. For example, in certain embodiments, when reconstituted according to the instructions provided, the RAGE fusion protein may exhibits less than 10%, or less than 5%, or less than 3% decomposition after one week at 40 degrees Centigrade. Also, the RAGE fusion protein formulation may be stable upon reconstitution in a diluent. In certain embodiments, less than about 10%, or about 5%, or about 4%, or about 3%, or about 2%, or about 1% of the RAGE fusion protein is present as an aggregate in the RAGE fusion protein formulation.

Also, in certain embodiments, when reconstituted according to the instructions provided, the reconstituted RAGE fusion protein formulation may be suitable for administration by various routes and as is required for treatment of the RAGE-mediated disorder of interest. In certain embodiments, the reconstituted RAGE fusion protein formulation is suitable for at least one of intravenous, intraperitoneal, or subcutaneous administration of the formulation to the subject.

In certain embodiments of the formulations, articles of manufacture, and methods of making formulations comprising a RAGE fusion protein, the RAGE fusion protein concentration in the reconstituted formulation may be at least 10 mg/mL, or at least 20 mg/mL, or at least 50 mg/mL. In alternate embodiments, the RAGE fusion protein concentration in the reconstituted formulation may be at least 100 mg/mL, or 200 mg/mL, or 400 mg/mL. For example, in alternate embodiments, the RAGE fusion protein concentration in the reconstituted formulation is at least about 0.5 to 400 mg/mL, or about 1 to 200 mg/mL, 40 to 400 mg/mL, 50 to 400 mg/mL, 40 to 100 mg/mL, 50 to 100 mg/mL, or about 40-50 mg/mL. For example, in one embodiment, the RAGE fusion protein is administered in a formulation as a sterile aqueous solution having a pH that ranges from about 5.0 to about 6.5 and comprising from about 1 mg/mL to about 200 mg/ml of RAGE fusion protein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

Any of the embodiments described herein may be used as the RAGE fusion protein in the formulations of the present invention. Thus, for each of the lyophilized formulations, reconstituted lyophilized formulations, or the methods of making the lyophilized formulations or reconstituted lyophilized formulations, or the articles of manufacture comprising either the lyophilized formulations or the reconstituted lyophilized formulations of the present invention, the RAGE fusion protein may comprise a sequence derived from a RAGE ligand binding site linked to an immunoglobulin polypeptide.

Thus, embodiments of the RAGE fusion protein may comprise a RAGE polypeptide directly linked to a polypeptide comprising a $C_H2$ domain of an immunoglobulin or a portion of a $C_H2$ domain of an immunoglobulin as described herein. In certain embodiments, the RAGE polypeptide may comprise a RAGE interdomain linker linked to a RAGE immunoglobulin domain such that the C-terminal amino acid of the RAGE immunoglobulin domain is linked to the N-terminal amino acid of the interdomain linker, and the C-terminal amino acid of the RAGE interdomain linker is directly linked to the N-terminal amino acid of a polypeptide comprising a $C_H2$ domain of an immunoglobulin, or a portion thereof. For example, certain embodiments of the fusion protein may comprise a first RAGE immunoglobulin domain and a first RAGE interdomain linker linked to a second RAGE immunoglobulin domain and a second RAGE interdomain linker, such that the N-terminal amino acid of the first interdomain linker is linked to the C-terminal amino acid of the first RAGE immunoglobulin domain, the N-terminal amino acid of the second RAGE immunoglobulin domain is linked to C-terminal amino acid of the first interdomain linker, the N-terminal amino acid of the second interdomain linker is linked to C-terminal amino acid of the second RAGE immunoglobulin domain, and the C-terminal amino acid of the RAGE second interdomain linker is directly linked to the N-terminal amino acid of the $C_H2$ immunoglobulin domain or a portion of a $C_H2$ domain of an immunoglobulin.

For example, in alternate embodiments, of the RAGE fusion protein, the RAGE polypeptide may comprise the amino acid sequence as set forth in SEQ ID NO: 10, or a sequence at least 90% identical thereto, or the amino acid sequence as set forth in SEQ ID NO: 47, or a sequence at least 70%, 75%, 80%, 85%, 90%, 95%, 96%, 97%, 98%, or 99% identical thereto. In other alternate embodiments, the RAGE fusion protein may comprise the amino acid sequence as set forth in at least one of SEQ ID NOs: 32, 33, 34, 35, 36, 37, 56, or 57, or a sequence at least 70%, 75%, 80%, 85%, 90%, 95%, 96%, 97%, 98%, or 99% identical thereto. For example, in certain embodiments, a sequence at least 90% identical to SEQ ID NOs: 32, 33, 34, 56, 35, 36, 37, or 57 comprises the polypeptide of SEQ ID NOs: 32, 33, 34, 56, 35, 36, 37, or 57 without the C-terminal lysine.

Preparation of Lyophilized Formulations

In another embodiment, the present invention provides a pre-lyophilized formulation, a lyophilized formulation, a reconstituted formulation, and methods for preparation thereof.

After preparation of a RAGE fusion protein of interest as described above, a "pre-lyophilized formulation" may be produced. The amount of RAGE fusion protein present in the pre-lyophilized formulation may be determined taking into account the desired dose volumes, mode(s) of administration etc. In an embodiment, the amount of fusion protein in the pre-lyophilized formulation may be greater than 1 mg/mL. Also in certain embodiments, the amount of fusion protein in the pre-lyophilized formulation may be less than about 5 mg/mL, 10 mg/mL, 50 mg/mL, 100 mg/mL, or 200 mg/mL.

In a further embodiment, the pre-lyophilized formulation may be a pH-buffered solution at a pH from about 4-8. In another embodiment, the pre-lyophilized formulation may be a pH-buffered solution at a pH from about 5-7. In another embodiment, the pre-lyophilized formulation may be a pH-buffered solution at a pH of less than 6.7. In another embodiment, the pre-lyophilized formulation may be a pH-buffered solution at a pH of about 6.0. Exemplary buffers include histidine, phosphate, Tris, citrate, succinate and other organic acids as described herein. The buffer concentration may be from about 1 mM to about 100 mM, or less than about 50 mM, or from about 2 mM to about 50 mM, or less than about 15 mM, or from about 3 mM to about 15 mM depending, for example, on the buffer and the desired isotonicity of the formulation (e.g. of the reconstituted formulation). In an embodiment, the buffer is histidine.

The lyoprotectant may be added to the pre-lyophilized formulation. In an embodiment, the lypoprotectant comprises a sugar. In another embodiment, the lyoprotectant comprises a non-reducing sugar. In another embodiment, the lyoprotectant comprises the non-reducing sugar sucrose. Or, the non-reducing sugar may comprise mannitol. Or, the non-reducing sugar may comprise trehalose. The amount of lyoprotectant in the pre-lyophilized formulation is generally such that upon reconstitution, the resulting formulation will be isotonic. However, a hypertonic reconstituted formulation may also be suitable, for example in formulations for peripheral parenteral administration. In addition, the amount of lyoprotectant should not be so low such that an unacceptable amount of degradation and/or aggregation of the protein occurs upon lyophilization. In alternate embodiments, an unacceptable amount of aggregation may be where 20%, or 10%, or 5% or more of the RAGE fusion protein is present as an aggregate in a formulation. An exemplary range of lyoprotectant concentration in the pre-lyophilized formulation may be less than about 400 mM. In another embodiment, the range of lyoprotectant concentration in the pre-lyophilized formulation is less than about 100 mM. In alternate embodiments, the range of lyoprotectant concentration in the pre-lyophilized formulation may therefore range from about 0.5 mM to 400 mM, or from about 2 mM to 200 mM, or from about 30 mM to about 150 mM, or from about 60-65 mM. Also, in some embodiments, the lyprotectant is added in an amount to render the reconstituted formulation isotonic.

The ratio of RAGE fusion protein to lyoprotectant in the pre-lyophilized formulation is selected for each RAGE fusion protein and lyoprotectant combination. In an embodiment of an isotonic reconstituted formulation with a high RAGE fusion protein concentration (e.g., greater than or equal to about 50 mg/mL), the molar ratio of lyoprotectant to RAGE fusion protein may be from about 50 to about 1500 moles lyoprotectant to 1 mole RAGE fusion protein. In another embodiment, the molar ratio of lyoprotectant to RAGE fusion protein may be from about 150 to about 1000 moles of lyoprotectant to 1 mole fusion protein. In another embodiment, the molar ratio of lyoprotectant to RAGE fusion protein may be from about 150 to about 300 moles of lyoprotectant to 1 mole RAGE fusion protein. For example, these ranges may be suitable where the lypoprotectant is a non-reducing sugar, such as sucrose, trehalose or mannitol.

In another embodiment of the invention, a surfactant may be added to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80) (Tween 20™ or Tween 80™); poloxamers (e.g. poloxamer 188). The amount of surfactant added is such that it reduces aggregation of the reconstituted protein and minimizes the formation of particulates after reconstitution. For example, the surfactant may be present in the pre-lyophilized formulation in an amount from about 0.001% to 0.5%. For example, in an embodiment where the surfactant comprises polysorbate 80, the surfactant may be present in the pre-lyophilized formulation in an amount from about 0.005% to 0.05%, or about 0.008% to 0.012%, or at about 0.01%. Alternatively, the surfactant may be present in the formulation so as to comprise a final concentration ranging from 0.001 mg/mL to about 100 mg/mL, or about 0.01 mg/mL to about 10 mg/mL.

In certain embodiments of the invention, a mixture of the lyoprotectant (such as sucrose or histidine) and a bulking agent (e.g. mannitol or glycine) may be used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counter ions such as sodium.

The RAGE fusion protein formulations of the present invention may also contain additional proteins as necessary for the particular indication being treated. The additional proteins may be selected such that the proteins each have complementary activities that do not adversely affect each other or the RAGE fusion protein. Such proteins are suitably present in combination in amounts that are effective for the purpose intended.

The RAGE fusion protein formulations of the present invention may be sterile for in vivo administration. This may be accomplished by filtration through sterile filtration membranes, prior to, or following, lyophilization and reconstitution.

After the RAGE fusion protein, lyoprotectant and other optional components are mixed together, the formulation may be lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −50 to 25° C. (provided the product remains frozen during primary drying) at a suitable pressure, ranging typically from about 50 to 250 mTorr. In an embodiment, the pressure is about 100 mTorr and the sample may be lyophilized between about −30 and 25° C. The formulation, size and type of the container holding the sample (e.g., glass vial) and the volume of liquid may dictate the time required for drying, which can range from a few hours to several days (e.g., 40-60 hrs). Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 2, 3, 5, 10, 20, 50, 100, or 250 cc vial. In an embodiment, the container is any container suitable to prepare a reconstituted formulation having a volume of less than or equal to 100 mL.

As a general proposition, lyophilization will result in a lyophilized formulation in which the moisture content thereof is less than about 5%. In an embodiment, the moisture content of the lyophilized formulation is less than about 3%. In another embodiment, the moisture content of the lyophilized formulation is less than about 1%.

Reconstitution of the Lyophilized Formulation

At the desired stage, typically when it is time to administer the RAGE fusion protein to a patient or subject, the lyophilized formulation may be reconstituted with a diluent such that the RAGE fusion protein concentration in the reconstituted formulation is about greater than 10 mg/mL, or greater than 20 mg/ml, or greater than 50 mg/mL, or about 30-50 mg/mL, or about 50 mg/mL. In alternate embodiments, the RAGE fusion protein concentration in the reconstituted formulation may be at least 100 mg/mL, or 200 mg/mL, or 400 mg/mL. For example, in alternate embodiments, the RAGE fusion protein concentration in the reconstituted formulation may be in the range of from about 1 mg/mL to about 600 mg/mL, or from about 1 mg/mL to about 500 mg/mL, or from about 1 mg/mL to about 400 mg/mL, or from about 1 mg/mL to about 200 mg/mL, or from about 10 mg/mL to about 400 mg/mL, or from about 10 mg/mL to about 200 mg/mL, or from about 40 mg/mL to about 400 mg/mL, or from about 40 mg/mL to about 200 mg/mL, or from about 50 mg/mL to about 400 mg/mL, or from about 50 mg/mL to about 200 mg/mL. In other embodiments, the RAGE fusion protein concentration in the reconstituted formulation is from about 40 mg/mL to about 100 mg/mL, or about 50 mg/mL to about 100 mg/mL, or about 40 mg/mL to about 50 mg/mL. Such RAGE fusion protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL RAGE fusion protein in the reconstituted formulation). Thus, in some embodiments, the concentration of fusion protein in the reconstituted formulation may the same or less than 2 times the concentration of the fusion protein in the pre-lyophilized formulation.

In certain embodiments, the fusion protein concentration in the reconstituted formulation is significantly higher than that in the pre-lyophilized formulation. For example, the fusion protein concentration in the reconstituted formulation may, in certain embodiments, be about 2-40, or 2-10, or 3-8 times that of the pre-lyophilized formulation. In an embodiment, the RAGE fusion protein concentration in the reconstituted formulation may be about 3-6 times that of the pre-lyophilized formulation. In another embodiment where the concentration of RAGE fusion protein in the pre-lyophilized formulation is about 15 mg/mL, the concentration of the RAGE fusion protein in the reconstituted formulation is greater than or equal to about 50 mg/mL (e.g., at least three fold or at least four fold greater).

The delivery of a high protein concentration is often advantageous or required for subcutaneous administration due to the volume limitations (less than or equal to 1.5 mL) and dosing requirements (greater than or equal to 100 mg). However, protein concentrations (greater than or equal to 50 mg/mL) may be difficult to achieve in the manufacturing process since at high concentrations, a protein may have a tendency to aggregate during processing and become difficult to manipulate (e.g. pump) and sterile filter. Alternatively, the lyophilization process may provide a method to allow concentration of a protein. For example, a RAGE fusion protein may be filled into vials at a volume (Vf) and then lyophilized. The lyophilized RAGE fusion protein is then reconstituted with a smaller volume (Vr) of water or preservative (e.g. BWFI) than the original volume (e.g. Vr=0.25 Vf) resulting in a higher RAGE fusion protein concentration in the reconstituted solution. This process also results in the concentration of the buffers and excipients. For subcutaneous administration, the solution is desirably isotonic.

Reconstitution generally takes place at a temperature of about 25° C. to ensure complete hydration, although other temperatures may be employed as desired. The time required for reconstitution may depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. In an embodiment, the diluent provides a reconstituted formulation suitable for injection. In another embodiment, where the diluent provides a reconstituted formulation suitable for injection, the diluent comprises water for injection (WFI). The diluent optionally contains a preservative. The amount of preservative employed may be determined by assessing different preservative concentrations for compatibility with the protein and preservative efficacy testing.

In alternate embodiments, the reconstituted formulation may have less than 8,000, or less than 6,000, or less that 4,000, or less than 2,000, or less than 1,000, or less than 600, or less than 400, or less than 200 or less than 100, or less than 50 particles that are equal to or greater than 10 μm in size per 50 mL container. In other embodiments, the reconstituted formulation may have less than 8,000, or less than 6,000, or less that 4,000, or less than 2,000, or less than 1,000, or less than 600, or less than 400, or less than 200 or less than 100, or less than 50 particles that are equal to or greater than 25 μm in size per 50 mL container.

Administration of the Reconstituted Formulation

The reconstituted formulation may be administered to a mammal in need of treatment with the RAGE fusion protein, such as a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In embodiments, the reconstituted formulation may be administered to the mammal by subcutaneous (i.e. beneath the skin) administration. For such purposes, the reconstituted formulation may be injected using a syringe. However, other devices for administration of the reconstituted formulation are available such as injection devices (e.g. the Inject-ease™ and Genject™ devices); injector pens (such as the GenPen™); needleless devices (e.g. MediJector™ and BioJector™); and subcutaneous patch delivery systems.

The appropriate dosage or therapeutically effective amount of the RAGE fusion protein will depend, for example, on the condition to be treated, the severity and course of the condition, whether the RAGE fusion protein is administered for preventive or therapeutic purposes, previous therapy, the patient's clinical history and response to the RAGE fusion protein, and the discretion of the attending physician. The RAGE fusion protein may be administered to the subject (e.g., patient) at one time or over a series of treatments or may be administered to the patient at any time from diagnosis onwards. The RAGE fusion protein may be administered as the sole treatment or in conjunction with other drugs or therapies useful in treating the condition in question. In an embodiment, a dosage from about 0.1-20 mg/kg is an initial candidate dosage for administration to the subject, whether, for example, by one or more separate administrations. As described above, other dosage regimens may be useful.

Articles of Manufacture

In another embodiment of the invention, an article of manufacture is provided which contains the lyophilized formulation of the present invention and provides instructions for its reconstitution and/or use. The article of manufacture may comprise a container. Suitable containers include, for example, bottles, vials (e.g. dual chamber vials), syringes (such as dual chamber syringes) and test tubes. The container may be formed from a variety of materials such as glass or plastic. The container may hold the lyophilized formulation. In certain embodiments, there may be a label affixed to, or associated with, the container. The label may indicate instructions for reconstitution and/or use. For example, in certain embodiments, the label may indicate that the lyophilized formulation is reconstituted to protein concentrations as described above. The label may further indicate that the formulation is useful or intended for subcutaneous administration.

The container holding the formulation may be a multi-use vial, which allows for repeat administrations (e.g., from 2-6, or 2-10, or 2-50 administrations) of the reconstituted formulation. The article of manufacture may further comprise a second container comprising a suitable diluent (e.g. WFI). Upon mixing of the diluent and the lyophilized formulation, the final RAGE fusion protein concentration in the reconstituted formulation will generally be at least 10 mg/mL. In one embodiment, the final RAGE fusion protein concentration in the reconstituted formulation is at least about 20 mg/mL. In another embodiment, the final RAGE fusion protein concentration in the reconstituted formulation is at least about 50 mg/mL. In alternate embodiments, the RAGE fusion protein concentration in the reconstituted formulation may be at least 100 mg/mL, or 200 mg/mL, or 400 mg/mL. In other embodiments, the final RAGE fusion protein concentration on the reconstituted formulation is between about 1-400 mg/mL, or 1-200 mg/mL, or 1-100 mg/mL, or 10-400 mg/mL, or 10-200 mg/mL, or 10-100 mg/mL, or from 40-400 mg/mL, or from 40-200 mg/mL, or from 40-100 mg/mL, or from 50-400 mg/mL, or from 50-200 mg/mL, or from 50-100 mg/mL, or from 40 mg/mL to 50 mg/mL. The article of manufacture may further include other materials desirable from a commercial and user standpoint, including other buffers, diluents, filters, needles, syringes, and package inserts with instructions for use.

EXAMPLES

Features and advantages of the inventive concept covered by the present invention are further illustrated in the examples which follow.

Example 1A

Production of RAGE Fusion Proteins

Two plasmids were constructed to express RAGE-IgG fusion proteins. Both plasmids were constructed by ligating different lengths of a 5' cDNA sequence from human RAGE with the same 3' cDNA sequence from human IgG Fc (γ1). These expression sequences (i.e., ligation products) were then inserted in pcDNA3.1 expression vector (Invitrogen, CA). The nucleic acid sequences that encode the RAGE fusion protein coding region are shown in FIGS. 2 and 3. For TTP-4000 RAGE fusion protein, the nucleic acid sequence from 1 to 753 (highlighted in bold) encodes the RAGE N-terminal protein sequence, whereas the nucleic acid sequence from 754 to 1386 encodes the IgG Fc protein sequence without the hinge (FIG. 2). For TTP-3000, the nucleic acid sequence from 1 to 408 (highlighted in bold) encodes the RAGE N-terminal protein sequence, whereas the nucleic acid sequence from 409 to 1041 encodes the IgG Fc protein sequence without the hinge (FIG. 3).

To produce the RAGE fusion proteins, the expression vectors comprising the nucleic acid sequences of either SEQ ID NO: 30 or SEQ ID NO: 31 were stably transfected into CHO cells. Positive transformants were selected for neomycin resistance conferred by the plasmid and cloned. High producing clones as detected by Western Blot analysis of supernatant were expanded and the gene product was purified by affinity chromatography using Protein A columns. Expression was optimized so that cells were producing recombinant TTP-4000 at levels of about 1.3 grams per liter.

Example 1B

Alternate Production of Four Domain RAGE Fusion Proteins

A plasmid was constructed to express RAGE-IgG fusion proteins. The plasmid was constructed by ligating a 5' cDNA sequence from human RAGE with a 3' cDNA sequence from human IgG Fc(γ1) without the Fc hinge region. PCR was used to amplify the cDNA. Further, on the 5' end, the PCR primer added an Eco RI restriction enzyme site from cloning and a Kozak consensus translation initiation sequence. On the 3' end, the PCR primer added a Xho I restriction just past the terminal codon. On the 3' end, the PCR primer also included two silent base changes that remove a cryptic RNA splice site in the immunoglobulin portion near the terminal codon. The codon encoding for proline (residue 459 based on numbering in the protein sequence in SEQ ID NO: 32) was changed from CCG to CCC, and the codon encoding for glycine (residue 460 based on numbering in the protein sequence in SEQ ID NO: 32) was changed from GGT to GGG. The PCR fragment was digested with Eco RI and Xho I and then inserted into a retrovector plasmid (pCNS-newMCS-WPRE (new ori), available from Gala, Inc.) that had been digested with Mfe I (to form a compatable end with Eco RI) and digested with Xho I. The inserted portion of the cloned plasmid and cloning junctions were sequenced to ensure that no mutations occurred during cloning.

To produce the RAGE-IgG fusion protein, the expression vector comprising the nucleic acid sequence SEQ ID NO: 54 was stably transfected in CHO cells.

The sequence of the isolated RAGE fusion protein TTP-4000 expressed by the transfected cells was confirmed by various characterization studies as either SEQ ID NO: 34 or SEQ ID NO: 56, or both SEQ ID NO: 34 and SEQ ID NO: 56. Thus, the signal sequence encoded by the first 23 amino acids of SEQ ID NO: 32 was cleaved and the N-terminal residue was glutamine (Q) or pyroglutamic acid (pE) or a mixture thereof. Characterization studies also showed glycosylation sites at N2 and N288 (based on numbering of SEQ ID NO: 34 or SEQ ID NO: 56) and showed that the $C_H3$ region of the RAGE fusion protein may have its C-terminal residue cleaved off through a post-translational modification when expressed in this recombinant system.

Example 1C

Alternate Production of Three Domain RAGE Fusion Proteins

A plasmid can be constructed to express three domain RAGE-IgG fusion proteins (e.g., one RAGE domain and two IgG domains) such as TTP-3000 in the manner described above for TTP-4000. The plasmid is constructed by ligating a 5' cDNA sequence from human RAGE encoding amino acids 1-136 of human RAGE with a 3' cDNA sequence from human IgG Fc(γ1) without the Fc hinge region. PCR can be used to amplify the cDNA. On the 5' end, a PCR primer may add a restriction site (e.g., an Eco RI restriction enzyme site as used for TTP-4000) for cloning and a Kozak consensus translation initiation sequence. On the 3' end, the PCR primer may also add a restriction site (e.g., a Xho I restriction site) just past the terminal codon. The PCR primers may also include silent base changes as may be needed to remove any cryptic RNA splice sites, such as the cryptic RNA splice sites located at the 3' end of the immunoglobulin $C_H2$ domain as describes in Example 1B. To remove these cryptic splice sites, the codon encoding for proline 344 of SEQ ID NO: 35 (i.e., residues 1030-1032 based on numbering in the DNA sequence in SEQ ID NO: 31) may be changed from CCG to CCC, and the codon encoding for glycine 345 of SEQ ID NO: 35 (residues 1033-1035 based on numbering in the DNA sequence in SEQ ID NO: 31) may be changed from GGT to GGG. The PCR fragment may then be digested with the appropriate restriction enzymes (e.g., Eco RI and Xho I), and inserted into the retrovector plasmid pCNS-newMCS-WPRE (new ori; available from Gala, Inc.). The vector may be digested with Mfe I to form a compatible end with Eco RI, and also digested with Xho I. The inserted portion of the cloned plasmid and cloning junctions can be sequenced to ensure that no mutations occurred during cloning.

To produce the RAGE-IgG fusion protein, the expression vector comprising the nucleic acid sequence SEQ ID NO: 55 (i.e., comprising the change in DNA sequence to remove cryptic splice sites) can be stably transfected in CHO cells as described in Example 1A and 1B.

The sequence of the isolated RAGE fusion protein TTP-3000 expressed by the transfected cells may be either SEQ ID NO: 36, SEQ ID NO: 37 or SEQ ID NO: 57, or a combination of SEQ ID NO: 36, SEQ ID NO: 37 and/or SEQ ID NO: 57. Thus, the signal sequence encoded by the first 22 and/or 23 amino acids of SEQ ID NO: 35 may be cleaved and the N-terminal residue may be glutamine (Q) or pyroglutamic acid (pE) or a mixture thereof. Glycosylation may occur at sites at N2 and N174 (based on numbering of SEQ ID NO: 37 or SEQ ID NO: 57) and/or other glycosylation sites that may be present. The $C_H3$ region of the RAGE fusion protein may have its C-terminal residue cleaved off through a post-translational modification when expressed in this recombinant system.

Example 2

Method for Testing Activity of a RAGE-IgG1 Fusion Protein

A. In Vitro Ligand Binding:

Known RAGE ligands were coated onto the surface of Maxisorb plates at a concentration of 5 micrograms per well. Plates were incubated at 4° C. overnight. Following ligand incubation, plates were aspirated and a blocking buffer of 1% BSA in 50 mM imidizole buffer (pH 7.2) was added to the plates for 1 hour at room temperature. The plates were then aspirated and/or washed with wash buffer (20 mM Imidizole, 150 mM NaCl, 0.05% Tween-20, 5 mM $CaCl_2$ and 5 mM $MgCl_2$, pH 7.2). A solution of TTP-3000 (TT3) at an initial concentration of 1.082 mg/mL and a solution of TTP-4000 (TT4) at an initial concentration of 370 μg/mL were prepared. The RAGE fusion protein was added at increasing dilutions of the initial sample. The RAGE fusion protein was allowed to incubate with the immobilized ligand at 37° C. for one hour after which the plate was washed and assayed for binding of the RAGE fusion protein. Binding was detected by the addition of an immunodetection complex containing a monoclonal mouse anti-human IgG1 diluted 1:11,000 to a final assay concentration (FAC) of 21 ng/100 μL, a biotinylated goat anti-mouse IgG diluted 1:500, to a FAC of 500 ng/μL, and an avidin-linked alkaline phosphatase. The complex was incubated with the immobilized RAGE fusion protein for one hour at room temperature after which the plate was washed and the alkaline phosphatase substrate para-nitrophenylphosphate (PNPP) was added. Binding of the complex to the immobilized RAGE fusion protein was quantified by measuring conversion of PNPP to para-nitrophenol (PNP) which was measured spectrophotometrically at 405 nm.

As illustrated in FIG. 7, the RAGE fusion proteins TTP-4000 (TT4) and TTP-3000 (TT3) specifically interact with known RAGE ligands amyloid-beta (Abeta), S100b (S100), and amphoterin (Ampho). In the absence of ligand, i.e., BSA coating alone (BSA or BSA+wash) there was no increase in absorbance over levels attributable to non-specific binding of the immunodetection complex. Where amyloid beta is used as the labeled ligand it may be necessary to preincubate the amyloid beta before the assay. Preincubation may allow the amyloid beta to self-aggregate into pleated sheet form, as amyloid beta may preferentially bind to RAGE in the form of a pleated sheet.

Additional evidence for a specific interaction between RAGE fusion proteins TTP-4000 and TTP-3000 with RAGE ligands is exemplified in studies showing that a RAGE ligand is able to effectively compete with a known RAGE ligand for binding to the RAGE fusion proteins. In these studies, amyloid-beta (A-beta) was immobilized on a Maxisorb plate and RAGE fusion protein added as described above. In addition, a RAGE ligand was added to some of the wells at the same time as the RAGE fusion protein.

It was found that the RAGE ligand could block binding of TTP-4000 (TT4) by about 25% to 30% where TTP-4000 was present at 123 μg/mL (1:3 dilution, FIG. 8). When the initial solution of TTP-4000 was diluted by a factor of 10 or 30 (1:10 or 1:30), binding of the RAGE fusion protein to the immobilized ligand was completely inhibited by the RAGE ligand. Similarly, the RAGE ligand blocked binding of TTP-3000 (TT3) by about 50% where TTP-3000 was present at 360 μg/mL (1:3 dilution, FIG. 9). When the initial solution of TTP-3000 was diluted by a factor of 10 (1:10), binding of the RAGE fusion protein to the immobilized ligand was completely inhibited by the RAGE ligand. Thus, specificity of binding of the RAGE fusion protein to the RAGE ligand was dose dependent. Also, as shown in FIGS. 8 and 9, there was essentially no binding detected in the absence of RAGE fusion protein, i.e., using only the immunodetection complex ("Complex alone").

B. Effect of RAGE Fusion Proteins in a Cell Based Assays

Previous work has shown that the myeloid THP-1 cells may secrete TNF-α in response to RAGE ligands. In this assay, THP-1 cells were cultured in RPMI-1640 media supplemented with 10% FBS using a protocol provided by ATCC. The cells were induced to secrete TNF-α via stimulation of RAGE with 0.1 mg/ml S100b both in the absence and the presence of the RAGE fusion proteins TTP-3000 (TT3) or TTP-4000 (TT4) (10 μg), sRAGE (10 μg), and a human IgG (10 μg) (i.e., as a negative control). The amount of TNF-α secreted by the THP-1 cells was measured 24 hours after the addition of the proteins to the cell culture using a commercially available ELISA kit for TNF-α (R&D Systems, Minneapolis, Minn.). The results in FIG. 10 demonstrate that the RAGE fusion proteins inhibit the S100b/RAGE-induced production of TNF-α in these cells. As shown in FIG. 10, upon addition of 10 μg TTP-3000 or TTP-4000

RAGE fusion protein, induction of TNF-α by S100b (0.1 mg/ml FAC) was reduced by about 45% to 70%, respectively. Fusion protein TTP-4000 may be at least as effective in blocking S100b induction of TNF-α as is sRAGE (FIG. 10). Specificity of the inhibition for the RAGE sequences of TTP-4000 and TTP-3000 is shown by the experiment in which IgG alone was added to S100b stimulated cells. Addition of IgG and S100b to the assay shows the same levels of TNF-α as S100b alone. Specificity of the inhibition of TNF-α induction by TTP-4000 and TTP-3000 for RAGE sequences of the RAGE fusion protein is shown by an experiment in which IgG alone was added to S100b stimulated cells. It can be seen that the addition of IgG, i.e., human IgG without the RAGE sequence (Sigma human IgG added at 10 μg/well), and S100b to the assay shows the same levels of TNF-α as S100b alone.

In another cell-based assay, the ability of TTP-4000 to prevent the RAGE ligand HMGB1 from interacting with RAGE and other HMGB1 receptors was evaluated. Unlike anti-RAGE antibodies that bind to RAGE and to prevent the interaction of a RAGE ligand with RAGE, TTP-4000 may block the interaction of a RAGE ligand with RAGE by binding to the RAGE ligand. HMGB1 has been reported to be a ligand for RAGE and the Toll-Like Receptors 2 and 4 (Park et al., *J Biol. Chem.*, 2004; 279(9):7370-7). All three of these receptors (RAGE, Toll-like receptor 2, and Toll-like receptor 4) are expressed on THP-1 cells (Parker, et al., *J. Immunol.*, 2004, 172(8):4977-86.).

In this experiment, THP-1 cells were stimulated to produce TNF-α by HMGB1 (50 mg/mL) in the presence or absence of either TTP4000 or anti-RAGE antibodies. Under the conditions used in the assay, HMGB1 should be the only inducer of TNF-α. The amount of TNF-α secreted by the THP-1 cells was measured 24 hours after the addition of the proteins to the cell culture using a commercially available ELISA kit for TNF-α (R&D Systems, Minneapolis, Minn.). The results in FIG. 11 demonstrate that the anti-RAGE antibody and RAGE fusion protein TTP-4000 block HMGB1 from interacting with RAGE expressed on the THP-1 cells, but that TTP-4000 inhibits HMGB1-induced TNF-α production to a greater extent than does the anti-RAGE antibody. Thus, the data indicate that TTP-4000 may inhibit HMGB1 activity to a greater extent than anti-RAGE antibody by inhibiting HMGB1 from interacting with Toll-like receptors 2 and 4, as well as RAGE present on THP-1 cells.

Example 3

Pharmacokinetic Profile of TTP-4000

To determine whether TTP-4000 would have a superior pharmacokinetic profile as compared to human sRAGE, rats and nonhuman primates were given an intravenous (IV) injection of TTP-4000 (5 mg/kg) and then plasma was assessed for the presence of TTP-4000. In these experiments, two naïve male monkeys received a single IV bolus dose of TTP-4000 (5 mg/ml/kg) in a peripheral vein followed by an approximate 1.0 milliliter (mL) saline flush. Blood samples (approximately 1.0 mL) were collected at pre-dose (i.e., prior to injection of the TTP-4000), or at 0.083, 0.25, 0.5, 2, 4, 8, 12, 24, 48, 72, 96, 120, 168, 240, 288, and 336 hours post dose into tubes containing (lithium heparin). Following collection, the tubes were placed on wet ice (maximum 30 minutes) until centrifugation under refrigeration (at 2 to 8° C.) at 1500×g for 15 minutes. Each harvested plasma sample was then stored frozen (−70° C.±10° C.) until assayed for RAGE polypeptide using an ELISA at various time-points following the injection, as described in Example 6.

The kinetic profile shown in FIG. 12 reveals that once TTP-4000 has saturated its ligands as evidenced by the fairly steep slope of the alpha phase in 2 animals, it retains a terminal half-life of greater than 300 hours. This half-life is significantly greater than the half-life of human sRAGE in plasma (generally about 2 hours) and provides an opportunity for single injections for acute and semi-chronic indications. In FIG. 12 each curve represents a different animal under the same experimental conditions.

Example 4

TTP-4000 Fc Activation

Experiments were performed to measure the activation of the Fc receptor by RAGE fusion protein TTP-4000 as compared to human IgG. Fc receptor activation was measured by measuring TNF-α secretion from THP-1 cells that express the Fc receptor. In these experiments, a 96 well plate was coated with 10 μg/well TTP-4000 or human IgG. Fc stimulation results in TNF-α secretion. The amount of TNF-α was measured by an Enzyme Linked Immunoabsorbent Assay (ELISA).

Thus, in this assay, the myeloid cell line, THP-1 (ATTC #TIB-202) was maintained in RPMI-1640 media supplemented with 10% fetal bovine serum per ATCC instructions. Typically, 40,000-80,000 cells per well were induced to secrete TNF-alpha via Fc receptor stimulation by precoating the well with 10 ug/well of either heat aggregated (63° C. for 30 min) TTP-4000 or human IgG1. The amount of TNF-alpha secreted by the THP-1 cells was measured in supernatants collected from 24 hours cultures of cells in the treated wells using a commercially available TNF ELISA kit (R&D Systems, Minneapolis, Minn. #DTA00C) per instructions. Results are shown in FIG. 13 where it can be seen that TTP-4000 generates less than 2 ng/well TNF and IgG generated greater than 40 ng/well.

Example 5

In Vivo Activity of TTP-4000

The activity of TTP-4000 was compared to sRAGE in several in vivo models of human disease.

A. TTP-4000 in an Animal Model of Restenosis

The RAGE fusion protein TTP-4000 was evaluated in a diabetic rat model of restenosis which involved measuring smooth muscle proliferation and intimal expansion 21 days following vascular injury. In these experiments, balloon injury of left common carotid artery was performed in Zucker diabetic and nondiabetic rats using standard procedure. A loading dose (3 mg/rat) of IgG, TTP-4000 or phosphate buffered saline (PBS) was administered intraperitoneally (EP) one day prior injury. A maintenance dose was delivered every other day until day 7 after injury (i.e., at day 1, 3, 5 and 7 after injury). The maintenance dose was high=1 mg/animal for one group, or low=0.3 mg/animal for the second group. To measure vascular smooth muscle cell (VSMC) proliferation, animals were sacrificed at 4 days and 21 days after injury.

For the measurement of cell proliferation, 4 day animals received intraperitoneal injection of bromodeoxyuridine (BrDdU) 50 mg/kg at 18, 12, and 2 hours before euthanasia. After sacrifice, the entire left and right carotid arteries were harvested. Specimens were stored in Histochoice for at least 24 hours before embedding. Assessment of VSMC proliferation was performed using mouse anti-BrdU monoclonal antibody. A fluorescence labeled goat anti-mouse secondary antibody was applied. The number of BrdU-positive nuclei per section were counted by two observers blinded to the treatment regimens.

The remaining rats were sacrificed at 21 days for morphometric analysis. Morphometric analyses were performed by an observer blinded to the study groups, using computerized digital microscopic planimetry software Image-Pro Plus on serial sections, (5 mm apart) carotid arteries stained by Van Gieson staining. All data were expressed as mean±SD. Statistical analysis was performed with use of SPSS software. Continuous variables were compared using unpaired t tests. A values of $P \leq 0.05$ was considered to be statistically significant.

As seen in FIGS. 14A and 14B, TTP-4000 treatment significantly reduced the intima/media ratio and vascular smooth muscle cell proliferation in a dose-responsive fashion. In FIG. 14B, the y-axis represents the number of BrdU proliferating cells.

B. TTP4000 in an Animal Model of AD

Experiments were performed to evaluate whether TTP-4000 could affect amyloid formation and cognitive dysfunction in a mouse model of AD. The experiments utilized transgenic mice expressing the human Swedish mutant amyloid precursor protein (APP) under the control of the PDGF-B chain promoter. Over time, these mice generate high levels of the RAGE ligand, amyloid beta (Aβ). Previously, sRAGE treatment for 3 months has been shown to reduce both amyloid plaque formation in the brain and the associated increase in inflammatory markers in this model.

The APP mice (male) used in this experiment were designed by microinjection of the human APP gene (with the Swedish and London mutations) into mouse eggs under the control of the platelet-derived growth factor B (PDGF-B) chain gene promoter. The mice were generated on a C57BL/6 background and were developed by Molecular Therapeutics Inc. Animals were fed ad libitum and maintained by brother sister mating. The mice generated from this construct develop amyloid deposits starting at 6 months of age. Animals were aged for 6 months and then maintained for 90 days and sacrificed for amyloid quantification.

APP transgenic mice were administered vehicle or TTP4000 every other day [qod (i.p.)] for 90 days starting at 6 months of age. At the end of the experiment, animals were sacrificed and examined for Aβ plaque burden in the brain (i.e., plaque number). A 6-month control APP group was used to determine the baseline of amyloid deposits. In addition, at the end of the study, the animals were subjected to behavioral (Morris water maze) analysis. The investigators were blinded to the study compounds. Samples were given to the mice at 0.25 ml/mouse/every other day. In addition, one group of mice were given 200 ug/day of human sRAGE.

1. Amyloid Beta Deposition

For histological examination, the animals were anesthetized with an intraperitoneal injection (IP) of sodium pentobarbital (50 mg/kg). The animals were transcardially perfused with 4° C., phosphate-buffered saline (PBS) followed by 4% paraformaldehyde. The brains were removed and placed in 4% paraformaldehyde over night. The brains were processed to paraffin and embedded. Ten serial 30-μm thick sections through the brain were obtained. Sections were subjected to primary antibody overnight at 4° C. (Aβ peptide antibody) in order to detect the amyloid deposits in the brain of the transgenic animals (Guo et al., *J. Neurosci.*, 22:5900-5909 (2002)). Sections were washed in Tris-buffered saline (TBS) and secondary antibody was added and incubated for 1 hour at room temperature. After washing, the sections were incubated as instructed in the Vector ABC Elite kit (Vector Laboratories) and stained with diaminobenzoic acid (DAB). The reactions were stopped in water and cover-slipped after treatment with xylene. The amyloid area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of amyloid was determined over the ten sections. A single operator blinded to treatment status performed all measurements. Summing the amyloid volumes of the sections and dividing by the total number of sections was done to calculate the amyloid volume.

For quantitative analysis, an enzyme-linked immunosorbent assay (ELISA) was used to measure the levels of human total Aβ, $Aβ_{total}$ and $Aβ_{1-42}$ in the brains of APP transgenic mice (Biosource International, Camarillo, Calif.). $Aβ_{total}$ and $Aβ_{1-42}$ were extracted from mouse brains by guanidine hydrochloride and quantified as described by the manufacturer. This assay extracts the total Aβ peptide from the brain (both soluble and aggregated).

2. Cognitive Function

The Morris water-maze testing was performed as follows. All mice were tested once in the Morris water maze test at the end of the experiment. Mice were trained in a 1.2 m open field water maze. The pool was filled to a depth of 30 cm with water and maintained at 25° C. The escape platform (10 cm square) was placed 1 cm below the surface of the water. During the trials, the platform was removed from the pool. The cued test was carried out in the pool surrounded with white curtains to hide any extra-maze cues. All animals underwent non-spatial pretraining (NSP) for three consecutive days. These trials are to prepare the animals for the final behavioral test to determine the retention of memory to find the platform. These trials were not recorded, but were for training purposes only. For the training and learning studies, the curtains were removed to extra maze cues (this allowed for identification of animals with swimming impairments). On day 1, the mice were placed on the hidden platform for 20 seconds (trial 1), for trials 2-3 animals were released in the water at a distance of 10 cm from the cued-platform or hidden platform (trial 4) and allowed to swim to the platform. On the second day of trails, the hidden platform was moved randomly between the center of the pool or the center of each quadrant. The animals were released into the pool, randomly facing the wall and were allowed 60 seconds to reach the platform (3 trials). In the third trial, animals were given three trials, two with a hidden platform and one with a cued platform. Two days following the NSP, animals were subjected to final behavioral trials (Morris water maze test). For these trials (3 per animal), the platform was placed in the center of one quadrant of the pool and the animals released facing the wall in a random fashion. The animal was allowed to find the platform or swim for 60 seconds (latency period, the time it takes to find the platform). All animals were tested within 4-6 hours of dosing and were randomly selected for testing by an operator blinded to the test group.

The results are expressed as the mean±standard deviations (SD). The significance of differences in the amyloid and behavioral studies were analyzed using a t-test. Comparisons were made between the 6-month-old APP control group and the TTP-4000 treated animals, as well as, the 9-month-old APP vehicle treated group and the TTP-4000 treated animals. Differences below 0.05 were considered significant. Percent changes in amyloid and behavior were determined by taking the summation of the data in each group and dividing by the comparison (i.e., 1, i.p./6 month control=% change).

FIGS. 15A and 15B show that mice treated for 3 months with either TTP-4000 or mouse sRAGE had fewer Aβ plaques and less cognitive dysfunction than vehicle and negative control human IgG1 (IgG1) treated animals. This data indicates that TTP-4000 is effective in reducing AD pathology in a transgenic mouse model. It was also found that like sRAGE, TTP-4000 can reduce the inflammatory cytokines IL-1 and TNF-α (data not shown).

C. Efficacy of TTP-4000 in an Animal Model of Stroke

TTP-4000 was also compared to sRAGE in a disease relevant animal model of stroke. In this model, the middle carotid artery of a mouse was ligated for 1 hour followed by 23 hours of reperfusion at which point the mice were sacrificed and the area of the infarct in the brain was assessed. Mice were treated with sRAGE or TTP-4000 or control immunoglobulin just prior to reperfusion.

In these experiments, male C57BL/6 were injected with vehicle at 250 µl/mouse or TTP test articles (TTP-3000, TTP-4000 at 250 µl/mouse). Mice were injected intraperitoneally, 1 hour after the initiation of ischemia. Mice were subjected to one hour of cerebral ischemia followed by 24 hours of reperfusion. To induce ischemia, each mouse was anesthetized and body temperature was maintained at 36-37° C. by external warming. The left common carotid artery (CCA) was exposed through a midline incision in the neck. A microsurgical clip was placed around the origin of the internal carotid artery (ICA). The distal end of the ECA was ligated with silk and transected. A 6-0 silk was tied loosely around the ECA stump. The fire-polished tip of a nylon suture was gently inserted into the ECA stump. The loop of the 6-0 silk was tightened around the stump and the nylon suture was advanced into and through the internal carotid artery (ICA), until it rested in the anterior cerebral artery, thereby occluding the anterior communicating and middle cerebral arteries. After the nylon suture had been in place for 1 hour, the animal was re-anesthetized, rectal temperature was recorded and the suture was removed and the incision closed.

Infarct volume was determined by anesthetizing the animals with an intraperitoneal injection of sodium pentobarbital (50 mg/kg) and then removing the brains. The brains were then sectioned into four 2-mm sections through the infracted region and placed in 2% triphenyltetrazolium chloride (TTC) for 30 minutes. After, the sections were placed in 4% paraformaldehyde over night. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume. The results are expressed as the mean±standard deviation (SD). The significance of difference in the infarct volume data was analyzed using a t-test.

As illustrated by the data in Table 2, TTP-4000 was more efficacious than sRAGE in limiting the area of infarct in these animals suggesting that TTP-4000, because of its better half-life in plasma, was able to maintain greater protection in these mice.

Example 6

Detection of RAGE Fusion Protein by ELISA

Initially, 50 uL of the RAGE specific monoclonal antibody 1HB1011 at a concentration of 10 ug/mL in 1×PBS pH 7.3 is coated on plates via overnight incubation. When ready for use, plates are washed three times with 300 uL of 1× Imidazole-Tween wash buffer and blocked with 1% BSA. The samples (diluted) and standard dilutions of known TTP-4000 dilutions are added at 100 uL final volume. The samples are allowed to incubate at room temperature for one hour. After incubation, the plates are plates are washed three times. A Goat Anti-human IgG1 1 (Sigma A3312) AP conjugate in 1×PBS with 1% BSA is added and allowed to incubate at room temperature for 1 hour. The plates are washed three times. Color was elucidated with paranitrophenylphosphate.

Example 7

Quantification of RAGE Ligand Binding to RAGE Fusion Protein

Figure 16:
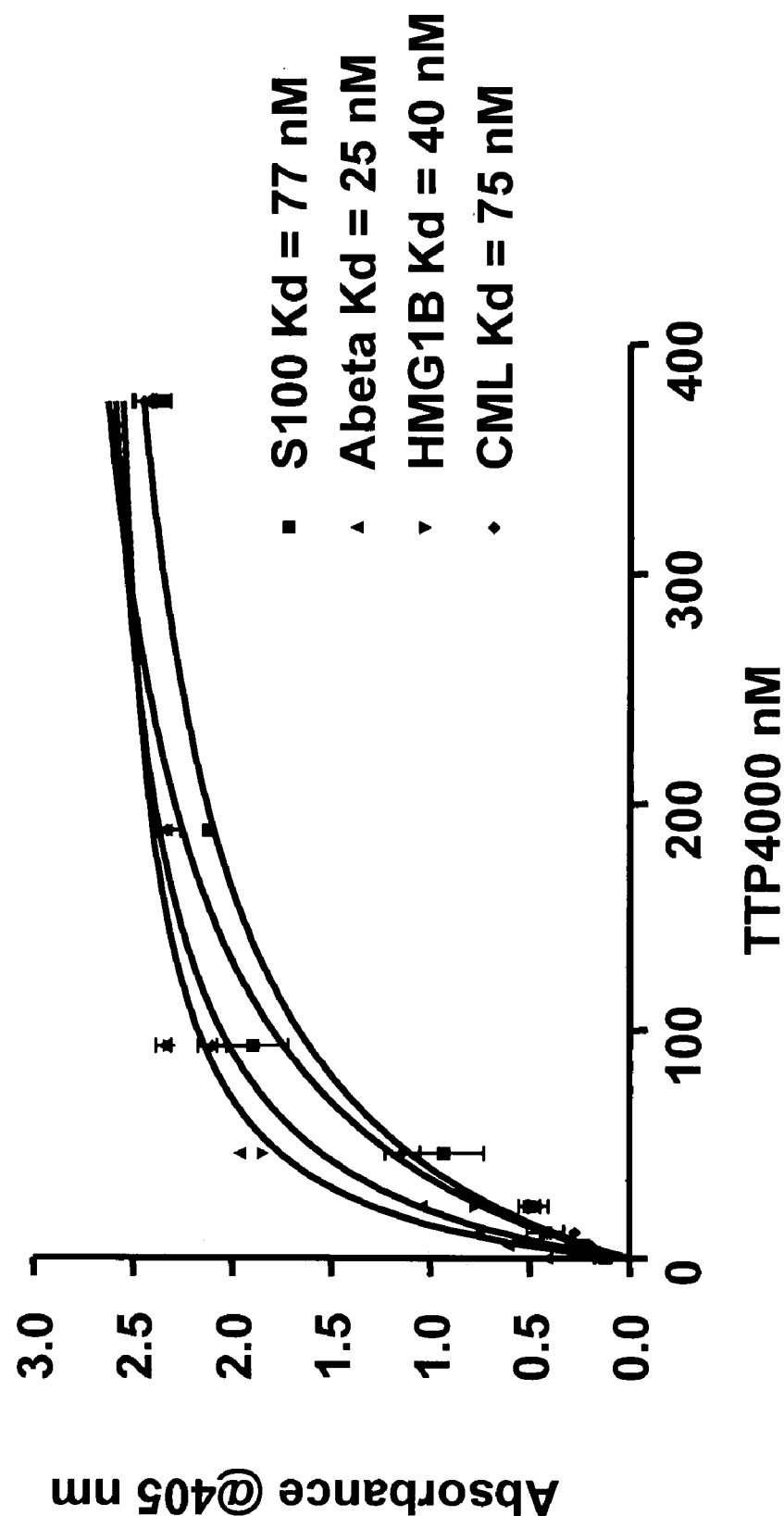
FIG. 16 shows saturation-binding curves with TTP-4000 to various immobilized known RAGE ligands in accordance with an embodiment of the present invention.

FIG. 16 shows saturation-binding curves with TTP-4000 to various immobilized known RAGE ligands. The ligands are immobilized on a microtiter plate and incubated in the presence of increasing concentrations of RAGE fusion protein from 0 to 360 nM. The RAGE fusion protein-ligand interaction is detected using a polyclonal antibody conjugated with alkaline phosphatase that is specific for the IgG portion of the fusion chimera. Relative Kds were calculated using Graphpad Prizm software and match with established literature values of RAGE-RAGE ligand values. HMG1B=Ampoterin, CML=Carboxymethyl Lysine, A beta=Amyloid beta 1-40.

Example 8

Use of RAGE Fusion Protein to Prevent Allogeneic Transplant Rejection

RAGE blockade may be expected to block allogeneic transplant rejection. These experiments explored whether blockade of ligand-RAGE interactions using a RAGE fusion protein of the invention would attenuate rejection of islet cells that had been transplanted from a healthy donor into a diabetic animal as measured by the length of time that the transplanted animals maintained a blood glucose level below a target concentration. As discussed herein, it was found that administration of a RAGE fusion protein (e.g., TTP-4000) to diabetic animals that had received islet cell transplants significantly delayed the recurrence of hyperglycemia and thus rejection of transplanted islet cells in two (allogeneic and syngeneic) animal models of transplant.

A. Allogeneic Islet Transplantation in Mice

The first set of experiments tested whether administration of a RAGE fusion protein (TTP-4000) would modulate the allogeneic rejection of transplanted islet cells and the recurrence of diabetes in a C57BL/6J (B6) mouse model of diabetes.

Animal Model of Diabetes

C57BL/6J (6-8 week old) (B6) mice were made diabetic by a single intravenous injection of streptozotocin (STZ) (Sigma Chemical Co., St. Louis, Mo.) at 200 mg/kg. BALB/cJ (6-8 week old) (BALB) mice served as donors for islet transplantation, thus providing an allo-mismatch for islet transplants.

Islet Isolation

Mice (BALB/c) were anesthetized with ketamine HCl/xylazine HCl solution (Sigma, St. Louis Mo.). After intraductal injection of 3 ml of cold Hank's balanced salt solution (HBSS, Gibco, Grand Island N.Y.) containing 1.5 mg/ml of collagenase P (Roche Diagnostics, Branchburg, N.J.), pancreata were surgically procured and digested at 37° C. for 20 mins. Islets were washed with HBSS and purified by discontinuous gradient centrifugation using Polysucrose 400 (Cellgro, Herndon Va.) having four different densities (26%, 23%, 20%, and 11%). The tissue fragments at the interface of the 20% and 23% layers were collected, washed and resuspended in HBSS. Individual islets, free of attached acinar, vascular and ductal tissues were handpicked under an inverted microscope, yielding highly purified islets for transplantation.

Islet Transplantation

Streptozotocin-induced diabetic C57BL/6 (B6) mice received islet grafts within 2 days of the diagnosis of diabetes. BALB/cJ (6-8 week old) (BALB) mice served as donors for allogeneic islet transplantation. For transplantation, 500-600 freshly isolated islets (i.e., approximately 550 islet equivalents) from donor mice were picked up with an infusion set and transplanted into the subcapular space of the right kidney of a recipient.

Treatment with Test Compounds

Test compounds were administered as soon as the islets were transplanted; administration continued for about 60 days, depending upon how the control animal was faring.

Mice were injected with 0.25 ml of either phosphate buffered saline (PBS), TTP-400 in PBS, or IgG in PBS according to the regimen below (Table 3).

TABLE 3

Administration of Test Compounds and/or Vehicle

| Test Group | Number of mice | Loading Dose | Maintenance Dose | Regimen |
|---|---|---|---|---|
| Untreated Control | 8 | | | |
| Control Vehicle (PBS) | 8 | 0.25 ml/dose/ mouse on day 1 | 0.25 ml/dose/ mouse starting on day 2 | Once every other day (QOD) × 60 days; IP |
| IgG | 8 | (300 μg) 0.25 ml/dose/ mouse on day 1 | (100 ug) 0.25 ml/dose/ mouse starting on day 2 | (100 ug) Once every other day (QOD) × 60 days; IP |
| TTP-4000 | 8 | (300 μg) 0.25 ml/dose/ mouse on day 1 | (100 ug) 0.25 ml/dose/ mouse starting on day 2 | (100 ug) Once every other day (QOD) × 60 days; IP |
| TTP-4000 | 8 | (300 μg) 0.25 ml/dose/ mouse on day 1 | (30 ug) 0.25 ml/dose/ mouse starting on day 2 | (30 ug) Once every other day (QOD) × 60 days; IP |

Monitoring of Islet Graft Function

Islet graft function was monitored by serial blood glucose measurements daily for the first 2 week after islet transplantation, followed by every other day thereafter. Reversal of diabetes was defined as blood a glucose level of less than 200 mg/dl on two consecutive measurements. Graft loss was determined when blood glucose exceeded 250 mg/dl on two consecutive measurements. The results are shown in Table 4.

TABLE 4

Effects Of TTP-4000 On Allograft Islet Transplant*

| | TTP-4000 300 ug LD + 100 ug qod ip (Group 1) | PBS (Group 2) | TTP-4000 300 ug + 30 ug qod ip (Group 3) | IgG 300 ug LD + 100 ug qod ip (Group 4) | Untreated control |
|---|---|---|---|---|---|
| | 14 | 9 | 13 | 8 | 9 |
| | 16 | 8 | 14 | 9 | 8 |
| | 13 | 10 | 12 | 10 | 9 |
| | 13 | 8 | 12 | 8 | 10 |
| | 12 | 11 | 11 | 8 | 9 |
| | 16 | 8 | 11 | 8 | 8 |
| | 15 | 8 | 8 | 9 | 11 |
| | 14 | 8 | 8 | 11 | 9 |
| | | | | | 7 |
| | | | | | 9 |
| | | | | | 8 |
| | | | | | 9 |
| Mean | 14.125 | 8.75 | 11.125 | 8.875 | 8.833333 |
| SD | 1.457738 | 1.164965 | 2.167124 | 1.125992 | 1.029857 |
| n | 8 | 8 | 8 | 8 | 12 |

*Values in Table 4 reflect the day of graft loss for each animal as defined by recurrence of increased blood glucose levels.

Figure 17:
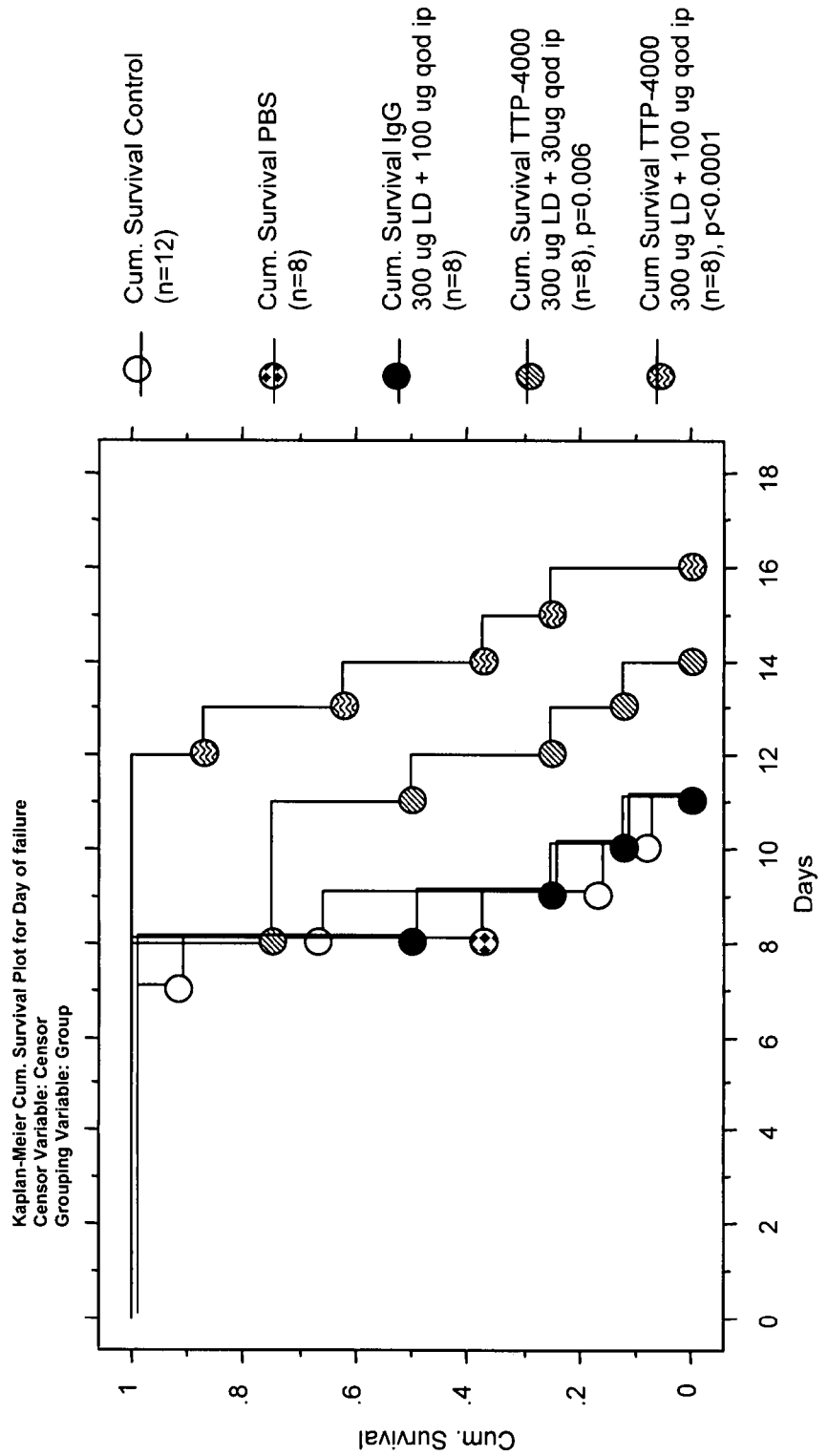
FIG. 17 shows the use of RAGE fusion protein TTP-4000 to reduce the rejection of allogeneic pancreatic islet cell transplants in accordance with alternate embodiments of the present invention where open (unfilled) circles designate untreated control animals; circles with diagonal hatching designate animals treated with TTP-4000 at a first dosage; circles with wavy hatching designate animals treated with TTP-4000 at a second dosage; diamond-filled circles designate animals treated with control PBS; and solid circles designate animals treated with control IgG.

The effects of administering TTP-4000 on allograft rejection for BALB/c islets in B6 mice are shown as a Kaplan-Meier Cumulative Survival Plot in FIG. 17. It can be seen that there is an increase in the time before detection of graft failure for animals treated with TTP-4000 (Groups 1 and 3) as opposed to animals that are not treated at all (Control) or animals treated with the vehicle (PBS) or (human IgG1). Using a variety of statistical analyses (Mantel-Cox Logrank, Breslow-Gehan-Wilcoxon; Tarone-Ware, Peto-Peto-Wilcoxin; and Harrington-Fleming) the differences between the Control and TTP-4000 (Groups 1 and 3) were significant (Table 5).

TABLE 5

| | Control vs Group 1 (TTP 4000) | | | Control vs Group 3 (TTP 4000) | | |
|---|---|---|---|---|---|---|
| Statistical Method | Chi-Square | DF* | P-value | Chi-Square | DF | P-value |
| Logrank (Mantel-Cox) | 18.777 | 1 | <0.0001 | 7.662 | 1 | 0.0056 |
| Breslow-Gehan-Wilcoxon | 15.092 | 1 | 0.0001 | 4.904 | 1 | 0.0268 |
| Tarone-Ware | 16.830 | 1 | <0.0001 | 6.212 | 1 | 0.0127 |
| Peto-Peto-Wilcoxon | 14.359 | 1 | 0.0002 | 4.315 | 1 | 0.0378 |
| Harrington-Fleming (rho = 0.5) | 16.830 | 1 | <0.0001 | 6.212 | 1 | 0.0127 |

*Degrees of Freedom

B. Islet Transplantation in NOD-Mice as a Model of Autoimmune Disease

The second set of experiments tested whether administration RAGE fusion protein (i.e. TTP-4000 or TTP-3000) would modulate the course of recurrent diabetes in NOD mice, using a syngeneic NOD transplant model.

Animal Model of Diabetes

Spontaneous autoimmune non-obese diabetic mice (NOD/LtJ) (12-25 weeks old) served as recipients for islet cells, while young pre-diabetic NOD/LtJ mice (6-7 weeks old) served as donors in syngeneic islet transplantation. Islets for transplantation were isolated as described above in Section A (Allogeneic Islet Transplantation).

Islet Transplantation:

Diabetic NOD/LtJ mice received islet grafts within 2 days of the diagnosis of diabetes. 500-600 freshly isolated islets (approximately 550 islet equivalents) from donor mice were picket up with an infusion set and transplanted into the subcapular space of the right kidney.

Treatment with Test Compounds

Test compounds were administered as soon as the islets were transplanted and continued for approximately 8 weeks. Mice were injected with 0.25 ml of either PBS, TTP-400 in PBS, or TTP-300 in PBS according to the regimen below (Table 6).

TABLE 6

| Group | No. mice | Loading Dose Volume | Maintenance Dose Volume | Regimen |
|---|---|---|---|---|
| TTP-4000 | 8 | (300 µg) 0.25 ml/dose/ mouse on day 1 | (100 µg) 0.25 ml/dose/ mouse starting on day 2 | (100 µg) Once every other day (QOD) × 8 weeks; IP |
| TTP-3000 | 8 | (300 µg) 0.25 ml/dose/ mouse on day 1 | (100 µg) 0.25 ml/dose/ mouse starting on day 2 | (100 µg) Once every other day (QOD) × 8 weeks; IP |
| PBS | 8 | 0.25 ml/dose/ mouse on day 1 | 0.25 ml/dose/ mouse starting on day 2 | Once every other day (QOD) × 8 weeks; IP |

Monitoring of Islet Graft Function

Islet graft function was monitored by serial blood glucose measurements daily for the first 2 weeks after islet transplantation, followed by every other day thereafter. Reversal of diabetes was defined as blood glucose less than 200 mg/dl on two consecutive measurements. Percentage graft loss was determined when blood glucose exceeded 250 mg/dl on two consecutive measurements. Results are shown in Table 7.

TABLE 7

Effects of TTP-4000 and TTP-3000 on Recurrent Diabetes In Syngeneic Islet Transplants In NOD Mice*

| | TTP-4000 300 ug LD + 100 ug qod ip (Group 1) | TTP-3000 300 ug + 100 ug qod ip (Group 2) | CONTROL |
|---|---|---|---|
| | 35 | 44 | 23 |
| | 38 | 46 | 25 |
| | 40 | 42 | 26 |
| | 43 | 41 | 22 |
| | 36 | 34 | 22 |
| | 45 | 32 | 24 |
| | 44 | 30 | 21 |
| | 38 | | 20 |
| | | | 22 |
| | | | 21 |
| | | | 24 |
| Mean | 39.875 | 38.42857 | 22.727273 |
| SD | 3.758324 | 6.32079 | 1.8488326 |
| n | 8 | 7 | 11 |

*Values reflect the day of graft loss for each animal as defined by recurrence of increased blood glucose levels.

Figure 18:
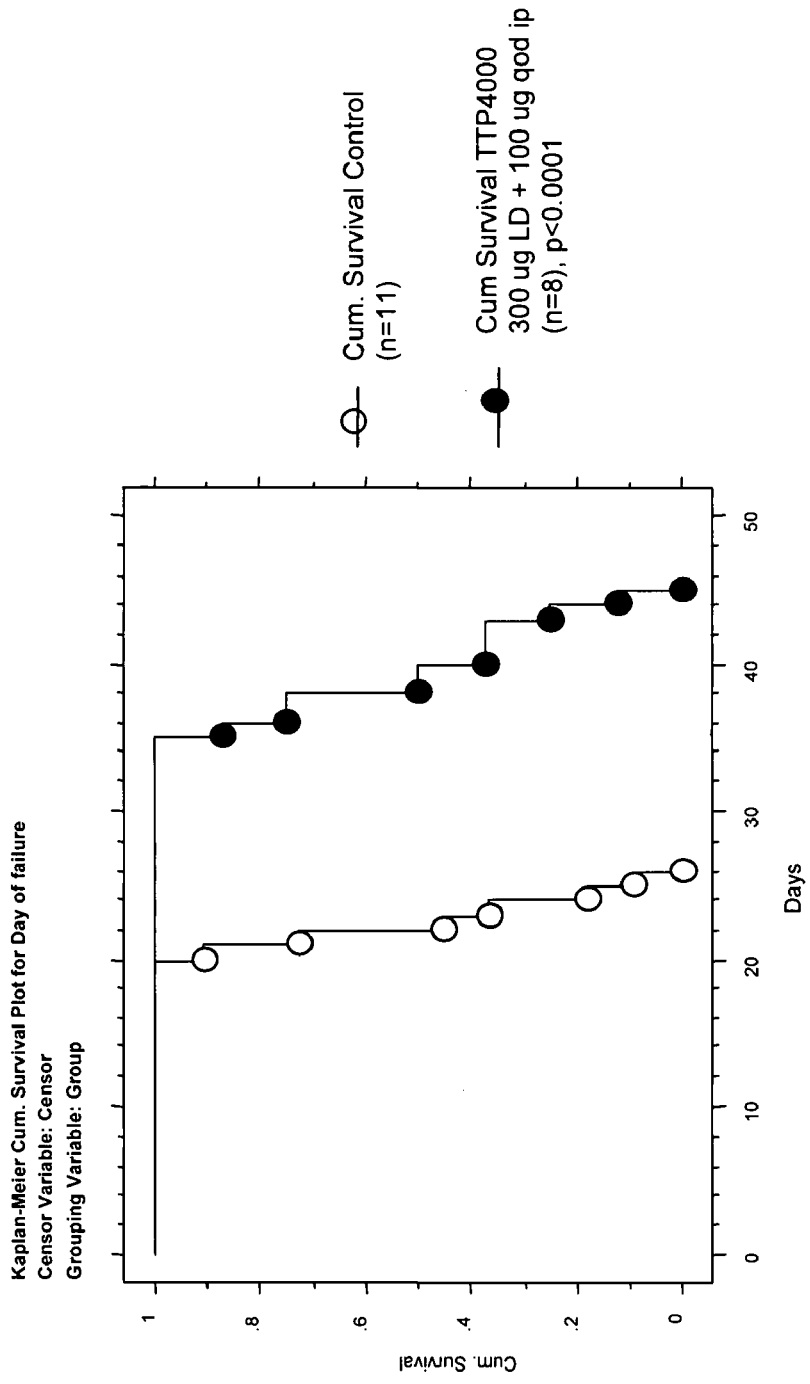
FIG. 18 shows the use of RAGE fusion proteins TTP-4000 to reduce the rejection of syngeneic pancreatic islet cell transplants in accordance with alternate embodiments of the present invention where open (unfilled) circles designate untreated control animals; and solid circles designate animals treated with TTP-4000.

The effects of administering TTP-4000 on rejection of syngeneic transplanted islets in diabetic NOD mice are shown as a Kaplan-Meier Cumulative Survival Plot in FIG. 18. As shown in the data of Table 7, there was an increase in the time before detection of graft failure for animals treated with TTP-4000 (Group 1) and TTP-3000 (Group 2) as opposed to animals that are not treated at all (Control). FIG. 18 shows the increase in time before detection of graft failure for animals treated with TTP-4000 (Group 1) and animals that are not treated at all. Using a variety of statistical analyses (Mantel-Cox Logrank, Breslow-Gehan-Wilcoxon; Tarone-Ware, Peto-Peto-Wilcoxin; Harrington-Fleming) the differences between the Control and TTP 4000 (Group 1) and the Control and TTP-3000 (Group 2) were significant (Table 8).

TABLE 8

| | Control vs Group 1 (TTP-4000) | | | Control vs Group 2 (TTP-3000) | | |
|---|---|---|---|---|---|---|
| Statistical Method | Chi-Square | DF* | P-value | Chi-Square | DF | P-value |
| Logrank (Mantel-Cox) | 18.410 | 1 | <0.0001 | 16.480 | 1 | <0.0001 |
| Breslow-Gehan-Wilcoxon | 14.690 | 1 | 0.0001 | 12.927 | 1 | 0.0001 |
| Tarone-Ware | 16.529 | 1 | <0.0001 | 14.686 | 1 | 0.0001 |
| Peto-Peto-Wilcoxon | 14.812 | 1 | 0.0001 | 13.027 | 1 | 0.0003 |
| Harrington-Fleming (rho = 0.5) | 16.529 | 1 | <0.0001 | 14.686 | 1 | 0.0001 |

*Degrees or Freedom

Example 9

RAGE Fusion Protein Lyophilized Formulation

In the development of a lyophilized formulation using the RAGE fusion protein TTP-4000, lyoprotectants and buffers were initially screened by measuring the stability of the protein after lyophilization and reconstitution. The lyophilized protein in each formulation was also subjected to accelerated stability studies to determine the potential stability of the protein over its shelf-life.

In initial screening studies, experiments were designed to evaluate formulation conditions that could provide appropriate solubility and stability of TTP-4000 formulated as a frozen bulk and provide reconstituted formulations having concentrations of RAGE fusion protein at about 50 mg/mL or higher. Formulations containing sodium acetate, sodium citrate, sodium phosphate, sodium succinate, histidine, and sodium chloride were tested along with sucrose and mannitol. Various pH's between 5.5 and 7.0 were also evaluated.

The biophysical and chemical stability of TTP-4000 was evaluated using size exclusion chromatography (SEC), SDS-Page, Fourier-Transform Infrared Spectroscopy (FTIR), circular dichroism (CD), peptide mapping, and ultra-violet-visible absorbance (UV-Vis).

Based on the solubility of the RAGE fusion protein in formulations containing one or more of sodium citrate, histidine, sucrose, mannitol, and Tween 80 at a pH of 7.0 or less, formulations containing one or more of these buffers, lyoprotectants, or surfactant were selected for further study.

Example 10

RAGE Fusion Protein Lyophilized Formulation

Based on the information collected in Example 9, additional formulations of TTP-4000 were studied. The studies focused on identifying the buffers and/or lyoprotectants useful to maintain a stable product through the freeze-drying process and potentially achieve a high concentration of TTP-4000 upon reconstitution (i.e., at about or above 50 mg/mL). Six formulations were studied during a 2 week accelerated stability study. The formulations are summarized in Table 9. Studies also focused on developing a freeze-drying cycle for larger doses of TTP-4000 (250 mg) as described below.

Following freeze-drying, the formulation development sample vials were crimped and placed into a 40° C. chamber for 2 weeks. The scale-up development samples were stored at 2-8° C. until testing was performed.

Sample Analysis Methods:

The concentration of TTP-4000 in samples was measured by UV-Vis spectrophotometry. An Aglient UV-Vis was used to obtain protein spectra as well as buffer blank spectra. Once acquired, absorbance values were corrected for any light scattering that may occur as a result of any protein aggregation.

Residual moisture was analyzed using a Karl Fisher titration method. Freeze-dried formulation development samples were reconstituted with the appropriate amount of WFI. The time for reconstitution was considered to be the time from when the water was added to the time when there were no visible solids. The pH of each sample was measured after reconstitution using a properly calibrated semi-micro probe.

Size Exclusion Chromatography (SEC) was performed using a TSKgel Super SW2000 column to analyze or monitor the physical stability (degradation and soluble aggregate formation) of TTP-4000 during freeze-drying and storage at accelerating conditions. Samples were injected into an Aglient 1100 series LC fitted with two TSKgel Super SW2000, 4.6×300 mm, 4 μm columns (Tosoh Bioscience, 18674).

To measure the particle count, a 1 mL sample was diluted 20-fold into 20 mL. The sample was degassed by sonication for about 30 seconds, and gently stirred by hand-swirling without introducing bubbles. Three aliquots, each 5 mL in volume, were withdrawn into the light obscuration counter sensor. With the instrument set to cumulative mode, particles were collected at settings of greater or equal to 10 μm and greater or equal to 25 μm.

Results:

Based on the preformulation studies in Example 9, two buffers were initially investigated: sodium citrate and L-histidine. The concentrated formulations 1-6 (Table 9) were prepared using centrifugal concentrators. The final protein concentration in the formulations 1-6 in Table 9 was in a range between about 4-15 mg/mL.

TABLE 9

Formulations of TTP-4000

| | Sodium Citrate (mM) | Histidine (mM) | Sucrose (mM) | Mannitol (mM) | Tween 80 (%) | pH |
|---|---|---|---|---|---|---|
| 1 | 10 | | 60 | | | 6.0 |
| 2 | 10 | | 30 | 50 | | 6.0 |
| 3 | 10 | | 60 | | 0.01 | 6.0 |
| 4 | | 10 | 60 | | | 6.0 |
| 5 | | 10 | 30 | 50 | | 6.0 |
| 6 | | 10 | 60 | | 0.01 | 6.0 |

Using formulations 1-6 in Table 9, vials (2 mL) were used with 0.7 mL fill volumes. The vial headspace was filled with air. Prior to drying, the samples were frozen at a shelf temperature of between −50° C. to −20° C. for approximately 12 hours. The samples were dried at a reduced pressure of 100 mTorr and a shelf temperature of between −20° C. and −10° C. for approximately 36 hours, followed by a shelf temperature of 20° C. for approximately 12 hours. Following freeze drying, the vials were stoppered, and the tops were crimped. Rugged cakes were produced from each formulation 1-6.

The freeze-dried products were subjected to accelerated stability study in order to access the chemical stability of the formulations. The freeze-dried products were placed in storage at 40° C. and 75% relative humidity for 2 weeks.

The freeze-dried products were reconstituted with 0.206 mL WFI. All freeze-dried products were reconstituted within 20 seconds or less. The pH remained consistent in all reconstituted formulations throughout the 2 week storage period. Residual moisture values determined at times 0 and 2 weeks for the freeze-dried products were between 3.0% and 0.8% and showed that the freeze-drying cycle was able to sufficiently dry the pre-lyophilized formulations. The osmolality of all the reconstituted formulations was within a desirable isotonic range between 250 mOsm/kg and 400 mOsm/kg (See Table 10). The viscosity of each reconstituted formulation was below 3.7 cP (centiPoise).

TABLE 10

Reconstituted formulations of TTP-4000 and osmolality

| | Sodium Citrate (mM) | Histidine (mM) | Sucrose (mM) | Mannitol (mM) | Tween 80 (%) | Osmolaltiy (mOsm/kg) |
|---|---|---|---|---|---|---|
| 1 | 10 | | 60 | | | 322 |
| 2 | 10 | | 30 | 50 | | 385 |
| 3 | 10 | | 60 | | 0.01 | 324 |
| 4 | | 10 | 60 | | | 264 |
| 5 | | 10 | 30 | 50 | | 336 |
| 6 | | 10 | 60 | | 0.01 | 262 |

SEC analysis was performed on samples of formulation 5 in Table 10 taken at various steps of the freeze-drying process and indicated that in these formulations, TTP-4000 was not particularly sensitive to any of the steps of the freeze-drying process based on the consistent low levels of aggregate and breakdown species.

SEC analysis was also performed on the pre-lyophilized formulations prior to freeze-drying as well as the reconstituted formulations at time zero and after a 2 week accelerated stability study. The amount of impurities (aggregate or breakdown product) were consistently low (i.e., below 4%) (Table 11).

TABLE 11

Reconstituted formulations of TTP-4000 and % intact protein

| | Sodium Citrate (mM) | Histidine (mM) | Sucrose (mM) | Mannitol (mM) | Tween 80 (%) | % intact protein (T = 0) | % intact protein (T = 2 wks.) |
|---|---|---|---|---|---|---|---|
| 1 | 10 | | 60 | | | 96.2 | 97.3 |
| 2 | 10 | | 30 | 50 | | 96.8 | 97.3 |
| 3 | 10 | | 60 | | 0.01 | 96.3 | 97.2 |
| 4 | | 10 | 60 | | | 97.4 | 97.0 |
| 5 | | 10 | 30 | 50 | | 97.9 | 96.9 |
| 6 | | 10 | 60 | | 0.01 | 97.7 | 96.9 |

Peptide mapping revealed no oxidation or deamidation of TTP-4000 due to freeze-drying and storage under accelerated conditions.

SDS-PAGE was run on formulations 1, 3, 4, and 6 and showed that TTP-4000 maintained physical stability throughout the freeze-drying and storage process in these formulations.

To scale-up the freeze-drying process for use with 50 mL lyo vials and a dosage of 250 mg of TTP-4000, samples were prepared by concentrating the solution to 15 mg/mL of TTP-4000 using ultrafiltration and then diafiltering the solution against 10 mM histidine and 65 mM sucrose at pH 6.0. Tween 80 was added to a final amount of 0.01% (vol/vol).

The pre-lyophilized formulation (16.67 mL) was added to each 50 mL vial. The samples were exposed to a freeze-drying cycle where the samples cooled at a shelf temperature of between 5° C. and −5° C. for 30 min, followed by cooling at a shelf temperature of −50° C. for approximately 3 hours. The samples were dried at a reduced pressure of 100 mTorr and a shelf temperature of between −20° C. and −10° C. for approximately 34 hours, followed by a shelf temperature of between 5° C. and 20° C. for approximately 11 hours. Following freeze drying, the vials were stoppered, and the tops were crimped. A pharmaceutically elegant, white cake was produced. The cake appeared rugged and did not lose its structure during handling and storage.

The concentration of the reconstituted sample as determined by absorbance at 280 nm was 40.5 mg/mL of TTP-4000. In additional studies under similar conditions, the concentration of TTP-4000 in the reconstituted sample was consistently about 50 mg/mL.

The reconstituted sample was measured for particulate content at 0, 2, and 6 hours of storage at room temperature. The results in Table 12 show that the reconstituted sample had a low amount of particulate content.

TABLE 12

Number of particles detected in reconstituted sample during storage

| | Particle size | Time = 0 | Time = 2 hrs. | Time = 6 hrs. |
|---|---|---|---|---|
| Particles per mL | >10 μm | 562 | 368 | 948 |
| | >25 μm | 8 | 16 | 20 |
| Particles per container | >10 μm | 2753 | 1803 | 4645 |
| | >25 μm | 39 | 78 | 98 |

In summary, TTP-4000 was formulated in citrate and histidine buffers containing one or more of sucrose, mannitol, and Tween 80. Testing showed that formulations containing sodium citrate or histidine had similar performance characteristics and that TTP-4000 may be more soluble in formulations containing histidine.

Formulations containing histidine were focused upon for further scale-up studies. Following a freeze-drying cycle, the chemical and physical stability of TTP-4000 was evaluated, and no significant differences between the histidine formulations were detected. Also, mannitol was eliminated from the formulation. The final formulation chosen from the formulation development study contained 10 mM histidine, 60 mM sucrose, and 0.01% Tween 80 at about pH 6.0. This formulation demonstrated a superior ability to keep TTP-4000 stable during freeze-drying and storage, and also provided the highest concentration of TTP-4000 during the study. In the scale up study, the sucrose level was raised to 65 mM to adjust the osmolality of the formulation closer to isotonicity. During the scale up study, it was also found that maintaining the pH of the TTP-4000 pre-lyophilized formulation and reconstituted formulation at or near pH 6.0 and less than 6.7 was useful pH to reduce protein precipitation or aggregation.

The foregoing is considered as illustrative only of the principal of the invention. Since numerous modifications and changes will readily occur to those skilled in the art, it is not intended to limit the invention to the exact embodiments shown and described, and all suitable modifications and equivalents falling within the scope of the appended claims are deemed within the present inventive concept.

What is claimed is:

1. A formulation comprising a lyophilized mixture of a lyoprotectant, a RAGE fusion protein, and a buffer, wherein the RAGE fusion protein comprises the amino acid sequence as set forth in one of SEQ ID NOs: 32, 33, 34, or 56 or a sequence at least 90% identical thereto, wherein the lyoprotectant comprises a non-reducing sugar, and wherein the amount of buffer is sufficient to provide a reconstituted formulation having a pH ranging from 6.0 to 6.7 when the concentration of the RAGE fusion protein in the reconstituted formulation is within the range from 1 mg/mL to 400 mg/mL.

2. The formulation of claim 1, wherein the non-reducing sugar comprises at least one of sucrose, mannitol, or trehalose.

3. The formulation of claim 1, wherein the buffer comprises histidine.

4. The formulation of claim 1, wherein the RAGE fusion protein comprises the amino acid sequence as set forth in SEQ ID NO: 32, or a sequence 98% identical thereto.

5. The formulation of claim 1, wherein the RAGE fusion protein comprises the amino acid sequence as set forth in SEQ ID NO: 33, or a sequence 98% identical thereto.

6. The formulation of claim 1, wherein the RAGE fusion protein comprises the amino acid sequence as set forth in SEQ ID NO: 34, or a sequence 98% identical thereto.

7. The formulation of claim 1, wherein the RAGE fusion protein comprises the amino acid sequence as set forth in SEQ ID NO: 56, or a sequence 98% identical thereto.

8. The formulation of claim 1, wherein the RAGE fusion protein is the amino acid sequence as set forth in one of SEQ ID NOs: 32, 33, 34, or 56.

9. The formulation of claim 1, wherein the sequence at least 90% identical to SEQ ID NOs: 32, 33, 34, or 56 comprises the polypeptide of SEQ ID NOs: 32, 33, 34, or 56 without the C-terminal lysine.

10. The formulation of claim 1, further comprising at least one of a surfactant, a chelating agent, or a bulking agent.

11. A reconstituted formulation comprising a lyophilized RAGE fusion protein reconstituted in a diluent, wherein the RAGE fusion protein concentration in the reconstituted formulation is within the range from about 1 mg/mL to about 400 mg/mL, wherein the reconstituted formulation comprises a lyoprotectant, the RAGE fusion protein, and a buffer, wherein the RAGE fusion protein comprises the amino acid sequence as set forth in one of SEQ ID NOs: 32, 33, 34, or 56 or a sequence at least 90% identical thereto, and wherein the lyoprotectant comprises a non-reducing sugar, and wherein the pH is in the range from 6.0 to 6.7.

12. The reconstituted formulation of claim 11, wherein the RAGE fusion protein comprises the amino acid sequence as set forth in SEQ ID NO: 32, or a sequence 98% identical thereto.

13. The reconstituted formulation of claim 11, wherein the RAGE fusion protein comprises the amino acid sequence as set forth in SEQ ID NO: 33, or a sequence 98% identical thereto.

14. The reconstituted formulation of claim 11, wherein the RAGE fusion protein comprises the amino acid sequence as set forth in SEQ ID NO: 34, or a sequence 98% identical thereto.

15. The reconstituted formulation of claim 11, wherein the RAGE fusion protein comprises the amino acid sequence as set forth in SEQ ID NO: 56, or a sequence 98% identical thereto.

16. The reconstituted formulation of claim 11, wherein the RAGE fusion protein is the amino acid sequence as set forth in one of SEQ ID NOs: 32, 33, 34, or 56 or a sequence at least 90% identical thereto.

17. The reconstituted formulation of claim 11, wherein the sequence at least 90% identical to SEQ ID NOs: 32, 33, 34, or 56 comprises the polypeptide of SEQ ID NOs: 32, 33, 34, or 56 without the C-terminal lysine.

18. The reconstituted formulation of claim 11, wherein the diluent comprises water for injection (WFI).

19. The reconstituted formulation of claim 11, wherein the reconstituted formulation is suitable for subcutaneous or intramuscular administration.

20. The reconstituted formulation of claim 11, wherein the reconstituted formulation is isotonic.

21. The reconstituted formulation of claim 11, wherein the formulation comprises about 1-400 mg/mL of RAGE fusion protein; about 1 mM to about 100 mM histidine buffer; about 60 mM to about 65 mM sucrose; about 0.001% to about 0.05% Tween 80; and a pH of about 6.0 to 6.5.

22. The reconstituted formulation of claim 11, wherein the formulation comprises about 40-50 mg/mL of RAGE fusion protein; about 10 mM histidine; about 65 mM sucrose; about 0.01% Tween 80; and a pH of about 6.0.

23. The reconstituted formulation of claim 11, wherein the formulation exhibits less than 5% decomposition after 1 week at 40 degrees Centigrade.

24. The reconstituted formulation of claim 11, wherein less than 10% of the RAGE fusion protein is present as an aggregate in the formulation upon reconstitution.

25. The reconstituted formulation of claim 11, wherein the non-reducing sugar comprises at least one of sucrose, mannitol, or trehalose.

26. The reconstituted formulation of claim 11, wherein the lyophylized formulation of the RAGE fusion protein comprises at least one of a surfactant, a chelating agent or a bulking agent.

27. An article of manufacture comprising a container which holds a lyophylized RAGE fusion protein comprising a lyophilized mixture of a lyoprotectant, a RAGE fusion protein, and a buffer, wherein the RAGE fusion protein comprises the amino acid sequence as set forth in one of SEQ ID NOs: 32, 33, 34, or 56 or a sequence at least 90% identical thereto, wherein the lyoprotectant comprises a non-reducing sugar, and wherein the amount of buffer is sufficient to provide a reconstituted formulation having a pH ranging from 6.0 to 6.7 when the concentration of the RAGE fusion protein in the reconstituted formulation is within the range from 1 mg/mL to 400 mg/mL, and instructions for reconstituting the lyophilized formulation with a diluent.

28. The article of manufacture of claim 27, wherein the RAGE fusion protein comprises the amino acid sequence as set forth in SEQ ID NO: 32, or a sequence 98% identical thereto.

29. The article of manufacture of claim 27, wherein the RAGE fusion protein comprises the amino acid sequence as set forth in SEQ ID NO: 33, or a sequence 98% identical thereto.

30. The article of manufacture of claim 27, wherein the RAGE fusion protein comprises the amino acid sequence as set forth in SEQ ID NO: 34, or a sequence 98% identical thereto.

31. The article of manufacture of claim 27, wherein the RAGE fusion protein comprises the amino acid sequence as set forth in SEQ ID NO: 56, or a sequence 98% identical thereto.

32. The article of manufacture of claim 27, wherein the RAGE fusion protein is the amino acid sequence as set forth in one of SEQ ID NOs: 32, 33, 34, or 56 or a sequence at least 90% identical thereto.

33. The article of manufacture of claim 27, wherein the sequence at least 90% identical to SEQ ID NOs: 32, 33, 34, or 56 comprises the polypeptide of SEQ ID NOs: 32, 33, 34, or 56 without the C-terminal lysine.

34. The article of manufacture of claim 27, wherein the diluent comprises water for injection (WFI).

35. The article of manufacture of claim 27, wherein the reconstituted formulation is suitable for subcutaneous or intramuscular administration.

36. The article of manufacture of claim 27, wherein the reconstituted formulation is isotonic.

37. The article of manufacture of claim 27, wherein upon reconstitution according to the instructions, the formulation comprises about 1-400 mg/mL of RAGE fusion protein; about 1 mM to about 100 mM histidine buffer; about 60 mM to about 65 mM sucrose; about 0.001% to about 0.05% Tween 80; and a pH of about 6.0 to 6.5.

38. The article of manufacture of claim 27, wherein upon reconstitution the formulation comprises about 40-50 mg/mL of RAGE fusion protein; about 10 mM histidine; about 65 mM sucrose; about 0.01% Tween 80; and a pH of about 6.0.

39. The article of manufacture of claim 27, wherein the instructions are for reconstituting the lyophilized formulation such that the RAGE fusion protein concentration in the reconstituted formulation is within the range from about 40 mg/mL to about 100 mg/mL.

40. The article of manufacture of claim 27, wherein the lyophilized formulation is sterile.

41. The article of manufacture of claim 27, further comprising a second container which holds a diluent for reconstituting the lyophilized formulation, wherein the diluent is water for injection (WFI).

42. The article of manufacture of claim 27, wherein upon reconstitution according to the instructions, the formulation exhibits less than 5% decomposition after 1 week at 40 degrees Centigrade.

43. The article of manufacture of claim 27, wherein less than 10% of the RAGE fusion protein is present as an aggregate in the formulation upon reconstitution.

44. The article of manufacture of claim 27, wherein the non-reducing sugar comprises at least one of sucrose, mannitol, or trehalose.

45. The article of manufacture of claim 27, wherein the lyophylized RAGE fusion protein comprises at least one of a surfactant, a chelating agent or a bulking agent.

46. A method for preparing a stable reconstituted formulation of a RAGE fusion protein comprising reconstituting a lyophilized mixture of the RAGE fusion protein, a lyoprotectant, and a buffer in a diluent such that the RAGE fusion protein concentration in the reconstituted formulation is in a range from about 1 mg/mL to about 400 mg/mL, and the pH is in the range from 6.0 to 6.7, wherein the RAGE fusion protein comprises the amino acid sequence as set forth in one of SEQ ID NOs: 32, 33, 34, or 56 or a sequence at least 90% identical thereto, and wherein the lyoprotectant comprises a non-reducing sugar.

47. The method of claim 46, wherein the lyoprotectant comprises at least one of sucrose, mannitol or trehalose.

48. The method of claim 46, wherein the lyophilized mixture further comprises at least one of a surfactant, a chelating agent or a bulking agent.

49. The method of claim 46, wherein the RAGE fusion protein is the amino acid sequence as set forth in one of SEQ ID NOs: 32, 33, 34, or 56 or a sequence at least 90% identical thereto.

50. The method of claim 49, wherein the sequence at least 90% identical to SEQ ID NOs: 32, 33, 34, or 56 comprises the polypeptide of SEQ ID NOs: 32, 33, 34, or 56 without the C-terminal lysine.

51. The method of claim 46, wherein the reconstituted formulation comprises about 40-100 mg/mL of RAGE fusion protein; about 2 mM to about 60 mM histidine; about 60 mM to about 65 mM sucrose; about 0.001% to about 0.05% Tween 80; and a pH of about 6.0 to 6.5.

52. The method of claim 46, further comprising preparing the lyophilized RAGE fusion protein by lyophilizing a mixture comprising a RAGE fusion protein and a lyoprotecting amount of a lyoprotectant.

* * * * *

UNITED STATES PATENT AND TRADEMARK OFFICE
CERTIFICATE OF CORRECTION

PATENT NO.        : 7,981,424 B2
APPLICATION NO.   : 11/789637
DATED             : July 19, 2011
INVENTOR(S)       : Adnan M. M. Mjalli et al.

Page 1 of 1

It is certified that error appears in the above-identified patent and that said Letters Patent is hereby corrected as shown below:

Column 139, Line 57, In Claim 11, Please delete "lyophylized", please insert -- lyophilized --.

Column 140, Line 63, In Claim 24, Please delete "10%", please insert -- about 10% --.

Column 141, Line 2, In Claim 26, Please delete "lyophylized", please insert -- lyophilized --.

Column 141, Line 6, In Claim 27, Please delete "lyophylized", please insert -- lyophilized --.

Column 142, Line 17, In Claim 43, Please delete "10%", please insert -- about 10% --.

Column 142, Line 23, In Claim 45, Please delete "lyophylized", please insert -- lyophilized --.

Signed and Sealed this
Twenty-ninth Day of November, 2011

David J. Kappos
*Director of the United States Patent and Trademark Office*